US011827714B2

(12) United States Patent
Chen et al.

(10) Patent No.: US 11,827,714 B2
(45) Date of Patent: Nov. 28, 2023

(54) ANTIBODIES AND CHIMERIC ANTIGEN RECEPTORS SPECIFIC FOR CD19

(71) Applicant: Juno Therapeutics, Inc., Seattle, WA (US)

(72) Inventors: Yan Chen, Lexington, MA (US); Steven M. Shamah, Acton, MA (US); Csaba Pazmany, Belmont, MA (US); Jui Dutta-Simmons, Lexington, MA (US)

(73) Assignee: Juno Therapeutics, Inc., Seattle, WA (US)

( * ) Notice: Subject to any disclaimer, the term of this patent is extended or adjusted under 35 U.S.C. 154(b) by 587 days.

(21) Appl. No.: 16/700,937

(22) Filed: Dec. 2, 2019

(65) Prior Publication Data

US 2020/0172630 A1 Jun. 4, 2020

Related U.S. Application Data

(62) Division of application No. 14/839,911, filed on Aug. 28, 2015, now Pat. No. 10,533,055.

(60) Provisional application No. 62/078,942, filed on Nov. 12, 2014, provisional application No. 62/043,273, filed on Aug. 28, 2014.

(51) Int. Cl.
*C07K 16/00* (2006.01)
*C12P 21/08* (2006.01)
*C07K 16/28* (2006.01)
*A61K 35/17* (2015.01)
*C07K 14/705* (2006.01)
*C07K 14/725* (2006.01)
*A61K 39/00* (2006.01)

(52) U.S. Cl.
CPC .......... *C07K 16/2896* (2013.01); *A61K 35/17* (2013.01); *C07K 14/7051* (2013.01); *C07K 14/70521* (2013.01); *C07K 16/2803* (2013.01); *A61K 2039/505* (2013.01); *C07K 2317/21* (2013.01); *C07K 2317/34* (2013.01); *C07K 2317/53* (2013.01); *C07K 2317/56* (2013.01); *C07K 2317/565* (2013.01); *C07K 2317/622* (2013.01); *C07K 2317/73* (2013.01); *C07K 2317/92* (2013.01); *C07K 2317/94* (2013.01); *C07K 2319/00* (2013.01); *C07K 2319/33* (2013.01)

(58) Field of Classification Search
None
See application file for complete search history.

(56) References Cited

U.S. PATENT DOCUMENTS

| | | |
|---|---|---|
| 4,235,871 A | 11/1980 | Papahadjopoulos et al. |
| 4,452,773 A | 6/1984 | Molday |
| 4,501,728 A | 2/1985 | Geho et al. |
| 4,690,915 A | 9/1987 | Rosenberg |
| 4,795,698 A | 1/1989 | Owen et al. |
| 4,837,028 A | 6/1989 | Allen |
| 5,019,369 A | 5/1991 | Presant et al. |
| 5,087,616 A | 2/1992 | Myers et al. |
| 5,200,084 A | 4/1993 | Liberti et al. |
| 5,208,020 A | 5/1993 | Chari et al. |
| 5,219,740 A | 6/1993 | Miller et al. |
| 5,416,064 A | 5/1995 | Chari et al. |
| 5,635,483 A | 6/1997 | Pettit et al. |
| 5,712,374 A | 1/1998 | Kuntsmann et al. |
| 5,714,586 A | 2/1998 | Kunstmann et al. |
| 5,739,116 A | 4/1998 | Hamann et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,877,296 A | 3/1999 | Hamann et al. |
| 6,040,177 A | 3/2000 | Riddell et al. |
| 6,207,453 B1 | 3/2001 | Maass et al. |
| 6,410,319 B1 | 6/2002 | Raubitschek et al. |
| 6,451,995 B1 | 9/2002 | Cheung et al. |
| 6,602,684 B1 | 8/2003 | Umana et al. |
| 6,630,579 B2 | 10/2003 | Chari et al. |
| 7,070,995 B2 | 7/2006 | Jensen |
| 7,109,304 B2 | 9/2006 | Hansen |
| 7,265,209 B2 | 9/2007 | Jensen |

(Continued)

FOREIGN PATENT DOCUMENTS

| | | |
|---|---|---|
| EP | 0425235 | 5/1991 |
| EP | 0452342 | 10/1991 |

(Continued)

OTHER PUBLICATIONS

US 8,252,592 B2, 08/2012, Sadelain (withdrawn)

(Continued)

*Primary Examiner* — Chun W Dahle

(74) *Attorney, Agent, or Firm* — Morrison & Foerster LLP

(57) ABSTRACT

Provided are CD19 binding molecules, including anti-CD19 antibodies, including antibody fragments such as single-chain fragments, and chimeric receptors including the antibodies, such as chimeric antigen receptors (CARs). Among the antibodies are human antibodies, including those that compete for binding to CD19 with reference antibodies, such as murine antibodies. In some embodiments, the antibodies display similar functional properties to the reference antibodies, such as comparable binding affinities and/or competitive inhibition properties. Also provided are genetically engineered cells expressing the chimeric receptors, and uses of the binding molecules and cells adoptive cell therapy.

31 Claims, 27 Drawing Sheets

Specification includes a Sequence Listing.

(56) References Cited

U.S. PATENT DOCUMENTS

| | | |
|---|---|---|
| 7,354,762 B2 | 4/2008 | Jensen |
| 7,446,179 B2 | 11/2008 | Jensen et al. |
| 7,446,190 B2 | 11/2008 | Sadelain et al. |
| 7,446,191 B2 | 11/2008 | Jensen |
| 7,498,298 B2 | 3/2009 | Doronina et al. |
| 7,521,541 B2 | 4/2009 | Eigenbrot et al. |
| 7,855,275 B2 | 12/2010 | Eigenbrot et al. |
| 8,324,353 B2 | 12/2012 | Jensen |
| 8,389,282 B2 | 3/2013 | Sadelain et al. |
| 8,399,645 B2 | 3/2013 | Campana et al. |
| 8,497,118 B2 | 7/2013 | Jensen |
| 8,822,647 B2 | 9/2014 | Jensen |
| 10,533,055 B2 | 1/2020 | Chen et al. |
| 2002/0131960 A1 | 9/2002 | Sadelain et al. |
| 2002/0164328 A1 | 11/2002 | Shinkawa et al. |
| 2003/0115614 A1 | 6/2003 | Kanda et al. |
| 2003/0157108 A1 | 8/2003 | Presta |
| 2003/0170238 A1 | 9/2003 | Gruenberg et al. |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2004/0259150 A1 | 12/2004 | Nakamura |
| 2005/0031613 A1 | 2/2005 | Nakamura |
| 2005/0123546 A1 | 6/2005 | Umana et al. |
| 2005/0272916 A1 | 12/2005 | Hanai |
| 2006/0270045 A1 | 11/2006 | Cregg et al. |
| 2007/0134759 A1 | 6/2007 | Nishiya |
| 2008/0241884 A1 | 10/2008 | Shitara |
| 2009/0203078 A1 | 8/2009 | Ogawa |
| 2009/0324630 A1 | 12/2009 | Jensen |
| 2011/0003380 A1 | 1/2011 | Miltenyi et al. |
| 2013/0149337 A1 | 6/2013 | Cooper et al. |
| 2013/0266551 A1 | 10/2013 | Campana |
| 2013/0287748 A1 | 10/2013 | June et al. |
| 2014/0271635 A1 | 9/2014 | Brogdon |
| 2014/0328812 A1 | 11/2014 | Campana |

FOREIGN PATENT DOCUMENTS

| | | |
|---|---|---|
| EP | 1331266 | 7/2003 |
| EP | 2537416 | 12/2012 |
| RU | 2495882 | 10/2013 |
| WO | WO 1994/011026 | 5/1994 |
| WO | WO 1997/030087 | 8/1997 |
| WO | WO 1998/058964 | 12/1998 |
| WO | WO 1999/022764 | 5/1999 |
| WO | WO 2000/014257 | 3/2000 |
| WO | WO 2000/061739 | 10/2000 |
| WO | WO 2001/029246 | 4/2001 |
| WO | WO 2002/031140 | 4/2002 |
| WO | WO 2002/077029 | 10/2002 |
| WO | WO 2003/084570 | 10/2003 |
| WO | WO 2003/085119 | 10/2003 |
| WO | WO 2004/056312 | 7/2004 |
| WO | WO 2005/012493 | 2/2005 |
| WO | WO 2005/035586 | 4/2005 |
| WO | WO 2005/035778 | 4/2005 |
| WO | WO 2005/053742 | 6/2005 |
| WO | WO 2009/054863 | 4/2009 |
| WO | WO 2009/072003 | 6/2009 |
| WO | WO 2009/091826 | 7/2009 |
| WO | WO 2010/011944 | 1/2010 |
| WO | WO 2010/033140 | 3/2010 |
| WO | WO 2010/095031 | 8/2010 |
| WO | WO 2012/129514 | 9/2012 |
| WO | WO 2012/170807 | 12/2012 |
| WO | WO 2013/071154 | 5/2013 |
| WO | WO 2013/123061 | 8/2013 |
| WO | WO 2013/126726 | 8/2013 |
| WO | WO 2013/166321 | 11/2013 |
| WO | WO 2014/031687 | 2/2014 |
| WO | WO 2014/055668 | 4/2014 |
| WO | WO 2014/134165 | 9/2014 |
| WO | WO 2015/066551 | 5/2015 |
| WO | WO 2015/092024 | 6/2015 |
| WO | WO 2015/095895 | 6/2015 |

OTHER PUBLICATIONS

Al-Lazikani et al., "Standard conformations for the canonical structures of immunoglobulins," JMB (1997) 273:927-948.

Almåsbak et al., "Inclusion of an IgG1-Fc spacer abrogates efficacy of CD19 Car T cells in a xenograft mouse model," Gene Ther. May 2015; 22(5):391-403.

Alonso-Camino et al., "CARbodies: Human Antibodies Against Cell Surface Tumor Antigens Selected From Repertoires Displayed on T Cell Chimeric Antigen Receptors," Mol Ther Nucl Acids (2013) 2: e93.

Boris-Lawrie et al., "Recent advances in retrovirus vector technology," Cur. Opin. Genet. Develop. (1993) 3:102-109.

Brash et al., "Strontium phosphate transfection of human cells in primary culture: stable expression of the simian virus 40 large-T-antigen gene in primary human bronchial epithelial cells," Mol. Cell Biol. (1987) 7: 2031-2034.

Brentjens et al., "CD19-targeted T cells rapidly induce molecular remissions in adults with chemotherapy-refractory acute lymphoblastic leukemia," Sci Transl Med. (2013) 5(177).

Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA (1993) 90:8033-8037.

Cardarelli et al., "A nonfucosylated human antibody to CD19 with potent B-cell depletive activity for therapy of B-cell malignancies," Cancer Immunol Immunother (2010) 59(2):257-265.

Carlens et al., "Ex vivo T lymphocyte expansion for retroviral transduction: influence of serum-free media on variations in cell expansion rates and lymphocyte subset distribution," Exp Hematol (2000) 28(10): 1137-46.

Carrillo et al., "The Multiple Sequence Alignment Problem in Biology," SIAM J Applied Math (1988) 48: 1073.

Cavalieri et al., "Human T lymphocytes transduced by lentiviral vectors in the absence of TCR activation maintain an intact immune competence," Blood (2003) 102(2): 497-505.

Chari et al., "Immunoconjugates containing novel maytansinoids: promising anticancer drugs," Cancer Res. (1992) 52:127-131.

Chicaybam et al., "An efficient low cost method for gene transfer to T lymphocytes," PLoS ONE (2013) 8(3): e60298.

Cho et al., "Human mammalian cell sorting using a highly integrated micro-fabricated fluorescence-activated cell sorter (microFACS)," Lab Chip (2010) 10: 1567-1573.

Chowdhury et al., "Engineering hot spots for affinity enhancement of antibodies," Methods Mol. Biol. (2008) 207:179-196.

Clackson et al., "Making antibody fragments using phage display libraries," Nature (1991) 352:624-628.

Cooper et al., "T-cell clones can be rendered specific for CD19: toward the selective augmentation of the graft-versus-B-lineage leukemia effect," Blood. (2003) 101:1637-1644.

Davila et al., "CD19 CAR-targeted T cells induce long-term remission and B Cell Aplasia in an immunocompetent mouse model of B cell acute lymphoblastic leukemia," PLoS ONE (2013) 8(4): e61338.

Dotti et al., "Design and Development of Therapies Using Chimeric Antigen Receptor-Expressing T Cells," Immunol Rev (2014) 257(1); 107-126.

Dubowchik et al., "Doxorubicin immunoconjugates containing bivalent, lysosomally-cleavable dipeptide linkages," Bioorg. & Med. Chem. Letters (2002) 12:1529-1532.

Endo et al., "High-throughput, genome-scale protein production method based on the wheat germ cell-free expression system," Biotechnol. Adv. (2003) 21: 695-713.

Fedorov et al., "PD-1- and CTLA-4-based inhibitory chimeric antigen receptors (iCARs) divert off-target immunotherapy responses," Sci. Transl. Medicine (2013) 5(215).

Flatman et al., "Process analytics for purification of monoclonal antibodies," J. Chromatogr. (2007) B 848:79-87.

(56) References Cited

OTHER PUBLICATIONS

Gerngross et al., "Advances in the production of human therapeutic proteins in yeasts and filamentous fungi," Nat. Biotech. (2004) 22:1409-1414.
Godin et al., "Microfluidics and photonics for Bio-System-on-a-Chip: a review of advancements in technology towards a microfluidic flow cytometry chip," J Biophoton. (2008) 1(5):355-376.
Hermans et al., "The VITAL assay: a versatile fluoro metric technique for assessing CTL- and NKT-mediated cytotoxicity against multiple targets in vitro and in vivo," J. Immunological Methods (2004) 285(1): 25-40.
Hinman et al., "Preparation and characterization of monoclonal antibody conjugates of the calicheamicins: a novel and potent family of antitumor antibiotics," Cancer Res. (1993) 53:3336-3342.
Honegger A and Plückthun A, "Yet another numbering scheme for immunoglobulin variable domains: an automatic modeling and analysis tool," J Mol Biol, (2001) 8;309(3):657-70.
Hoogenboom et al., "Overview of antibody phage-display technology and its applications," Methods in Molecular Biology (2002) 178:1-37.
Huang et al., "DNA transposons for modification of human primary T lymphocytes," Methods Mol Biol (2009) 506: 115-126.
Hudecek et al., "Receptor affinity and extracellular domain modifications affect tumor Yecognition by ROR1-specific chimeric antigen receptor T cells," Clin. Cancer Res. (2013) 19:3153.
Janeway et al. "Structure of the Antibody Molecule and Immunoglobulin genes," Immunology 3rd Edition p. 3:1-3:11.
Jeffrey et al., "Dipeptide-based highly potent doxorubicin antibody conjugates," Bioorganic& Med. Chem. Letters (2006) 16:358-362.
Jensen et al., "Antitransgene Rejection Responses Contribute to Attenuated Persistence of Adoptively Transferred CD20/CD19-specific Chimeric Antigen Receptor Redirected T Cells in Humans," Biol Blood Marrow Transplant (2010) 16 (9); 1245-1256.
Johnston, et al., "Biolistic transformation: microbes to mice," Nature (1990) 346:776-777.
Junghans et al., "Anti-Tac-H, a humanized antibody to the interleukin 2 receptor with new features for immunotherapy in malignant and immune disorders," Cancer Res. (1990) 50:1495-1502.
Juno Therapeutics, "Juno's Investigational CAR T Cell Product Candidates JCAR014 and JCAR018 Demonstrate Encouraging Clinical Responses in Patients with B-Cell Cancers," Published on Dec. 6, 2015. Retrieved on http://ir.junotherapeutics.com/news-releases/news-release-details/junos-investigational-car-t-cell-product-candidates-jcar014-and Retrieved on Mar. 6, 2018.
Kanda, Y. et al., "Comparison of cell lines for stable production of fucose-negative antibodies with enhanced ADCC," Biotechnol. Bioeng. (2006) 94(4):680-688.
Kindt et al., Kuby Immunology 6th ed., W.H. Freeman and Co. (2007) p. 91.
King et al., "Monoclonal antibody conjugates of doxorubicin prepared with branched peptide linkers: inhibition of aggregation by methoxytriethyleneglycol chains," J. Med. Chem. (2002) 45:4336-4343.
Klebanoff et al., "Immunotherapy: Treatment of aggressive lymphomas with anti-CD19 CAR T cells," Nat Rev Clin Oncol. Dec. 2014;11 (12):685-6.
Klebanoff et al., "Sorting through subsets: which T-cell populations mediate highly effective adoptive immunotherapy?," J Immunother. (2012) 35(9): 651-660.
Kochenderfer et al., "B cell depletion and remissions of malignancy a long with cytokine associated toxicity in a clinical trial of anti-CD 19 chimeric-antigen receptor-transduced T cells," Blood (2012) 119(12):2709-2720.
Kochenderfer et al., "Chemotherapy-refractory diffuse large B-cell lymphoma and indolent B-cell malignancies can be effectively treated with autologous T cells expressing an anti-CD19 chimeric antigen receptor," J Clin Oncol. Feb. 20 2015;33(6):540-9.
Kochenderfer et al., "Construction and preclinical evaluation of an anti-CD19 chimeric antigen receptor," J. Immunotherapy (2009) 32(7): 689-702.
Koste et al., "T-cell receptor transfer into human T cells with ecotropic retroviral vectors," Gene Therapy (2014) 21: 533-538.
Kratz et al., "Prodrugs of anthracyclines in cancer chemotherapy," Current Med. Chem. (2006) 13:477-523.
Lamers et al., "Immune Responses to Transgene and Retroviral Vector in Patients Treated With Ex Vivo-Engineered T Cells," Blood (2011) 117 (1); 72-82.
Lefranc et al., "IMGT unique numbering for immunoglobulin and T cell receptor variable domains and Ig superfamily V-like domains," Dev Comp Immunol (2003) 27(1):55-77.
Levine, "Performance-enhancing drugs: design and production of redirected chimeric antigen receptor (CAR) T cells," Cancer Gene Ther. Mar. 2015;22(2):79-84.
Li et al., "Optimization of humanized IgGs in glycoengineered Pichia pastoris," Nat. Biotech. (2006) 24:210-215.
Lode et al., "Targeted therapy with a novel enediyene antibiotic calicheamicin theta(I) 1 effectively suppresses growth and dissemination of liver metastases in a syngeneic model of murine neuroblastoma," Cancer Res. (1998) 58:2925-2928.
MacCallum et al., "Antibody-antigen interactions: Contact analysis and binding site topography," J. Mol. Biol. (1996) 262, 732-745.
Manuri et al., "piggyBac transposon/transposase system to generate CD19-specific T cells for the treatment of B-lineage malignancies," Hum Gene Ther (2010) 21(4): 427-437.
Miller et al., "Improved retroviral vectors for gene transfer and expression," BioTechniques (1989) 7:980-990.
Miller et al., "Retrovirus packaging cells," Human Gene Therapy (1990) 1:5-14.
Mullen et al., "Transfer of the bacterial gene for cytosine deaminase to mammalian cells confers lethal sensitivity to 5-fluorocytosine: a negative selection system," Proc. Natl. Acad. Sci. USA (1992) 89:33.
Nagy et al., "Stability of cytotoxic luteinizing hormone-releasing hormone conjugate (AN-152) containing doxorubicin 14-O-hemiglutarate in mouse and human serum in vitro implications for the design of preclinical studies," Proc. Natl. Acad. Sci. USA (2000) 97:829-834.
Okazaki et al., "Fucose depletion from human IgG1 oligosaccharide enhances binding enthalpy and association rate between IgG1 and FcgammaRIIIa," J. Mol. Biol. (2004) 336:1239-1249.
Park et al., "Are all chimeric antigen receptors created equal?" J Clin Oncol. Feb. 20, 2015;33(6):651-3.
Park et al., "Treating cancer with genetically engineered T cells," Trends Biotechnol. (2011) 29(11): 550-557.
Portolano et al., "Lack of promiscuity in autoantigen-specific H and L chain combinations as revealed by human H and L chain "roulette"," J. Immunol. (1993) 150:880-887.
Rader et al., "A phage display approach for rapid antibody humanization: Designed combinatorial V gene libraries," PNAS (1998) 95:8910-8915.
Ripka et al., "Two Chinese hamster ovary glycosylation mutants affected in the conversion of GDP-mannose to GDP-fucose," Arch. Biochem. Biophys. (1986) 249:533-545.
Rosenberg, et al., "Cell transfer immunotherapy for metastatic solid cancer—what clinicians need to know," Nat Rev Clin Oncol. (2011) 8(10):577-85).
Rosenberg, et al., "Use of tumor-infiltrating lymphocytes and interleukin-2 in the immunotherapy of patients with metastatic melanoma. A preliminary report," N Engl J Med. (1988) 319:1676-1680.
Rudikoff et al., "Single amino acid substitution altering antigen-binding specificity," ONAS (1982) 79(6): 1979-1983.
Sadelain et al., "The basic principles of chimeric antigen receptor design," Cancer Discov. (2013) 3(4): 388-398.
Scarpa et al., "Characterization of recombinant helper retroviruses from Moloney-based vectors in ecotropic and amphotropic packaging cell lines," Virology (1991) 180:849-852.
Sharma et al., "Efficient sleeping beauty DNA transposition from DNA minicircles," Molec Ther Nucl Acids (2013) 2, e74.
Sitaraman et al., "High-throughput protein expression using cell-free system," Methods Mol. Biol. (2009) 498: 229-44.
Sommermeyer, et al."Fully human CD19-specific chimeric antigen receptors for T cell therapy," Leukemia. (2017) 31(10):2191-2199.

(56) References Cited

OTHER PUBLICATIONS

Spirin, et al., "High-throughput cell-free systems for synthesis of functionally active proteins," Trends Biotechnol. (2004) 22: 538-45.

Szoka et al., "Comparative properties and methods of preparation of lipid vesicles Kliposomes)," Ann. Rev. Biophys. Bioeng. (1980) 9: 467.

Tedder et al., "Isolation of cDNAs encoding the CD19 antigen of human and mouse B Tymphocytes," J Immunology (1989) 143: 712-717.

Terakura et al., "Generation of CD19-chimeric antigen receptor modified CD8+T cells derived from virus-specific central memory T cells," Blood (2012) 1:72-82.

Themeli et al., "Generation of tumor-targeted human T lymphocytes from induced pluripotent stem cells for cancer therapy," Nat Biotechnol. (2013) 31 (10): 928-933.

Torgov et al., "Generation of an intensely potent anthracycline by a monoclonal antibody-beta-galactosidase conjugate," Bioconj. Chem. (2005) 16:717-721.

Tsukahara et al., "CD19 target-engineered T-cells accumulate at tumor lesions in human B-cell lymphoma xenograft mouse models," Biochem Biophys Res Commun K2013) 438(1): 84-9.

Turtle et al., "CD19 CAR-T cells of defined CD4+:CD8+ composition in adult B cell ALL patients," J Clin Invest. (2016) 126(6):2123-2138.

Turtle et al., "Engineered T cells for anti-cancer therapy," Curr. Opin. Immunol. (2012) 24(5): 633-39.

Van Tendeloo et al., "High-level transgene expression in primary human T Tymphocytes and adult bone marrow CD34+ cells via electroporation-mediated gene delivery," Gene Therapy (2000) 7(16): 1431-1437).

Verhoeyen et al., "Lentiviral vector gene transfer into human T cells," Methods Mol Biol. (2009) 506: 97-114.

Vitetta et al., "Redesigning nature's poisons to create anti-tumor reagents," Science (1987) 238:1098.

Wadhwa et al., "Receptor mediated glycotargeting," J. Drug Targeting (1995) 3: 111.

Wang et al., "Phenotypic and functional attributes of lentivirus-modified CD19-specific human CD8+ central memory T cells manufactured at clinical scale," J Immunother. (2012) 35(9):689-701.

Wigler et al., "Transfer of purified herpes virus thymidine kinase gene to cultured mouse cells," Cell (1997) 11: 223-232.

Wu et al., "Adoptive T-cell therapy using autologous tumor-infiltrating lymphocytes for metastatic melanoma: current status and future outlook," Cancer (2012) 18(2): 160-75.

Yam et al., "Design of HIV vectors for efficient gene delivery into human hematopoietic cells," Mol. Ther. (2002) 5:479.

Yamane-Ohnuki et al., "Establishment of FUT8 knockout Chinese hamster ovary cells: an ideal host cell line for producing completely defucosylated antibodies with enhanced antibody-dependent cellular cytotoxicity," Biotech. Bioeng. (2004) 87: 614.

Zhou et al., "Structure of the genes encoding the CD19 antigen of human and mouse B lymphocytes," Immunogenetics (1992) 35: 102-111.

Zola H et al., "Preparation and characterization of a chimeric CD19 monoclonal antibody," Immunol Cell Biol. (1991) 69 (6):411-22.

Borlee et al., "Pseudomonas aeruginosa uses a cyclic-di-GMP-regulated adhesin to reinforce the biofilm extracellular matrix," Mol Microbiol. (2010) 75(4) 827-42.

Jiang et al., "Preparation of genetic engineering antibody anti-CD19(Fab)-LDM and its biological activity," Chinese Pharmacological Bulletin (2013) 29(10):1363-1368 (English abstract only).

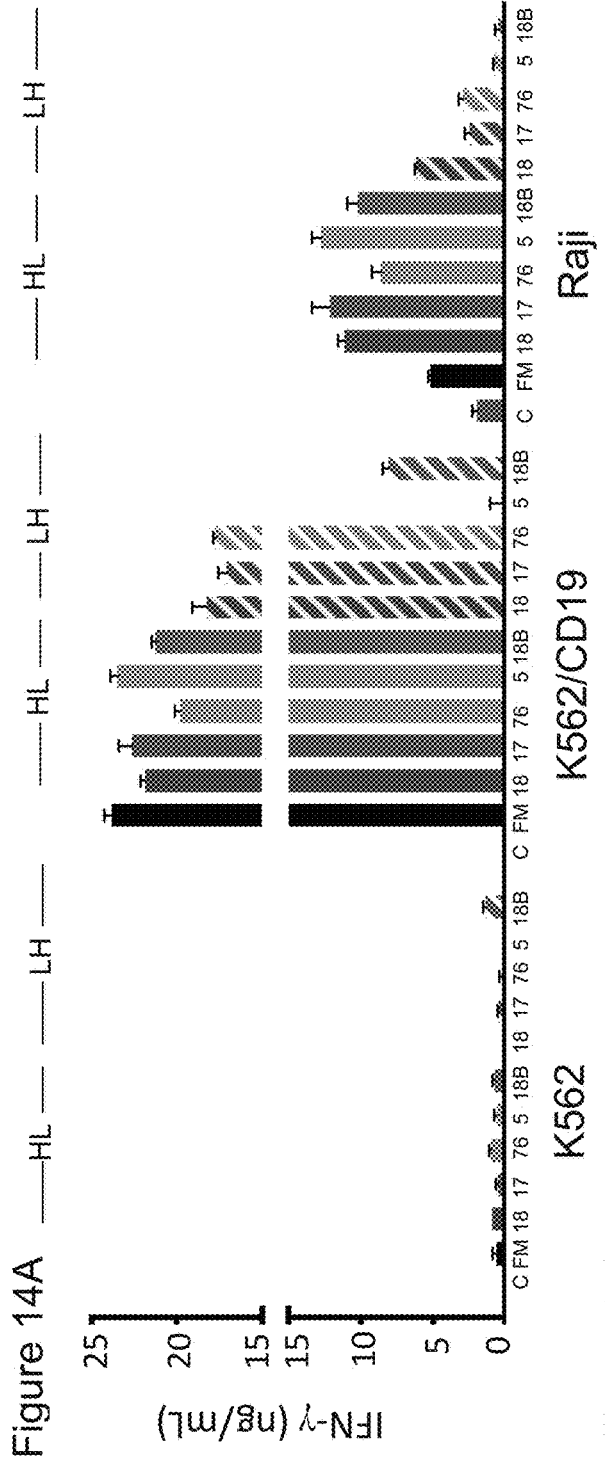
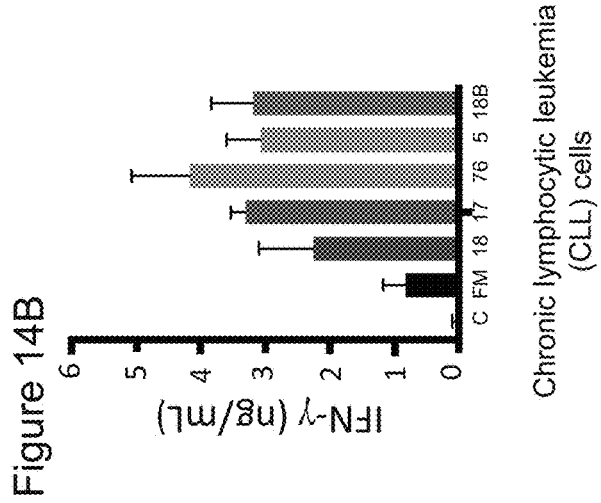
Figure 14A
Figure 14B

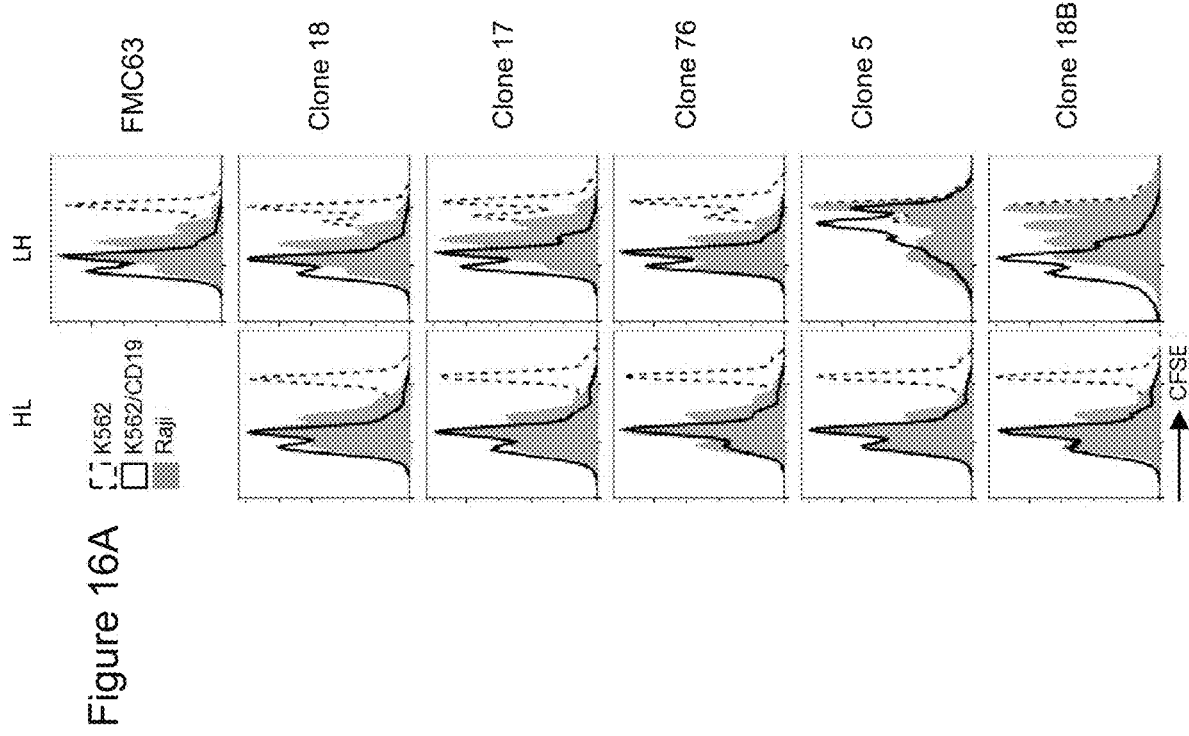

v1: HPKGPKS-LLSLELKDDRPARDMWVMETGLLLIPRATAQDAGKYYCHRGNLTMSFHLEITARPVLMHWLLRTGGWK
v2: RPKGPKSSLLSLELKDDRPRDMWVVDTGLLLITRATAQDAGKYYCHRGNLTMSFHLEITARPVLMHWLLRTGGWK
v3: HPKGPKS-LLSLELKDDRPARDMWVMETGLLLIPRATAQDAGKYYCHRGNWTKSFYLEITARPALMHWLLRIGGWK

SEQUENCE LISTING

<160> NUMBER OF SEQ ID NOS: 228

<210> SEQ ID NO 1
<211> LENGTH: 738
<212> TYPE: DNA
<213> ORGANISM: Homo sapiens
<220> FEATURE:
<223> OTHER INFORMATION: Clone 18 scFv (nt)

<400> SEQUENCE: 1

```
gaagtgcagc tggtggagtc tgggggaggc ttggtacagc ctggcaggtc cctgagactc       60
tcctgtgcag cctctggatt cacctttgat gattatgcca tgcactgggt ccggcaagct      120
ccagggaagg gcctggagtg ggtctcaggt attagttgga atagtggtag gataggctat      180
gcggactctg taaagggccg attcaccatc tccagagaca cgccaagaa ctccctgttt       240
ctgcaaatga acagtctgag agctgaggac acggccgtgt attactgtgc gagagatcag      300
gggtatcatt actatgatag tgccgaacat gcttttgata tctggggcca agggacagtg      360
gtcaccgtct cctcaggtgg aggcggttca ggcggaggtg gctctggcgg tggcggatcg      420
cagtctgccc tgactcagcc tcgctcagtg tccggctttc ctggacaatc agtcaccatc      480
tcctgcactg gaaccaccag tgatgatgtc tcctggtacc aacaacaccc aggcaaagcc      540
ccccaactta tgctttatga tgtcagtaag cggccctccg ggtccctca tcgcttctct        600
ggctccaggt ctggcagagc ggcctccctg atcatctctg gctccagac tgaggatgag      660
gctgattatt tctgctgctc atatgcaggc cgatacaact ctgtcctttt cggcggaggg      720
accaagctga ccgtccta                                                    738
```

<210> SEQ ID NO 2
<211> LENGTH: 246
<212> TYPE: PRT
<213> ORGANISM: Homo sapiens
<220> FEATURE:
<223> OTHER INFORMATION: Clone 18 scFv (aa)

<400> SEQUENCE: 2

```
Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
            20                  25                  30
```

Ala Met His Trp Val Arg Gln Ala Pro Gly Lys Gly Leu Glu Trp Val
            35                  40                  45

Ser Gly Ile Ser Trp Asn Ser Gly Arg Ile Gly Tyr Ala Asp Ser Val
 50                  55                  60

Lys Gly Arg Phe Thr Ile Ser Arg Asp Asn Ala Lys Asn Ser Leu Phe
 65                  70                  75                  80

Leu Gln Met Asn Ser Leu Arg Ala Glu Asp Thr Ala Val Tyr Tyr Cys
                 85                  90                  95

Ala Arg Asp Gln Gly Tyr His Tyr Tyr Asp Ser Ala Glu His Ala Phe
                100                 105                 110

Asp Ile Trp Gly Gln Gly Thr Val Val Thr Val Ser Ser Gly Gly Gly
            115                 120                 125

Gly Ser Gly Gly Gly Gly Ser Gly Gly Gly Gly Ser Gln Ser Ala Leu
130                 135                 140

Thr Gln Pro Arg Ser Val Ser Gly Phe Pro Gly Gln Ser Val Thr Ile
145                 150                 155                 160

Ser Cys Thr Gly Thr Thr Ser Asp Asp Val Ser Trp Tyr Gln Gln His
            165                 170                 175

Pro Gly Lys Ala Pro Gln Leu Met Leu Tyr Asp Val Ser Lys Arg Pro
            180                 185                 190

Ser Gly Val Pro His Arg Phe Ser Gly Ser Arg Ser Gly Arg Ala Ala
            195                 200                 205

Ser Leu Ile Ile Ser Gly Leu Gln Thr Glu Asp Glu Ala Asp Tyr Phe
            210                 215                 220

Cys Cys Ser Tyr Ala Gly Arg Tyr Asn Ser Val Leu Phe Gly Gly Gly
225                 230                 235                 240

Thr Lys Leu Thr Val Leu
            245

<210> SEQ ID NO 3
<211> LENGTH: 738
<212> TYPE: DNA
<213> ORGANISM: Homo sapiens
<220> FEATURE:
<223> OTHER INFORMATION: Clone 18B scFv (nt)

<400> SEQUENCE: 3
gaagtgcagc tggtggagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg ggtctcaggt attagttgga atagtggtag ataggctat     180 gcggactctg taaagggccg attcaccatc tccagagaca acgccaagaa ctccctgttt     240
ctgcaaatga acagtctgag agctgaggac acggccgtgt attactgtgc gagagatcag     300
gggtatcatt actatgatag tgccgaacat gcttttgata tctggggcca agggacagtg     360
gtcaccgtct cctcaggtgg aggcggttca ggcggaggtg gctctggcgg tggcggatcg     420
cagtctgccc tgactcagcc tcgctcagtg tccggctttc ctggacaatc agtcaccatc     480
tcctgcactg gaaccaccag tgatgatgtc tcctggtacc aacaacaccc aggcaaagcc     540
ccccaactta tgctttatga tgtcagtaag cggccctccg ggtccctca tcgcttctct     600 ggctccaggt ctggcagagc ggcctccctg atcatctctg ggctccagac tgaggatgag     660
gctgattatt tctgcagctc atatgcaggc cgatacaact ctgtcctttt cggcggaggg     720
accaagctga ccgtccta                                                  738

<210> SEQ ID NO 4
<211> LENGTH: 246
<212> TYPE: PRT
<213> ORGANISM: Homo sapiens
<220> FEATURE:
<223> OTHER INFORMATION: Clone 18B scFv (aa)

<400> SEQUENCE: 4

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
            100                 105                 110

Asp Ile Trp Gly Gln Gly Thr Val Val Thr Val Ser Ser Gly Gly Gly
        115                 120                 125

Gly Ser Gly Gly Gly Gly Ser Gly Gly Gly Gly Ser Gln Ser Ala Leu
    130                 135                 140

Thr Gln Pro Arg Ser Val Ser Gly Phe Pro Gly Gln Ser Val Thr Ile
145                 150                 155                 160

Ser Cys Thr Gly Thr Thr Ser Asp Asp Val Ser Trp Tyr Gln Gln His
                165                 170                 175

Pro Gly Lys Ala Pro Gln Leu Met Leu Tyr Asp Val Ser Lys Arg Pro
            180                 185                 190

Ser Gly Val Pro His Arg Phe Ser Gly Ser Arg Ser Gly Arg Ala Ala
        195                 200                 205

Ser Leu Ile Ile Ser Gly Leu Gln Thr Glu Asp Glu Ala Asp Tyr Phe
    210                 215                 220

Cys Ser Ser Tyr Ala Gly Arg Tyr Asn Ser Val Leu Phe Gly Gly Gly
225                 230                 235                 240

Thr Lys Leu Thr Val Leu
                245
```

<210> SEQ ID NO 5
<211> LENGTH: 750
<212> TYPE: DNA
<213> ORGANISM: Homo sapiens
<220> FEATURE:
<223> OTHER INFORMATION: Clone 17 scFv (nt)

<400> SEQUENCE: 5

```
gaagtgcagc tggtggagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg gtctcaggt attagttgga atagtggtag gataggctat      180
gcggactctg taaagggccg attcaccatc tccagagaca acgccaagaa ctccctgttt     240
ctgcaaatga acagtctgag agctgaggac acggccgtgt attactgtgc gagagatcag     300
gggtatcatt actatgatag tgccgaacat gcttttgata tctggggcca aggacaatg      360
```

```
gtcaccgtct cctcaggtgg aggcggttca ggcggaggtg gctctggcgg tggcggatcg      420
cagtctgccc tgactcagcc tgcctccgtg tctgggtctc ctggacagtc gatcaccatc      480
ttctgcactg gaaccagcag tgacgttggt ggttataact atgtctcctg gtaccagcag      540
ctcccaggaa cggcccccaa actcctcatc tatagtaata atcagcggcc ctcaggggtc      600
cctgaccgat tctctggctc caagtctggc acctcagcct ccctggccat cagtgggctc      660
cggtccgagg atgaggctga ttattactgt gcagcatggg atgacagcct gagtgtggta      720
ttcggcggag ggaccaagct gaccgtcctc                                      750
```

<210> SEQ ID NO 6
<211> LENGTH: 250
<212> TYPE: PRT
<213> ORGANISM: Homo sapiens
<220> FEATURE:
<223> OTHER INFORMATION: Clone 17 scFv (aa)

<400> SEQUENCE: 6

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
            100                 105                 110

Asp Ile Trp Gly Gln Gly Thr Met Val Thr Val Ser Ser Gly Gly Gly
        115                 120                 125

Gly Ser Gly Gly Gly Gly Ser Gly Gly Gly Gly Ser Gln Ser Ala Leu
    130                 135                 140

Thr Gln Pro Ala Ser Val Ser Gly Ser Pro Gly Gln Ser Ile Thr Ile
145                 150                 155                 160

Phe Cys Thr Gly Thr Ser Ser Asp Val Gly Gly Tyr Asn Tyr Val Ser
                165                 170                 175

Trp Tyr Gln Gln Leu Pro Gly Thr Ala Pro Lys Leu Leu Ile Tyr Ser
            180                 185                 190

Asn Asn Gln Arg Pro Ser Gly Val Pro Asp Arg Phe Ser Gly Ser Lys
        195                 200                 205

Ser Gly Thr Ser Ala Ser Leu Ala Ile Ser Gly Leu Arg Ser Glu Asp
    210                 215                 220

Glu Ala Asp Tyr Tyr Cys Ala Ala Trp Asp Asp Ser Leu Ser Val Val
225                 230                 235                 240

Phe Gly Gly Gly Thr Lys Leu Thr Val Leu
                245                 250
```

<210> SEQ ID NO 7
<211> LENGTH: 747
<212> TYPE: DNA
<213> ORGANISM: Homo sapiens
<220> FEATURE:
<223> OTHER INFORMATION: Clone 76 scFv (nt)

<400> SEQUENCE: 7

```
gaagtgcagc tggtggagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg ggtctcaggt attagttgga atagtggtag gataggctat     180
gcggactctg taaagggccg attcaccatc tccagagaca acgccaagaa ctccctgttt     240
ctgcaaatga acagtctgag agctgaggac acggccgtgt attactgtgc gagagatcag     300
gggtatcatt actatgatag tgccgaacat gcttttgata tctggggcca agggacagtg     360
gtcaccgtct cctcaggtgg aggcggttca ggcggaggtg gctctggcgg tggcggatcg     420
cagtctgtgc tgacgcagcc gccctcagtg tctgcggccc caggacagga ggtcaccatc     480
tcctgctctg gaagcagctc aacattggga ataattatg tatcctggta ccagcaactc      540
ccaggaacag ccccccaaact cctcatttat gacaatgata agcgaccctc agggattcct     600
gaccgattct ctggctccaa gtctggcacg tcagccaccc tgggcatcac cggactccag     660
actggggacg aggccgatta ttactgcgga acatgggatg caatctgag tgctgtattc      720
ggcggaggga ccaaggtgac cgtccta                                          747
```

<210> SEQ ID NO 8
<211> LENGTH: 249
<212> TYPE: PRT
<213> ORGANISM: Homo sapiens
<220> FEATURE:
<223> OTHER INFORMATION: Clone 76 scFv (aa)

<400> SEQUENCE: 8

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
            100                 105                 110

Asp Ile Trp Gly Gln Gly Thr Val Val Thr Val Ser Ser Gly Gly Gly
        115                 120                 125

Gly Ser Gly Gly Gly Gly Ser Gly Gly Gly Gly Ser Gln Ser Val Leu
    130                 135                 140

Thr Gln Pro Pro Ser Val Ser Ala Ala Pro Gly Gln Glu Val Thr Ile
145                 150                 155                 160

Ser Cys Ser Gly Ser Ser Ser Asn Ile Gly Asn Asn Tyr Val Ser Trp
                165                 170                 175

Tyr Gln Gln Leu Pro Gly Thr Ala Pro Lys Leu Leu Ile Tyr Asp Asn
            180                 185                 190

Asp Lys Arg Pro Ser Gly Ile Pro Asp Arg Phe Ser Gly Ser Lys Ser
        195                 200                 205

Gly Thr Ser Ala Thr Leu Gly Ile Thr Gly Leu Gln Thr Gly Asp Glu
```

Ala Asp Tyr Tyr Cys Gly Thr Trp Asp Gly Asn Leu Ser Ala Val Phe
225                 230                 235                 240

Gly Gly Gly Thr Lys Val Thr Val Leu
                245

<210> SEQ ID NO 9
<211> LENGTH: 744
<212> TYPE: DNA
<213> ORGANISM: Homo sapiens
<220> FEATURE:
<223> OTHER INFORMATION: Clone 5 scFv (nt)

<400> SEQUENCE: 9
gaagtgcagc tggtggagtc tgggggaggc ttggtacagc ctggcaggtc cctgagactc    60
tcctgtgcag cctctggatt cacctttgat gattatgcca tgcactgggt ccggcaagct   120
ccagggaagg gcctggagtg ggtctcaggt attagttgga atagtggtag gataggctat   180
gcggactctg taaagggccg attcaccatc tccagagaca acgccaagaa ctccctgttt   240
ctgcaaatga acagtctgag agctgaggac acggccgtgt attactgtgc gagagatcag   300
gggtatcatt actatgatag tgccgaacat gcttttgata tctggggcca agggacaatg   360
gtcaccgtct cctcaggtgg aggcggttca ggcggaggtg gctctggcgg tggcggatcg   420
tcctatgagc tgactcagga ccctgctgtg tctgtggcct tgggacagac agtcaggatc   480
acatgccaag agacagcct cagaagctat tatgcaagct ggtaccagca gaagccagga   540
caggcccctg tacttgtcat ctatgataaa acaaccggc cctcagggat cccagaccga   600
ttctctggct ccagctcagg aaacacagct tccttgacca tcactggggc tcaggcggaa   660
gatgaggctg actactactg caactcccgg gacagcagtg taacaattg gtgttcggc   720 ggagggacca gctgaccgt ccta                                           744

<210> SEQ ID NO 10
<211> LENGTH: 248
<212> TYPE: PRT
<213> ORGANISM: Homo sapiens
<220> FEATURE:
<223> OTHER INFORMATION: Clone 5 scFv (aa)

<400> SEQUENCE: 10

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
            85                  90                  95

Ala Arg Asp Gln Gly Tyr His Tyr Tyr Asp Ser Ala Glu His Ala Phe
        100                 105                 110

Asp Ile Trp Gly Gln Gly Thr Met Val Thr Val Ser Ser Gly Gly Gly
    115                 120                 125

Gly Ser Gly Gly Gly Gly Ser Gly Gly Gly Gly Ser Ser Tyr Glu Leu

```
Thr Gln Asp Pro Ala Val Ser Val Ala Leu Gly Gln Thr Val Arg Ile
145                 150                 155                 160

Thr Cys Gln Gly Asp Ser Leu Arg Ser Tyr Tyr Ala Ser Trp Tyr Gln
                165                 170                 175

Gln Lys Pro Gly Gln Ala Pro Val Leu Val Ile Tyr Asp Lys Asn Asn
                180                 185                 190

Arg Pro Ser Gly Ile Pro Asp Arg Phe Ser Gly Ser Ser Ser Gly Asn
            195                 200                 205

Thr Ala Ser Leu Thr Ile Thr Gly Ala Gln Ala Glu Asp Glu Ala Asp
        210                 215                 220

Tyr Tyr Cys Asn Ser Arg Asp Ser Ser Gly Asn Asn Trp Val Phe Gly
225                 230                 235                 240

Gly Gly Thr Lys Leu Thr Val Leu
                245

<210> SEQ ID NO 11
<211> LENGTH: 125
<212> TYPE: PRT
<213> ORGANISM: Homo sapiens
<220> FEATURE:
<223> OTHER INFORMATION: VH
      (clones 18, 18B reversion, 76, 285)
      (aa)

<400> SEQUENCE: 11

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Arg Ile Gly Tyr Ala Asp Ser Val
        50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
                100                 105                 110

Asp Ile Trp Gly Gln Gly Thr Val Val Thr Val Ser Ser
        115                 120                 125

<210> SEQ ID NO 12
<211> LENGTH: 125
<212> TYPE: PRT
<213> ORGANISM: Homo sapiens
<220> FEATURE:
<223> OTHER INFORMATION: VH (clones 17, 5, 1, 192)
      (aa)

<400> SEQUENCE: 12

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45
```

```
Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
                100                 105                 110

Asp Ile Trp Gly Gln Gly Thr Met Val Thr Val Ser Ser
                115                 120                 125

<210> SEQ ID NO 13
<211> LENGTH: 106
<212> TYPE: PRT
<213> ORGANISM: Homo sapiens
<220> FEATURE:
<223> OTHER INFORMATION: VL Clone 18 (aa)

<400> SEQUENCE: 13

Gln Ser Ala Leu Thr Gln Pro Arg Ser Val Ser Gly Phe Pro Gly Gln
1               5                   10                  15

Ser Val Thr Ile Ser Cys Thr Gly Thr Thr Ser Asp Asp Val Ser Trp
                20                  25                  30

Tyr Gln Gln His Pro Gly Lys Ala Pro Gln Leu Met Leu Tyr Asp Val
                35                  40                  45

Ser Lys Arg Pro Ser Gly Val Pro His Arg Phe Ser Gly Ser Arg Ser
    50                  55                  60

Gly Arg Ala Ala Ser Leu Ile Ile Ser Gly Leu Gln Thr Glu Asp Glu
65                  70                  75                  80

Ala Asp Tyr Phe Cys Cys Ser Tyr Ala Gly Arg Tyr Asn Ser Val Leu
                85                  90                  95

Phe Gly Gly Gly Thr Lys Leu Thr Val Leu
                100                 105

<210> SEQ ID NO 14
<211> LENGTH: 106
<212> TYPE: PRT
<213> ORGANISM: Homo sapiens
<220> FEATURE:
<223> OTHER INFORMATION: VL, Clone 18B
      (aa)

<400> SEQUENCE: 14

Gln Ser Ala Leu Thr Gln Pro Arg Ser Val Ser Gly Phe Pro Gly Gln
1               5                   10                  15

Ser Val Thr Ile Ser Cys Thr Gly Thr Thr Ser Asp Asp Val Ser Trp
                20                  25                  30

Tyr Gln Gln His Pro Gly Lys Ala Pro Gln Leu Met Leu Tyr Asp Val
                35                  40                  45

Ser Lys Arg Pro Ser Gly Val Pro His Arg Phe Ser Gly Ser Arg Ser
    50                  55                  60

Gly Arg Ala Ala Ser Leu Ile Ile Ser Gly Leu Gln Thr Glu Asp Glu
65                  70                  75                  80

Ala Asp Tyr Phe Cys Ser Ser Tyr Ala Gly Arg Tyr Asn Ser Val Leu
                85                  90                  95

Phe Gly Gly Gly Thr Lys Leu Thr Val Leu
                100                 105
```

```
<210> SEQ ID NO 15
<211> LENGTH: 110
<212> TYPE: PRT
<213> ORGANISM: Homo sapiens
<220> FEATURE:
<223> OTHER INFORMATION: VL, Clone 17 (aa)

<400> SEQUENCE: 15

Gln Ser Ala Leu Thr Gln Pro Ala Ser Val Ser Gly Ser Pro Gly Gln
1               5                   10                  15

Ser Ile Thr Ile Phe Cys Thr Gly Thr Ser Ser Asp Val Gly Gly Tyr
            20                  25                  30

Asn Tyr Val Ser Trp Tyr Gln Gln Leu Pro Gly Thr Ala Pro Lys Leu
        35                  40                  45

Leu Ile Tyr Ser Asn Asn Gln Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Ser Val Val Phe Gly Gly Gly Thr Lys Leu Thr Val Leu
            100                 105                 110

<210> SEQ ID NO 16
<211> LENGTH: 109
<212> TYPE: PRT
<213> ORGANISM: Homo sapiens
<220> FEATURE:
<223> OTHER INFORMATION: VL, Clone 76 (aa)

<400> SEQUENCE: 16

Gln Ser Val Leu Thr Gln Pro Pro Ser Val Ser Ala Ala Pro Gly Gln
1               5                   10                  15

Glu Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asp Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Gly Asn Leu
                85                  90                  95

Ser Ala Val Phe Gly Gly Gly Thr Lys Val Thr Val Leu
            100                 105

<210> SEQ ID NO 17
<211> LENGTH: 108
<212> TYPE: PRT
<213> ORGANISM: Homo sapiens
<220> FEATURE:
<223> OTHER INFORMATION: VL, Clone 5 (aa)

<400> SEQUENCE: 17

Ser Tyr Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45
```

```
Asp Lys Asn Asn Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Asn Asn
                85                  90                  95

Trp Val Phe Gly Gly Gly Thr Lys Leu Thr Val Leu
            100                 105

<210> SEQ ID NO 18
<211> LENGTH: 5
<212> TYPE: PRT
<213> ORGANISM: Artificial Sequence
<220> FEATURE:
<223> OTHER INFORMATION: Synthetic
<220> FEATURE:
<223> OTHER INFORMATION: CDR-H1 (aa)

<400> SEQUENCE: 18

Asp Tyr Ala Met His
1               5

<210> SEQ ID NO 19
<211> LENGTH: 17
<212> TYPE: PRT
<213> ORGANISM: Artificial Sequence
<220> FEATURE:
<223> OTHER INFORMATION: Synthetic
<220> FEATURE:
<223> OTHER INFORMATION: CDR-H2 (aa)

<400> SEQUENCE: 19

Gly Ile Ser Trp Asn Ser Gly Arg Ile Gly Tyr Ala Asp Ser Val Lys
1               5                   10                  15

Gly

<210> SEQ ID NO 20
<211> LENGTH: 16
<212> TYPE: PRT
<213> ORGANISM: Artificial Sequence
<220> FEATURE:
<223> OTHER INFORMATION: Synthetic
<220> FEATURE:
<223> OTHER INFORMATION: CDR-H3 (aa)

<400> SEQUENCE: 20

Asp Gln Gly Tyr His Tyr Tyr Asp Ser Ala Glu His Ala Phe Asp Ile
1               5                   10                  15

<210> SEQ ID NO 21
<211> LENGTH: 9
<212> TYPE: PRT
<213> ORGANISM: Homo sapiens
<220> FEATURE:
<223> OTHER INFORMATION: Clones 18, 18B CDR-L1 (aa)

<400> SEQUENCE: 21

Thr Gly Thr Thr Ser Asp Asp Val Ser
1               5

<210> SEQ ID NO 22
<211> LENGTH: 7
<212> TYPE: PRT
<213> ORGANISM: Homo sapiens
<220> FEATURE:
```

```
<223> OTHER INFORMATION: Clones 18, 18B CDR-L2 (aa)

<400> SEQUENCE: 22

Asp Val Ser Lys Arg Pro Ser
1               5

<210> SEQ ID NO 23
<211> LENGTH: 11
<212> TYPE: PRT
<213> ORGANISM: Homo sapiens
<220> FEATURE:
<223> OTHER INFORMATION: Clone 18 CDR-L3 (aa)

<400> SEQUENCE: 23

Cys Ser Tyr Ala Gly Arg Tyr Asn Ser Val Leu
1               5                   10

<210> SEQ ID NO 24
<211> LENGTH: 11
<212> TYPE: PRT
<213> ORGANISM: Homo sapiens
<220> FEATURE:
<223> OTHER INFORMATION: Clone 18B CDR-L3 (aa)

<400> SEQUENCE: 24

Ser Ser Tyr Ala Gly Arg Tyr Asn Ser Val Leu
1               5                   10

<210> SEQ ID NO 25
<211> LENGTH: 14
<212> TYPE: PRT
<213> ORGANISM: Homo sapiens
<220> FEATURE:
<223> OTHER INFORMATION: Clone 17 CDR-L1 (aa)

<400> SEQUENCE: 25

Thr Gly Thr Ser Ser Asp Val Gly Gly Tyr Asn Tyr Val Ser
1               5                   10

<210> SEQ ID NO 26
<211> LENGTH: 7
<212> TYPE: PRT
<213> ORGANISM: Homo sapiens
<220> FEATURE:
<223> OTHER INFORMATION: Clone 17 CDR-L2 (aa)

<400> SEQUENCE: 26

Ser Asn Asn Gln Arg Pro Ser
1               5

<210> SEQ ID NO 27
<211> LENGTH: 10
<212> TYPE: PRT
<213> ORGANISM: Homo sapiens
<220> FEATURE:
<223> OTHER INFORMATION: Clone 17 CDR-L3 (aa)

<400> SEQUENCE: 27

Ala Ala Trp Asp Asp Ser Leu Ser Val Val
1               5                   10

<210> SEQ ID NO 28
<211> LENGTH: 13
<212> TYPE: PRT
<213> ORGANISM: Homo sapiens
<220> FEATURE:
<223> OTHER INFORMATION: Clone 76 CDR-L1 (aa)
```

```
<400> SEQUENCE: 28

Ser Gly Ser Ser Ser Asn Ile Gly Asn Asn Tyr Val Ser
1               5                   10

<210> SEQ ID NO 29
<211> LENGTH: 7
<212> TYPE: PRT
<213> ORGANISM: Homo sapiens
<220> FEATURE:
<223> OTHER INFORMATION: Clone 76 CDR-L2 (aa)

<400> SEQUENCE: 29

Asp Asn Asp Lys Arg Pro Ser
1               5

<210> SEQ ID NO 30
<211> LENGTH: 10
<212> TYPE: PRT
<213> ORGANISM: Homo sapiens
<220> FEATURE:
<223> OTHER INFORMATION: Clone 76 CDR-L3 (aa)

<400> SEQUENCE: 30

Gly Thr Trp Asp Gly Asn Leu Ser Ala Val
1               5                   10

<210> SEQ ID NO 31
<211> LENGTH: 11
<212> TYPE: PRT
<213> ORGANISM: Homo sapiens
<220> FEATURE:
<223> OTHER INFORMATION: Clone 5 CDR-L1 (aa)

<400> SEQUENCE: 31

Gln Gly Asp Ser Leu Arg Ser Tyr Tyr Ala Ser
1               5                   10

<210> SEQ ID NO 32
<211> LENGTH: 7
<212> TYPE: PRT
<213> ORGANISM: Homo sapiens
<220> FEATURE:
<223> OTHER INFORMATION: Clone 5 CDR-L2 (aa)

<400> SEQUENCE: 32

Asp Lys Asn Asn Arg Pro Ser
1               5

<210> SEQ ID NO 33
<211> LENGTH: 11
<212> TYPE: PRT
<213> ORGANISM: Homo sapiens
<220> FEATURE:
<223> OTHER INFORMATION: Clone 5 CDR-L3 (aa)

<400> SEQUENCE: 33

Asn Ser Arg Asp Ser Ser Gly Asn Asn Trp Val
1               5                   10

<210> SEQ ID NO 34
<211> LENGTH: 15
<212> TYPE: PRT
<213> ORGANISM: Artificial Sequence
<220> FEATURE:
<223> OTHER INFORMATION: Synthetic
<220> FEATURE:
```

```
<223> OTHER INFORMATION: Linker (aa)

<400> SEQUENCE: 34

Gly Gly Gly Gly Ser Gly Gly Gly Gly Ser Gly Gly Gly Ser
1               5                   10                  15

<210> SEQ ID NO 35
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: CDR-H2

<400> SEQUENCE: 35

Gly Ile Ser Trp Asn Ser Gly Arg Ile Gly Tyr
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Synthetic
<220> FEATURE:
<223> OTHER INFORMATION: CDR-L1 consensus
<220> FEATURE:
<221> NAME/KEY: VARIANT
<222> LOCATION: 1
<223> OTHER INFORMATION: Xaa = Thr, Ser or Gln
<220> FEATURE:
<221> NAME/KEY: VARIANT
<222> LOCATION: 3
<223> OTHER INFORMATION: Xaa = Thr, Ser or Asp
<220> FEATURE:
<221> NAME/KEY: VARIANT
<222> LOCATION: 4
<223> OTHER INFORMATION: Xaa = Thr or Ser
<220> FEATURE:
<221> NAME/KEY: VARIANT
<222> LOCATION: 5
<223> OTHER INFORMATION: Xaa = null or Ser
<220> FEATURE:
<221> NAME/KEY: VARIANT
<222> LOCATION: 6
<223> OTHER INFORMATION: Xaa = null, Asp or Asn
<220> FEATURE:
<221> NAME/KEY: VARIANT
<222> LOCATION: 7
<223> OTHER INFORMATION: Xaa = null or Val
<220> FEATURE:
<221> NAME/KEY: VARIANT
<222> LOCATION: 8
<223> OTHER INFORMATION: Xaa = null, Gly or Ile
<220> FEATURE:
<221> NAME/KEY: VARIANT
<222> LOCATION: 9
<223> OTHER INFORMATION: Xaa = null, Gly or Arg
<220> FEATURE:
<221> NAME/KEY: VARIANT
<222> LOCATION: 10
<223> OTHER INFORMATION: Xaa = Ser, Tyr or Asn
<220> FEATURE:
<221> NAME/KEY: VARIANT
<222> LOCATION: 11
<223> OTHER INFORMATION: Xaa = Asp or Asn
<220> FEATURE:
<221> NAME/KEY: VARIANT
<222> LOCATION: 12
<223> OTHER INFORMATION: Xaa = Asp or Tyr
<220> FEATURE:
<221> NAME/KEY: VARIANT
<222> LOCATION: 13
<223> OTHER INFORMATION: Xaa = Val or Ala
```

-continued

```
<400> SEQUENCE: 36

Xaa Gly Xaa Xaa Xaa Xaa Xaa Xaa Xaa Xaa Xaa Xaa Ser
1               5                   10

<210> SEQ ID NO 37
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: CDR-L2 consensus
<220> FEATURE:
<221> NAME/KEY: VARIANT
<222> LOCATION: 1
<223> OTHER INFORMATION: Xaa = Asp or Ser
<220> FEATURE:
<221> NAME/KEY: VARIANT
<222> LOCATION: 2
<223> OTHER INFORMATION: Xaa = Val, Asn or Lys
<220> FEATURE:
<221> NAME/KEY: VARIANT
<222> LOCATION: 3
<223> OTHER INFORMATION: Xaa = Ser, Asn or Asp
<220> FEATURE:
<221> NAME/KEY: VARIANT
<222> LOCATION: 4
<223> OTHER INFORMATION: Xaa = Lys, Gln or Asn

<400> SEQUENCE: 37

Xaa Xaa Xaa Xaa Arg Pro Ser
1               5

<210> SEQ ID NO 38
<211> LENGTH: 12
<212> TYPE: PRT
<213> ORGANISM: Artificial Sequence
<220> FEATURE:
<223> OTHER INFORMATION: Synthetic
<220> FEATURE:
<223> OTHER INFORMATION: CDR-L3
<220> FEATURE:
<221> NAME/KEY: VARIANT
<222> LOCATION: 1
<223> OTHER INFORMATION: Xaa = Cys, Ser, Ala, Gly or Asn
<220> FEATURE:
<221> NAME/KEY: VARIANT
<222> LOCATION: 2
<223> OTHER INFORMATION: Xaa = Ser, Ala or Thr
<220> FEATURE:
<221> NAME/KEY: VARIANT
<222> LOCATION: 3
<223> OTHER INFORMATION: Xaa = Tyr, Trp or Arg
<220> FEATURE:
<221> NAME/KEY: VARIANT
<222> LOCATION: 4
<223> OTHER INFORMATION: Xaa = Ala or Asp
<220> FEATURE:
<221> NAME/KEY: VARIANT
<222> LOCATION: 5
<223> OTHER INFORMATION: Xaa = Gly, Asp or Ser
<220> FEATURE:
<221> NAME/KEY: VARIANT
<222> LOCATION: 6
<223> OTHER INFORMATION: Xaa = Arg, Ser or Asn
<220> FEATURE:
<221> NAME/KEY: VARIANT
<222> LOCATION: 7
<223> OTHER INFORMATION: Xaa = Tyr, Leu or Gly
<220> FEATURE:
<221> NAME/KEY: VARIANT
<222> LOCATION: 8
<223> OTHER INFORMATION: Xaa = Asn or Ser
<220> FEATURE:
```

```
<221> NAME/KEY: VARIANT
<222> LOCATION: 9
<223> OTHER INFORMATION: Xaa = Ser or null
<220> FEATURE:
<221> NAME/KEY: VARIANT
<222> LOCATION: 10
<223> OTHER INFORMATION: Xaa = Val, Ala or Asn
<220> FEATURE:
<221> NAME/KEY: VARIANT
<222> LOCATION: 11
<223> OTHER INFORMATION: Xaa = Trp or null
<220> FEATURE:
<221> NAME/KEY: VARIANT
<222> LOCATION: 12
<223> OTHER INFORMATION: Xaa = Leu or Val

<400> SEQUENCE: 38

Xaa Xaa Xaa Xaa Xaa Xaa Xaa Xaa Xaa Xaa Xaa Xaa
1               5                   10

<210> SEQ ID NO 39
<211> LENGTH: 120
<212> TYPE: PRT
<213> ORGANISM: Mus musculus
<220> FEATURE:
<223> OTHER INFORMATION: FMC63 VH

<400> SEQUENCE: 39

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120

<210> SEQ ID NO 40
<211> LENGTH: 107
<212> TYPE: PRT
<213> ORGANISM: Mus musculus
<220> FEATURE:
<223> OTHER INFORMATION: FMC63VL

<400> SEQUENCE: 40

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80
```

```
Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105

<210> SEQ ID NO 41
<211> LENGTH: 122
<212> TYPE: PRT
<213> ORGANISM: Mus musculus
<220> FEATURE:
<223> OTHER INFORMATION: SJ25C1VH

<400> SEQUENCE: 41

Glu Val Lys Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Tyr Pro Gly Asp Gly Asp Thr Asn Tyr Asn Gly Lys Phe
    50                  55                  60

Lys Gly Gln Ala Thr Leu Thr Ala Asp Lys Ser Ser Ser Thr Ala Tyr
65                  70                  75                  80

Met Gln Leu Ser Gly Leu Thr Ser Glu Asp Ser Ala Val Tyr Phe Cys
                85                  90                  95

Ala Arg Lys Thr Ile Ser Ser Val Val Asp Phe Tyr Phe Asp Tyr Trp
                100                 105                 110

Gly Gln Gly Thr Thr Val Thr Val Ser Ser
            115                 120

<210> SEQ ID NO 42
<211> LENGTH: 106
<212> TYPE: PRT
<213> ORGANISM: Mus musculus
<220> FEATURE:
<223> OTHER INFORMATION: SJ25C1 VL

<400> SEQUENCE: 42

Asp Ile Glu Leu Thr Gln Ser Pro Lys Phe Met Ser Thr Ser Val Gly
1               5                   10                  15

Asp Arg Val Ser Val Thr Cys Lys Ala Ser Gln Asn Val Gly Thr Asn
                20                  25                  30

Val Ala Trp Tyr Gln Gln Lys Pro Gly Gln Ser Pro Lys Pro Leu Ile
            35                  40                  45

Tyr Ser Ala Thr Tyr Arg Asn Ser Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Lys Asp Leu Ala Asp Tyr Phe Cys Gln Gln Tyr Asn Arg Tyr Pro Tyr
                85                  90                  95

Thr Ser Gly Gly Gly Thr Lys Leu Glu Ile
            100                 105

<210> SEQ ID NO 43
<211> LENGTH: 18
<212> TYPE: PRT
<213> ORGANISM: Artificial Sequence
<220> FEATURE:
<223> OTHER INFORMATION: Synthetic
```

```
<220> FEATURE:
<223> OTHER INFORMATION: Linker

<400> SEQUENCE: 43

Gly Ser Thr Ser Gly Ser Gly Lys Pro Gly Ser Gly Glu Gly Ser Thr
1               5                   10                  15

Lys Gly

<210> SEQ ID NO 44
<211> LENGTH: 747
<212> TYPE: DNA
<213> ORGANISM: Homo sapiens
<220> FEATURE:
<223> OTHER INFORMATION: Clone 488 scFv (nt)

<400> SEQUENCE: 44
gaagtgcagc tggtgcagtc tgggggaggc ttggtacagc ctggcaggtc cctgagactc        60
tcctgtgcag cctctggatt cacctttgat gattatgcca tgcactgggt ccggcaagct       120
ccagggaagg gcctggagtg ggtctcaggt attagttgga atagtggtag cataggctat       180
gcggactctg tgaagggccg attcaccatc tccagagaca acgccaagaa ctccctgtat       240
ctgcaaatga acagtctgag agctgaggac accgccgtgt attactgtgc gagagatcag       300
gggtatcatt actatgatag tgccgaacat gcttttgata tctggggcca agggacagtg       360
gtcaccgtct cctcaggtgg aggcggttca ggcggaggtg gctctggcgg tggcggatcg       420
gaaattgtgt tgacgcagtc tccagccacc ctgtctttgt ctccagggga gaccgccacc       480
ctctcctgca gggccagtca gagtattaac cactacttag cctggtacca acagaaacct       540
ggccaggctc ccggctcct catctatgat gcctccaaca gggccactgg catcccagcc        600
aggttcagtg gcagtgggtc tgggacagac ttcactctca ccatcagcag cctagagcct       660
gaagattttg caacttacta ctgtcaacag agttacagtc ccctcgaat gtacactttt        720 ggccagggga ccaaactgga tatcaaa                                           747

<210> SEQ ID NO 45
<211> LENGTH: 249
<212> TYPE: PRT
<213> ORGANISM: Homo sapiens
<220> FEATURE:
<223> OTHER INFORMATION: Clone 488 scFv (aa)

<400> SEQUENCE: 45

Glu Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
            100                 105                 110

Asp Ile Trp Gly Gln Gly Thr Val Thr Val Ser Ser Gly Gly Gly
            115                 120                 125
```

```
Gly Ser Gly Gly Gly Ser Gly Gly Gly Ser Glu Ile Val Leu
        130                 135                 140

Thr Gln Ser Pro Ala Thr Leu Ser Leu Ser Pro Gly Glu Thr Ala Thr
145                 150                 155                 160

Leu Ser Cys Arg Ala Ser Gln Ser Ile Asn His Tyr Leu Ala Trp Tyr
                165                 170                 175

Gln Gln Lys Pro Gly Gln Ala Pro Arg Leu Leu Ile Tyr Asp Ala Ser
            180                 185                 190

Asn Arg Ala Thr Gly Ile Pro Ala Arg Phe Ser Gly Ser Gly Ser Gly
        195                 200                 205

Thr Asp Phe Thr Leu Thr Ile Ser Ser Leu Glu Pro Glu Asp Phe Ala
    210                 215                 220

Thr Tyr Tyr Cys Gln Gln Ser Tyr Ser His Pro Arg Met Tyr Thr Phe
225                 230                 235                 240

Gly Gln Gly Thr Lys Leu Asp Ile Lys
                245
```

<210> SEQ ID NO 46
<211> LENGTH: 747
<212> TYPE: DNA
<213> ORGANISM: Homo sapiens
<220> FEATURE:
<223> OTHER INFORMATION: Clone 1304 scFv (nt)

<400> SEQUENCE: 46

```
cagatgcagc tggtgcagtc tgggggaggc ttggtacagc ctggcaggtc cctgagactc      60
tcctgtgcag cctctggatt cacctttgat gattatgcca tgcactgggt ccggcaagct    120
ccagggaagg gcctggagtg ggtctcaggt attagttgga atagtggtag cataggctat    180
gcggactctg tgaagggccg attcaccatc tccagagaca acgccaagaa ctccctgtat    240
ctgcaaatga acagtctgag agctgaggac acggccgtgt attactgtgc gagagatcag    300
gggtatcatt actatgatag tgccgaacat gcttttgata tctggggcca agggacagtg    360
gtcaccgtct cctcaggtgg aggcggttca ggcggaggtg gctctggcgg tggcggatcg    420
gccatccgga tgacccagtc tccatcctcc ctgtctgcat ctgtaggaga cagagtcacc    480
gtcacttgcc aggcgagtca ggacattagc aactatttaa attggtatca gcagaaacca    540
ggaagagccc ctaagctcct gatctacgat gcatccaatg tgaaagcagg ggtcccatca    600
aggttcagtg ggggtggatc tgggacagat ttcactctca ccatcagcag tctgcaacct    660
gaagattttg caacttacta ctgtcaacag agttacagta cccctcaggc gtacactttt    720
ggccagggga ccaagctgga gatcaaa                                         747
```

<210> SEQ ID NO 47
<211> LENGTH: 249
<212> TYPE: PRT
<213> ORGANISM: Homo sapiens
<220> FEATURE:
<223> OTHER INFORMATION: Clone 1304 scFv (aa)

<400> SEQUENCE: 47

```
Gln Met Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45
```

```
Ser Gly Ile Ser Trp Asn Ser Gly Ser Ile Gly Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gln Gly Tyr His Tyr Tyr Asp Ser Ala Glu His Ala Phe
                100                 105                 110

Asp Ile Trp Gly Gln Gly Thr Val Val Thr Val Ser Ser Gly Gly Gly
            115                 120                 125

Gly Ser Gly Gly Gly Gly Ser Gly Gly Gly Gly Ser Ala Ile Arg Met
        130                 135                 140

Thr Gln Ser Pro Ser Ser Leu Ser Ala Ser Val Gly Asp Arg Val Thr
145                 150                 155                 160

Val Thr Cys Gln Ala Ser Gln Asp Ile Ser Asn Tyr Leu Asn Trp Tyr
                165                 170                 175

Gln Gln Lys Pro Gly Arg Ala Pro Lys Leu Leu Ile Tyr Asp Ala Ser
            180                 185                 190

Asn Val Lys Ala Gly Val Pro Ser Arg Phe Ser Gly Gly Ser Gly
        195                 200                 205

Thr Asp Phe Thr Leu Thr Ile Ser Ser Leu Gln Pro Glu Asp Phe Ala
    210                 215                 220

Thr Tyr Tyr Cys Gln Gln Ser Tyr Ser Thr Pro Gln Ala Tyr Thr Phe
225                 230                 235                 240

Gly Gln Gly Thr Lys Leu Glu Ile Lys
                245

<210> SEQ ID NO 48
<211> LENGTH: 756
<212> TYPE: DNA
<213> ORGANISM: Homo sapiens
<220> FEATURE:
<223> OTHER INFORMATION: Clone 285 scFv (nt)

<400> SEQUENCE: 48
gaggtgcagc tggtggagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg ggtctcaggt attagttgga atagtggtag ataggctat     180 gcggactctg taaagggccg attcaccatc tccagagaca cgccaagaa ctccctgttt     240 ctgcaaatga acagtctgag agctgaggac acggccgtgt attactgtgc gagagatcag     300
gggtatcatt actatgatag tgccgaacat gcttttgata tctggggcca agggacagtg     360
gtcaccgtct cctcaggtgg aggcggttca ggcggaggtg gctctggcgg tggcggatcg     420
cagtctgccc tgactcagcc tcctccgtg tctgggtctc ctggacagtc gatcaccatc     480
tcctgcactg gaaccagcag tgaccttggt ggttacaatt atgtctcctg gtatcaacac     540
cgcccaggca agccccccaa actcatcatt tatgatgtca ctgttcggcc ctcaggggtt     600
tctgatcgct tctctggctc caagtctggc aacacggcct ccctgaccat ctctgggctc     660
caggctgagg acgaggctga ttattactgc ggctcatata caagcagtag cactcttctt     720
tgggtgttcg gcggagggac caagctcacc gtccta                                756

<210> SEQ ID NO 49
<211> LENGTH: 252
```

```
<212> TYPE: PRT
<213> ORGANISM: Homo sapiens
<220> FEATURE:
<223> OTHER INFORMATION: Clone 285 scFv (aa)

<400> SEQUENCE: 49

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
                100                 105                 110

Asp Ile Trp Gly Gln Gly Thr Val Val Thr Val Ser Ser Gly Gly Gly
            115                 120                 125

Gly Ser Gly Gly Gly Gly Ser Gly Gly Gly Gly Ser Gln Ser Ala Leu
    130                 135                 140

Thr Gln Pro Ala Ser Val Ser Gly Ser Pro Gly Gln Ser Ile Thr Ile
145                 150                 155                 160

Ser Cys Thr Gly Thr Ser Ser Asp Leu Gly Gly Tyr Asn Tyr Val Ser
                165                 170                 175

Trp Tyr Gln His Arg Pro Gly Lys Ala Pro Lys Leu Ile Ile Tyr Asp
                180                 185                 190

Val Thr Val Arg Pro Ser Gly Val Ser Asp Arg Phe Ser Gly Ser Lys
            195                 200                 205

Ser Gly Asn Thr Ala Ser Leu Thr Ile Ser Gly Leu Gln Ala Glu Asp
    210                 215                 220

Glu Ala Asp Tyr Tyr Cys Gly Ser Tyr Thr Ser Ser Ser Thr Leu Leu
225                 230                 235                 240

Trp Val Phe Gly Gly Gly Thr Lys Leu Thr Val Leu
                245                 250

<210> SEQ ID NO 50
<211> LENGTH: 753
<212> TYPE: DNA
<213> ORGANISM: Homo sapiens
<220> FEATURE:
<223> OTHER INFORMATION: Clone 192B scFv (nt)

<400> SEQUENCE: 50
caggtgcagc tggtggagtc tgggggaggc ttggtacagc ctggcaggtc cctgagactc      60
tcctgtgcag cctctggatt cacctttgat gattatgcca tgcactgggt ccggcaagct    120
ccagggaagg gcctggagtg ggtctcaggt attagttgga atagtggtag gataggctat    180
gcggactctg taaagggccg attcaccatc tccagagaca cgccaagaa ctccctgttt    240 ctgcaaatga acagtctgag agctgaggac acggccgtgt attactgtgc gagagatcag    300
gggtatcatt actatgatag tgccgaacat gcttttgata tctggggcca agggacaatg    360
gtcaccgtct cctcaggtgg aggcggttca ggcggaggtg gctctggcgg tggcggatcg    420
```

| | |
|---|---|
| caggctgtgc tgactcagcc tcgctcagtg tccgggtctc ctggacagtc agtcaccatc | 480 |
| tcctgcactg gaatcagcag tggtgttgat agtcataggt atgtctcctg gtaccaacac | 540 |
| cacccaggca aagcccccaa actcatgatt tatgatttca gtaagcggcc ctcaggggtc | 600 |
| cctgatcgtt tctctggctc caagtctggc aacacggcct ccctgaccat ctctgggctc | 660 |
| caggctgagg atgaggctga ttactattgc agctcatatg cagccatctc ccctaattat | 720 |
| gtcttcggaa ctgggaccaa gctcaccgtc cta | 753 |

```
<210> SEQ ID NO 51
<211> LENGTH: 251
<212> TYPE: PRT
<213> ORGANISM: Homo sapiens
<220> FEATURE:
<223> OTHER INFORMATION: Clone 192B scFv (aa)

<400> SEQUENCE: 51

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
            100                 105                 110

Asp Ile Trp Gly Gln Gly Thr Met Val Thr Val Ser Ser Gly Gly Gly
        115                 120                 125

Gly Ser Gly Gly Gly Gly Ser Gly Gly Gly Gly Ser Gln Ala Val Leu
    130                 135                 140

Thr Gln Pro Arg Ser Val Ser Gly Ser Pro Gly Gln Ser Val Thr Ile
145                 150                 155                 160

Ser Cys Thr Gly Ile Ser Ser Gly Val Asp Ser His Arg Tyr Val Ser
                165                 170                 175

Trp Tyr Gln His His Pro Gly Lys Ala Pro Lys Leu Met Ile Tyr Asp
            180                 185                 190

Phe Ser Lys Arg Pro Ser Gly Val Pro Asp Arg Phe Ser Gly Ser Lys
        195                 200                 205

Ser Gly Asn Thr Ala Ser Leu Thr Ile Ser Gly Leu Gln Ala Glu Asp
    210                 215                 220

Glu Ala Asp Tyr Tyr Cys Ser Ser Tyr Ala Ala Ile Ser Pro Asn Tyr
225                 230                 235                 240

Val Phe Gly Thr Gly Thr Lys Leu Thr Val Leu
                245                 250

<210> SEQ ID NO 52
<211> LENGTH: 750
<212> TYPE: DNA
<213> ORGANISM: Homo sapiens
<220> FEATURE:
<223> OTHER INFORMATION: Clone 328 scFv (nt)

<400> SEQUENCE: 52
```

```
caggtgcagc tggtggagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg ggtctcaggt attagttgga atagtggtag ataggctat      180 gcggactctg taaagggccg attcaccatc tccagagaca cgccaagaa ctccctgttt      240 ctgcaaatga acagtctgag agctgaggac acggccgtgt attactgtgc gagagatcag     300
gggtatcatt actatgatag tgccgaacat gctttttgata tctggggcca agggacagtg     360
gtcaccgtct cctcaggtgg aggcggttca ggcggaggtg gctctggcgg tggcggatcg     420
cagtctgccc tgactcagcc tgcctccgtg tctgggtctc ctggacattc gatcaccatc     480
tcctgcactg gaaccagaag tgacgtcggt ggttttgatt atgtctcctg gtaccagcat     540
aacccaggca agcccccaa actcataatt tatgatgtca ctaagcggcc ctcaggggtc      600
tctaatcgct tctctggcgc caagtctggc atcacggcct ccctgaccat ctctgggctc     660
caggctgagg acgaggctga ttattactgc acctcatata gacccggtcc aacatttgtc     720
ttcggcaccg ggaccaagct caccgtccta                                      750
```

<210> SEQ ID NO 53  
<211> LENGTH: 250  
<212> TYPE: PRT  
<213> ORGANISM: Homo sapiens

<400> SEQUENCE: 53

```
Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
            100                 105                 110

Asp Ile Trp Gly Gln Gly Thr Val Val Thr Val Ser Ser Gly Gly Gly
        115                 120                 125

Gly Ser Gly Gly Gly Gly Ser Gly Gly Gly Gly Ser Gln Ser Ala Leu
    130                 135                 140

Thr Gln Pro Ala Ser Val Ser Gly Ser Pro Gly His Ser Ile Thr Ile
145                 150                 155                 160

Ser Cys Thr Gly Thr Arg Ser Asp Val Gly Gly Phe Asp Tyr Val Ser
                165                 170                 175

Trp Tyr Gln His Asn Pro Gly Lys Ala Pro Lys Leu Ile Ile Tyr Asp
            180                 185                 190

Val Thr Lys Arg Pro Ser Gly Val Ser Asn Arg Phe Ser Gly Ala Lys
        195                 200                 205

Ser Gly Ile Thr Ala Ser Leu Thr Ile Ser Gly Leu Gln Ala Glu Asp
    210                 215                 220

Glu Ala Asp Tyr Tyr Cys Thr Ser Tyr Arg Pro Gly Pro Thr Phe Val
225                 230                 235                 240
```

```
Phe Gly Thr Gly Thr Lys Leu Thr Val Leu
                245                 250

<210> SEQ ID NO 54
<211> LENGTH: 741
<212> TYPE: DNA
<213> ORGANISM: Homo sapiens
<220> FEATURE:
<223> OTHER INFORMATION: Clone 227 scFv (nt)

<400> SEQUENCE: 54
gaagtgcagc tggtgcagtc tgggggaggc ttggtacagc ctggcaggtc cctgagactc     60
tcctgtgcag cctctggatt cacctttgat gattatgcca tgcactgggt ccggcaagct    120
ccagggaagg gcctggagtg ggtctcaggt attagttgga atagtggtag cataggctat    180
gcggactctg tgaagggccg attcaccatc tccagagaca acgccaagaa ctccctgtat    240
ctgcaaatga acagtctgag agctgaggac acggccgtgt attactgtgc gagagatcag    300
gggtatcatt actatgatag tgccgaacat gcttttgata tctggggcca agggacagtg    360
gtcaccgtct cctcaggtgg aggcggttca ggcggaggtg gctctggcgg tggcggatcg    420
gacatccagt tgacccagtc tccttccacc ctgtctgcat ctgtaggaga cagagtcacc    480
atcacttgcc gggccagtca gagtattagt aggtggttgg cctggtatca gcagaaacca    540
gggaaagccc ctaagctcct gatctacgat gcatccaatt tggaaacagg ggtcccatcc    600
aggttcagtg gaagtggatc tgggacagat tttactttca ccatcagcag cctgcagcct    660
gaagatattg caacatatta ctgtcaacag tatgataatc tccctctcac tttcggcgga    720
gggaccaagg tggagatcaa a                                              741

<210> SEQ ID NO 55
<211> LENGTH: 247
<212> TYPE: PRT
<213> ORGANISM: Homo sapiens
<220> FEATURE:
<223> OTHER INFORMATION: Clone 227 scFv (aa)

<400> SEQUENCE: 55

Glu Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
            100                 105                 110

Asp Ile Trp Gly Gln Gly Thr Val Val Thr Val Ser Ser Gly Gly Gly
        115                 120                 125

Gly Ser Gly Gly Gly Gly Ser Gly Gly Gly Gly Ser Asp Ile Gln Leu
    130                 135                 140

Thr Gln Ser Pro Ser Thr Leu Ser Ala Ser Val Gly Asp Arg Val Thr
145                 150                 155                 160
```

Ile Thr Cys Arg Ala Ser Gln Ser Ile Ser Arg Trp Leu Ala Trp Tyr
            165                 170                 175

Gln Gln Lys Pro Gly Lys Ala Pro Lys Leu Leu Ile Tyr Asp Ala Ser
            180                 185                 190

Asn Leu Glu Thr Gly Val Pro Ser Arg Phe Ser Gly Ser Gly Ser Gly
            195                 200                 205

Thr Asp Phe Thr Phe Thr Ile Ser Ser Leu Gln Pro Glu Asp Ile Ala
            210                 215                 220

Thr Tyr Tyr Cys Gln Gln Tyr Asp Asn Leu Pro Leu Thr Phe Gly Gly
225                 230                 235                 240

Gly Thr Lys Val Glu Ile Lys
            245

<210> SEQ ID NO 56
<211> LENGTH: 744
<212> TYPE: DNA
<213> ORGANISM: Homo sapiens
<220> FEATURE:
<223> OTHER INFORMATION: Clone 1300 scFv (nt)

<400> SEQUENCE: 56
cagatgcagc tggtgcagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg gtctcaggt attagttgga atagtggtag cataggctat     180
gcggactctg tgaagggccg attcaccatc tccagacaca cgccaagaa ctccctgtat     240 ctgcaaatga acagtctgag agctgaggac acggccgtgt attactgtgc gagagatcag     300
gggtatcatt actatgatag tgccgaacat gctttgata tctggggcca agggacagtg     360
gtcaccgtct cctcaggtgg aggcggttca ggcggaggtg gctctggcgg tggcggatcg     420
gccatccgga tgacccagtc tccttccacc ctgtctgcat ctgtgggaga cagagtcacc     480
atcacttgcc gggccagtca gagcattagt cactacttgg cctggtatca acagaaacca     540
gggaaagccc ctaagctcct gatctttgat gcctcccgtt tggcaagtgg ggtcccatca     600
aggttcagtg gcagtggatc tgggacagat ttcactctca ccatcagcag tctgcaacct     660
gaagattttg cgacatacta ctgtcaacag agttacggtg cccctatgtt cactttcggc     720
cctgggacca gagtggatct caaa                                             744

<210> SEQ ID NO 57
<211> LENGTH: 248
<212> TYPE: PRT
<213> ORGANISM: Homo sapiens
<220> FEATURE:
<223> OTHER INFORMATION: Clone 1300 scFv (aa)

<400> SEQUENCE: 57

Gln Met Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
            100                 105                 110

Asp Ile Trp Gly Gln Gly Thr Val Val Thr Val Ser Ser Gly Gly Gly
        115                 120                 125

Gly Ser Gly Gly Gly Gly Ser Gly Gly Gly Ser Ala Ile Arg Met
    130                 135                 140

Thr Gln Ser Pro Ser Thr Leu Ser Ala Ser Val Gly Asp Arg Val Thr
145                 150                 155                 160

Ile Thr Cys Arg Ala Ser Gln Ser Ile Ser His Tyr Leu Ala Trp Tyr
            165                 170                 175

Gln Gln Lys Pro Gly Lys Ala Pro Lys Leu Leu Ile Phe Asp Ala Ser
        180                 185                 190

Arg Leu Ala Ser Gly Val Pro Ser Arg Phe Ser Gly Ser Gly Ser Gly
    195                 200                 205

Thr Asp Phe Thr Leu Thr Ile Ser Ser Leu Gln Pro Glu Asp Phe Ala
    210                 215                 220

Thr Tyr Tyr Cys Gln Gln Ser Tyr Gly Ala Pro Met Phe Thr Phe Gly
225                 230                 235                 240

Pro Gly Thr Arg Val Asp Leu Lys
            245

<210> SEQ ID NO 58
<211> LENGTH: 753
<212> TYPE: DNA
<213> ORGANISM: Homo sapiens
<220> FEATURE:
<223> OTHER INFORMATION: Clone 1 scFv (nt)

<400> SEQUENCE: 58
gaagtgcagc tggtggagtc tgggggaggc ttggtacagc ctggcaggtc cctgagactc    60
tcctgtgcag cctctggatt cacctttgat gattatgcca tgcactgggt ccggcaagct   120
ccagggaagg gcctggagtg gtctcaggt attagttgga atagtggtag ataggctat     180 gcggactctg taaagggccg attcaccatc tccagagaca cgccaagaa ctccctgttt    240 ctgcaaatga acagtctgag agctgaggac acggccgtgt attactgtgc gagagatcag   300
gggtatcatt actatgatag tgccgaacat gcttttgata tctggggcca agggacaatg   360
gtcacagtct cctcaggtgg aggcggttca ggcggaggtg gctctggcgg tggcggatcg   420
cagtctgccc tgactcagcc cgcctccgtg tctgggtctc ctggacagtc gatcaccatc   480
tcctgcactg gaaccagcag tgacgttggt gcttataact ttgtctcctg gtaccagcag   540
ctcccaggaa cagcccccaa attcctcatt tatgacaata taaacgacc cccagggatt    600 cctgaccgat tctctggctc caagtctggc acgtcagcca ccctgggcat caccggactc   660
cagactgggg acgaggccga ttattactgc gcaacatggg atagcggcct gagtgctgtg   720
gtattcggcg agggaccaa gctgaccgtc cta                                  753

<210> SEQ ID NO 59
<211> LENGTH: 251
<212> TYPE: PRT
<213> ORGANISM: Homo sapiens
<220> FEATURE:
<223> OTHER INFORMATION: Clone 1 scFv (aa)

<400> SEQUENCE: 59

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
            35                  40                  45

Ser Gly Ile Ser Trp Asn Ser Gly Arg Ile Gly Tyr Ala Asp Ser Val
50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
            85                  90                  95

Ala Arg Asp Gln Gly Tyr His Tyr Tyr Asp Ser Ala Glu His Ala Phe
            100                 105                 110

Asp Ile Trp Gly Gln Gly Thr Met Val Thr Val Ser Ser Gly Gly Gly
            115                 120                 125

Gly Ser Gly Gly Gly Gly Ser Gly Gly Gly Gly Ser Gln Ser Ala Leu
            130                 135                 140

Thr Gln Pro Ala Ser Val Ser Gly Ser Pro Gly Gln Ser Ile Thr Ile
145                 150                 155                 160

Ser Cys Thr Gly Thr Ser Ser Asp Val Gly Ala Tyr Asn Phe Val Ser
            165                 170                 175

Trp Tyr Gln Gln Leu Pro Gly Thr Ala Pro Lys Phe Leu Ile Tyr Asp
            180                 185                 190

Asn Asn Lys Arg Pro Pro Gly Ile Pro Asp Arg Phe Ser Gly Ser Lys
            195                 200                 205

Ser Gly Thr Ser Ala Thr Leu Gly Ile Thr Gly Leu Gln Thr Gly Asp
            210                 215                 220

Glu Ala Asp Tyr Tyr Cys Ala Thr Trp Asp Ser Gly Leu Ser Ala Val
225                 230                 235                 240

Val Phe Gly Gly Gly Thr Lys Leu Thr Val Leu
            245                 250

<210> SEQ ID NO 60
<211> LENGTH: 125
<212> TYPE: PRT
<213> ORGANISM: Homo sapiens
<220> FEATURE:
<223> OTHER INFORMATION: VH Clone 192B (aa)

<400> SEQUENCE: 60

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
            35                  40                  45

Ser Gly Ile Ser Trp Asn Ser Gly Arg Ile Gly Tyr Ala Asp Ser Val
50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
            85                  90                  95

Ala Arg Asp Gln Gly Tyr His Tyr Tyr Asp Ser Ala Glu His Ala Phe
            100                 105                 110
```

-continued

Asp Ile Trp Gly Gln Gly Thr Met Val Thr Val Ser Ser
        115                 120                 125

<210> SEQ ID NO 61
<211> LENGTH: 125
<212> TYPE: PRT
<213> ORGANISM: Homo sapiens
<220> FEATURE:
<223> OTHER INFORMATION: VH Clone 328 (aa)

<400> SEQUENCE: 61

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
            100                 105                 110

Asp Ile Trp Gly Gln Gly Thr Val Val Thr Val Ser Ser
        115                 120                 125

<210> SEQ ID NO 62
<211> LENGTH: 125
<212> TYPE: PRT
<213> ORGANISM: Homo sapiens
<220> FEATURE:
<223> OTHER INFORMATION: VH Clone 1304 Clone 1300 (aa)

<400> SEQUENCE: 62

Gln Met Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
            100                 105                 110

Asp Ile Trp Gly Gln Gly Thr Val Val Thr Val Ser Ser
        115                 120                 125

<210> SEQ ID NO 63
<211> LENGTH: 125
<212> TYPE: PRT
<213> ORGANISM: Homo sapiens
<220> FEATURE:
<223> OTHER INFORMATION: VH Clones 227, 488, 241 (aa)

```
<400> SEQUENCE: 63

Glu Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
            100                 105                 110

Asp Ile Trp Gly Gln Gly Thr Val Val Thr Val Ser Ser
            115                 120                 125

<210> SEQ ID NO 64
<211> LENGTH: 111
<212> TYPE: PRT
<213> ORGANISM: Homo sapiens
<220> FEATURE:
<223> OTHER INFORMATION: VL Clone 192B (aa)

<400> SEQUENCE: 64

Gln Ala Val Leu Thr Gln Pro Arg Ser Val Ser Gly Ser Pro Gly Gln
1               5                   10                  15

Ser Val Thr Ile Ser Cys Thr Gly Ile Ser Ser Gly Val Asp Ser His
            20                  25                  30

Arg Tyr Val Ser Trp Tyr Gln His Pro Gly Lys Ala Pro Lys Leu
        35                  40                  45

Met Ile Tyr Asp Phe Ser Lys Arg Pro Ser Gly Val Pro Asp Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ala Ala Ile
                85                  90                  95

Ser Pro Asn Tyr Val Phe Gly Thr Gly Thr Lys Leu Thr Val Leu
            100                 105                 110

<210> SEQ ID NO 65
<211> LENGTH: 112
<212> TYPE: PRT
<213> ORGANISM: Homo sapiens
<220> FEATURE:
<223> OTHER INFORMATION: VL Clone 285 (aa)

<400> SEQUENCE: 65

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Leu Gly Gly Tyr
            20                  25                  30

Asn Tyr Val Ser Trp Tyr Gln His Arg Pro Gly Lys Ala Pro Lys Leu
        35                  40                  45

Ile Ile Tyr Asp Val Thr Val Arg Pro Ser Gly Val Ser Asp Arg Phe
50                  55                  60
```

-continued

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Thr Ser Ser
                85                  90                  95

Ser Thr Leu Leu Trp Val Phe Gly Gly Gly Thr Lys Leu Thr Val Leu
            100                 105                 110

<210> SEQ ID NO 66
<211> LENGTH: 110
<212> TYPE: PRT
<213> ORGANISM: Homo sapiens
<220> FEATURE:
<223> OTHER INFORMATION: VL Clone 328 (aa)

<400> SEQUENCE: 66

Gln Ser Ala Leu Thr Gln Pro Ala Ser Val Ser Gly Ser Pro Gly His
1               5                   10                  15

Ser Ile Thr Ile Ser Cys Thr Gly Thr Arg Ser Asp Val Gly Gly Phe
            20                  25                  30

Asp Tyr Val Ser Trp Tyr Gln His Asn Pro Gly Lys Ala Pro Lys Leu
        35                  40                  45

Ile Ile Tyr Asp Val Thr Lys Arg Pro Ser Gly Val Ser Asn Arg Phe
    50                  55                  60

Ser Gly Ala Lys Ser Gly Ile Thr Ala Ser Leu Thr Ile Ser Gly Leu
65                  70                  75                  80

Gln Ala Glu Asp Glu Ala Asp Tyr Tyr Cys Thr Ser Tyr Arg Pro Gly
                85                  90                  95

Pro Thr Phe Val Phe Gly Thr Gly Thr Lys Leu Thr Val Leu
            100                 105                 110

<210> SEQ ID NO 67
<211> LENGTH: 111
<212> TYPE: PRT
<213> ORGANISM: Homo sapiens
<220> FEATURE:
<223> OTHER INFORMATION: VL Clone 1 (aa)

<400> SEQUENCE: 67

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ala Tyr
            20                  25                  30

Asn Phe Val Ser Trp Tyr Gln Gln Leu Pro Gly Thr Ala Pro Lys Phe
        35                  40                  45

Leu Ile Tyr Asp Asn Asn Lys Arg Pro Pro Gly Ile Pro Asp Arg Phe
    50                  55                  60

Ser Gly Ser Lys Ser Gly Thr Ser Ala Thr Leu Gly Ile Thr Gly Leu
65                  70                  75                  80

Gln Thr Gly Asp Glu Ala Asp Tyr Tyr Cys Ala Thr Trp Asp Ser Gly
                85                  90                  95

Leu Ser Ala Val Val Phe Gly Gly Gly Thr Lys Leu Thr Val Leu
            100                 105                 110

<210> SEQ ID NO 68
<211> LENGTH: 109
<212> TYPE: PRT
<213> ORGANISM: Homo sapiens
<220> FEATURE:
<223> OTHER INFORMATION: VL Clone 1304 (aa)

-continued

<400> SEQUENCE: 68

Ala Ile Arg Met Thr Gln Ser Pro Ser Ser Leu Ser Ala Ser Val Gly
1               5                   10                  15

Asp Arg Val Thr Val Thr Cys Gln Ala Ser Gln Asp Ile Ser Asn Tyr
            20                  25                  30

Leu Asn Trp Tyr Gln Gln Lys Pro Gly Arg Ala Pro Lys Leu Leu Ile
        35                  40                  45

Tyr Asp Ala Ser Asn Val Lys Ala Gly Val Pro Ser Arg Phe Ser Gly
    50                  55                  60

Gly Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Gln
                85                  90                  95

Ala Tyr Thr Phe Gly Gln Gly Thr Lys Leu Glu Ile Lys
            100                 105

<210> SEQ ID NO 69
<211> LENGTH: 108
<212> TYPE: PRT
<213> ORGANISM: Homo sapiens
<220> FEATURE:
<223> OTHER INFORMATION: VL Clone 1300 (aa)

<400> SEQUENCE: 69

Ala Ile Arg Met Thr Gln Ser Pro Ser Thr Leu Ser Ala Ser Val Gly
1               5                   10                  15

Asp Arg Val Thr Ile Thr Cys Arg Ala Ser Gln Ser Ile Ser His Tyr
            20                  25                  30

Leu Ala Trp Tyr Gln Gln Lys Pro Gly Lys Ala Pro Lys Leu Leu Ile
        35                  40                  45

Phe Asp Ala Ser Arg Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Gly Ala Pro Met
                85                  90                  95

Phe Thr Phe Gly Pro Gly Thr Arg Val Asp Leu Lys
            100                 105

<210> SEQ ID NO 70
<211> LENGTH: 107
<212> TYPE: PRT
<213> ORGANISM: Homo sapiens
<220> FEATURE:
<223> OTHER INFORMATION: VL Clone 227 (aa)

<400> SEQUENCE: 70

Asp Ile Gln Leu Thr Gln Ser Pro Ser Thr Leu Ser Ala Ser Val Gly
1               5                   10                  15

Asp Arg Val Thr Ile Thr Cys Arg Ala Ser Gln Ser Ile Ser Arg Trp
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

```
Glu Asp Ile Ala Thr Tyr Tyr Cys Gln Gln Tyr Asp Asn Leu Pro Leu
                85                  90                  95

Thr Phe Gly Gly Gly Thr Lys Val Glu Ile Lys
            100                 105

<210> SEQ ID NO 71
<211> LENGTH: 109
<212> TYPE: PRT
<213> ORGANISM: Homo sapiens
<220> FEATURE:
<223> OTHER INFORMATION: VL Clone 488 (aa)

<400> SEQUENCE: 71

Glu Ile Val Leu Thr Gln Ser Pro Ala Thr Leu Ser Leu Ser Pro Gly
1               5                   10                  15

Glu Thr Ala Thr Leu Ser Cys Arg Ala Ser Gln Ser Ile Asn His Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Thr Tyr Tyr Cys Gln Gln Ser Tyr Ser His Pro Arg
                85                  90                  95

Met Tyr Thr Phe Gly Gln Gly Thr Lys Leu Asp Ile Lys
            100                 105

<210> SEQ ID NO 72
<211> LENGTH: 17
<212> TYPE: PRT
<213> ORGANISM: Homo sapiens
<220> FEATURE:
<223> OTHER INFORMATION: CDR-H2 Clone 1304 Clone 1300 Clone 227 Clone
      488 Clone 241 (aa)

<400> SEQUENCE: 72

Gly Ile Ser Trp Asn Ser Gly Ser Ile Gly Tyr Ala Asp Ser Val Lys
1               5                   10                  15

Gly

<210> SEQ ID NO 73
<211> LENGTH: 14
<212> TYPE: PRT
<213> ORGANISM: Homo sapiens
<220> FEATURE:
<223> OTHER INFORMATION: CDR-L1 Clone 192B Clone 192 (aa)

<400> SEQUENCE: 73

Thr Gly Ile Ser Ser Gly Val Asp Ser His Arg Tyr Val Ser
1               5                   10

<210> SEQ ID NO 74
<211> LENGTH: 14
<212> TYPE: PRT
<213> ORGANISM: Homo sapiens
<220> FEATURE:
<223> OTHER INFORMATION: CDR-L1 Clone 285 (aa)

<400> SEQUENCE: 74

Thr Gly Thr Ser Ser Asp Leu Gly Gly Tyr Asn Tyr Val Ser
1               5                   10
```

<210> SEQ ID NO 75
<211> LENGTH: 14
<212> TYPE: PRT
<213> ORGANISM: Homo sapiens
<220> FEATURE:
<223> OTHER INFORMATION: CDR-L1 Clone 328 (aa)

<400> SEQUENCE: 75

Thr Gly Thr Arg Ser Asp Val Gly Gly Phe Asp Tyr Val Ser
1               5                   10

<210> SEQ ID NO 76
<211> LENGTH: 14
<212> TYPE: PRT
<213> ORGANISM: Homo sapiens
<220> FEATURE:
<223> OTHER INFORMATION: CDR-L1 Clone 1 (aa)

<400> SEQUENCE: 76

Thr Gly Thr Ser Ser Asp Val Gly Ala Tyr Asn Phe Val Ser
1               5                   10

<210> SEQ ID NO 77
<211> LENGTH: 11
<212> TYPE: PRT
<213> ORGANISM: Homo sapiens
<220> FEATURE:
<223> OTHER INFORMATION: CDR-L1 Clone 1304 Clone 241 (aa)

<400> SEQUENCE: 77

Gln Ala Ser Gln Asp Ile Ser Asn Tyr Leu Asn
1               5                   10

<210> SEQ ID NO 78
<211> LENGTH: 11
<212> TYPE: PRT
<213> ORGANISM: Homo sapiens
<220> FEATURE:
<223> OTHER INFORMATION: CDR-L1 Clone 1300 (aa)

<400> SEQUENCE: 78

Arg Ala Ser Gln Ser Ile Ser His Tyr Leu Ala
1               5                   10

<210> SEQ ID NO 79
<211> LENGTH: 11
<212> TYPE: PRT
<213> ORGANISM: Homo sapiens
<220> FEATURE:
<223> OTHER INFORMATION: CDR-L1 Clone 227 (aa)

<400> SEQUENCE: 79

Arg Ala Ser Gln Ser Ile Ser Arg Trp Leu Ala
1               5                   10

<210> SEQ ID NO 80
<211> LENGTH: 11
<212> TYPE: PRT
<213> ORGANISM: Homo sapiens
<220> FEATURE:
<223> OTHER INFORMATION: CDR-L1 Clone 488 (aa)

<400> SEQUENCE: 80

Arg Ala Ser Gln Ser Ile Asn His Tyr Leu Ala
1               5                   10

```
<210> SEQ ID NO 81
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: CDR-H2

<400> SEQUENCE: 81

Gly Ile Ser Trp Asn Ser Gly Arg Ile Gly
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: CDR-H2

<400> SEQUENCE: 82

Gly Ile Ser Trp Asn Ser Gly Ser Ile Gly
1               5                   10

<210> SEQ ID NO 83
<211> LENGTH: 14
<212> TYPE: PRT
<213> ORGANISM: Artificial Sequence
<220> FEATURE:
<223> OTHER INFORMATION: Synthetic
<220> FEATURE:
<223> OTHER INFORMATION: CDR-L1
      Consensus
<220> FEATURE:
<221> NAME/KEY: VARIANT
<222> LOCATION: 1
<223> OTHER INFORMATION: Xaa = Thr, Gln or Arg
<220> FEATURE:
<221> NAME/KEY: VARIANT
<222> LOCATION: 2
<223> OTHER INFORMATION: Xaa = Gly or Ala
<220> FEATURE:
<221> NAME/KEY: VARIANT
<222> LOCATION: 3
<223> OTHER INFORMATION: Xaa = Ile, Thr or Ser
<220> FEATURE:
<221> NAME/KEY: VARIANT
<222> LOCATION: 4
<223> OTHER INFORMATION: Xaa = Ser, Arg or Gln
<220> FEATURE:
<221> NAME/KEY: VARIANT
<222> LOCATION: 5
<223> OTHER INFORMATION: Xaa = null or Ser
<220> FEATURE:
<221> NAME/KEY: VARIANT
<222> LOCATION: 6
<223> OTHER INFORMATION: Xaa = null, Asp or Gly
<220> FEATURE:
<221> NAME/KEY: VARIANT
<222> LOCATION: 7
<223> OTHER INFORMATION: Xaa = null, Val or Leu
<220> FEATURE:
<221> NAME/KEY: VARIANT
<222> LOCATION: 8
<223> OTHER INFORMATION: Xaa = Asp, Gly or Ser
<220> FEATURE:
<221> NAME/KEY: VARIANT
<222> LOCATION: 9
<223> OTHER INFORMATION: Xaa = Ser, Gly, Ala or Ile
<220> FEATURE:
<221> NAME/KEY: VARIANT
<222> LOCATION: 10
```

-continued

```
<223> OTHER INFORMATION: Xaa = His, Tyr, Phe, Ser or Asn
<220> FEATURE:
<221> NAME/KEY: VARIANT
<222> LOCATION: 11
<223> OTHER INFORMATION: Xaa = Arg, Asn, Asp or His
<220> FEATURE:
<221> NAME/KEY: VARIANT
<222> LOCATION: 12
<223> OTHER INFORMATION: Xaa = Tyr, Phe or Trp
<220> FEATURE:
<221> NAME/KEY: VARIANT
<222> LOCATION: 13
<223> OTHER INFORMATION: Xaa = Val or Leu
<220> FEATURE:
<221> NAME/KEY: VARIANT
<222> LOCATION: 14
<223> OTHER INFORMATION: Xaa = Ser, Asn or Ala

<400> SEQUENCE: 83

Xaa Xaa Xaa Xaa Xaa Xaa Xaa Xaa Xaa Xaa Xaa Xaa Xaa Xaa
 1               5                  10

<210> SEQ ID NO 84
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: CDR-L2 Consensus
<220> FEATURE:
<221> NAME/KEY: VARIANT
<222> LOCATION: 2
<223> OTHER INFORMATION: Xaa = Phe, Val, Asn or Ala
<220> FEATURE:
<221> NAME/KEY: VARIANT
<222> LOCATION: 3
<223> OTHER INFORMATION: Xaa = Ser, Thr or Asn
<220> FEATURE:
<221> NAME/KEY: VARIANT
<222> LOCATION: 4
<223> OTHER INFORMATION: Xaa = Lys, Val, Asn or Arg
<220> FEATURE:
<221> NAME/KEY: VARIANT
<222> LOCATION: 5
<223> OTHER INFORMATION: Xaa = Arg, Val or Leu
<220> FEATURE:
<221> NAME/KEY: VARIANT
<222> LOCATION: 6
<223> OTHER INFORMATION: Xaa = Pro, Lys, Ala or Glu
<220> FEATURE:
<221> NAME/KEY: VARIANT
<222> LOCATION: 7
<223> OTHER INFORMATION: Xaa = Ser, Pro, Ala or Thr

<400> SEQUENCE: 84

Asp Xaa Xaa Xaa Xaa Xaa Xaa
 1               5

<210> SEQ ID NO 85
<211> LENGTH: 12
<212> TYPE: PRT
<213> ORGANISM: Artificial Sequence
<220> FEATURE:
<223> OTHER INFORMATION: Synthetic
<220> FEATURE:
<223> OTHER INFORMATION: CDR-L3 Consensus
<220> FEATURE:
<221> NAME/KEY: VARIANT
<222> LOCATION: 1
<223> OTHER INFORMATION: Xaa = Ser, Gly, Thr, Ala or Gln
<220> FEATURE:
<221> NAME/KEY: VARIANT
<222> LOCATION: 2
<223> OTHER INFORMATION: Xaa = Ser, Thr or Gln
```

```
<220> FEATURE:
<221> NAME/KEY: VARIANT
<222> LOCATION: 3
<223> OTHER INFORMATION: Xaa = Tyr, Trp or Ser
<220> FEATURE:
<221> NAME/KEY: VARIANT
<222> LOCATION: 4
<223> OTHER INFORMATION: Xaa = Ala, Thr, Arg, Asp or Tyr
<220> FEATURE:
<221> NAME/KEY: VARIANT
<222> LOCATION: 5
<223> OTHER INFORMATION: Xaa = Ala, Ser, Pro, Gly or Asn
<220> FEATURE:
<221> NAME/KEY: VARIANT
<222> LOCATION: 6
<223> OTHER INFORMATION: Xaa = Ile, Ser, Gly, Thr, Leu, Ala or His
<220> FEATURE:
<221> NAME/KEY: VARIANT
<222> LOCATION: 7
<223> OTHER INFORMATION: Xaa = Ser, Pro or Leu
<220> FEATURE:
<221> NAME/KEY: VARIANT
<222> LOCATION: 8
<223> OTHER INFORMATION: Xaa = Pro, Thr, Ser, Gln, Met, Arg or null
<220> FEATURE:
<221> NAME/KEY: VARIANT
<222> LOCATION: 9
<223> OTHER INFORMATION: Xaa = Asn, Leu, Ala, Met or null
<220> FEATURE:
<221> NAME/KEY: VARIANT
<222> LOCATION: 10
<223> OTHER INFORMATION: Xaa = Leu or null
<220> FEATURE:
<221> NAME/KEY: VARIANT
<222> LOCATION: 11
<223> OTHER INFORMATION: Xaa = Tyr, Trp, Phe, Val or Leu
<220> FEATURE:
<221> NAME/KEY: VARIANT
<222> LOCATION: 12
<223> OTHER INFORMATION: Xaa = Val or Thr

<400> SEQUENCE: 85

Xaa Xaa Xaa Xaa Xaa Xaa Xaa Xaa Xaa Xaa Xaa Xaa
1               5                   10

<210> SEQ ID NO 86
<211> LENGTH: 753
<212> TYPE: DNA
<213> ORGANISM: Homo sapiens
<220> FEATURE:
<223> OTHER INFORMATION: Clone 192 scFv (nt)

<400> SEQUENCE: 86
gaagtgcagc tggtggagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg ggtctcaggt attagttgga atagtggtag ataggctat     180 gcggactctg taaagggccg attcaccatc tccagagaca cgccaagaa ctccctgttt     240 ctgcaaatga acagtctgag agctgaggac acggccgtgt attactgtgc gagagatcag    300
gggtatcatt actatgatag tgccgaacat gcttttgata tctggggcca agggacaatg    360
gtcaccgtct cctcaggtgg aggcggttca ggcggaggtg gctctggcgg tggcggatcg    420
caggctgtgc tgactcagcc tcgctcagtg tccgggtctc ctggacagtc agtcaccatc    480
tcctgcactg gaatcagcag tggtgttgat agtcataggt atgtctcctg gtaccaacac    540
cacccaggca agccccccaa actcatgatt tatgatttca gtaagcggcc ctcagggtc     600 cctgatcgtt tctctggctc caagtctggc aacacggcct ccctgaccat ctctgggctc    660
caggctgagg atgaggctga ttactattgc tgctcatatg cagccatctc ccctaattat    720
```
gtcttcggaa ctgggaccaa gctgaccgtc cta    753

<210> SEQ ID NO 87
<211> LENGTH: 251
<212> TYPE: PRT
<213> ORGANISM: Homo sapiens
<220> FEATURE:
<223> OTHER INFORMATION: Clone 192 scFv (aa)

<400> SEQUENCE: 87

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
            100                 105                 110

Asp Ile Trp Gly Gln Gly Thr Met Val Thr Val Ser Ser Gly Gly Gly
        115                 120                 125

Gly Ser Gly Gly Gly Gly Ser Gly Gly Gly Gly Ser Gln Ala Val Leu
    130                 135                 140

Thr Gln Pro Arg Ser Val Ser Gly Ser Pro Gly Gln Ser Val Thr Ile
145                 150                 155                 160

Ser Cys Thr Gly Ile Ser Ser Gly Val Asp Ser His Arg Tyr Val Ser
                165                 170                 175

Trp Tyr Gln His His Pro Gly Lys Ala Pro Lys Leu Met Ile Tyr Asp
            180                 185                 190

Phe Ser Lys Arg Pro Ser Gly Val Pro Asp Arg Phe Ser Gly Ser Lys
        195                 200                 205

Ser Gly Asn Thr Ala Ser Leu Thr Ile Ser Gly Leu Gln Ala Glu Asp
    210                 215                 220

Glu Ala Asp Tyr Tyr Cys Cys Ser Tyr Ala Ala Ile Ser Pro Asn Tyr
225                 230                 235                 240

Val Phe Gly Thr Gly Thr Lys Leu Thr Val Leu
                245                 250

<210> SEQ ID NO 88
<211> LENGTH: 747
<212> TYPE: DNA
<213> ORGANISM: Homo sapiens
<220> FEATURE:
<223> OTHER INFORMATION: Clone 241 scFv (nt)

<400> SEQUENCE: 88
gaagtgcagc tggtgcagtc tgggggaggc ttggtacagc ctggcaggtc cctgagactc    60
tcctgtgcag cctctggatt cacctttgat gattatgcca tgcactgggt ccggcaagct    120
ccagggaagg gcctggagtg ggtctcaggt attagttgga atagtggtag cataggctat    180
gcggactctg tgaagggccg attcaccatc tccagagaca acgccaagaa ctccctgtat    240

-continued

```
ctgcaaatga acagtctgag agctgaggac acggccgtgt attactgtgc gagagatcag      300
gggtatcatt actatgatag tgccgaacat gctttgata tctggggcca agggacagtg       360
gtcaccgtct cctcaggtgg aggcggttca ggcggaggtg gctctggcgg tggcggatcg      420
gccatccgga tgacccagtc tccatcctcc ctgtctgcat ctgtaggaga cagagtcacc      480
gtcacttgcc aggcgagtca ggacattagc aactatttaa attggtatca gcagaaacca     540
gggagagccc ctaagctcct gatctacgat gcatccaatg tgaaagcagg gtcccatca      600 aggttcagtg ggggtggatc tgggacagat ttcactctca ccatcagcag tctgcaacct     660
gaagattttg caacttacta ctgtcaacag agttacagta cccctcaggc gtacactttt     720
ggccagggga ccaagctgga tatcaaa                                          747
```

<210> SEQ ID NO 89
<211> LENGTH: 249
<212> TYPE: PRT
<213> ORGANISM: Homo sapiens
<220> FEATURE:
<223> OTHER INFORMATION: Clone 241 scFv (aa)

<400> SEQUENCE: 89

```
Glu Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
            100                 105                 110

Asp Ile Trp Gly Gln Gly Thr Val Val Thr Val Ser Ser Gly Gly Gly
        115                 120                 125

Gly Ser Gly Gly Gly Gly Ser Gly Gly Gly Gly Ser Ala Ile Arg Met
    130                 135                 140

Thr Gln Ser Pro Ser Ser Leu Ser Ala Ser Val Gly Asp Arg Val Thr
145                 150                 155                 160

Val Thr Cys Gln Ala Ser Gln Asp Ile Ser Asn Tyr Leu Asn Trp Tyr
                165                 170                 175

Gln Gln Lys Pro Gly Arg Ala Pro Lys Leu Leu Ile Tyr Asp Ala Ser
            180                 185                 190

Asn Val Lys Ala Gly Val Pro Ser Arg Phe Ser Gly Gly Ser Gly
        195                 200                 205

Thr Asp Phe Thr Leu Thr Ile Ser Ser Leu Gln Pro Glu Asp Phe Ala
    210                 215                 220

Thr Tyr Tyr Cys Gln Gln Ser Tyr Ser Thr Pro Gln Ala Tyr Thr Phe
225                 230                 235                 240

Gly Gln Gly Thr Lys Leu Asp Ile Lys
                245
```

<210> SEQ ID NO 90
<211> LENGTH: 109

```
<212> TYPE: PRT
<213> ORGANISM: Homo sapiens
<220> FEATURE:
<223> OTHER INFORMATION: VL Clone 241 (aa)

<400> SEQUENCE: 90

Ala Ile Arg Met Thr Gln Ser Pro Ser Ser Leu Ser Ala Ser Val Gly
1               5                   10                  15

Asp Arg Val Thr Val Thr Cys Gln Ala Ser Gln Asp Ile Ser Asn Tyr
            20                  25                  30

Leu Asn Trp Tyr Gln Gln Lys Pro Gly Arg Ala Pro Lys Leu Leu Ile
        35                  40                  45

Tyr Asp Ala Ser Asn Val Lys Ala Gly Val Pro Ser Arg Phe Ser Gly
    50                  55                  60

Gly Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Gln
                85                  90                  95

Ala Tyr Thr Phe Gly Gln Gly Thr Lys Leu Asp Ile Lys
            100                 105

<210> SEQ ID NO 91
<211> LENGTH: 111
<212> TYPE: PRT
<213> ORGANISM: Homo sapiens
<220> FEATURE:
<223> OTHER INFORMATION: VL Clone 192

<400> SEQUENCE: 91

Gln Ala Val Leu Thr Gln Pro Arg Ser Val Ser Gly Ser Pro Gly Gln
1               5                   10                  15

Ser Val Thr Ile Ser Cys Thr Gly Ile Ser Ser Gly Val Asp Ser His
            20                  25                  30

Arg Tyr Val Ser Trp Tyr Gln His His Pro Gly Lys Ala Pro Lys Leu
        35                  40                  45

Met Ile Tyr Asp Phe Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Ala Ile
                85                  90                  95

Ser Pro Asn Tyr Val Phe Gly Thr Gly Thr Lys Leu Thr Val Leu
            100                 105                 110

<210> SEQ ID NO 92
<211> LENGTH: 556
<212> TYPE: PRT
<213> ORGANISM: Homo sapiens
<220> FEATURE:
<223> OTHER INFORMATION: CD19 Accession No. P15391

<400> SEQUENCE: 92

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
```

```
                50             55             60
Ser Leu Gly Leu Pro Gly Leu Gly Ile His Met Arg Pro Leu Ala Ile
 65                     70                 75                 80

Trp Leu Phe Ile Phe Asn Val Ser Gln Gln Met Gly Gly Phe Tyr Leu
                    85                 90                 95

Cys Gln Pro Gly Pro Pro Ser Glu Lys Ala Trp Gln Pro Gly Trp Thr
                100                105                110

Val Asn Val Glu Gly Ser Gly Glu Leu Phe Arg Trp Asn Val Ser Asp
                115                120                125

Leu Gly Gly Leu Gly Cys Gly Leu Lys Asn Arg Ser Ser Glu Gly Pro
                130                135                140

Ser Ser Pro Ser Gly Lys Leu Met Ser Pro Lys Leu Tyr Val Trp Ala
145                    150                155                160

Lys Asp Arg Pro Glu Ile Trp Glu Gly Glu Pro Pro Cys Leu Pro Pro
                    165                170                175

Arg Asp Ser Leu Asn Gln Ser Leu Ser Gln Asp Leu Thr Met Ala Pro
                180                185                190

Gly Ser Thr Leu Trp Leu Ser Cys Gly Val Pro Pro Asp Ser Val Ser
                    195                200                205

Arg Gly Pro Leu Ser Trp Thr His Val His Pro Lys Gly Pro Lys Ser
                210                215                220

Leu Leu Ser Leu Glu Leu Lys Asp Asp Arg Pro Ala Arg Asp Met Trp
225                    230                235                240

Val Met Glu Thr Gly Leu Leu Leu Pro Arg Ala Thr Ala Gln Asp Ala
                    245                250                255

Gly Lys Tyr Tyr Cys His Arg Gly Asn Leu Thr Met Ser Phe His Leu
                260                265                270

Glu Ile Thr Ala Arg Pro Val Leu Trp His Trp Leu Leu Arg Thr Gly
                    275                280                285

Gly Trp Lys Val Ser Ala Val Thr Leu Ala Tyr Leu Ile Phe Cys Leu
                290                295                300

Cys Ser Leu Val Gly Ile Leu His Leu Gln Arg Ala Leu Val Leu Arg
305                    310                315                320

Arg Lys Arg Lys Arg Met Thr Asp Pro Thr Arg Arg Phe Phe Lys Val
                    325                330                335

Thr Pro Pro Pro Gly Ser Gly Pro Gln Asn Gln Tyr Gly Asn Val Leu
                340                345                350

Ser Leu Pro Thr Pro Thr Ser Gly Leu Gly Arg Ala Gln Arg Trp Ala
                355                360                365

Ala Gly Leu Gly Gly Thr Ala Pro Ser Tyr Gly Asn Pro Ser Ser Asp
                370                375                380

Val Gln Ala Asp Gly Ala Leu Gly Ser Arg Ser Pro Pro Gly Val Gly
385                    390                395                400

Pro Glu Glu Glu Glu Gly Glu Gly Tyr Glu Glu Pro Asp Ser Glu Glu
                    405                410                415

Asp Ser Glu Phe Tyr Glu Asn Asp Ser Asn Leu Gly Gln Asp Gln Leu
                420                425                430

Ser Gln Asp Gly Ser Gly Tyr Glu Asn Pro Glu Asp Glu Pro Leu Gly
                435                440                445

Pro Glu Asp Glu Asp Ser Phe Ser Asn Ala Glu Ser Tyr Glu Asn Glu
                450                455                460

Asp Glu Glu Leu Thr Gln Pro Val Ala Arg Thr Met Asp Phe Leu Ser
465                    470                475                480
```

```
Pro His Gly Ser Ala Trp Asp Pro Ser Arg Glu Ala Thr Ser Leu Gly
            485                 490                 495

Ser Gln Ser Tyr Glu Asp Met Arg Gly Ile Leu Tyr Ala Ala Pro Gln
        500                 505                 510

Leu Arg Ser Ile Arg Gly Gln Pro Gly Pro Asn His Glu Glu Asp Ala
    515                 520                 525

Asp Ser Tyr Glu Asn Met Asp Asn Pro Asp Gly Pro Asp Pro Ala Trp
530                 535                 540

Gly Gly Gly Gly Arg Met Gly Thr Trp Ser Thr Arg
545                 550                 555

<210> SEQ ID NO 93
<211> LENGTH: 7
<212> TYPE: PRT
<213> ORGANISM: Homo sapiens
<220> FEATURE:
<223> OTHER INFORMATION: CDR-L2 Clone 192B, Clone 192

<400> SEQUENCE: 93

Asp Phe Ser Lys Arg Pro Ser
1               5

<210> SEQ ID NO 94
<211> LENGTH: 7
<212> TYPE: PRT
<213> ORGANISM: Homo sapiens
<220> FEATURE:
<223> OTHER INFORMATION: CDR-L2 Clone 285

<400> SEQUENCE: 94

Asp Val Thr Val Arg Pro Ser
1               5

<210> SEQ ID NO 95
<211> LENGTH: 7
<212> TYPE: PRT
<213> ORGANISM: Homo sapiens
<220> FEATURE:
<223> OTHER INFORMATION: CDR-L2 Clone 328

<400> SEQUENCE: 95

Asp Val Thr Lys Arg Pro Ser
1               5

<210> SEQ ID NO 96
<211> LENGTH: 7
<212> TYPE: PRT
<213> ORGANISM: Homo sapiens
<220> FEATURE:
<223> OTHER INFORMATION: CDR-L2 Clone 1

<400> SEQUENCE: 96

Asp Asn Asn Lys Arg Pro Pro
1               5

<210> SEQ ID NO 97
<211> LENGTH: 7
<212> TYPE: PRT
<213> ORGANISM: Homo sapiens
<220> FEATURE:
<223> OTHER INFORMATION: CDR-L2 Clone 1304 Clone 241

<400> SEQUENCE: 97

Asp Ala Ser Asn Val Lys Ala
```

<210> SEQ ID NO 98
<211> LENGTH: 7
<212> TYPE: PRT
<213> ORGANISM: Homo sapiens
<220> FEATURE:
<223> OTHER INFORMATION: CDR-L2 Clone 1300

<400> SEQUENCE: 98

Asp Ala Ser Arg Leu Ala Ser
1               5

<210> SEQ ID NO 99
<211> LENGTH: 7
<212> TYPE: PRT
<213> ORGANISM: Homo sapiens
<220> FEATURE:
<223> OTHER INFORMATION: CDR-L2 Clone 227

<400> SEQUENCE: 99

Asp Ala Ser Asn Leu Glu Thr
1               5

<210> SEQ ID NO 100
<211> LENGTH: 7
<212> TYPE: PRT
<213> ORGANISM: Homo sapiens
<220> FEATURE:
<223> OTHER INFORMATION: CDR-L2 Clone 488

<400> SEQUENCE: 100

Asp Ala Ser Asn Arg Ala Thr
1               5

<210> SEQ ID NO 101
<211> LENGTH: 11
<212> TYPE: PRT
<213> ORGANISM: Homo sapiens
<220> FEATURE:
<223> OTHER INFORMATION: CDR-L3 Clone 192B

<400> SEQUENCE: 101

Ser Ser Tyr Ala Ala Ile Ser Pro Asn Tyr Val
1               5                   10

<210> SEQ ID NO 102
<211> LENGTH: 11
<212> TYPE: PRT
<213> ORGANISM: Homo sapiens
<220> FEATURE:
<223> OTHER INFORMATION: CDR-L3 Clone 192

<400> SEQUENCE: 102

Cys Ser Tyr Ala Ala Ile Ser Pro Asn Tyr Val
1               5                   10

<210> SEQ ID NO 103
<211> LENGTH: 12
<212> TYPE: PRT
<213> ORGANISM: Homo sapiens
<220> FEATURE:
<223> OTHER INFORMATION: CDR-L3 Clone 285

<400> SEQUENCE: 103

Gly Ser Tyr Thr Ser Ser Ser Thr Leu Leu Trp Val
1               5                   10

<210> SEQ ID NO 104
<211> LENGTH: 10
<212> TYPE: PRT
<213> ORGANISM: Homo sapiens
<220> FEATURE:
<223> OTHER INFORMATION: CDR-L3 Clone 328

<400> SEQUENCE: 104

Thr Ser Tyr Arg Pro Gly Pro Thr Phe Val
1               5                   10

<210> SEQ ID NO 105
<211> LENGTH: 11
<212> TYPE: PRT
<213> ORGANISM: Homo sapiens
<220> FEATURE:
<223> OTHER INFORMATION: CDR-L3 Clone 1

<400> SEQUENCE: 105

Ala Thr Trp Asp Ser Gly Leu Ser Ala Val Val
1               5                   10

<210> SEQ ID NO 106
<211> LENGTH: 11
<212> TYPE: PRT
<213> ORGANISM: Homo sapiens
<220> FEATURE:
<223> OTHER INFORMATION: CDR-L3 Clone 1304 Clone 241

<400> SEQUENCE: 106

Gln Gln Ser Tyr Ser Thr Pro Gln Ala Tyr Thr
1               5                   10

<210> SEQ ID NO 107
<211> LENGTH: 10
<212> TYPE: PRT
<213> ORGANISM: Homo sapiens
<220> FEATURE:
<223> OTHER INFORMATION: CDR-L3 Clone 1300

<400> SEQUENCE: 107

Gln Gln Ser Tyr Gly Ala Pro Met Phe Thr
1               5                   10

<210> SEQ ID NO 108
<211> LENGTH: 9
<212> TYPE: PRT
<213> ORGANISM: Homo sapiens
<220> FEATURE:
<223> OTHER INFORMATION: CDR-L3 Clone 227

<400> SEQUENCE: 108

Gln Gln Tyr Asp Asn Leu Pro Leu Thr
1               5

<210> SEQ ID NO 109
<211> LENGTH: 11
<212> TYPE: PRT
<213> ORGANISM: Homo sapiens
<220> FEATURE:
<223> OTHER INFORMATION: CDR-L3 Clone 488

<400> SEQUENCE: 109

Gln Gln Ser Tyr Ser His Pro Arg Met Tyr Thr
1               5                   10

```
<210> SEQ ID NO 110
<211> LENGTH: 14
<212> TYPE: PRT
<213> ORGANISM: Artificial Sequence
<220> FEATURE:
<223> OTHER INFORMATION: Synthetic
<220> FEATURE:
<223> OTHER INFORMATION: CDR-L1 consensus
<220> FEATURE:
<221> NAME/KEY: VARIANT
<222> LOCATION: 1
<223> OTHER INFORMATION: Xaa = Thr, Gln, Ser or Arg
<220> FEATURE:
<221> NAME/KEY: VARIANT
<222> LOCATION: 2
<223> OTHER INFORMATION: Xaa = Gly or Ala
<220> FEATURE:
<221> NAME/KEY: VARIANT
<222> LOCATION: 3
<223> OTHER INFORMATION: Xaa = Ile, Thr, Asp or Ser
<220> FEATURE:
<221> NAME/KEY: VARIANT
<222> LOCATION: 4
<223> OTHER INFORMATION: Xaa = Ser, Arg, Thr or Gln
<220> FEATURE:
<221> NAME/KEY: VARIANT
<222> LOCATION: 5
<223> OTHER INFORMATION: Xaa = null or Ser
<220> FEATURE:
<221> NAME/KEY: VARIANT
<222> LOCATION: 6
<223> OTHER INFORMATION: Xaa = null, Asp, Asn or Gly
<220> FEATURE:
<221> NAME/KEY: VARIANT
<222> LOCATION: 7
<223> OTHER INFORMATION: Xaa = null, Val or Leu
<220> FEATURE:
<221> NAME/KEY: VARIANT
<222> LOCATION: 8
<223> OTHER INFORMATION: Xaa = any amino acid or null
<220> FEATURE:
<221> NAME/KEY: VARIANT
<222> LOCATION: 9
<223> OTHER INFORMATION: Xaa = any amino acid or null
<220> FEATURE:
<221> NAME/KEY: VARIANT
<222> LOCATION: 10
<223> OTHER INFORMATION: Xaa = any amino acid
<220> FEATURE:
<221> NAME/KEY: VARIANT
<222> LOCATION: 11
<223> OTHER INFORMATION: Xaa = any amino acid
<220> FEATURE:
<221> NAME/KEY: VARIANT
<222> LOCATION: 12
<223> OTHER INFORMATION: Xaa = Tyr, Phe, Asp or Trp
<220> FEATURE:
<221> NAME/KEY: VARIANT
<222> LOCATION: 13
<223> OTHER INFORMATION: Xaa = Val, Ala or Leu
<220> FEATURE:
<221> NAME/KEY: VARIANT
<222> LOCATION: 14
<223> OTHER INFORMATION: Xaa = Ser, Asn or Ala

<400> SEQUENCE: 110

Xaa Xaa Xaa Xaa Xaa Xaa Xaa Xaa Xaa Xaa Xaa Xaa Xaa Xaa
1               5                   10

<210> SEQ ID NO 111
<211> LENGTH: 14
<212> TYPE: PRT
<213> ORGANISM: Artificial Sequence
<220> FEATURE:
<223> OTHER INFORMATION: Synthetic
<220> FEATURE:
```

```
<223> OTHER INFORMATION: CDR-L1 consensus
<220> FEATURE:
<221> NAME/KEY: VARIANT
<222> LOCATION: 1
<223> OTHER INFORMATION: Xaa = Thr, Gln, Ser or Arg
<220> FEATURE:
<221> NAME/KEY: VARIANT
<222> LOCATION: 2
<223> OTHER INFORMATION: Xaa = Gly or Ala
<220> FEATURE:
<221> NAME/KEY: VARIANT
<222> LOCATION: 3
<223> OTHER INFORMATION: Xaa = Ile, Thr, Asp or Ser
<220> FEATURE:
<221> NAME/KEY: VARIANT
<222> LOCATION: 4
<223> OTHER INFORMATION: Xaa = Ser, Arg, Thr or Gln
<220> FEATURE:
<221> NAME/KEY: VARIANT
<222> LOCATION: 5
<223> OTHER INFORMATION: Xaa = null or Ser
<220> FEATURE:
<221> NAME/KEY: VARIANT
<222> LOCATION: 6
<223> OTHER INFORMATION: Xaa = Gly, Asp, Asn or null
<220> FEATURE:
<221> NAME/KEY: VARIANT
<222> LOCATION: 7
<223> OTHER INFORMATION: Xaa = null, Val or Leu
<220> FEATURE:
<221> NAME/KEY: VARIANT
<222> LOCATION: 8
<223> OTHER INFORMATION: Xaa = Asp, Gly, Ile, Leu, Ser or null
<220> FEATURE:
<221> NAME/KEY: VARIANT
<222> LOCATION: 9
<223> OTHER INFORMATION: Xaa = Ser, Gly, Ala, Ile, Arg or null
<220> FEATURE:
<221> NAME/KEY: VARIANT
<222> LOCATION: 10
<223> OTHER INFORMATION: Xaa = His, Tyr, Phe, Ser or Asn
<220> FEATURE:
<221> NAME/KEY: VARIANT
<222> LOCATION: 11
<223> OTHER INFORMATION: Xaa = Arg, Asn, Asp, His or Tyr
<220> FEATURE:
<221> NAME/KEY: VARIANT
<222> LOCATION: 12
<223> OTHER INFORMATION: Xaa = Tyr, Phe, Asp or Trp
<220> FEATURE:
<221> NAME/KEY: VARIANT
<222> LOCATION: 13
<223> OTHER INFORMATION: Xaa = Val, Ala, Leu
<220> FEATURE:
<221> NAME/KEY: VARIANT
<222> LOCATION: 14
<223> OTHER INFORMATION: Xaa = Ser, Asn or Ala

<400> SEQUENCE: 111

Xaa Xaa Xaa Xaa Xaa Xaa Xaa Xaa Xaa Xaa Xaa Xaa Xaa Xaa
1               5                   10

<210> SEQ ID NO 112
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: CDR-L2 Consensus
<220> FEATURE:
<221> NAME/KEY: VARIANT
<222> LOCATION: 1
<223> OTHER INFORMATION: Xaa = Asp or Ser
<220> FEATURE:
<221> NAME/KEY: VARIANT
<222> LOCATION: 2
```

<223> OTHER INFORMATION: Xaa = Phe, Val, Asn, Lys or Ala
<220> FEATURE:
<221> NAME/KEY: VARIANT
<222> LOCATION: 3
<223> OTHER INFORMATION: Xaa = Ser, Thr, Asp or Asn
<220> FEATURE:
<221> NAME/KEY: VARIANT
<222> LOCATION: 4
<223> OTHER INFORMATION: Xaa = Lys, Val, Asn, Gln or Arg
<220> FEATURE:
<221> NAME/KEY: VARIANT
<222> LOCATION: 5
<223> OTHER INFORMATION: Xaa = Arg, Val or Leu
<220> FEATURE:
<221> NAME/KEY: VARIANT
<222> LOCATION: 6
<223> OTHER INFORMATION: Xaa = Pro, Lys, Ala or Glu
<220> FEATURE:
<221> NAME/KEY: VARIANT
<222> LOCATION: 7
<223> OTHER INFORMATION: Xaa = Ser, Pro, Ala or Thr

<400> SEQUENCE: 112

Xaa Xaa Xaa Xaa Xaa Xaa Xaa
1               5

<210> SEQ ID NO 113
<211> LENGTH: 11
<212> TYPE: PRT
<213> ORGANISM: Artificial Sequence
<220> FEATURE:
<223> OTHER INFORMATION: Synthetic
<220> FEATURE:
<223> OTHER INFORMATION: CDR-L3
<220> FEATURE:
<221> NAME/KEY: VARIANT
<222> LOCATION: 1
<223> OTHER INFORMATION: Xaa = Cys, Ser, Ala, Gly or Asn
<220> FEATURE:
<221> NAME/KEY: VARIANT
<222> LOCATION: 2
<223> OTHER INFORMATION: Xaa = Ser, Ala or Thr
<220> FEATURE:
<221> NAME/KEY: VARIANT
<222> LOCATION: 3
<223> OTHER INFORMATION: Xaa = Tyr, Trp or Arg
<220> FEATURE:
<221> NAME/KEY: VARIANT
<222> LOCATION: 4
<223> OTHER INFORMATION: Xaa = Ala or Asp
<220> FEATURE:
<221> NAME/KEY: VARIANT
<222> LOCATION: 5
<223> OTHER INFORMATION: Xaa = Gly, Asp or Ser
<220> FEATURE:
<221> NAME/KEY: VARIANT
<222> LOCATION: 6
<223> OTHER INFORMATION: Xaa = Arg, Ser or Asn
<220> FEATURE:
<221> NAME/KEY: VARIANT
<222> LOCATION: 7
<223> OTHER INFORMATION: Xaa = Tyr, Leu or Gly
<220> FEATURE:
<221> NAME/KEY: VARIANT
<222> LOCATION: 8
<223> OTHER INFORMATION: Xaa = Asn or Ser
<220> FEATURE:
<221> NAME/KEY: VARIANT
<222> LOCATION: 9
<223> OTHER INFORMATION: Xaa = Ser, Asn or null
<220> FEATURE:
<221> NAME/KEY: VARIANT
<222> LOCATION: 10
<223> OTHER INFORMATION: Xaa = Val, Ala or Trp
<220> FEATURE:
<221> NAME/KEY: VARIANT
<222> LOCATION: 11

```
<223> OTHER INFORMATION: Xaa = Leu or Val

<400> SEQUENCE: 113

Xaa Xaa Xaa Xaa Xaa Xaa Xaa Xaa Xaa Xaa Xaa
1               5                   10

<210> SEQ ID NO 114
<211> LENGTH: 12
<212> TYPE: PRT
<213> ORGANISM: Artificial Sequence
<220> FEATURE:
<223> OTHER INFORMATION: Synthetic
<220> FEATURE:
<223> OTHER INFORMATION: CDR-L3 consensus
<220> FEATURE:
<221> NAME/KEY: VARIANT
<222> LOCATION: 1
<223> OTHER INFORMATION: Xaa = Ser, Gly, Thr, Ala, Gln, Cys or Asn
<220> FEATURE:
<221> NAME/KEY: VARIANT
<222> LOCATION: 2
<223> OTHER INFORMATION: Xaa = Ser, Gln, Ala or Thr
<220> FEATURE:
<221> NAME/KEY: VARIANT
<222> LOCATION: 3
<223> OTHER INFORMATION: Xaa = Tyr, Ser, Trp or Arg
<220> FEATURE:
<221> NAME/KEY: VARIANT
<222> LOCATION: 4
<223> OTHER INFORMATION: Xaa = Ala, Asp, Arg, Thr or Tyr
<220> FEATURE:
<221> NAME/KEY: VARIANT
<222> LOCATION: 5
<223> OTHER INFORMATION: Xaa = Ala, Ser, Pro, Gly, Asn or Asp
<220> FEATURE:
<221> NAME/KEY: VARIANT
<222> LOCATION: 6
<223> OTHER INFORMATION: Xaa = Ile, Ser, Gly, Thr, Ala, Leu, His, Arg or
      Asn
<220> FEATURE:
<221> NAME/KEY: VARIANT
<222> LOCATION: 7
<223> OTHER INFORMATION: Xaa = Ser, Pro, Leu, Tyr or Gly
<220> FEATURE:
<221> NAME/KEY: VARIANT
<222> LOCATION: 8
<223> OTHER INFORMATION: Xaa = Pro, Thr, Ser, Gln, Met, Arg, Asn or null
<220> FEATURE:
<221> NAME/KEY: VARIANT
<222> LOCATION: 9
<223> OTHER INFORMATION: Xaa = Ser, Leu, Asn, Ala, Met or null
<220> FEATURE:
<221> NAME/KEY: VARIANT
<222> LOCATION: 10
<223> OTHER INFORMATION: Xaa = Leu or null
<220> FEATURE:
<221> NAME/KEY: VARIANT
<222> LOCATION: 11
<223> OTHER INFORMATION: Xaa = Tyr, Trp, Phe, Val, Ala or Leu
<220> FEATURE:
<221> NAME/KEY: VARIANT
<222> LOCATION: 12
<223> OTHER INFORMATION: Xaa = Val, Thr or Leu

<400> SEQUENCE: 114

Xaa Xaa Xaa Xaa Xaa Xaa Xaa Xaa Xaa Xaa Xaa Xaa
1               5                   10

<210> SEQ ID NO 115
<211> LENGTH: 12
<212> TYPE: PRT
<213> ORGANISM: Artificial Sequence
<220> FEATURE:
<223> OTHER INFORMATION: Synthetic
<220> FEATURE:
```

```
<223> OTHER INFORMATION: CDR-L3 consensus
<220> FEATURE:
<221> NAME/KEY: VARIANT
<222> LOCATION: 1
<223> OTHER INFORMATION: Xaa = any amino acid
<220> FEATURE:
<221> NAME/KEY: VARIANT
<222> LOCATION: 2
<223> OTHER INFORMATION: Xaa = Ser, Gln, Ala or Thr
<220> FEATURE:
<221> NAME/KEY: VARIANT
<222> LOCATION: 3
<223> OTHER INFORMATION: Xaa = Tyr, Ser, Trp or Arg
<220> FEATURE:
<221> NAME/KEY: VARIANT
<222> LOCATION: 4
<223> OTHER INFORMATION: Xaa = Ala, Asp, Arg, Thr or Tyr
<220> FEATURE:
<221> NAME/KEY: VARIANT
<222> LOCATION: 5
<223> OTHER INFORMATION: Xaa = any amino acid
<220> FEATURE:
<221> NAME/KEY: VARIANT
<222> LOCATION: 6
<223> OTHER INFORMATION: Xaa = any amino acid
<220> FEATURE:
<221> NAME/KEY: VARIANT
<222> LOCATION: 7
<223> OTHER INFORMATION: Xaa = Ser, Pro, Leu, Tyr or Gly
<220> FEATURE:
<221> NAME/KEY: VARIANT
<222> LOCATION: 8
<223> OTHER INFORMATION: Xaa = any amino acid or null
<220> FEATURE:
<221> NAME/KEY: VARIANT
<222> LOCATION: 9
<223> OTHER INFORMATION: Xaa = any amino acid or null
<220> FEATURE:
<221> NAME/KEY: VARIANT
<222> LOCATION: 10
<223> OTHER INFORMATION: Xaa = Leu or null
<220> FEATURE:
<221> NAME/KEY: VARIANT
<222> LOCATION: 11
<223> OTHER INFORMATION: Xaa = any amino acid
<220> FEATURE:
<221> NAME/KEY: VARIANT
<222> LOCATION: 12
<223> OTHER INFORMATION: Xaa = Val, Thr or Leu

<400> SEQUENCE: 115

Xaa Xaa Xaa Xaa Xaa Xaa Xaa Xaa Xaa Xaa Xaa Xaa
1               5                   10

<210> SEQ ID NO 116
<211> LENGTH: 11
<212> TYPE: PRT
<213> ORGANISM: Homo sapiens
<220> FEATURE:
<223> OTHER INFORMATION: CDR-L3 Clone 79

<400> SEQUENCE: 116

Gly Thr Trp Asp Ile Ser Leu Arg Phe Gly Val
1               5                   10

<210> SEQ ID NO 117
<211> LENGTH: 11
<212> TYPE: PRT
<213> ORGANISM: Homo sapiens
<220> FEATURE:
<223> OTHER INFORMATION: CDR-L3 Clone 835

<400> SEQUENCE: 117

Cys Ser Tyr Glu Ala Pro Thr His Thr Tyr Val
```

```
1               5                   10

<210> SEQ ID NO 118
<211> LENGTH: 10
<212> TYPE: PRT
<213> ORGANISM: Homo sapiens
<220> FEATURE:
<223> OTHER INFORMATION: CDR-L3 Clone 184

<400> SEQUENCE: 118

Ala Ala Trp Asp Asp Ser Leu Asn Val Val
1               5                   10

<210> SEQ ID NO 119
<211> LENGTH: 11
<212> TYPE: PRT
<213> ORGANISM: Homo sapiens
<220> FEATURE:
<223> OTHER INFORMATION: CDR-L3 Clone 505

<400> SEQUENCE: 119

Cys Ser Tyr Ala Gly Ser Tyr Thr Phe Glu Val
1               5                   10

<210> SEQ ID NO 120
<211> LENGTH: 11
<212> TYPE: PRT
<213> ORGANISM: Homo sapiens
<220> FEATURE:
<223> OTHER INFORMATION: CDR-L3 Clone 506

<400> SEQUENCE: 120

Cys Ser Phe Ala Gly Tyr Tyr Thr Tyr Trp Leu
1               5                   10

<210> SEQ ID NO 121
<211> LENGTH: 9
<212> TYPE: PRT
<213> ORGANISM: Homo sapiens
<220> FEATURE:
<223> OTHER INFORMATION: CDR-L3 Clone 305
<220> FEATURE:
<221> NAME/KEY: VARIANT
<222> LOCATION: 3
<223> OTHER INFORMATION: Xaa = any amino acid

<400> SEQUENCE: 121

Ser Ser Xaa Ala Gly Arg Lys Tyr Val
1               5

<210> SEQ ID NO 122
<211> LENGTH: 4
<212> TYPE: PRT
<213> ORGANISM: Artificial Sequence
<220> FEATURE:
<223> OTHER INFORMATION: Synthetic
<220> FEATURE:
<223> OTHER INFORMATION: Linker

<400> SEQUENCE: 122

Gly Gly Gly Ser
1

<210> SEQ ID NO 123
<211> LENGTH: 5
<212> TYPE: PRT
<213> ORGANISM: Artificial Sequence
<220> FEATURE:
```

```
<223> OTHER INFORMATION: Synthetic
<220> FEATURE:
<223> OTHER INFORMATION: Linker

<400> SEQUENCE: 123

Gly Gly Gly Gly Ser
1               5

<210> SEQ ID NO 124
<211> LENGTH: 12
<212> TYPE: PRT
<213> ORGANISM: Homo sapiens
<220> FEATURE:
<223> OTHER INFORMATION: spacer (IgG4hinge) (aa)

<400> SEQUENCE: 124

Glu Ser Lys Tyr Gly Pro Pro Cys Pro Pro Cys Pro
1               5                   10

<210> SEQ ID NO 125
<211> LENGTH: 36
<212> TYPE: PRT
<213> ORGANISM: Homo sapiens
<220> FEATURE:
<223> OTHER INFORMATION: spacer (IgG4hinge) (nt)

<400> SEQUENCE: 125

Gly Ala Ala Thr Cys Thr Ala Ala Gly Thr Ala Cys Gly Gly Ala Cys
1               5                   10                  15

Cys Gly Cys Cys Cys Thr Gly Cys Cys Cys Cys Cys Thr Thr Gly
            20                  25                  30

Cys Cys Cys Thr
            35

<210> SEQ ID NO 126
<211> LENGTH: 119
<212> TYPE: PRT
<213> ORGANISM: Homo sapiens
<220> FEATURE:
<223> OTHER INFORMATION: Hinge-CH3 spacer

<400> SEQUENCE: 126

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Glu Gly Asn Val Phe Ser
                85                  90                  95

Cys Ser Val Met His Glu Ala Leu His Asn His Tyr Thr Gln Lys Ser
            100                 105                 110

Leu Ser Leu Ser Leu Gly Lys
        115

<210> SEQ ID NO 127
<211> LENGTH: 229
<212> TYPE: PRT
```

```
<213> ORGANISM: Homo sapiens
<220> FEATURE:
<223> OTHER INFORMATION: Hinge-CH2-CH3 spacer

<400> SEQUENCE: 127

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 128
<211> LENGTH: 282
<212> TYPE: PRT
<213> ORGANISM: Homo sapiens
<220> FEATURE:
<223> OTHER INFORMATION: IgD-hinge-Fc

<400> SEQUENCE: 128

Arg Trp Pro Glu Ser Pro Lys Ala Gln Ala Ser Ser Val Pro Thr Ala
1               5                   10                  15

Gln Pro Gln Ala Glu Gly Ser Leu Ala Lys Ala Thr Thr Ala Pro Ala
            20                  25                  30

Thr Thr Arg Asn Thr Gly Arg Gly Gly Glu Glu Lys Lys Lys Glu Lys
        35                  40                  45

Glu Lys Glu Glu Gln Glu Glu Arg Glu Thr Lys Thr Pro Glu Cys Pro
    50                  55                  60

Ser His Thr Gln Pro Leu Gly Val Tyr Leu Leu Thr Pro Ala Val Gln
65                  70                  75                  80

Asp Leu Trp Leu Arg Asp Lys Ala Thr Phe Thr Cys Phe Val Val Gly
                85                  90                  95
```

-continued

```
Ser Asp Leu Lys Asp Ala His Leu Thr Trp Glu Val Ala Gly Lys Val
            100                 105                 110
Pro Thr Gly Gly Val Glu Glu Gly Leu Leu Glu Arg His Ser Asn Gly
        115                 120                 125
Ser Gln Ser Gln His Ser Arg Leu Thr Leu Pro Arg Ser Leu Trp Asn
    130                 135                 140
Ala Gly Thr Ser Val Thr Cys Thr Leu Asn His Pro Ser Leu Pro Pro
145                 150                 155                 160
Gln Arg Leu Met Ala Leu Arg Glu Pro Ala Ala Gln Ala Pro Val Lys
                165                 170                 175
Leu Ser Leu Asn Leu Leu Ala Ser Ser Asp Pro Pro Glu Ala Ala Ser
            180                 185                 190
Trp Leu Leu Cys Glu Val Ser Gly Phe Ser Pro Pro Asn Ile Leu Leu
        195                 200                 205
Met Trp Leu Glu Asp Gln Arg Glu Val Asn Thr Ser Gly Phe Ala Pro
    210                 215                 220
Ala Arg Pro Pro Gln Pro Gly Ser Thr Thr Phe Trp Ala Trp Ser
225                 230                 235                 240
Val Leu Arg Val Pro Ala Pro Ser Pro Gln Pro Ala Thr Tyr Thr
                245                 250                 255
Cys Val Val Ser His Glu Asp Ser Arg Thr Leu Leu Asn Ala Ser Arg
            260                 265                 270
Ser Leu Glu Val Ser Tyr Val Thr Asp His
        275                 280
```

<210> SEQ ID NO 129
<211> LENGTH: 27
<212> TYPE: PRT
<213> ORGANISM: Homo sapiens
<220> FEATURE:
<223> OTHER INFORMATION: CD28 (amino acids 153-179 of Accession No. P10747)

<400> SEQUENCE: 129

```
Phe Trp Val Leu Val Val Val Gly Gly Val Leu Ala Cys Tyr Ser Leu
1               5                   10                  15
Leu Val Thr Val Ala Phe Ile Ile Phe Trp Val
            20                  25
```

<210> SEQ ID NO 130
<211> LENGTH: 66
<212> TYPE: PRT
<213> ORGANISM: Homo sapiens
<220> FEATURE:
<223> OTHER INFORMATION: CD28 (amino acids 114-179 of Accession No. P10747)

<400> SEQUENCE: 130

```
Ile Glu Val Met Tyr Pro Pro Pro Tyr Leu Asp Asn Glu Lys Ser Asn
1               5                   10                  15
Gly Thr Ile Ile His Val Lys Gly Lys His Leu Cys Pro Ser Pro Leu
            20                  25                  30
Phe Pro Gly Pro Ser Lys Pro Phe Trp Val Leu Val Val Val Gly Gly
        35                  40                  45
Val Leu Ala Cys Tyr Ser Leu Leu Val Thr Val Ala Phe Ile Ile Phe
    50                  55                  60
Trp Val
65
```

<210> SEQ ID NO 131
<211> LENGTH: 41
<212> TYPE: PRT
<213> ORGANISM: Homo sapiens
<220> FEATURE:
<223> OTHER INFORMATION: CD28 (amino acids 180-220 of P10747)

<400> SEQUENCE: 131

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 132
<211> LENGTH: 41
<212> TYPE: PRT
<213> ORGANISM: Homo sapiens
<220> FEATURE:
<223> OTHER INFORMATION: CD28 (LL to GG)

<400> SEQUENCE: 132

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 133
<211> LENGTH: 42
<212> TYPE: PRT
<213> ORGANISM: Homo sapiens
<220> FEATURE:
<223> OTHER INFORMATION: 4-1BB (amino acids 214-255 of Q07011.1)

<400> SEQUENCE: 133

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 134
<211> LENGTH: 112
<212> TYPE: PRT
<213> ORGANISM: Homo sapiens
<220> FEATURE:
<223> OTHER INFORMATION: CD3 zeta

<400> SEQUENCE: 134

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 135
<211> LENGTH: 112
<212> TYPE: PRT
<213> ORGANISM: Homo sapiens
<220> FEATURE:
<223> OTHER INFORMATION: CD3 zeta

<400> SEQUENCE: 135

Arg Val Lys Phe Ser Arg Ser Ala Glu Pro Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 136
<211> LENGTH: 112
<212> TYPE: PRT
<213> ORGANISM: Homo sapiens
<220> FEATURE:
<223> OTHER INFORMATION: CD3 zeta

<400> SEQUENCE: 136

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 137
<211> LENGTH: 24
<212> TYPE: PRT
<213> ORGANISM: Artificial Sequence
<220> FEATURE:
<223> OTHER INFORMATION: Synthetic
<220> FEATURE:

<223> OTHER INFORMATION: T2A

<400> SEQUENCE: 137

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 138
<211> LENGTH: 357
<212> TYPE: PRT
<213> ORGANISM: Artificial Sequence
<220> FEATURE:
<223> OTHER INFORMATION: Synthetic
<220> FEATURE:
<223> OTHER INFORMATION: tEGFR

<400> SEQUENCE: 138

Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
    210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
    290                 295                 300

```
Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
            325                 330                 335

Thr Gly Met Val Gly Ala Leu Leu Leu Leu Val Val Ala Leu Gly
        340                 345                 350

Ile Gly Leu Phe Met
        355

<210> SEQ ID NO 139
<211> LENGTH: 557
<212> TYPE: PRT
<213> ORGANISM: Macaca mulatta
<220> FEATURE:
<223> OTHER INFORMATION: Accession No. F7F486

<400> SEQUENCE: 139

Met Pro Pro Pro Cys Leu Leu Phe Phe Leu Leu Phe Leu Thr Pro Met
1               5                   10                  15

Glu Val Arg Pro Gln Glu Pro Leu Val Val Lys Val Glu Glu Gly Asp
            20                  25                  30

Asn Ala Val Leu Gln Cys Leu Glu Gly Thr Ser Asp Gly Pro Thr Gln
        35                  40                  45

Gln Leu Val Trp Cys Arg Asp Ser Pro Phe Glu Pro Phe Leu Asn Leu
    50                  55                  60

Ser Leu Gly Leu Pro Gly Met Gly Ile Arg Met Gly Pro Leu Gly Ile
65                  70                  75                  80

Trp Leu Leu Ile Phe Asn Val Ser Asn Gln Thr Gly Gly Phe Tyr Leu
                85                  90                  95

Cys Gln Pro Gly Leu Pro Ser Glu Lys Ala Trp Gln Pro Gly Trp Thr
            100                 105                 110

Val Ser Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Asn Ser Ser Gln Leu Tyr Val Trp Ala
145                 150                 155                 160

Lys Asp Arg Pro Glu Met Trp Glu Gly Glu Pro Val Cys Gly Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val Arg Pro Lys Gly Pro Lys Ser
    210                 215                 220

Ser Leu Leu Ser Leu Glu Leu Lys Asp Asp Arg Pro Asp Arg Asp Met
225                 230                 235                 240

Trp Val Val Asp Thr Gly Leu Leu Leu Thr Arg Ala Thr Ala Gln Asp
                245                 250                 255

Ala Gly Lys Tyr Tyr Cys His Arg Gly Asn Trp Thr Lys Ser Phe Tyr
            260                 265                 270

Leu Glu Ile Thr Ala Arg Pro Ala Leu Trp His Trp Leu Leu Arg Ile
        275                 280                 285

Gly Gly Trp Lys Val Pro Ala Val Thr Leu Thr Tyr Leu Ile Phe Cys
    290                 295                 300
```

Leu Cys Ser Leu Val Gly Ile Leu Gln Leu Gln Arg Ala Leu Val Leu
305                 310                 315                 320

Arg Arg Lys Arg Lys Arg Met Thr Asp Pro Thr Arg Arg Phe Phe Lys
            325                 330                 335

Val Thr Pro Pro Pro Gly Ser Gly Pro Gln Asn Gln Tyr Gly Asn Val
            340                 345                 350

Leu Ser Leu Pro Thr Pro Thr Ser Gly Leu Gly Arg Ala Gln Arg Trp
        355                 360                 365

Ala Ala Gly Leu Gly Gly Thr Ala Pro Ser Tyr Gly Asn Pro Ser Ser
    370                 375                 380

Asp Val Gln Val Asp Gly Ala Val Gly Ser Arg Ser Pro Pro Gly Ala
385                 390                 395                 400

Gly Pro Glu Glu Glu Gly Glu Gly Tyr Glu Glu Pro Asp Ser Glu
            405                 410                 415

Glu Gly Ser Glu Phe Tyr Glu Asn Asp Ser Asn Phe Gly Gln Asp Gln
            420                 425                 430

Leu Ser Gln Asp Gly Ser Gly Tyr Glu Asn Pro Glu Asp Glu Pro Leu
        435                 440                 445

Gly Pro Glu Asp Glu Asp Ser Phe Ser Asn Ala Glu Ser Tyr Glu Asn
450                 455                 460

Glu Asp Glu Glu Leu Thr Gln Pro Val Ala Arg Thr Met Asp Phe Leu
465                 470                 475                 480

Ser Pro His Gly Ser Ala Trp Asp Pro Ser Arg Glu Ala Thr Ser Leu
            485                 490                 495

Gly Ser Gln Ser Tyr Glu Asp Met Arg Gly Leu Leu Tyr Ala Ala Pro
        500                 505                 510

Gln Leu Arg Thr Ile Arg Gly Gln Pro Gly Pro Asn His Glu Glu Asp
            515                 520                 525

Ala Asp Ser Tyr Glu Asn Met Asp Asn Pro Asp Gly Pro Asp Pro Ala
530                 535                 540

Trp Gly Gly Gly Gly Arg Met Gly Thr Trp Ser Ala Arg
545                 550                 555

<210> SEQ ID NO 140
<211> LENGTH: 74
<212> TYPE: PRT
<213> ORGANISM: Artificial Sequence
<220> FEATURE:
<223> OTHER INFORMATION: Synthetic
<220> FEATURE:
<223> OTHER INFORMATION: V1 chimeric rhesus/human

<400> SEQUENCE: 140

His Pro Lys Gly Pro Lys Ser Leu Leu Ser Leu Glu Leu Lys Asp Asp
1               5                   10                  15

Arg Pro Ala Arg Asp Met Trp Val Met Glu Thr Gly Leu Leu Leu Pro
            20                  25                  30

Arg Ala Thr Ala Gln Asp Ala Gly Lys Tyr Tyr Cys His Arg Gly Asn
        35                  40                  45

Leu Thr Met Ser Phe His Leu Glu Ile Thr Ala Arg Pro Val Leu Trp
    50                  55                  60

His Trp Leu Leu Arg Thr Gly Gly Trp Lys
65                  70

<210> SEQ ID NO 141
<211> LENGTH: 75
<212> TYPE: PRT

```
<213> ORGANISM: Artificial Sequence
<220> FEATURE:
<223> OTHER INFORMATION: Synthetic
<220> FEATURE:
<223> OTHER INFORMATION: V2 chimeric rhesus/human

<400> SEQUENCE: 141

Arg Pro Lys Gly Pro Lys Ser Ser Leu Leu Ser Leu Glu Leu Lys Asp
1               5                   10                  15

Asp Arg Pro Asp Arg Asp Met Trp Val Val Asp Thr Gly Leu Leu Leu
            20                  25                  30

Thr Arg Ala Thr Ala Gln Asp Ala Gly Lys Tyr Tyr Cys His Arg Gly
        35                  40                  45

Asn Leu Thr Met Ser Phe His Leu Glu Ile Thr Ala Arg Pro Val Leu
    50                  55                  60

Trp His Trp Leu Leu Arg Thr Gly Gly Trp Lys
65                  70                  75

<210> SEQ ID NO 142
<211> LENGTH: 74
<212> TYPE: PRT
<213> ORGANISM: Artificial Sequence
<220> FEATURE:
<223> OTHER INFORMATION: Synthetic
<220> FEATURE:
<223> OTHER INFORMATION: V3 chimeric rhesus/human

<400> SEQUENCE: 142

His Pro Lys Gly Pro Lys Ser Leu Leu Ser Leu Glu Leu Lys Asp Asp
1               5                   10                  15

Arg Pro Ala Arg Asp Met Trp Val Met Glu Thr Gly Leu Leu Leu Pro
            20                  25                  30

Arg Ala Thr Ala Gln Asp Ala Gly Lys Tyr Tyr Cys His Arg Gly Asn
        35                  40                  45

Trp Thr Lys Ser Phe Tyr Leu Glu Ile Thr Ala Arg Pro Ala Leu Trp
    50                  55                  60

His Trp Leu Leu Arg Ile Gly Gly Trp Lys
65                  70

<210> SEQ ID NO 143
<211> LENGTH: 32
<212> TYPE: PRT
<213> ORGANISM: Artificial Sequence
<220> FEATURE:
<223> OTHER INFORMATION: Synthetic

<400> SEQUENCE: 143

His Pro Lys Gly Pro Lys Ser Leu Leu Ser Leu Glu Leu Lys Asp Asp
1               5                   10                  15

Arg Pro Ala Arg Asp Met Trp Val Met Glu Thr Gly Leu Leu Leu Pro
            20                  25                  30

<210> SEQ ID NO 144
<211> LENGTH: 33
<212> TYPE: PRT
<213> ORGANISM: Artificial Sequence
<220> FEATURE:
<223> OTHER INFORMATION: Synthetic

<400> SEQUENCE: 144

Arg Pro Lys Gly Pro Lys Ser Ser Leu Leu Ser Leu Glu Leu Lys Asp
1               5                   10                  15
```

Asp Arg Pro Asp Arg Asp Met Trp Val Val Asp Thr Gly Leu Leu Leu
            20                  25                  30

Thr

<210> SEQ ID NO 145
<211> LENGTH: 16
<212> TYPE: PRT
<213> ORGANISM: Homo sapiens
<220> FEATURE:
<223> OTHER INFORMATION: CDR-H3 clone 305
<220> FEATURE:
<221> NAME/KEY: VARIANT
<222> LOCATION: 4
<223> OTHER INFORMATION: Xaa = any amino acid
<220> FEATURE:
<221> NAME/KEY: VARIANT
<222> LOCATION: 6
<223> OTHER INFORMATION: Xaa = any amino acid
<220> FEATURE:
<221> NAME/KEY: VARIANT
<222> LOCATION: 15
<223> OTHER INFORMATION: Xaa = any amino acid

<400> SEQUENCE: 145

Asp Gln Gly Xaa His Xaa Tyr Asp Ser Ala Glu His Ala Phe Xaa Ile
1               5                   10                  15

<210> SEQ ID NO 146
<211> LENGTH: 11
<212> TYPE: PRT
<213> ORGANISM: Homo sapiens
<220> FEATURE:
<223> OTHER INFORMATION: CDR-L1 Clone 255

<400> SEQUENCE: 146

Gln Ala Ser Gln Asp Ile Ser Asn Tyr Leu Asn
1               5                   10

<210> SEQ ID NO 147
<211> LENGTH: 14
<212> TYPE: PRT
<213> ORGANISM: Homo sapiens
<220> FEATURE:
<223> OTHER INFORMATION: CDR-L1 Clone 305

<400> SEQUENCE: 147

Thr Gly Thr Gly Arg Asp Ile Gly Ala Tyr Asp Tyr Val Ser
1               5                   10

<210> SEQ ID NO 148
<211> LENGTH: 14
<212> TYPE: PRT
<213> ORGANISM: Homo sapiens
<220> FEATURE:
<223> OTHER INFORMATION: CDR-L1 Clone 327

<400> SEQUENCE: 148

Thr Glu Thr Ser Ser Asp Leu Gly Gly Tyr Asn Tyr Val Ser
1               5                   10

<210> SEQ ID NO 149
<211> LENGTH: 14
<212> TYPE: PRT
<213> ORGANISM: Homo sapiens
<220> FEATURE:
<223> OTHER INFORMATION: CDR-L1 Clone 505

<400> SEQUENCE: 149

Thr Gly Ala Ser Thr Asp Val Gly Gly Tyr Asn Tyr Val Ser
1               5                   10

<210> SEQ ID NO 150
<211> LENGTH: 14
<212> TYPE: PRT
<213> ORGANISM: Homo sapiens
<220> FEATURE:
<223> OTHER INFORMATION: CDR-L1 Clone 506

<400> SEQUENCE: 150

Thr Gly Ala Ser Ser Asp Val Gly Gly Tyr Asp His Val Ser
1               5                   10

<210> SEQ ID NO 151
<211> LENGTH: 13
<212> TYPE: PRT
<213> ORGANISM: Homo sapiens
<220> FEATURE:
<223> OTHER INFORMATION: CDR-L1 Clone 184

<400> SEQUENCE: 151

Ser Gly Ser Ser Ser Asn Ile Gly Ser Asn Thr Val Asn
1               5                   10

<210> SEQ ID NO 152
<211> LENGTH: 14
<212> TYPE: PRT
<213> ORGANISM: Homo sapiens
<220> FEATURE:
<223> OTHER INFORMATION: CDR-L1 Clone 835

<400> SEQUENCE: 152

Thr Gly Pro Ile Ser Gly Val Gly Asp Tyr Thr Ser Val Ser
1               5                   10

<210> SEQ ID NO 153
<211> LENGTH: 7
<212> TYPE: PRT
<213> ORGANISM: Homo sapiens
<220> FEATURE:
<223> OTHER INFORMATION: CDR-L2 Clone 272

<400> SEQUENCE: 153

Asp Asn Asn Lys Arg Pro Ser
1               5

<210> SEQ ID NO 154
<211> LENGTH: 7
<212> TYPE: PRT
<213> ORGANISM: Homo sapiens
<220> FEATURE:
<223> OTHER INFORMATION: CDR-L2 Clone 305

<400> SEQUENCE: 154

Gly Val Asn Lys Arg Pro Ser
1               5

<210> SEQ ID NO 155
<211> LENGTH: 7
<212> TYPE: PRT
<213> ORGANISM: Homo sapiens
<220> FEATURE:
<223> OTHER INFORMATION: CDR-L2 Clone 505

<400> SEQUENCE: 155

Asp Val Asn Lys Arg Pro Ser

<210> SEQ ID NO 156
<211> LENGTH: 7
<212> TYPE: PRT
<213> ORGANISM: Homo sapiens
<220> FEATURE:
<223> OTHER INFORMATION: CDR-L2 Clone 79

<400> SEQUENCE: 156

Asp Asn Asn Lys Arg Pro Ser
1               5

<210> SEQ ID NO 157
<211> LENGTH: 7
<212> TYPE: PRT
<213> ORGANISM: Homo sapiens
<220> FEATURE:
<223> OTHER INFORMATION: CDR-L2 Clone 835

<400> SEQUENCE: 157

Asp Val Thr Gln Arg Pro Ser
1               5

<210> SEQ ID NO 158
<211> LENGTH: 12
<212> TYPE: PRT
<213> ORGANISM: Homo sapiens
<220> FEATURE:
<223> OTHER INFORMATION: CDR-L3
      Clone 272

<400> SEQUENCE: 158

Gly Thr Trp Asp Ser Ser Leu Asn Arg Asp Trp Val
1               5                   10

<210> SEQ ID NO 159
<211> LENGTH: 11
<212> TYPE: PRT
<213> ORGANISM: Homo sapiens
<220> FEATURE:
<223> OTHER INFORMATION: CDR-L3 Clone 508

<400> SEQUENCE: 159

Cys Ser Tyr Ala Gly Arg Tyr Asn Ser Val Pro
1               5                   10

<210> SEQ ID NO 160
<211> LENGTH: 7
<212> TYPE: PRT
<213> ORGANISM: Homo sapiens
<220> FEATURE:
<223> OTHER INFORMATION: CDR-H1 Clone 1265

<400> SEQUENCE: 160

Thr Ser Gly Val Gly Val Gly
1               5

<210> SEQ ID NO 161
<211> LENGTH: 16
<212> TYPE: PRT
<213> ORGANISM: Homo sapiens
<220> FEATURE:
<223> OTHER INFORMATION: CDR-H2 Clone 1265

<400> SEQUENCE: 161

Leu Ile Tyr Trp Asp Asp Asp Lys Arg Tyr Ser Pro Ser Leu Lys Ser

-continued

```
1               5                    10                   15
```

<210> SEQ ID NO 162
<211> LENGTH: 20
<212> TYPE: PRT
<213> ORGANISM: Homo sapiens
<220> FEATURE:
<223> OTHER INFORMATION: CDR-H3 Clone 1265

<400> SEQUENCE: 162

```
Ile Asp Tyr Gly Ser Gly Ser Tyr Ser Pro Arg Thr Ser Tyr Tyr Tyr
1               5                   10                  15

Tyr Met Ser Val
            20
```

<210> SEQ ID NO 163
<211> LENGTH: 11
<212> TYPE: PRT
<213> ORGANISM: Homo sapiens
<220> FEATURE:
<223> OTHER INFORMATION: CDR-L1 Clone 1265

<400> SEQUENCE: 163

```
Arg Ala Ser Gln Gly Ile Ser Ser Tyr Leu Asn
1               5                   10
```

<210> SEQ ID NO 164
<211> LENGTH: 7
<212> TYPE: PRT
<213> ORGANISM: Homo sapiens
<220> FEATURE:
<223> OTHER INFORMATION: CDR-L2 Clone 1265

<400> SEQUENCE: 164

```
Ala Ala Ser Asn Leu Gln Ser
1               5
```

<210> SEQ ID NO 165
<211> LENGTH: 9
<212> TYPE: PRT
<213> ORGANISM: Homo sapiens
<220> FEATURE:
<223> OTHER INFORMATION: CDR-L3 Clone 1265

<400> SEQUENCE: 165

```
Gln Gln Gly Asp Ala Phe Pro Leu Thr
1               5
```

<210> SEQ ID NO 166
<211> LENGTH: 130
<212> TYPE: PRT
<213> ORGANISM: Homo sapiens
<220> FEATURE:
<223> OTHER INFORMATION: VH Clone 1265

<400> SEQUENCE: 166

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asp Asp Lys Arg Tyr Ser Pro Ser
    50                  55                  60
```

```
Leu Lys Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala His Ile Asp Tyr Gly Ser Gly Ser Tyr Ser Pro Arg Thr Ser
                100                 105                 110

Tyr Tyr Tyr Tyr Met Ser Val Trp Gly Lys Gly Thr Thr Val Thr Val
            115                 120                 125

Ser Ser
    130

<210> SEQ ID NO 167
<211> LENGTH: 125
<212> TYPE: PRT
<213> ORGANISM: Homo sapiens
<220> FEATURE:
<223> OTHER INFORMATION: VH Clone 213

<400> SEQUENCE: 167

Gln Val Gln Leu Val Gln Ser Gly Gly Gly Val Val Gln Pro Gly Arg
 1               5                  10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
             35                  40                  45

Ser Gly Ile Ser Trp Asn Ser Gly Ser Ile Gly Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gln Gly Tyr His Tyr Tyr Asp Ser Ala Glu His Ala Phe
                100                 105                 110

Asp Ile Trp Gly Gln Gly Thr Val Val Thr Val Ser Ser
            115                 120                 125

<210> SEQ ID NO 168
<211> LENGTH: 125
<212> TYPE: PRT
<213> ORGANISM: Homo sapiens
<220> FEATURE:
<223> OTHER INFORMATION: VH Clone 255

<400> SEQUENCE: 168

Glu Val Gln Leu Val Gln Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
             35                  40                  45

Ser Gly Ile Ser Trp Asn Ser Gly Ser Ile Gly Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gln Gly Tyr His Tyr Tyr Asp Ser Ala Glu His Ala Phe
                100                 105                 110
```

Asp Ile Trp Gly Gln Gly Thr Val Val Thr Val Ser Ser
        115                 120                 125

<210> SEQ ID NO 169
<211> LENGTH: 125
<212> TYPE: PRT
<213> ORGANISM: Homo sapiens
<220> FEATURE:
<223> OTHER INFORMATION: VH Clone 272

<400> SEQUENCE: 169

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
            100                 105                 110

Asp Ile Trp Gly Gln Gly Thr Val Val Thr Val Ser Ser
        115                 120                 125

<210> SEQ ID NO 170
<211> LENGTH: 125
<212> TYPE: PRT
<213> ORGANISM: Homo sapiens
<220> FEATURE:
<223> OTHER INFORMATION: VH Clone 283

<400> SEQUENCE: 170

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
            100                 105                 110

Asp Ile Trp Gly Gln Gly Thr Val Val Thr Val Ser Ser
        115                 120                 125

<210> SEQ ID NO 171
<211> LENGTH: 125
<212> TYPE: PRT
<213> ORGANISM: Homo sapiens
<220> FEATURE:
<223> OTHER INFORMATION: VH Clone 302

<400> SEQUENCE: 171

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
            100                 105                 110

Asp Ile Trp Gly Gln Gly Thr Val Val Thr Val Ser Ser
            115                 120                 125

<210> SEQ ID NO 172
<211> LENGTH: 98
<212> TYPE: PRT
<213> ORGANISM: Homo sapiens
<220> FEATURE:
<223> OTHER INFORMATION: VH Clone 305
<220> FEATURE:
<221> NAME/KEY: VARIANT
<222> LOCATION: 64
<223> OTHER INFORMATION: Xaa = any amino acid
<220> FEATURE:
<221> NAME/KEY: VARIANT
<222> LOCATION: 65
<223> OTHER INFORMATION: Xaa = any amino acid
<220> FEATURE:
<221> NAME/KEY: VARIANT
<222> LOCATION: 68
<223> OTHER INFORMATION: Xaa = any amino acid
<220> FEATURE:
<221> NAME/KEY: VARIANT
<222> LOCATION: 69
<223> OTHER INFORMATION: Xaa = any amino acid
<220> FEATURE:
<221> NAME/KEY: VARIANT
<222> LOCATION: 93
<223> OTHER INFORMATION: Xaa = any amino acid
<220> FEATURE:
<221> NAME/KEY: VARIANT
<222> LOCATION: 98
<223> OTHER INFORMATION: Xaa = any amino acid

<400> SEQUENCE: 172

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Xaa
    50                  55                  60

Xaa Gly Arg Xaa Xaa Ile Ser Arg Asp Asn Ala Lys Asn Ser Leu Phe
65                  70                  75                  80

Leu Gln Met Asn Ser Leu Arg Ala Glu Asp Thr Ala Xaa Tyr Tyr Cys
                85                  90                  95

Ala Xaa

<210> SEQ ID NO 173
<211> LENGTH: 125
<212> TYPE: PRT
<213> ORGANISM: Homo sapiens
<220> FEATURE:
<223> OTHER INFORMATION: VH Clone 314

<400> SEQUENCE: 173

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
            100                 105                 110

Asp Ile Trp Gly Gln Gly Thr Val Val Thr Val Ser Ser
        115                 120                 125

<210> SEQ ID NO 174
<211> LENGTH: 125
<212> TYPE: PRT
<213> ORGANISM: Homo sapiens
<220> FEATURE:
<223> OTHER INFORMATION: VH Clone 379

<400> SEQUENCE: 174

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
            100                 105                 110

Asp Ile Trp Gly Gln Gly Thr Val Val Thr Val Ser Ser
        115                 120                 125

<210> SEQ ID NO 175
<211> LENGTH: 125
<212> TYPE: PRT
<213> ORGANISM: Homo sapiens
<220> FEATURE:
<223> OTHER INFORMATION: VH Clone 324

<400> SEQUENCE: 175

-continued

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
            100                 105                 110

Asp Ile Trp Gly Gln Gly Thr Val Val Thr Val Ser Ser
        115                 120                 125

<210> SEQ ID NO 176
<211> LENGTH: 125
<212> TYPE: PRT
<213> ORGANISM: Homo sapiens
<220> FEATURE:
<223> OTHER INFORMATION: VH Clone 327
<220> FEATURE:
<221> NAME/KEY: VARIANT
<222> LOCATION: 76
<223> OTHER INFORMATION: Xaa = any amino acid

<400> SEQUENCE: 176

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Xaa Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
            100                 105                 110

Asp Ile Trp Gly Gln Gly Thr Val Val Thr Val Ser Ser
        115                 120                 125

<210> SEQ ID NO 177
<211> LENGTH: 125
<212> TYPE: PRT
<213> ORGANISM: Homo sapiens
<220> FEATURE:
<223> OTHER INFORMATION: VH Clone 336

<400> SEQUENCE: 177

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

```
Ala Met His Trp Val Arg Gln Ala Pro Gly Lys Gly Leu Glu Trp Val
            35                  40                  45

Ser Gly Ile Ser Trp Asn Ser Gly Arg Ile Gly Tyr Ala Asp Ser Val
 50                  55                  60

Lys Gly Arg Phe Thr Ile Ser Arg Asp Asn Ala Lys Asn Ser Leu Phe
 65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
                100                 105                 110

Asp Ile Trp Gly Gln Gly Thr Val Val Thr Val Ser Ser
                115                 120                 125

<210> SEQ ID NO 178
<211> LENGTH: 125
<212> TYPE: PRT
<213> ORGANISM: Homo sapiens
<220> FEATURE:
<223> OTHER INFORMATION: VH Clone 440

<400> SEQUENCE: 178

Gln Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Arg Ile Gly Tyr Ala Asp Ser Val
 50                  55                  60

Lys Gly Arg Phe Thr Ile Ser Arg Asp Asn Ala Lys Asn Ser Leu Phe
 65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
                100                 105                 110

Asp Ile Trp Gly Gln Gly Thr Val Val Thr Val Ser Ser
                115                 120                 125

<210> SEQ ID NO 179
<211> LENGTH: 125
<212> TYPE: PRT
<213> ORGANISM: Homo sapiens
<220> FEATURE:
<223> OTHER INFORMATION: VH Clone 448

<400> SEQUENCE: 179

Gln Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Arg Ile Gly Tyr Ala Asp Ser Val
 50                  55                  60

Lys Gly Arg Phe Thr Ile Ser Arg Asp Asn Ala Lys Asn Ser Leu Phe
 65                  70                  75                  80

Leu Gln Met Asn Ser Leu Arg Ala Glu Asp Thr Ala Val Tyr Tyr Cys
                85                  90                  95
```

Ala Arg Asp Gln Gly Tyr His Tyr Tyr Asp Ser Ala Glu His Ala Phe
            100                 105                 110

Asp Ile Trp Gly Gln Gly Thr Val Val Thr Val Ser Ser
            115                 120                 125

<210> SEQ ID NO 180
<211> LENGTH: 125
<212> TYPE: PRT
<213> ORGANISM: Homo sapiens
<220> FEATURE:
<223> OTHER INFORMATION: VH Clone 505

<400> SEQUENCE: 180

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
            100                 105                 110

Asp Ile Trp Gly Gln Gly Thr Met Val Thr Val Ser Ser
            115                 120                 125

<210> SEQ ID NO 181
<211> LENGTH: 125
<212> TYPE: PRT
<213> ORGANISM: Homo sapiens
<220> FEATURE:
<223> OTHER INFORMATION: VH Clone 506

<400> SEQUENCE: 181

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
            100                 105                 110

Asp Ile Trp Gly Gln Gly Thr Met Val Thr Val Ser Ser
            115                 120                 125

<210> SEQ ID NO 182
<211> LENGTH: 125
<212> TYPE: PRT

```
<213> ORGANISM: Homo sapiens
<220> FEATURE:
<223> OTHER INFORMATION: VH Clone 508

<400> SEQUENCE: 182

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
            100                 105                 110

Asp Ile Trp Gly Gln Gly Thr Val Val Thr Val Ser Ser
        115                 120                 125

<210> SEQ ID NO 183
<211> LENGTH: 125
<212> TYPE: PRT
<213> ORGANISM: Homo sapiens
<220> FEATURE:
<223> OTHER INFORMATION: VH Clone 184

<400> SEQUENCE: 183

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
            100                 105                 110

Asp Ile Trp Gly Gln Gly Thr Met Val Thr Val Ser Ser
        115                 120                 125

<210> SEQ ID NO 184
<211> LENGTH: 125
<212> TYPE: PRT
<213> ORGANISM: Homo sapiens
<220> FEATURE:
<223> OTHER INFORMATION: VH Clone 79

<400> SEQUENCE: 184

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30
```

Ala Met His Trp Val Arg Gln Ala Pro Gly Lys Gly Leu Glu Trp Val
            35                  40                  45

Ser Gly Ile Ser Trp Asn Ser Gly Arg Ile Gly Tyr Ala Asp Ser Val
        50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
            100                 105                 110

Asp Ile Trp Gly Gln Gly Thr Val Val Thr Val Ser Ser
            115                 120                 125

<210> SEQ ID NO 185
<211> LENGTH: 125
<212> TYPE: PRT
<213> ORGANISM: Homo sapiens
<220> FEATURE:
<223> OTHER INFORMATION: VH Clone 835

<400> SEQUENCE: 185

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Leu Ala Pro Gly Lys Gly Leu Glu Trp Val
            35                  40                  45

Ser Gly Ile Ser Trp Asn Ser Gly Arg Ile Gly Tyr Ala Asp Ser Val
        50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Lys Asp Thr Ala Val Tyr Tyr Cys
                85                  90                  95

Ala Arg Asp Gln Gly Tyr His Tyr Tyr Asp Ser Ala Glu His Ala Phe
            100                 105                 110

Asp Ile Trp Gly Gln Gly Thr Met Val Thr Val Ser Ser
            115                 120                 125

<210> SEQ ID NO 186
<211> LENGTH: 107
<212> TYPE: PRT
<213> ORGANISM: Homo sapiens
<220> FEATURE:
<223> OTHER INFORMATION: VL Clone 1265

<400> SEQUENCE: 186

Ala Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Asn Trp Tyr Gln Gln Arg Ala Gly Lys Ala Pro Glu Leu Leu Ile
            35                  40                  45

Tyr Ala Ala Ser Asn Leu Gln Ser Gly Val Pro Ser Arg Phe Ser Gly
        50                  55                  60

Ser Gly Ser Gly Thr Asp Phe Thr Leu Thr Ile Thr Ser Val Gln Pro
65                  70                  75                  80

Glu Asp Phe Ala Thr Tyr Phe Cys Gln Gln Gly Asp Ala Phe Pro Leu

```
                85                  90                  95
Thr Phe Gly Pro Gly Thr Lys Val Thr Ile Arg
            100                 105

<210> SEQ ID NO 187
<211> LENGTH: 109
<212> TYPE: PRT
<213> ORGANISM: Homo sapiens
<220> FEATURE:
<223> OTHER INFORMATION: VL Clone 213

<400> SEQUENCE: 187

Glu Ile Val Leu Thr Gln Ser Pro Ala Thr Leu Ser Leu Ser Pro Gly
1               5                   10                  15

Glu Thr Ala Thr Leu Ser Cys Arg Ala Ser Gln Ser Ile Asn His Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Thr Tyr Tyr Cys Gln Gln Ser Tyr Ser His Pro Arg
                85                  90                  95

Met Tyr Thr Phe Gly Gln Gly Thr Lys Leu Glu Ile Lys
            100                 105

<210> SEQ ID NO 188
<211> LENGTH: 109
<212> TYPE: PRT
<213> ORGANISM: Homo sapiens
<220> FEATURE:
<223> OTHER INFORMATION: VL Clone 255

<400> SEQUENCE: 188

Ala Ile Arg Met Thr Gln Ser Pro Ser Ser Leu Ser Ala Ser Val Gly
1               5                   10                  15

Asp Arg Val Thr Val Thr Cys Gln Ala Ser Gln Asp Ile Ser Asn Tyr
            20                  25                  30

Leu Asn Trp Tyr Gln Gln Lys Pro Gly Arg Ala Pro Lys Leu Leu Ile
        35                  40                  45

Tyr Asp Ala Ser Asn Val Lys Ala Gly Val Pro Ser Arg Phe Ser Gly
    50                  55                  60

Gly Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Gln
                85                  90                  95

Ala Tyr Thr Phe Gly Gln Gly Thr Lys Leu Asp Ile Lys
            100                 105

<210> SEQ ID NO 189
<211> LENGTH: 111
<212> TYPE: PRT
<213> ORGANISM: Homo sapiens
<220> FEATURE:
<223> OTHER INFORMATION: VL Clone 272

<400> SEQUENCE: 189

Gln Ser Val Leu Thr Gln Pro Pro Ser Val Ser Ala Ala Pro Gly Gln
1               5                   10                  15
```

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Asn Arg Asp Trp Val Phe Gly Gly Gly Thr Lys Leu Thr Val Leu
            100                 105                 110

<210> SEQ ID NO 190
<211> LENGTH: 112
<212> TYPE: PRT
<213> ORGANISM: Homo sapiens
<220> FEATURE:
<223> OTHER INFORMATION: VL Clone 283

<400> SEQUENCE: 190

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Leu Gly Gly Tyr
            20                  25                  30

Asn Tyr Val Ser Trp Tyr Gln His Arg Pro Gly Lys Ala Pro Lys Leu
        35                  40                  45

Ile Ile Tyr Asp Val Thr Val Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Thr Ser Ser
                85                  90                  95

Ser Thr Leu Leu Trp Val Phe Gly Gly Gly Thr Lys Leu Thr Val Leu
            100                 105                 110

<210> SEQ ID NO 191
<211> LENGTH: 112
<212> TYPE: PRT
<213> ORGANISM: Homo sapiens
<220> FEATURE:
<223> OTHER INFORMATION: VL Clone 302

<400> SEQUENCE: 191

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Leu Gly Gly Tyr
            20                  25                  30

Asn Tyr Val Ser Trp Tyr Gln His Arg Pro Gly Lys Ala Pro Lys Leu
        35                  40                  45

Ile Ile Tyr Asp Val Thr Val Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Thr Ser Ser
                85                  90                  95

Ser Thr Leu Leu Trp Val Phe Gly Gly Gly Thr Lys Leu Thr Val Leu 100                 105                 110

<210> SEQ ID NO 192
<211> LENGTH: 109
<212> TYPE: PRT
<213> ORGANISM: Homo sapiens
<220> FEATURE:
<223> OTHER INFORMATION: VL Clone 305
<220> FEATURE:
<221> NAME/KEY: VARIANT
<222> LOCATION: 5, 6, 8, 9, 93, 104
<223> OTHER INFORMATION: Xaa = any amino acid

<400> SEQUENCE: 192

Gln Ser Val Leu Xaa Xaa Pro Xaa Xaa Ala Ser Gly Ser Pro Gly Gln
1               5                   10                  15

Ser Val Thr Val Ser Cys Thr Gly Thr Gly Arg Asp Ile Gly Ala Tyr
            20                  25                  30

Asp Tyr Val Ser Trp Tyr Gln Gln His Pro Gly Lys Ala Pro Lys Leu
        35                  40                  45

Leu Ile Tyr Gly Val Asn Lys Arg Pro Ser Gly Val Pro Asp Arg Phe
    50                  55                  60

Ser Gly Ser Lys Ser Asp Asn Thr Ala Ser Leu Thr Val Ser Gly Leu
65                  70                  75                  80

Gln Val Glu Asp Glu Ala Asp Tyr Tyr Cys Ser Ser Xaa Ala Gly Arg
                85                  90                  95

Lys Tyr Val Phe Gly Thr Gly Xaa Lys Val Thr Val Leu
            100                 105

<210> SEQ ID NO 193
<211> LENGTH: 112
<212> TYPE: PRT
<213> ORGANISM: Homo sapiens
<220> FEATURE:
<223> OTHER INFORMATION: VL Clone 314

<400> SEQUENCE: 193

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Leu Gly Gly Tyr
            20                  25                  30

Asn Tyr Val Ser Trp Tyr Gln His Arg Pro Gly Lys Ala Pro Lys Leu
        35                  40                  45

Ile Ile Tyr Asp Val Thr Val Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Thr Ser Ser
                85                  90                  95

Ser Thr Leu Leu Trp Val Phe Gly Gly Gly Thr Lys Leu Thr Val Leu
            100                 105                 110

<210> SEQ ID NO 194
<211> LENGTH: 112
<212> TYPE: PRT
<213> ORGANISM: Homo sapiens
<220> FEATURE:
<223> OTHER INFORMATION: VL Clone 379

<400> SEQUENCE: 194

Gln Ser Ala Leu Thr Gln Pro Ala Ser Val Ser Gly Ser Pro Gly Gln

```
            1               5              10              15

Ser Ile Thr Ile Ser Cys Thr Gly Thr Ser Ser Asp Leu Gly Gly Tyr
                20                  25                  30

Asn Tyr Val Ser Trp Tyr Gln His Arg Pro Gly Lys Ala Pro Lys Leu
            35                  40                  45

Ile Ile Tyr Asp Val Thr Val Arg Pro Ser Gly Val Ser Asp Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Thr Ser Ser
                85                  90                  95

Ser Thr Leu Leu Trp Val Phe Gly Gly Gly Thr Lys Leu Thr Val Leu
                100                 105                 110
```

<210> SEQ ID NO 195
<211> LENGTH: 112
<212> TYPE: PRT
<213> ORGANISM: Homo sapiens
<220> FEATURE:
<223> OTHER INFORMATION: VL Clone 324

<400> SEQUENCE: 195

```
Gln Ser Ala Leu Thr Gln Pro Ala Ser Val Ser Gly Ser Pro Gly Gln
1               5                  10                  15

Ser Ile Thr Ile Ser Cys Thr Gly Thr Ser Ser Asp Leu Gly Gly Tyr
                20                  25                  30

Asn Tyr Val Ser Trp Tyr Gln His Arg Pro Gly Lys Ala Pro Lys Leu
            35                  40                  45

Ile Ile Tyr Asp Val Thr Val Arg Pro Ser Gly Val Ser Asp Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Thr Ser Ser
                85                  90                  95

Ser Thr Leu Leu Trp Val Phe Gly Gly Gly Thr Lys Leu Thr Val Leu
                100                 105                 110
```

<210> SEQ ID NO 196
<211> LENGTH: 112
<212> TYPE: PRT
<213> ORGANISM: Homo sapiens
<220> FEATURE:
<223> OTHER INFORMATION: VL Clone 327
<220> FEATURE:
<221> NAME/KEY: VARIANT
<222> LOCATION: 61
<223> OTHER INFORMATION: Xaa = any amino acid

<400> SEQUENCE: 196

```
Gln Ser Ala Leu Thr Gln Pro Ala Ser Val Ser Gly Ser Pro Gly Gln
1               5                  10                  15

Ser Ile Thr Ile Ser Cys Thr Glu Thr Ser Ser Asp Leu Gly Gly Tyr
                20                  25                  30

Asn Tyr Val Ser Trp Tyr Gln His Arg Pro Gly Lys Ala Pro Lys Leu
            35                  40                  45

Ile Ile Tyr Asp Val Thr Val Arg Pro Ser Gly Val Xaa Asp Arg Phe
        50                  55                  60

Ser Gly Ser Lys Ser Gly Asn Thr Ala Ser Leu Thr Ile Ser Gly Leu
65                  70                  75                  80
```

Gln Ala Glu Asp Glu Ala Asp Tyr Tyr Cys Gly Ser Tyr Thr Ser Ser
                85                  90                  95

Ser Thr Leu Leu Trp Val Phe Gly Gly Gly Thr Lys Leu Thr Val Leu
            100                 105                 110

<210> SEQ ID NO 197
<211> LENGTH: 112
<212> TYPE: PRT
<213> ORGANISM: Homo sapiens
<220> FEATURE:
<223> OTHER INFORMATION: VL Clone 336

<400> SEQUENCE: 197

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Leu Gly Gly Tyr
            20                  25                  30

Asn Tyr Val Ser Trp Tyr Gln His Arg Pro Gly Lys Ala Pro Lys Leu
        35                  40                  45

Ile Ile Tyr Asp Val Thr Val Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Thr Ser Ser
                85                  90                  95

Ser Thr Leu Leu Trp Val Phe Gly Gly Gly Thr Lys Leu Thr Val Leu
            100                 105                 110

<210> SEQ ID NO 198
<211> LENGTH: 110
<212> TYPE: PRT
<213> ORGANISM: Homo sapiens
<220> FEATURE:
<223> OTHER INFORMATION: VL Clone 440

<400> SEQUENCE: 198

Gln Ser Ala Leu Thr Gln Pro Ala Ser Val Ser Gly Ser Pro Gly His
1               5                   10                  15

Ser Ile Thr Ile Ser Cys Thr Gly Thr Arg Ser Asp Val Gly Gly Phe
            20                  25                  30

Asp Tyr Val Ser Trp Tyr Gln His Asn Pro Gly Lys Ala Pro Lys Leu
        35                  40                  45

Ile Ile Tyr Asp Val Thr Lys Arg Pro Ser Gly Val Ser Asn Arg Phe
    50                  55                  60

Ser Gly Ala Lys Ser Gly Ile Thr Ala Ser Leu Thr Ile Ser Gly Leu
65                  70                  75                  80

Gln Ala Glu Asp Glu Ala Asp Tyr Tyr Cys Thr Ser Tyr Arg Pro Gly
                85                  90                  95

Pro Thr Phe Val Phe Gly Thr Gly Thr Lys Leu Asp Ile Lys
            100                 105                 110

<210> SEQ ID NO 199
<211> LENGTH: 112
<212> TYPE: PRT
<213> ORGANISM: Homo sapiens
<220> FEATURE:
<223> OTHER INFORMATION: VL Clone 448

<400> SEQUENCE: 199

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Leu Gly Gly Tyr
            20                  25                  30

Asn Tyr Val Ser Trp Tyr Gln His Arg Pro Gly Lys Ala Pro Lys Leu
        35                  40                  45

Ile Ile Tyr Asp Val Thr Val Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Thr Ser Ser
                85                  90                  95

Ser Thr Leu Leu Trp Val Phe Gly Gly Gly Thr Lys Leu Asp Ile Lys
            100                 105                 110
```

<210> SEQ ID NO 200
<211> LENGTH: 111
<212> TYPE: PRT
<213> ORGANISM: Homo sapiens
<220> FEATURE:
<223> OTHER INFORMATION: VL Clone 505

<400> SEQUENCE: 200

```
Gln Ser Val Leu Thr Gln Pro Arg Ser Leu Ser Gly Ser Pro Gly Gln
1               5                   10                  15

Ser Val Thr Ile Ala Cys Thr Gly Ala Ser Thr Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Asn Lys Arg Pro Ser Gly Val Pro Asp Arg Phe
    50                  55                  60

Ser Gly Ser Lys Ser Gly Asn Thr Ala Phe Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Phe Glu Val Phe Gly Gly Gly Thr Lys Leu Thr Val Leu
            100                 105                 110
```

<210> SEQ ID NO 201
<211> LENGTH: 111
<212> TYPE: PRT
<213> ORGANISM: Homo sapiens
<220> FEATURE:
<223> OTHER INFORMATION: VL Clone 506

<400> SEQUENCE: 201

```
Gln Leu Val Leu Thr Gln Pro Pro Ser Val Ser Gly Ser Pro Gly Gln
1               5                   10                  15

Ser Val Thr Phe Ser Cys Thr Gly Ala Ser Ser Asp Val Gly Gly Tyr
            20                  25                  30

Asp His Val Ser Trp Tyr Gln His His Pro Gly Lys Gly Pro Lys Leu
        35                  40                  45

Leu Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Phe Ala Gly Tyr
                85                  90                  95
```

```
Tyr Thr Tyr Trp Leu Phe Gly Gly Gly Thr Lys Val Thr Val Leu
            100                 105                 110
```

<210> SEQ ID NO 202
<211> LENGTH: 106
<212> TYPE: PRT
<213> ORGANISM: Homo sapiens
<220> FEATURE:
<223> OTHER INFORMATION: VL Clone 508

<400> SEQUENCE: 202

```
Gln Ser Ala Leu Thr Gln Pro Arg Ser Val Ser Gly Phe Pro Gly Gln
1               5                   10                  15

Ser Val Thr Ile Ser Cys Thr Gly Thr Thr Ser Asp Asp Val Ser Trp
            20                  25                  30

Tyr Gln Gln His Pro Gly Lys Ala Pro Gln Leu Met Leu Tyr Asp Val
        35                  40                  45

Ser Lys Arg Pro Ser Gly Val Pro His Arg Phe Ser Gly Ser Arg Ser
    50                  55                  60

Gly Arg Ala Ala Ser Leu Ile Ile Ser Gly Leu Gln Thr Glu Asp Glu
65                  70                  75                  80

Ala Asp Tyr Phe Cys Cys Ser Tyr Ala Gly Arg Tyr Asn Ser Val Pro
                85                  90                  95

Phe Gly Gly Gly Thr Lys Leu Thr Val Leu
            100                 105
```

<210> SEQ ID NO 203
<211> LENGTH: 99
<212> TYPE: PRT
<213> ORGANISM: Homo sapiens
<220> FEATURE:
<223> OTHER INFORMATION: VL Clone 184

<400> SEQUENCE: 203

```
Ser Tyr Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Phe Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Glu Tyr Tyr Cys Ala Ala Trp Asp Asp Ser Leu
                85                  90                  95

Asn Val Val
```

<210> SEQ ID NO 204
<211> LENGTH: 110
<212> TYPE: PRT
<213> ORGANISM: Homo sapiens
<220> FEATURE:
<223> OTHER INFORMATION: VL Clone 79

<400> SEQUENCE: 204

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
```

```
                    20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Gly Asp Tyr Tyr Cys Gly Thr Trp Asp Ile Ser Leu
                85                  90                  95

Arg Phe Gly Val Phe Gly Gly Gly Thr Lys Val Thr Val Leu
            100                 105                 110
```

<210> SEQ ID NO 205
<211> LENGTH: 111
<212> TYPE: PRT
<213> ORGANISM: Homo sapiens
<220> FEATURE:
<223> OTHER INFORMATION: VL Clone 835

<400> SEQUENCE: 205

```
Gln Ser Val Leu Thr Gln Pro Arg Ser Val Ser Gly Ser Pro Gly Gln
1               5                   10                  15

Ser Val Thr Ile Ser Cys Thr Gly Pro Ile Ser Gly Val Gly Asp Tyr
            20                  25                  30

Thr Ser Val Ser Trp Tyr Gln His Tyr Pro Gly Lys Thr Pro Lys Leu
            35                  40                  45

Ile Ile Tyr Asp Val Thr Gln Arg Pro Ser Gly Val Pro Asn Arg Phe
        50                  55                  60

Ser Gly Ser Lys Ser Gly Asn Thr Ala Ser Leu Thr Ile Ser Gly Leu
65                  70                  75                  80

Gln Ala Asp Asp Glu Ala Asp Tyr Tyr Cys Cys Ser Tyr Glu Ala Pro
                85                  90                  95

Thr His Thr Tyr Val Phe Gly Thr Gly Thr Lys Leu Thr Val Leu
            100                 105                 110
```

<210> SEQ ID NO 206
<211> LENGTH: 252
<212> TYPE: PRT
<213> ORGANISM: Homo sapiens
<220> FEATURE:
<223> OTHER INFORMATION: scFv Clone 1265

<400> SEQUENCE: 206

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
            35                  40                  45

Trp Leu Ala Leu Ile Tyr Trp Asp Asp Lys Arg Tyr Ser Pro Ser
        50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Ile Asp Tyr Gly Ser Gly Ser Tyr Ser Pro Arg Thr Ser
            100                 105                 110
```

Tyr Tyr Tyr Tyr Met Ser Val Trp Gly Lys Gly Thr Thr Val Thr Val
            115                 120                 125

Ser Ser Gly Gly Gly Gly Ser Gly Gly Gly Ser Gly Gly Gly Gly
130                 135                 140

Ser Ala Ile Gln Leu Thr Gln Ser Pro Ser Phe Leu Ser Ala Ser Val
145                 150                 155                 160

Gly Asp Arg Val Thr Ile Thr Cys Arg Ala Ser Gln Gly Ile Ser Ser
                165                 170                 175

Tyr Leu Asn Trp Tyr Gln Gln Arg Ala Gly Lys Ala Pro Glu Leu Leu
            180                 185                 190

Ile Tyr Ala Ala Ser Asn Leu Gln Ser Gly Val Pro Ser Arg Phe Ser
        195                 200                 205

Gly Ser Gly Ser Gly Thr Asp Phe Thr Leu Thr Ile Thr Ser Val Gln
    210                 215                 220

Pro Glu Asp Phe Ala Thr Tyr Phe Cys Gln Gln Gly Asp Ala Phe Pro
225                 230                 235                 240

Leu Thr Phe Gly Pro Gly Thr Lys Val Thr Ile Arg
                245                 250

<210> SEQ ID NO 207
<211> LENGTH: 249
<212> TYPE: PRT
<213> ORGANISM: Homo sapiens
<220> FEATURE:
<223> OTHER INFORMATION: scFv Clone 213

<400> SEQUENCE: 207

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Asp Gln Gly Tyr His Tyr Tyr Asp Ser Ala Glu His Ala Phe
        100                 105                 110

Asp Ile Trp Gly Gln Gly Thr Val Val Thr Val Ser Ser Gly Gly Gly
    115                 120                 125

Gly Ser Gly Gly Gly Gly Ser Gly Gly Gly Gly Ser Glu Ile Val Leu
130                 135                 140

Thr Gln Ser Pro Ala Thr Leu Ser Leu Ser Pro Gly Glu Thr Ala Thr
145                 150                 155                 160

Leu Ser Cys Arg Ala Ser Gln Ser Ile Asn His Tyr Leu Ala Trp Tyr
                165                 170                 175

Gln Gln Lys Pro Gly Gln Ala Pro Arg Leu Leu Ile Tyr Asp Ala Ser
            180                 185                 190

Asn Arg Ala Thr Gly Ile Pro Ala Arg Phe Ser Gly Ser Gly Ser Gly
        195                 200                 205

Thr Asp Phe Thr Leu Thr Ile Ser Ser Leu Glu Pro Glu Asp Phe Ala
    210                 215                 220

Thr Tyr Tyr Cys Gln Gln Ser Tyr Ser His Pro Arg Met Tyr Thr Phe
225                 230                 235                 240

Gly Gln Gly Thr Lys Leu Glu Ile Lys
                245

<210> SEQ ID NO 208
<211> LENGTH: 249
<212> TYPE: PRT
<213> ORGANISM: Homo sapiens
<220> FEATURE:
<223> OTHER INFORMATION: scFv Clone 255

<400> SEQUENCE: 208

Glu Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
            100                 105                 110

Asp Ile Trp Gly Gln Gly Thr Val Val Thr Val Ser Ser Gly Gly Gly
        115                 120                 125

Gly Ser Gly Gly Gly Gly Ser Gly Gly Gly Gly Ser Ala Ile Arg Met
    130                 135                 140

Thr Gln Ser Pro Ser Ser Leu Ser Ala Ser Val Gly Asp Arg Val Thr
145                 150                 155                 160

Val Thr Cys Gln Ala Ser Gln Asp Ile Ser Asn Tyr Leu Asn Trp Tyr
                165                 170                 175

Gln Gln Lys Pro Gly Arg Ala Pro Lys Leu Leu Ile Tyr Asp Ala Ser
            180                 185                 190

Asn Val Lys Ala Gly Val Pro Ser Arg Phe Ser Gly Gly Ser Gly
        195                 200                 205

Thr Asp Phe Thr Leu Thr Ile Ser Ser Leu Gln Pro Glu Asp Phe Ala
    210                 215                 220

Thr Tyr Tyr Cys Gln Gln Ser Tyr Ser Thr Pro Gln Ala Tyr Thr Phe
225                 230                 235                 240

Gly Gln Gly Thr Lys Leu Asp Ile Lys
                245

<210> SEQ ID NO 209
<211> LENGTH: 251
<212> TYPE: PRT
<213> ORGANISM: Homo sapiens
<220> FEATURE:
<223> OTHER INFORMATION: scFv Clone 272

<400> SEQUENCE: 209

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

```
Ala Met His Trp Val Arg Gln Ala Pro Gly Lys Gly Leu Glu Trp Val
            35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Lys Asn Ser Leu Phe
 65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
                100                 105                 110

Asp Ile Trp Gly Gln Gly Thr Val Val Thr Val Ser Ser Gly Gly Gly
            115                 120                 125

Gly Ser Gly Gly Gly Gly Ser Gly Gly Gly Gly Ser Gln Ser Val Leu
    130                 135                 140

Thr Gln Pro Pro Ser Val Ser Ala Ala Pro Gly Gln Lys Val Thr Ile
145                 150                 155                 160

Ser Cys Ser Gly Ser Ser Ser Asn Ile Gly Asn Asn Tyr Val Ser Trp
                165                 170                 175

Tyr Gln Gln Leu Pro Gly Thr Ala Pro Lys Leu Leu Ile Tyr Asp Asn
                180                 185                 190

Asn Lys Arg Pro Ser Gly Ile Pro Asp Arg Phe Ser Gly Ser Lys Ser
            195                 200                 205

Gly Thr Ser Ala Thr Leu Gly Ile Thr Gly Leu Gln Thr Gly Asp Glu
    210                 215                 220

Ala Asp Tyr Tyr Cys Gly Thr Trp Asp Ser Ser Leu Asn Arg Asp Trp
225                 230                 235                 240

Val Phe Gly Gly Gly Thr Lys Leu Thr Val Leu
                245                 250
```

<210> SEQ ID NO 210
<211> LENGTH: 252
<212> TYPE: PRT
<213> ORGANISM: Homo sapiens
<220> FEATURE:
<223> OTHER INFORMATION: scFv Clone 283

<400> SEQUENCE: 210

```
Gln Val Gln Leu Val Glu Ser Gly Gly Gly Leu Val Gln Pro Gly Arg
  1               5                  10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Lys Asn Ser Leu Phe
 65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
                100                 105                 110

Asp Ile Trp Gly Gln Gly Thr Val Val Thr Val Ser Ser Gly Gly Gly
            115                 120                 125

Gly Ser Gly Gly Gly Gly Ser Gly Gly Gly Gly Ser Gln Ser Ala Leu
    130                 135                 140
```

Thr Gln Pro Ala Ser Val Ser Gly Ser Pro Gly Gln Ser Ile Thr Ile
145                 150                 155                 160

Ser Cys Thr Gly Thr Ser Ser Asp Leu Gly Gly Tyr Asn Tyr Val Ser
                165                 170                 175

Trp Tyr Gln His Arg Pro Gly Lys Ala Pro Lys Leu Ile Ile Tyr Asp
            180                 185                 190

Val Thr Val Arg Pro Ser Gly Val Ser Asp Arg Phe Ser Gly Ser Lys
        195                 200                 205

Ser Gly Asn Thr Ala Ser Leu Thr Ile Ser Gly Leu Gln Ala Glu Asp
    210                 215                 220

Glu Ala Asp Tyr Tyr Cys Gly Ser Tyr Thr Ser Ser Ser Thr Leu Leu
225                 230                 235                 240

Trp Val Phe Gly Gly Gly Thr Lys Leu Thr Val Leu
                245                 250

<210> SEQ ID NO 211
<211> LENGTH: 252
<212> TYPE: PRT
<213> ORGANISM: Homo sapiens
<220> FEATURE:
<223> OTHER INFORMATION: scFv Clone 302

<400> SEQUENCE: 211

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
            100                 105                 110

Asp Ile Trp Gly Gln Gly Thr Val Val Thr Val Ser Ser Gly Gly Gly
        115                 120                 125

Gly Ser Gly Gly Gly Gly Ser Gly Gly Gly Gly Ser Gln Ser Ala Leu
    130                 135                 140

Thr Gln Pro Ala Ser Val Ser Gly Ser Pro Gly Gln Ser Ile Thr Ile
145                 150                 155                 160

Ser Cys Thr Gly Thr Ser Ser Asp Leu Gly Gly Tyr Asn Tyr Val Ser
                165                 170                 175

Trp Tyr Gln His Arg Pro Gly Lys Ala Pro Lys Leu Ile Ile Tyr Asp
            180                 185                 190

Val Thr Val Arg Pro Ser Gly Val Ser Asp Arg Phe Ser Gly Ser Lys
        195                 200                 205

Ser Gly Asn Thr Ala Ser Leu Thr Ile Ser Gly Leu Gln Ala Glu Asp
    210                 215                 220

Glu Ala Asp Tyr Tyr Cys Gly Ser Tyr Thr Ser Ser Ser Thr Leu Leu
225                 230                 235                 240

Trp Val Phe Gly Gly Gly Thr Lys Leu Thr Val Leu
                245                 250

```
<210> SEQ ID NO 212
<211> LENGTH: 249
<212> TYPE: PRT
<213> ORGANISM: Homo sapiens
<220> FEATURE:
<223> OTHER INFORMATION: scFv Clone 305
<220> FEATURE:
<221> NAME/KEY: VARIANT
<222> LOCATION: 64, 65, 68, 69, 93, 98, 102, 104, 113, 145, 146, 148,
      149, 233, 244
<223> OTHER INFORMATION: Xaa = any amino acid

<400> SEQUENCE: 212

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Xaa
    50                  55                  60

Xaa Gly Arg Xaa Xaa Ile Ser Arg Asp Asn Ala Lys Asn Ser Leu Phe
65                  70                  75                  80

Leu Gln Met Asn Ser Leu Arg Ala Glu Asp Thr Ala Xaa Tyr Tyr Cys
                85                  90                  95

Ala Xaa Asp Gln Gly Xaa His Xaa Tyr Asp Ser Ala Glu His Ala Phe
            100                 105                 110

Xaa Ile Trp Gly Gln Gly Thr Val Thr Val Ser Ser Gly Gly Gly Gly
        115                 120                 125

Gly Ser Gly Gly Gly Gly Ser Gly Gly Gly Gly Ser Gln Ser Val Leu
    130                 135                 140

Xaa Xaa Pro Xaa Xaa Ala Ser Gly Ser Pro Gly Gln Ser Val Thr Val
145                 150                 155                 160

Ser Cys Thr Gly Thr Gly Arg Asp Ile Gly Ala Tyr Asp Tyr Val Ser
                165                 170                 175

Trp Tyr Gln Gln His Pro Gly Lys Ala Pro Lys Leu Leu Ile Tyr Gly
            180                 185                 190

Val Asn Lys Arg Pro Ser Gly Val Pro Asp Arg Phe Ser Gly Ser Lys
        195                 200                 205

Ser Asp Asn Thr Ala Ser Leu Thr Val Ser Gly Leu Gln Val Glu Asp
    210                 215                 220

Glu Ala Asp Tyr Tyr Cys Ser Ser Xaa Ala Gly Arg Lys Tyr Val Phe
225                 230                 235                 240

Gly Thr Gly Xaa Lys Val Thr Val Leu
            245

<210> SEQ ID NO 213
<211> LENGTH: 252
<212> TYPE: PRT
<213> ORGANISM: Homo sapiens
<220> FEATURE:
<223> OTHER INFORMATION: scFv Clone 314

<400> SEQUENCE: 213

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30
```

Ala Met His Trp Val Arg Gln Ala Pro Gly Lys Gly Leu Glu Trp Val
            35                  40                  45

Ser Gly Ile Ser Trp Asn Ser Gly Arg Ile Gly Tyr Ala Asp Ser Val
        50                  55                  60

Lys Gly Arg Phe Thr Ile Ser Arg Asp Asn Ala Lys Asn Ser Leu Phe
 65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
                    100                 105                 110

Asp Ile Trp Gly Gln Gly Thr Val Val Thr Val Ser Ser Gly Gly Gly
            115                 120                 125

Gly Ser Gly Gly Gly Gly Ser Gly Gly Gly Gly Ser Gln Ser Ala Leu
        130                 135                 140

Thr Gln Pro Ala Ser Val Ser Gly Ser Pro Gly Gln Ser Ile Thr Ile
145                 150                 155                 160

Ser Cys Thr Gly Thr Ser Ser Asp Leu Gly Gly Tyr Asn Tyr Val Ser
                165                 170                 175

Trp Tyr Gln His Arg Pro Gly Lys Ala Pro Lys Leu Ile Ile Tyr Asp
                    180                 185                 190

Val Thr Val Arg Pro Ser Gly Val Ser Asp Arg Phe Ser Gly Ser Lys
            195                 200                 205

Ser Gly Asn Thr Ala Ser Leu Thr Ile Ser Gly Leu Gln Ala Glu Asp
        210                 215                 220

Glu Ala Asp Tyr Tyr Cys Gly Ser Tyr Thr Ser Ser Thr Leu Leu
225                 230                 235                 240

Trp Val Phe Gly Gly Gly Thr Lys Leu Thr Val Leu
                245                 250

<210> SEQ ID NO 214
<211> LENGTH: 252
<212> TYPE: PRT
<213> ORGANISM: Homo sapiens
<220> FEATURE:
<223> OTHER INFORMATION: scFv Clone 379

<400> SEQUENCE: 214

Glu Val Gln Leu Val Glu Ser Gly Gly Gly Leu Val Gln Pro Gly Arg
 1                   5                  10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Arg Ile Gly Tyr Ala Asp Ser Val
        50                  55                  60

Lys Gly Arg Phe Thr Ile Ser Arg Asp Asn Ala Lys Asn Ser Leu Phe
 65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
                    100                 105                 110

Asp Ile Trp Gly Gln Gly Thr Val Val Thr Val Ser Ser Gly Gly Gly
            115                 120                 125

Gly Ser Gly Gly Gly Gly Ser Gly Gly Gly Gly Ser Gln Ser Ala Leu
        130                 135                 140

```
Thr Gln Pro Ala Ser Val Ser Gly Ser Pro Gly Gln Ser Ile Thr Ile
145                 150                 155                 160

Ser Cys Thr Gly Thr Ser Ser Asp Leu Gly Gly Tyr Asn Tyr Val Ser
                165                 170                 175

Trp Tyr Gln His Arg Pro Gly Lys Ala Pro Lys Leu Ile Ile Tyr Asp
            180                 185                 190

Val Thr Val Arg Pro Ser Gly Val Ser Asp Arg Phe Ser Gly Ser Lys
        195                 200                 205

Ser Gly Asn Thr Ala Ser Leu Thr Ile Ser Gly Leu Gln Ala Glu Asp
    210                 215                 220

Glu Ala Asp Tyr Tyr Cys Gly Ser Tyr Thr Ser Ser Ser Thr Leu Leu
225                 230                 235                 240

Trp Val Phe Gly Gly Gly Thr Lys Leu Thr Val Leu
                245                 250

<210> SEQ ID NO 215
<211> LENGTH: 252
<212> TYPE: PRT
<213> ORGANISM: Homo sapiens
<220> FEATURE:
<223> OTHER INFORMATION: scFv Clone 324

<400> SEQUENCE: 215

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
            100                 105                 110

Asp Ile Trp Gly Gln Gly Thr Val Val Thr Val Ser Ser Gly Gly Gly
        115                 120                 125

Gly Ser Gly Gly Gly Gly Ser Gly Gly Gly Gly Ser Gln Ser Ala Leu
    130                 135                 140

Thr Gln Pro Ala Ser Val Ser Gly Ser Pro Gly Gln Ser Ile Thr Ile
145                 150                 155                 160

Ser Cys Thr Gly Thr Ser Ser Asp Leu Gly Gly Tyr Asn Tyr Val Ser
                165                 170                 175

Trp Tyr Gln His Arg Pro Gly Lys Ala Pro Lys Leu Ile Ile Tyr Asp
            180                 185                 190

Val Thr Val Arg Pro Ser Gly Val Ser Asp Arg Phe Ser Gly Ser Lys
        195                 200                 205

Ser Gly Asn Thr Ala Ser Leu Thr Ile Ser Gly Leu Gln Ala Glu Asp
    210                 215                 220

Glu Ala Asp Tyr Tyr Cys Gly Ser Tyr Thr Ser Ser Ser Thr Leu Leu
225                 230                 235                 240

Trp Val Phe Gly Gly Gly Thr Lys Leu Thr Val Leu
                245                 250
```

<210> SEQ ID NO 216
<211> LENGTH: 252
<212> TYPE: PRT
<213> ORGANISM: Homo sapiens
<220> FEATURE:
<223> OTHER INFORMATION: scFv Clone 327
<220> FEATURE:
<221> NAME/KEY: VARIANT
<222> LOCATION: 76, 201
<223> OTHER INFORMATION: Xaa = any amino acid

<400> SEQUENCE: 216

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Xaa Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
            100                 105                 110

Asp Ile Trp Gly Gln Gly Thr Val Val Thr Val Ser Ser Gly Gly Gly
        115                 120                 125

Gly Ser Gly Gly Gly Gly Ser Gly Gly Gly Gly Ser Gln Ser Ala Leu
    130                 135                 140

Thr Gln Pro Ala Ser Val Ser Gly Ser Pro Gly Gln Ser Ile Thr Ile
145                 150                 155                 160

Ser Cys Thr Glu Thr Ser Ser Asp Leu Gly Gly Tyr Asn Tyr Val Ser
                165                 170                 175

Trp Tyr Gln His Arg Pro Gly Lys Ala Pro Lys Leu Ile Ile Tyr Asp
            180                 185                 190

Val Thr Val Arg Pro Ser Gly Val Xaa Asp Arg Phe Ser Gly Ser Lys
        195                 200                 205

Ser Gly Asn Thr Ala Ser Leu Thr Ile Ser Gly Leu Gln Ala Glu Asp
    210                 215                 220

Glu Ala Asp Tyr Tyr Cys Gly Ser Tyr Thr Ser Ser Ser Thr Leu Leu
225                 230                 235                 240

Trp Val Phe Gly Gly Gly Thr Lys Leu Thr Val Leu
                245                 250

<210> SEQ ID NO 217
<211> LENGTH: 252
<212> TYPE: PRT
<213> ORGANISM: Homo sapiens
<220> FEATURE:
<223> OTHER INFORMATION: scFv Clone 336

<400> SEQUENCE: 217

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

```
Ala Met His Trp Val Arg Gln Ala Pro Gly Lys Gly Leu Glu Trp Val
            35                  40                  45

Ser Gly Ile Ser Trp Asn Ser Gly Arg Ile Gly Tyr Ala Asp Ser Val
 50                      55                  60

Lys Gly Arg Phe Thr Ile Ser Arg Asp Asn Ala Lys Asn Ser Leu Phe
 65                  70                  75                  80

Leu Gln Met Asn Ser Leu Arg Ala Glu Asp Thr Ala Val Tyr Tyr Cys
                 85                  90                  95

Ala Arg Asp Gln Gly Tyr His Tyr Tyr Asp Ser Ala Glu His Ala Phe
                100                 105                 110

Asp Ile Trp Gly Gln Gly Thr Val Val Thr Val Ser Ser Gly Gly Gly
            115                 120                 125

Gly Ser Gly Gly Gly Gly Ser Gly Gly Gly Gly Ser Gln Ser Ala Leu
    130                 135                 140

Thr Gln Pro Ala Ser Val Ser Gly Ser Pro Gly Gln Ser Ile Thr Ile
145                 150                 155                 160

Ser Cys Thr Gly Thr Ser Ser Asp Leu Gly Gly Tyr Asn Tyr Val Ser
                165                 170                 175

Trp Tyr Gln His Arg Pro Gly Lys Ala Pro Lys Leu Ile Ile Tyr Asp
                180                 185                 190

Val Thr Val Arg Pro Ser Gly Val Ser Asp Arg Phe Ser Gly Ser Lys
            195                 200                 205

Ser Gly Asn Thr Ala Ser Leu Thr Ile Ser Gly Leu Gln Ala Glu Asp
    210                 215                 220

Glu Ala Asp Tyr Tyr Cys Gly Ser Tyr Thr Ser Ser Thr Leu Leu
225                 230                 235                 240

Trp Val Phe Gly Gly Gly Thr Lys Leu Thr Val Leu
                245                 250
```

<210> SEQ ID NO 218
<211> LENGTH: 250
<212> TYPE: PRT
<213> ORGANISM: Homo sapiens
<220> FEATURE:
<223> OTHER INFORMATION: scFv Clone 440

<400> SEQUENCE: 218

```
Gln Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
            35                  40                  45

Ser Gly Ile Ser Trp Asn Ser Gly Arg Ile Gly Tyr Ala Asp Ser Val
 50                      55                  60

Lys Gly Arg Phe Thr Ile Ser Arg Asp Asn Ala Lys Asn Ser Leu Phe
 65                  70                  75                  80

Leu Gln Met Asn Ser Leu Arg Ala Glu Asp Thr Ala Val Tyr Tyr Cys
                 85                  90                  95

Ala Arg Asp Gln Gly Tyr His Tyr Tyr Asp Ser Ala Glu His Ala Phe
                100                 105                 110

Asp Ile Trp Gly Gln Gly Thr Val Val Thr Val Ser Ser Gly Gly Gly
            115                 120                 125

Gly Ser Gly Gly Gly Gly Ser Gly Gly Gly Gly Ser Gln Ser Ala Leu
    130                 135                 140
```

```
Thr Gln Pro Ala Ser Val Gly Ser Pro Gly His Ser Ile Thr Ile
145                 150                 155                 160

Ser Cys Thr Gly Thr Arg Ser Asp Val Gly Gly Phe Asp Tyr Val Ser
            165                 170                 175

Trp Tyr Gln His Asn Pro Gly Lys Ala Pro Lys Leu Ile Ile Tyr Asp
                180                 185                 190

Val Thr Lys Arg Pro Ser Gly Val Ser Asn Arg Phe Ser Gly Ala Lys
            195                 200                 205

Ser Gly Ile Thr Ala Ser Leu Thr Ile Ser Gly Leu Gln Ala Glu Asp
            210                 215                 220

Glu Ala Asp Tyr Tyr Cys Thr Ser Tyr Arg Pro Gly Pro Thr Phe Val
225                 230                 235                 240

Phe Gly Thr Gly Thr Lys Leu Asp Ile Lys
                245                 250

<210> SEQ ID NO 219
<211> LENGTH: 252
<212> TYPE: PRT
<213> ORGANISM: Homo sapiens
<220> FEATURE:
<223> OTHER INFORMATION: scFv Clone 448

<400> SEQUENCE: 219

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
            100                 105                 110

Asp Ile Trp Gly Gln Gly Thr Val Val Thr Val Ser Ser Gly Gly Gly
        115                 120                 125

Gly Ser Gly Gly Gly Gly Ser Gly Gly Gly Gly Ser Gln Ser Ala Leu
    130                 135                 140

Thr Gln Pro Ala Ser Val Gly Ser Pro Gly Gln Ser Ile Thr Ile
145                 150                 155                 160

Ser Cys Thr Gly Thr Ser Ser Asp Leu Gly Gly Tyr Asn Tyr Val Ser
            165                 170                 175

Trp Tyr Gln His Arg Pro Gly Lys Ala Pro Lys Leu Ile Ile Tyr Asp
                180                 185                 190

Val Thr Val Arg Pro Ser Gly Val Ser Asp Arg Phe Ser Gly Ser Lys
            195                 200                 205

Ser Gly Asn Thr Ala Ser Leu Thr Ile Ser Gly Leu Gln Ala Glu Asp
            210                 215                 220

Glu Ala Asp Tyr Tyr Cys Gly Ser Tyr Thr Ser Ser Thr Leu Leu
225                 230                 235                 240

Trp Val Phe Gly Gly Thr Lys Leu Asp Ile Lys
                245                 250
```

```
<210> SEQ ID NO 220
<211> LENGTH: 236
<212> TYPE: PRT
<213> ORGANISM: Homo sapiens
<220> FEATURE:
<223> OTHER INFORMATION: scFv Clone 505

<400> SEQUENCE: 220

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
            100                 105                 110

Asp Ile Trp Gly Gln Gly Thr Met Val Thr Val Ser Ser Gln Ser Val
        115                 120                 125

Leu Thr Gln Pro Arg Ser Leu Ser Gly Ser Pro Gly Gln Ser Val Thr
    130                 135                 140

Ile Ala Cys Thr Gly Ala Ser Thr Asp Val Gly Gly Tyr Asn Tyr Val
145                 150                 155                 160

Ser Trp Tyr Gln Gln His Pro Gly Lys Ala Pro Lys Leu Met Ile Tyr
                165                 170                 175

Asp Val Asn Lys Arg Pro Ser Gly Val Pro Asp Arg Phe Ser Gly Ser
            180                 185                 190

Lys Ser Gly Asn Thr Ala Phe Leu Thr Ile Ser Gly Leu Gln Ala Glu
        195                 200                 205

Asp Glu Ala Asp Tyr Tyr Cys Cys Ser Tyr Ala Gly Ser Tyr Thr Phe
    210                 215                 220

Glu Val Phe Gly Gly Gly Thr Lys Leu Thr Val Leu
225                 230                 235

<210> SEQ ID NO 221
<211> LENGTH: 251
<212> TYPE: PRT
<213> ORGANISM: Homo sapiens
<220> FEATURE:
<223> OTHER INFORMATION: scFv Clone 506

<400> SEQUENCE: 221

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Lys Asn Ser Leu Phe
65                  70                  75                  80
```

```
Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
            100                 105                 110

Asp Ile Trp Gly Gln Gly Thr Met Val Thr Val Ser Ser Gly Gly Gly
        115                 120                 125

Gly Ser Gly Gly Gly Gly Ser Gly Gly Gly Gly Ser Gln Leu Val Leu
    130                 135                 140

Thr Gln Pro Pro Ser Val Ser Gly Ser Pro Gly Gln Ser Val Thr Phe
145                 150                 155                 160

Ser Cys Thr Gly Ala Ser Ser Asp Val Gly Gly Tyr Asp His Val Ser
                165                 170                 175

Trp Tyr Gln His His Pro Gly Lys Gly Pro Lys Leu Leu Ile Tyr Asp
            180                 185                 190

Val Ser Lys Arg Pro Ser Gly Val Pro Asp Arg Phe Ser Gly Ser Lys
        195                 200                 205

Ser Gly Asn Thr Ala Ser Leu Thr Ile Ser Gly Leu Gln Ala Glu Asp
    210                 215                 220

Glu Ala Asp Tyr Tyr Cys Cys Ser Phe Ala Gly Tyr Tyr Thr Tyr Trp
225                 230                 235                 240

Leu Phe Gly Gly Gly Thr Lys Val Thr Val Leu
                245                 250

<210> SEQ ID NO 222
<211> LENGTH: 246
<212> TYPE: PRT
<213> ORGANISM: Homo sapiens
<220> FEATURE:
<223> OTHER INFORMATION: scFv Clone 508

<400> SEQUENCE: 222

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
            100                 105                 110

Asp Ile Trp Gly Gln Gly Thr Val Val Thr Val Ser Ser Gly Gly Gly
        115                 120                 125

Gly Ser Gly Gly Gly Gly Ser Gly Gly Gly Gly Ser Gln Ser Ala Leu
    130                 135                 140

Thr Gln Pro Arg Ser Val Ser Gly Phe Pro Gly Gln Ser Val Thr Ile
145                 150                 155                 160

Ser Cys Thr Gly Thr Thr Ser Asp Asp Val Ser Trp Tyr Gln Gln His
                165                 170                 175

Pro Gly Lys Ala Pro Gln Leu Met Leu Tyr Asp Val Ser Lys Arg Pro
            180                 185                 190
```

-continued

Ser Gly Val Pro His Arg Phe Ser Gly Ser Arg Ser Gly Arg Ala Ala
        195                 200                 205

Ser Leu Ile Ile Ser Gly Leu Gln Thr Glu Asp Glu Ala Asp Tyr Phe
        210                 215                 220

Cys Cys Ser Tyr Ala Gly Arg Tyr Asn Ser Val Pro Phe Gly Gly Gly
225                 230                 235                 240

Thr Lys Leu Thr Val Leu
                245

<210> SEQ ID NO 223
<211> LENGTH: 239
<212> TYPE: PRT
<213> ORGANISM: Homo sapiens
<220> FEATURE:
<223> OTHER INFORMATION: scFv Clone 184

<400> SEQUENCE: 223

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
            100                 105                 110

Asp Ile Trp Gly Gln Gly Thr Met Val Thr Val Ser Ser Gly Gly Gly
        115                 120                 125

Gly Ser Gly Gly Gly Gly Ser Gly Gly Gly Gly Ser Ser Tyr Val Leu
    130                 135                 140

Thr Gln Pro Pro Ser Ala Ser Gly Thr Pro Gly Gln Arg Val Thr Ile
145                 150                 155                 160

Ser Cys Ser Gly Ser Ser Asn Ile Gly Ser Asn Thr Val Asn Trp
                165                 170                 175

Tyr Gln Gln Phe Pro Gly Thr Ala Pro Lys Leu Leu Ile Tyr Ser Asn
            180                 185                 190

Asn Gln Arg Pro Ser Gly Val Pro Asp Arg Phe Ser Gly Ser Lys Ser
        195                 200                 205

Gly Thr Ser Ala Ser Leu Ala Ile Ser Gly Leu Gln Ser Glu Asp Glu
    210                 215                 220

Ala Glu Tyr Tyr Cys Ala Ala Trp Asp Asp Ser Leu Asn Val Val
225                 230                 235

<210> SEQ ID NO 224
<211> LENGTH: 250
<212> TYPE: PRT
<213> ORGANISM: Homo sapiens
<220> FEATURE:
<223> OTHER INFORMATION: scFv Clone 79

<400> SEQUENCE: 224

Glu Val Gln Leu Val Glu Ser Gly Gly Gly Leu Val Gln Pro Gly Arg

-continued

```
1               5                   10                  15
Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
            35                  40                  45

Ser Gly Ile Ser Trp Asn Ser Gly Arg Ile Gly Tyr Ala Asp Ser Val
        50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Asp Gln Gly Tyr His Tyr Tyr Asp Ser Ala Glu His Ala Phe
            100                 105                 110

Asp Ile Trp Gly Gln Gly Thr Val Val Thr Val Ser Ser Gly Gly Gly
            115                 120                 125

Gly Ser Gly Gly Gly Gly Ser Gly Gly Gly Gly Ser Gln Ser Val Leu
        130                 135                 140

Thr Gln Pro Pro Ser Val Ser Ala Ala Pro Gly Gln Lys Val Thr Ile
145                 150                 155                 160

Ser Cys Ser Gly Ser Ser Ser Asn Ile Gly Asn Asn Tyr Val Ser Trp
                165                 170                 175

Tyr Gln Gln Leu Pro Gly Thr Ala Pro Lys Leu Leu Ile Tyr Asp Asn
            180                 185                 190

Asn Lys Arg Pro Ser Gly Ile Pro Asp Arg Phe Ser Gly Ser Lys Ser
            195                 200                 205

Gly Thr Ser Ala Thr Leu Gly Ile Thr Gly Leu Gln Thr Gly Asp Glu
        210                 215                 220

Gly Asp Tyr Tyr Cys Gly Thr Trp Asp Ile Ser Leu Arg Phe Gly Val
225                 230                 235                 240

Phe Gly Gly Gly Thr Lys Val Thr Val Leu
            245                 250
```

<210> SEQ ID NO 225
<211> LENGTH: 251
<212> TYPE: PRT
<213> ORGANISM: Homo sapiens
<220> FEATURE:
<223> OTHER INFORMATION: scFv Clone 835

<400> SEQUENCE: 225

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Leu Ala Pro Gly Lys Gly Leu Glu Trp Val
            35                  40                  45

Ser Gly Ile Ser Trp Asn Ser Gly Arg Ile Gly Tyr Ala Asp Ser Val
        50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Lys Asp Thr Ala Val Tyr Tyr Cys
                85                  90                  95

Ala Arg Asp Gln Gly Tyr His Tyr Tyr Asp Ser Ala Glu His Ala Phe
            100                 105                 110

Asp Ile Trp Gly Gln Gly Thr Met Val Thr Val Ser Ser Gly Gly Gly
```

```
                115                 120                 125
Gly Ser Gly Gly Gly Ser Gly Gly Gly Ser Gln Ser Val Leu
            130                 135                 140

Thr Gln Pro Arg Ser Val Ser Gly Ser Pro Gly Gln Ser Val Thr Ile
145                 150                 155                 160

Ser Cys Thr Gly Pro Ile Ser Gly Val Gly Asp Tyr Thr Ser Val Ser
                165                 170                 175

Trp Tyr Gln His Tyr Pro Gly Lys Thr Pro Lys Leu Ile Ile Tyr Asp
            180                 185                 190

Val Thr Gln Arg Pro Ser Gly Val Pro Asn Arg Phe Ser Gly Ser Lys
            195                 200                 205

Ser Gly Asn Thr Ala Ser Leu Thr Ile Ser Gly Leu Gln Ala Asp Asp
        210                 215                 220

Glu Ala Asp Tyr Tyr Cys Cys Ser Tyr Glu Ala Pro Thr His Thr Tyr
225                 230                 235                 240

Val Phe Gly Thr Gly Thr Lys Leu Thr Val Leu
                245                 250

<210> SEQ ID NO 226
<211> LENGTH: 14
<212> TYPE: PRT
<213> ORGANISM: Artificial Sequence
<220> FEATURE:
<223> OTHER INFORMATION: Synthetic
<220> FEATURE:
<223> OTHER INFORMATION: CDR-L1 consensus
<220> FEATURE:
<221> NAME/KEY: VARIANT
<222> LOCATION: 1
<223> OTHER INFORMATION: Xaa = Thr, Gln, Arg or Ser
<220> FEATURE:
<221> NAME/KEY: VARIANT
<222> LOCATION: 2
<223> OTHER INFORMATION: Xaa = Gly, Ala or Glu
<220> FEATURE:
<221> NAME/KEY: VARIANT
<222> LOCATION: 3
<223> OTHER INFORMATION: Xaa = Ile, Thr, Ser, Asp, Ala or Pro
<220> FEATURE:
<221> NAME/KEY: VARIANT
<222> LOCATION: 4
<223> OTHER INFORMATION: Xaa = Ser, Arg, Gln, Thr, Gly or Ile
<220> FEATURE:
<221> NAME/KEY: VARIANT
<222> LOCATION: 5
<223> OTHER INFORMATION: Xaa = null, Ser, Arg or Thr
<220> FEATURE:
<221> NAME/KEY: VARIANT
<222> LOCATION: 6
<223> OTHER INFORMATION: Xaa = Gly, Asp, Asn or null
<220> FEATURE:
<221> NAME/KEY: VARIANT
<222> LOCATION: 7
<223> OTHER INFORMATION: Xaa = Val, Leu, null or Ile
<220> FEATURE:
<221> NAME/KEY: VARIANT
<222> LOCATION: 8
<223> OTHER INFORMATION: Xaa = Asp, Gly, Ser, Ile, Leu or null
<220> FEATURE:
<221> NAME/KEY: VARIANT
<222> LOCATION: 9
<223> OTHER INFORMATION: Xaa = Ser, Gly, Ala, Ile, null or Asp
<220> FEATURE:
<221> NAME/KEY: VARIANT
<222> LOCATION: 10
<223> OTHER INFORMATION: Xaa = His, Tyr, Phe, Ser or Asn
<220> FEATURE:
<221> NAME/KEY: VARIANT
<222> LOCATION: 11
<223> OTHER INFORMATION: Xaa = Arg, Asn, Asp, His, Tyr or Thr
```

-continued

```
<220> FEATURE:
<221> NAME/KEY: VARIANT
<222> LOCATION: 12
<223> OTHER INFORMATION: Xaa = Tyr, Phe, Trp, Asp, His, Thr or Ser
<220> FEATURE:
<221> NAME/KEY: VARIANT
<222> LOCATION: 13
<223> OTHER INFORMATION: Xaa = Val, Ala or Leu
<220> FEATURE:
<221> NAME/KEY: VARIANT
<222> LOCATION: 14
<223> OTHER INFORMATION: Xaa = Ser, Asn or Ala

<400> SEQUENCE: 226

Xaa Xaa Xaa Xaa Xaa Xaa Xaa Xaa Xaa Xaa Xaa Xaa Xaa Xaa
1               5                   10

<210> SEQ ID NO 227
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: CDR-L2 consensus
<220> FEATURE:
<221> NAME/KEY: VARIANT
<222> LOCATION: 1
<223> OTHER INFORMATION: Xaa = Asp, Ser or Gly
<220> FEATURE:
<221> NAME/KEY: VARIANT
<222> LOCATION: 2
<223> OTHER INFORMATION: Xaa = Phe, Val, Asn, Lys or Ala
<220> FEATURE:
<221> NAME/KEY: VARIANT
<222> LOCATION: 3
<223> OTHER INFORMATION: Xaa = Ser, Thr, Asn or Asp
<220> FEATURE:
<221> NAME/KEY: VARIANT
<222> LOCATION: 4
<223> OTHER INFORMATION: Xaa = Lys, Val, Asn, Arg or Gln
<220> FEATURE:
<221> NAME/KEY: VARIANT
<222> LOCATION: 5
<223> OTHER INFORMATION: Xaa = Arg, Val or Leu
<220> FEATURE:
<221> NAME/KEY: VARIANT
<222> LOCATION: 6
<223> OTHER INFORMATION: Xaa = Pro, Lys, Ala or Glu
<220> FEATURE:
<221> NAME/KEY: VARIANT
<222> LOCATION: 7
<223> OTHER INFORMATION: Xaa = Ser, Pro, Ala or Thr

<400> SEQUENCE: 227

Xaa Xaa Xaa Xaa Xaa Xaa Xaa
1               5

<210> SEQ ID NO 228
<211> LENGTH: 12
<212> TYPE: PRT
<213> ORGANISM: Artificial Sequence
<220> FEATURE:
<223> OTHER INFORMATION: Synthetic
<220> FEATURE:
<223> OTHER INFORMATION: CDR-L3 consensus
<220> FEATURE:
<221> NAME/KEY: VARIANT
<222> LOCATION: 1
<223> OTHER INFORMATION: Xaa = Ser, Gly, Thr, Ala, Gln, Cys or Asn
<220> FEATURE:
<221> NAME/KEY: VARIANT
<222> LOCATION: 2
<223> OTHER INFORMATION: Xaa = Ser, Gln, Ala or Thr
<220> FEATURE:
```

```
<221> NAME/KEY: VARIANT
<222> LOCATION: 3
<223> OTHER INFORMATION: Xaa = Tyr, Ser, Trp or Arg
<220> FEATURE:
<221> NAME/KEY: VARIANT
<222> LOCATION: 4
<223> OTHER INFORMATION: Xaa = Ala, Asp, Arg, Thr or Tyr
<220> FEATURE:
<221> NAME/KEY: VARIANT
<222> LOCATION: 5
<223> OTHER INFORMATION: Xaa = Ala, Ser, Pro, Gly, Asn or Asp
<220> FEATURE:
<221> NAME/KEY: VARIANT
<222> LOCATION: 6
<223> OTHER INFORMATION: Xaa = Ile, Ser, Gly, Thr, Ala, Leu, His, Arg or
      Asn
<220> FEATURE:
<221> NAME/KEY: VARIANT
<222> LOCATION: 7
<223> OTHER INFORMATION: Xaa = Ser, Pro, Leu, Tyr or Gly
<220> FEATURE:
<221> NAME/KEY: VARIANT
<222> LOCATION: 8
<223> OTHER INFORMATION: Xaa = Pro, Thr, Ser, Gln, Met, Arg or Asn
<220> FEATURE:
<221> NAME/KEY: VARIANT
<222> LOCATION: 9
<223> OTHER INFORMATION: Xaa = Ser, Leu, Asn, Ala, Met, null or Arg
<220> FEATURE:
<221> NAME/KEY: VARIANT
<222> LOCATION: 10
<223> OTHER INFORMATION: Xaa = Leu, null or Asp
<220> FEATURE:
<221> NAME/KEY: VARIANT
<222> LOCATION: 11
<223> OTHER INFORMATION: Xaa = Tyr, Trp, Phe, Val, Ala, Leu
<220> FEATURE:
<221> NAME/KEY: VARIANT
<222> LOCATION: 12
<223> OTHER INFORMATION: Xaa = Val, Thr, Leu or Pro

<400> SEQUENCE: 228

Xaa Xaa Xaa Xaa Xaa Xaa Xaa Xaa Xaa Xaa Xaa Xaa
1               5                   10
```

ANTIBODIES AND CHIMERIC ANTIGEN RECEPTORS SPECIFIC FOR CD19

CROSS-REFERENCE TO RELATED APPLICATIONS

This application is a divisional of U.S. application Ser. No. 14/839,911 filed Aug. 28, 2015 which claims priority from U.S. provisional application No. 62/043,273 filed Aug. 28, 2014, entitled "Antibodies and Chimeric Antigen Receptors Specific for CD19," and U.S. provisional application No. 62/078,942 filed Nov. 12, 2014, entitled "Antibodies and Chimeric Antigen Receptors Specific for CD19," the contents of which are incorporated by reference in their entirety.

INCORPORATION BY REFERENCE OF SEQUENCE LISTING

The present application is being filed with a Sequence Listing in electronic format. The Sequence Listing is provided as a file entitled 735042000710SubSeqList.txt, created Feb. 10, 2020, which is 219,287 bytes in size. The information in electronic format of the Sequence Listing is incorporated by reference in its entirety.

FIELD

The present disclosure relates in some aspects to CD19 binding molecules, in particular, to anti-CD19 antibodies, including antibody fragments. The present disclosure further relates to recombinant receptors containing such antibodies, including chimeric antigen receptors (CARs), which contain such antibodies. The disclosure further relates to genetically engineered cells expressing such receptors and antibodies, and use thereof in adoptive cell therapy.

BACKGROUND

CD19 is expressed on normal B cells and by cells and tissues of various diseases and conditions, including most B cell malignancies. Most patients with B cell malignancies are not cured by available therapies, including therapies targeting CD19 and/or other B cell markers. Various CD19-binding molecules, including anti-CD19 antibodies, and chimeric antigen receptors containing anti-CD19 antibody portions, and cells expressing such chimeric receptors, are available. Improved CD19-binding molecules and engineered CD19-targeting cells are needed. For example, there is a need for molecules and cells with reduced immunogenicity and/or human antibodies, including antibody fragments that specifically bind to CD19 and chimeric receptors expressing such human antibodies for use in adoptive cell therapy. Provided are embodiments that meet such needs.

SUMMARY

Provided are CD19-binding molecules, including polypeptides, such as anti-CD19 antibodies, including antigen-binding antibody fragments such as single-chain fragments including scFv fragments, and polypeptides containing such antibodies, including fusion proteins, receptors, e.g., recombinant receptors, including chimeric receptors such as chimeric antigen receptors (CARs) containing the antibody as an antigen-recognition component. In particular embodiments, the antibodies are human antibodies, such as human single-chain fragments including scFvs.

Provided are antibodies or antigen-binding fragments thereof, including those that specifically bind to CD19. In some embodiments, the antibodies contain particular complementarity determining regions (CDRs), including heavy chain CDRs (CDR-Hs) and light chain CDRs (CDR-Ls). In some embodiments, the CDRs have or include amino acid sequences of CDRs of a reference antibody or chain or sequence thereof.

In some embodiments, the antibody or antigen-binding fragment thereof includes a heavy chain variable (VH) region and a light chain variable (VL) region. In some embodiments, the antibody, e.g., the VH region thereof, includes a heavy chain complementarity determining region 3 (CDR-H3) comprising the amino acid sequence set forth as SEQ ID NO: 20. In some embodiments, the VH region comprises at least at or about 90% sequence identity to the VH region amino acid sequence set forth in SEQ ID NO: 11, 12, 60, 61, 63, or 62, e.g., at least at or about 91%, 92%, 93%, 94%, 95%, 96%, 97%, 98%, or 99% sequence identity thereto. In some embodiments, the antibody or fragment includes a CDR-H1 of SEQ ID NO: 18 and a CDR-H3 of SEQ ID NO: 20. In some embodiments, the antibody or fragment further includes a CDR-H2 sequence comprising SEQ ID NO: 81, 82, 19 or 72.

In some embodiments, the antibody has a CDR-H1, a CDR-H2, and/or a CDR-H3 that respectively include the amino acid sequences of CDR 1, 2, and 3 sequences contained within the heavy chain variable ($V_H$) region of a reference antibody. In some embodiments, the VH region of the reference antibody has the amino acid sequence set forth in SEQ ID NO: 11 or 12. In some embodiments, it has the amino acid sequence set forth in SEQ ID NO: 11, 12, 60, 61, 63, or 62.

In some embodiments, the antibody has, e.g., further includes, a CDR-L1, a CDR-L2, and/or a CDR-L3, respectively comprising the amino acid sequences of CDR 1, 2, and 3 sequences contained within the light chain variable ($V_L$) region of a reference antibody. In some embodiments, the VL of the reference antibody has the amino acid sequence set forth in SEQ ID NO: 13, 14, 15, 16, or 17. In some embodiments, the VL of the reference antibody has the amino acid sequence set forth in SEQ ID NO: 13, 14, 15, 16, 17, 71, 65, 64, 66, 70, 69, 67, 90 or 91.

In some embodiments, the CDR within the reference antibody, VH, or VL refers to the CDR as defined by any numbering scheme, e.g., those defined herein. In some embodiments, the CDR in the reference antibody or VH or VL refers to the CDR as defined by Kabat numbering scheme as described herein, the CDR as defined by the Chothia scheme as described herein, or the Contact scheme as described herein.

In some embodiments, the antibody contains a VH chain that includes a CDR-H1, CDR-H2 and/or CDR-H3 in which the CDR-H1 comprises the amino acid sequence of DYAMH (SEQ ID NO: 18) or a sequence having at least or at least about 90%, 91%, 92%, 93%, 94%, 95%, 96%, 97%, 98%, or 99% amino acid sequence identity to SEQ ID NO: 18; the CDR-H2 comprises the amino acid sequence of SEQ ID NO: 81 or 82 or 19 or 72 or a sequence having at least or at least about 90%, 91%, 92%, 93%, 94%, 95%, 96%, 97%, 98%, or 99% amino acid sequence identity to SEQ ID NO: 81 or to SEQ ID NO: 82 or to SEQ ID NO: 19 or to SEQ ID NO: 72; and/or the CDR-H3 comprises the amino acid sequence of SEQ ID NO: 20 or a sequence having at least or at least about 90%, 91%, 92%, 93%, 94%, 95%, 96%, 97%, 98%, or 99% amino acid sequence identity to SEQ ID NO: 20.

In some embodiments, the antibody comprises a CDR-H1 comprising the amino acid sequence of SEQ ID NO: 18, a CDR-H2 comprising the amino acid sequence of SEQ ID NO: 81 or 82, and a CDR-H3 comprising the amino acid sequence set forth as SEQ ID NO: 20.

In some embodiments, the antibody has a CDR-1 comprising the amino acid sequence of $X_1X_2X_3X_4X_5X_6X_7X_8X_9X_{10}X_{11}X_{12}X_{13}X_{14}$ (SEQ ID NO: 110), wherein $X_1$ is T, W, S or R; $X_2$ is G or A; $X_3$ is I, T, D or S; $X_4$ is S, R, T or Q; $X_5$ is null or S; $X_6$ is null, D, N or G; $X_7$ is null, V or L; $X_8$ is X or null; $X_9$ is X or null; $X_{10}$ is X; $X_{11}$ is X; $X_{12}$ is Y, F, D or W; $X_{13}$ is V, A or L and $X_{14}$ is S, N or A. For example, in some embodiments, the antibody has a CDR-L1 comprising the amino acid sequence of $X_1X_2X_3X_4X_5X_6X_7X_8X_9X_{10}X_{11}X_{12}X_{13}X_{14}$ (SEQ ID NO: 111), wherein $X_1$ is T, Q, S, or R; $X_2$ is G or A; $X_3$ is I, T, D, or S; $X_4$ is S, R, T, or Q; $X_5$ is null or S; $X_6$ is G, D, N, or null; $X_7$ is null, V, or L; $X_8$ is D, G, I, L, S, or null; $X_9$ is S, G, A, I, R, or null; $X_{10}$ is H, Y, F, S, or N; $X_{11}$ is R, N, D, H, or Y; $X_{12}$ is Y, F, D, or W; $X_{13}$ is V, A, or L; and $X_{14}$ is S, N, or A; and/or a CDR-L2 comprising the amino acid sequence of $X_1X_2X_3X_4X_5X_6X_7$ (SEQ ID NO: 112), wherein $X_1$ is D or S; $X_2$ is F, V, N, K, or A; $X_3$ is S, T, D, or N; $X_4$ is K, V, N, Q, or R; $X_5$ is R, V, or L; $X_6$ is P, K, A, or E; and $X_7$ is S, P, A, or T, and/or a CDR-L3 comprising the amino acid sequence of $X_1X_2X_3X_4X_5X_6X_7X_8X_9X_{10}X_{11}X_{12}$ (SEQ ID NO: 115), wherein $X_1$ is X; $X_2$ is S, Q, A, or T; $X_3$ is Y, S, W, R; $X_4$ is A, D, R, T, or Y; $X_5$ is X; $X_6$ is X; $X_7$ is S, P, L, Y, G; $X_8$ is X or null; $X_9$ is X or null; $X_{10}$ is L or null; $X_{11}$ is X; and $X_{12}$ is V, T, or L. For example, in some embodiments, the antibody has a CDR-L3 comprising the amino acid sequence $X_1X_2X_3X_4X_5X_6X_7X_8X_9X_{10}X_{11}X_{12}$ (SEQ ID NO: 114), wherein $X_1$ is S, G, T, A, Q, C or N; $X_2$ is S, Q, A, or T; $X_3$ is Y, S, W, R; $X_4$ is A, D, R, T, or Y; $X_5$ is A, S, P, G, N or D; $X_6$ is I, S, G, T, A, L, H, R, N; $X_7$ is S, P, L, Y, G; $X_8$ is P, T, S, Q, M, R, N or null; $X_9$ is S, L, N, A, M or null; $X_{10}$ is L or null; $X_{11}$ is Y, W, F, V, A or L; and $X_{12}$ is V, T, or L.

In some such embodiments, in said CDR-L1, $X_3$ is I, T, or S; $X_4$ is S, T, or Q; $X_8$ is D, G, I, S, or null; $X_9$ is S, G, I, or null; $X_{10}$ is H, Y, S, or N; $X_{11}$ is R, N, D, or H; $X_{12}$ is Y or D; and $X_{13}$ is V or L; and/or in said CDR-L2, $X_1$ is D; $X_4$ is K, V, N, Q, or R; $X_6$ is P, K, or A; and $X_7$ is S, A, or T; and/or in said CDR-L3, $X_1$ is S, G, T, A, Q, C, or N; $X_5$ is A, S, P, G, N, or D; $X_6$ is I, S, G, T, A, L, H, R, or N; $X_8$ is P, T, S, Q, M, R, N, or null; $X_9$ is S, L, N, A, M or null; and $X_{11}$ is Y, W, F, V, A, or L. In some embodiments, in said CDR-L3, $X_1$ is S, G, Q, or N; $X_2$ is S, Q, or T; $X_4$ is A, D, T, or Y; $X_5$ is A, S, or G; and $X_6$ is I, S, N, R, A, H, or T.

In some embodiments, the CDR-H2 comprises the amino acid sequence set forth in SEQ ID NO: 19 (GISWNSGRIGYADSVKG); or the CDR-H2 comprises the amino acid sequence set forth in SEQ ID NO: 72 (GISWNSGSIGYADSVKG).

In some embodiments, the CDR-L1 comprises the amino acid sequence set forth in SEQ ID NO: 80, 77, 74, 73, 75, 79, 78, 76, 21, 25, 28, or 31. In some embodiments, the CDR-L1 comprises the amino acid sequence set forth in SEQ ID NO: 80, 77, 74, 73, 78, 21, or 28.

In some embodiments, the CDR-L2 comprises the amino acid sequence set forth in SEQ ID NO: 100, 97, 94, 93, 95, 99, 98, 96, 22, 26, 29, or 32. In some embodiments, the CDR-L2 comprises the amino acid sequence set forth in SEQ ID NO: 100, 97, 94, 93, 98, 22, or 29.

In some embodiments, the CDR-L3 comprises the amino acid sequence set forth in SEQ ID NO: 109, 106, 103, 101, 104, 108, 107, 105, 102, 23, 24, 27, 30, or 33. In some embodiments, the CDR-L3 comprises the amino acid sequence set forth in SEQ ID NO: 109, 106, 103, 101, 107, 24 or 30.

In some embodiments, the CDR-L1, CDR-L2, and CDR-L3 comprise the sequences of SEQ ID NOs: 21, 22, and 23, respectively or sequences having at least or at least about 90%, 91%, 92%, 93%, 94%, 95%, 96%, 97%, 98%, or 99% amino acid sequence identity, respectively, thereto; the CDR-L1, CDR-L2, and CDR-L3 comprise the sequences of SEQ ID NOs: 21, 22, and 24 or sequences having at least or at least about 90%, 91%, 92%, 93%, 94%, 95%, 96%, 97%, 98%, or 99% amino acid sequence identity, respectively, thereto, respectively; the CDR-L1, CDR-L2, and CDR-L3 comprise the sequences of SEQ ID NOs: 25, 26, and 27, respectively or sequences having at least or at least about 90%, 91%, 92%, 93%, 94%, 95%, 96%, 97%, 98%, or 99% amino acid sequence identity, respectively, thereto; the CDR-L1, CDR-L2, and CDR-L3 comprise the sequences of SEQ ID NOs: 28, 29 and 30, respectively or sequences having at least or at least about 90%, 91%, 92%, 93%, 94%, 95%, 96%, 97%, 98%, or 99% amino acid sequence identity, respectively, thereto; the CDR-L1, CDR-L2, and CDR-L3 comprise the sequences of SEQ ID NOs: 31, 32, and 33, respectively or sequences having at least or at least about 90%, 91%, 92%, 93%, 94%, 95%, 96%, 97%, 98%, or 99% amino acid sequence identity, respectively, thereto; the CDR-L1, CDR-L2, and CDR-L3 comprise the sequences of SEQ ID NOs: 80, 100, and 109, respectively or sequences having at least or at least about 90%, 91%, 92%, 93%, 94%, 95%, 96%, 97%, 98%, or 99% amino acid sequence identity, respectively, thereto; the CDR-L1, CDR-L2, and CDR-L3 comprise the sequences of SEQ ID NOs:77, 97, and 106, respectively or sequences having at least or at least about 90%, 91%, 92%, 93%, 94%, 95%, 96%, 97%, 98%, or 99% amino acid sequence identity, respectively, thereto; the CDR-L1, CDR-L2, and CDR-L3 comprise the sequences of SEQ ID NOs: 74, 94, and 103, respectively, or sequences having at least or at least about 90%, 91%, 92%, 93%, 94%, 95%, 96%, 97%, 98%, or 99% amino acid sequence identity, respectively, thereto; the CDR-L1, CDR-L2, and CDR-L3 comprise the sequences of SEQ ID NOs: 73, 93, and 101, respectively or sequences having at least or at least about 90%, 91%, 92%, 93%, 94%, 95%, 96%, 97%, 98%, or 99% amino acid sequence identity, respectively, thereto; the CDR-L1, CDR-L2, and CDR-L3 comprise the sequences of SEQ ID NOs:75, 95, and 104, respectively or sequences having at least or at least about 90%, 91%, 92%, 93%, 94%, 95%, 96%, 97%, 98%, or 99% amino acid sequence identity, respectively; the CDR-L1, CDR-L2, and CDR-L3 comprise the sequences of SEQ ID NOs: 79, 99, and 108, respectively or sequences having at least or at least about 90%, 91%, 92%, 93%, 94%, 95%, 96%, 97%, 98%, or 99% amino acid sequence identity, respectively, thereto; the CDR-L1, CDR-L2, and CDR-L3 comprise the sequences of SEQ ID NOs: 78, 98, and 107, respectively or sequences having at least or at least about 90%, 91%, 92%, 93%, 94%, 95%, 96%, 97%, 98%, or 99% amino acid sequence identity, respectively, thereto; the CDR-L1, CDR-L2, and CDR-L3 comprise the sequences of SEQ ID NOs: 76, 96, and 105, respectively or sequences having at least or at least about 90%, 91%, 92%, 93%, 94%, 95%, 96%, 97%, 98%, or 99% amino acid sequence identity, respectively, thereto; the CDR-L1, CDR-L2, and CDR-L3 comprise the sequences of SEQ ID NOs: 73, 93, and 102, respectively or sequences having at least or at least about 90%, 91%, 92%, 93%, 94%, 95%, 96%, 97%, 98%, or 99% amino acid sequence identity, respectively, thereto; or the CDR-L1, CDR-L2, and CDR-L3 comprise the sequences of SEQ ID NOs: 77, 97, and 106, respectively or sequences having at least or at least about 90%, 91%, 92%, 93%, 94%, 95%, 96%, 97%, 98%, or 99% amino acid sequence identity, respectively, thereto.

In some embodiments, the CDR-L3 comprises the amino acid sequence set forth as SEQ ID NO: 116, 117, 118, 119, 120, or 121, or a sequence having at least or at least about 90%, 91%, 92%, 93%, 94%, 95%, 96%, 97%, 98%, or 99% amino acid sequence identity, respectively, thereto.

In some embodiments, the CDR-H1, CDR-H2, and CDR-H3 comprise the sequences of SEQ ID NOs: 18, 81, and 20, respectively or sequences having at least or at least about 90%, 91%, 92%, 93%, 94%, 95%, 96%, 97%, 98%, or 99% amino acid sequence identity, respectively, thereto; the CDR-H1, CDR-H2, and CDR-H3 comprise the sequences of SEQ ID NOs: 18, 19, and 20, respectively or sequences having at least or at least about 90%, 91%, 92%, 93%, 94%, 95%, 96%, 97%, 98%, or 99% amino acid sequence identity, respectively, thereto; the CDR-H1, CDR-H2, and CDR-H3 comprise the sequences of SEQ ID NOs: 18, 82, and 20, respectively or sequences having at least or at least about 90%, 91%, 92%, 93%, 94%, 95%, 96%, 97%, 98%, or 99% amino acid sequence identity, respectively, thereto; or the CDR-H1, CDR-H2, and CDR-H3 comprise the sequences of SEQ ID NOs: 18, 72, and 20, respectively or sequences having at least or at least about 90%, 91%, 92%, 93%, 94%, 95%, 96%, 97%, 98%, or 99% amino acid sequence identity, respectively, thereto.

In some embodiments, the antibody has a CDR-L1 comprising the amino acid sequence $X_1GX_3X_4X_5X_6X_7X_8X_9X_{10}X_{11}X_{12}X_{13}S$ (SEQ ID NO: 36), wherein X1 is T, S, or Q, X3 is T, S, or D, X4 is T or S, X5 is null or S, X6 is null, D, or N, X7 is null or V, X8 is null, G, or I, X9 is null, G, or R, X10 is S, Y, or N, X11 is D or N, X12 is D or Y, X13 is V or A; the CDR-L2 comprises the amino acid sequence $X_1X_2X_3X_4RPS$ (SEQ ID NO: 37), wherein X1 is D or S, X2 is V, N, or K, X3 is S, N, or D, and X4 is K, Q, or N; and/or the CDR-L3 comprises the amino acid sequence $X_1X_2X_3X_4X_5X_6X_7X_8X_9X_{10}X_{11}$ (SEQ ID NO: 113), wherein X1 is C, S, A, G, or N; X2 is S, A, or T; X3 is Y, W, or R; X4 is A or D; X5 is G, D, or S; X6 is R, S, or N; X7 is Y, L, or G; X8 is N or S; X9 is S, N, or null; X10 V, A, or W; and X11 is L or V.

In some embodiments, the antibody has a CDR-L1 comprising the amino acid sequence $X_1GX_3X_4X_5X_6X_7X_8X_9X_{10}X_{11}X_{12}X_{13}S$ (SEQ ID NO: 36), wherein X1 is T, S, or Q, X3 is T, S, or D, X4 is T or S, X5 is null or S, X6 is null, D, or N, X7 is null or V, X8 is null, G, or I, X9 is null, G, or R, X10 is S, Y, or N, X11 is D or N, X12 is D or Y, X13 is V or A; the CDR-L2 comprises the amino acid sequence $X_1X_2X_3X_4RPS$ (SEQ ID NO: 37), wherein X1 is D or S, X2 is V, N, or K, X3 is S, N, or D, and X4 is K, Q, or N; and/or the CDR-L3 comprises the amino acid sequence $X_1X_2X_3X_4X_5X_6X_7X_8X_9X_{10}X_{11}X_{12}$ (SEQ ID NO: 38), wherein X1 is C, S, A, G, or N; X2 is S, A, or T; X3 is Y, W, or R; X4 is A or D; X5 is G, D, or S; X6 is R, S, or N; X7 is Y, L, or G; X8 is N or S; X9 is S or null; X10 is V, A or N; X11 is W or null; and X12 is L or V.

In some such embodiments, in the CDR-L1, X1 is T or S, X3 is T or S, X11 is D or N, and X13 is V; and/or in the CDR-L2, X2 is V or N and X4 is K or Q.

In some embodiments, the CDR-H2 comprises the amino acid sequence set forth in SEQ ID NO: 19 (GISWNSGRIGYADSVKG) or a sequence having at least or at least about 90%, 91%, 92%, 93%, 94%, 95%, 96%, 97%, 98%, or 99% amino acid sequence identity to SEQ ID NO: 19.

In some embodiments, the CDR-L1 comprises the sequence set forth in SEQ ID NO: 21, 25, 28, or 31 or a sequence having at least or at least about 90%, 91%, 92%, 93%, 94%, 95%, 96%, 97%, 98%, or 99% amino acid sequence identity thereto; and/or the CDR-L2 comprises the sequence set forth in SEQ ID NO: 22, 26, 29, or 32 or a sequence having at least or at least about 90%, 91%, 92%, 93%, 94%, 95%, 96%, 97%, 98%, or 99% amino acid sequence identity thereto; and/or the CDR-L3 comprises the sequence set forth in SEQ ID NO: 23, 24, 27, 30, or 33 or a sequence having at least or at least about 90%, 91%, 92%, 93%, 94%, 95%, 96%, 97%, 98%, or 99% amino acid sequence identity thereto.

In some embodiments, the CDR-L1, CDR-L2, and/or CDR-L3 comprise the sequences of SEQ ID NOs: 21, 22, and/or 23, respectively or sequences having at least or at least about 90%, 91%, 92%, 93%, 94%, 95%, 96%, 97%, 98%, or 99% amino acid sequence identity thereto, respectively.

In some embodiments, the CDR-L1, CDR-L2, and CDR-L3 comprise the sequences of SEQ ID NOs: 21, 22, and 24, respectively, or sequences having at least or at least about 90%, 91%, 92%, 93%, 94%, 95%, 96%, 97%, 98%, or 99% amino acid sequence identity thereto, respectively.

In some embodiments, the CDR-L1, CDR-L2, and CDR-L3 comprise the sequences of SEQ ID NOs: 25, 26, and 27, respectively or sequences having at least or at least about 90%, 91%, 92%, 93%, 94%, 95%, 96%, 97%, 98%, or 99% amino acid sequence identity thereto, respectively.

In some embodiments, the CDR-L1, CDR-L2, and CDR-L3 comprise the sequences of SEQ ID NOs: 28, 29, and 30, respectively, or sequences having at least or at least about 90%, 91%, 92%, 93%, 94%, 95%, 96%, 97%, 98%, or 99% amino acid sequence identity thereto, respectively. In some embodiments, the CDR-L1, CDR-L2, and CDR-L3 comprise the sequences of SEQ ID NOs: 31, 32, and 33, respectively, or sequences having at least or at least about 90%, 91%, 92%, 93%, 94%, 95%, 96%, 97%, 98%, or 99% amino acid sequence identity thereto.

In some embodiments, the heavy and light chain CDRs are any combination of the aforementioned CDR-L and CDR-H sequences, including sequences having at least or at least about 90%, 91%, 92%, 93%, 94%, 95%, 96%, 97%, 98%, or 99% amino acid sequence identity thereto.

In particular embodiments, the antibody or fragment comprises a VH region comprising the amino acid sequence of SEQ ID NO: 11 or a sequence having at least or at least about 90%, 91%, 92%, 93%, 94%, 95%, 96%, 97%, 98%, or 99% amino acid sequence identity thereto.

In particular embodiments, the antibody or fragment comprises a VH region comprising the amino acid sequence of SEQ ID NO: 12 or a sequence having at least or at least about 90%, 91%, 92%, 93%, 94%, 95%, 96%, 97%, 98%, or 99% amino acid sequence identity thereto.

In particular embodiments, the antibody or fragment comprises a VL region comprising the amino acid sequence of SEQ ID NO: 13 or a sequence having at least or at least about 90%, 91%, 92%, 93%, 94%, 95%, 96%, 97%, 98%, or 99% amino acid sequence identity thereto.

In particular embodiments, the antibody or fragment comprises a VL region comprising the amino acid sequence of SEQ ID NO: 14 or a sequence having at least or at least about 90%, 91%, 92%, 93%, 94%, 95%, 96%, 97%, 98%, or 99% amino acid sequence identity thereto.

In particular embodiments, the antibody or fragment comprises a VL region comprising the amino acid sequence of SEQ ID NO: 15 or a sequence having at least or at least about 90%, 91%, 92%, 93%, 94%, 95%, 96%, 97%, 98%, or 99% amino acid sequence identity thereto.

In particular embodiments, the antibody or fragment comprises a VL region comprising the amino acid sequence of SEQ ID NO: 16 or a sequence having at least or at least about 90%, 91%, 92%, 93%, 94%, 95%, 96%, 97%, 98%, or 99% amino acid sequence identity thereto.

In particular embodiments, the antibody or fragment comprises a VL region comprising the amino acid sequence of SEQ ID NO: 17 or a sequence having at least or at least about 90%, 91%, 92%, 93%, 94%, 95%, 96%, 97%, 98%, or 99% amino acid sequence identity thereto.

In particular embodiments, the antibody or fragment comprises a VH region comprising the amino acid sequence of SEQ ID NO: 63 or a sequence having at least or at least about 90%, 91%, 92%, 93%, 94%, 95%, 96%, 97%, 98%, or 99% amino acid sequence identity thereto.

In particular embodiments, the antibody or fragment comprises a VH region comprising the amino acid sequence of SEQ ID NO: 60 or a sequence having at least or at least about 90%, 91%, 92%, 93%, 94%, 95%, 96%, 97%, 98%, or 99% amino acid sequence identity thereto.

In particular embodiments, the antibody or fragment comprises a VH region comprising the amino acid sequence of SEQ ID NO: 61 or a sequence having at least or at least about 90%, 91%, 92%, 93%, 94%, 95%, 96%, 97%, 98%, or 99% amino acid sequence identity thereto.

In particular embodiments, the antibody or fragment comprises a VH region comprising the amino acid sequence of SEQ ID NO: 63 or a sequence having at least or at least about 90%, 91%, 92%, 93%, 94%, 95%, 96%, 97%, 98%, or 99% amino acid sequence identity thereto.

In particular embodiments, the antibody or fragment comprises a VH region comprising the amino acid sequence of SEQ ID NO: 62 or a sequence having at least or at least about 90%, 91%, 92%, 93%, 94%, 95%, 96%, 97%, 98%, or 99% amino acid sequence identity thereto.

In particular embodiments, the antibody or fragment comprises a VL region comprising the amino acid sequence of SEQ ID NO: 71 or a sequence having at least or at least about 90%, 91%, 92%, 93%, 94%, 95%, 96%, 97%, 98%, or 99% amino acid sequence identity thereto.

In particular embodiments, the antibody or fragment comprises a VL region comprising the amino acid sequence of SEQ ID NO: 90 or a sequence having at least or at least about 90%, 91%, 92%, 93%, 94%, 95%, 96%, 97%, 98%, or 99% amino acid sequence identity thereto.

In particular embodiments, the antibody or fragment comprises a VL region comprising the amino acid sequence of SEQ ID NO: 91 or a sequence having at least or at least about 90%, 91%, 92%, 93%, 94%, 95%, 96%, 97%, 98%, or 99% amino acid sequence identity thereto.

In particular embodiments, the antibody or fragment comprises a VL region comprising the amino acid sequence of SEQ ID NO: 68 or a sequence having at least or at least about 90%, 91%, 92%, 93%, 94%, 95%, 96%, 97%, 98%, or 99% amino acid sequence identity thereto.

In particular embodiments, the antibody or fragment comprises a VL region comprising the amino acid sequence of SEQ ID NO: 65 or a sequence having at least or at least about 90%, 91%, 92%, 93%, 94%, 95%, 96%, 97%, 98%, or 99% amino acid sequence identity thereto.

In particular embodiments, the antibody or fragment comprises a VL region comprising the amino acid sequence of SEQ ID NO: 64 or a sequence having at least or at least about 90%, 91%, 92%, 93%, 94%, 95%, 96%, 97%, 98%, or 99% amino acid sequence identity thereto.

In particular embodiments, the antibody or fragment comprises a VL region comprising the amino acid sequence of SEQ ID NO: 66 or a sequence having at least or at least about 90%, 91%, 92%, 93%, 94%, 95%, 96%, 97%, 98%, or 99% amino acid sequence identity thereto.

In particular embodiments, the antibody or fragment comprises a VL region comprising the amino acid sequence of SEQ ID NO: 70 or a sequence having at least or at least about 90%, 91%, 92%, 93%, 94%, 95%, 96%, 97%, 98%, or 99% amino acid sequence identity thereto.

In particular embodiments, the antibody or fragment comprises a VL region comprising the amino acid sequence of SEQ ID NO: 69 or a sequence having at least or at least about 90%, 91%, 92%, 93%, 94%, 95%, 96%, 97%, 98%, or 99% amino acid sequence identity thereto.

In particular embodiments, the antibody or fragment comprises a VL region comprising the amino acid sequence of SEQ ID NO: 67 or a sequence having at least or at least about 90%, 91%, 92%, 93%, 94%, 95%, 96%, 97%, 98%, or 99% amino acid sequence identity thereto.

In particular embodiments, the VH region of the antibody or fragment comprises the amino acid sequence of SEQ ID NO: 11, 60, 63, or 62 or a sequence having at least or at least about 90%, 91%, 92%, 93%, 94%, 95%, 96%, 97%, 98%, or 99% amino acid sequence identity thereto; and/or the VL region of the antibody or fragment comprises the amino acid sequence of SEQ ID NO: 14, 16, 71, 90, 65, 64, or 69 or a sequence having at least or at least about 90%, 91%, 92%, 93%, 94%, 95%, 96%, 97%, 98%, or 99% amino acid sequence identity thereto.

In some embodiments, the VH and VL regions of the antibody or fragment comprise the amino acid sequences of SEQ ID NOs: 12 and 17, respectively, or sequences having at least or at least about 90%, 91%, 92%, 93%, 94%, 95%, 96%, 97%, 98%, or 99% amino acid sequence identity thereto, respectively;

the VH and VL regions of the antibody or fragment comprise the amino acid sequences of SEQ ID NOs: 12 and 15, respectively, or sequences having at least or at least about 90%, 91%, 92%, 93%, 94%, 95%, 96%, 97%, 98%, or 99% amino acid sequence identity thereto, respectively;

the VH and VL regions of the antibody or fragment comprise the amino acid sequences of SEQ ID NOs: 11 and 13, respectively, or sequences having at least or at least about 90%, 91%, 92%, 93%, 94%, 95%, 96%, 97%, 98%, or 99% amino acid sequence identity thereto, respectively;

the VH and VL regions of the antibody or fragment comprise the amino acid sequences of SEQ ID NOs: 11 and 14, respectively, or sequences having at least or at least about 90%, 91%, 92%, 93%, 94%, 95%, 96%, 97%, 98%, or 99% amino acid sequence identity thereto, respectively;

the VH and VL regions of the antibody or fragment comprise the amino acid sequences of SEQ ID NOs: 11 and 16, respectively, or sequences having at least or at least about 90%, 91%, 92%, 93%, 94%, 95%, 96%, 97%, 98%, or 99% amino acid sequence identity thereto, respectively;

the VH and VL regions of the antibody or fragment comprise the amino acid sequences of SEQ ID NOs: 63 and 71, respectively, or sequences having at least or at least about 90%, 91%, 92%, 93%, 94%, 95%, 96%, 97%, 98%, or 99% amino acid sequence identity thereto, respectively;

the VH and VL regions of the antibody or fragment comprise the amino acid sequences of SEQ ID NOs: 62 and 68, respectively, or sequences having at least or at least about 90%, 91%, 92%, 93%, 94%, 95%, 96%, 97%, 98%, or 99% amino acid sequence identity thereto, respectively;

the VH and VL regions of the antibody or fragment comprise the amino acid sequences of SEQ ID NOs: 11 and 65, respectively, or sequences having at least or at least about 90%, 91%, 92%, 93%, 94%, 95%, 96%, 97%, 98%, or 99% amino acid sequence identity thereto, respectively;

the VH and VL regions of the antibody or fragment comprise the amino acid sequences of SEQ ID NOs: 60 and 64, respectively, or sequences having at least or at least about 90%, 91%, 92%, 93%, 94%, 95%, 96%, 97%, 98%, or 99% amino acid sequence identity thereto, respectively;

the VH and VL regions of the antibody or fragment comprise the amino acid sequences of SEQ ID NOs: 61 and 66, respectively, or sequences having at least or at least about 90%, 91%, 92%, 93%, 94%, 95%, 96%, 97%, 98%, or 99% amino acid sequence identity thereto, respectively;

the VH and VL regions of the antibody or fragment comprise the amino acid sequences of SEQ ID NOs: 63 and 70, respectively, or sequences having at least or at least about 90%, 91%, 92%, 93%, 94%, 95%, 96%, 97%, 98%, or 99% amino acid sequence identity thereto, respectively;

the VH and VL regions of the antibody or fragment comprise the amino acid sequences of SEQ ID NOs: 62 and 69, respectively, or sequences having at least or at least about 90%, 91%, 92%, 93%, 94%, 95%, 96%, 97%, 98%, or 99% amino acid sequence identity thereto, respectively;

the VH and VL regions of the antibody or fragment comprise the amino acid sequences of SEQ ID NOs: 12 and 67, respectively, or sequences having at least or at least about 90%, 91%, 92%, 93%, 94%, 95%, 96%, 97%, 98%, or 99% amino acid sequence identity thereto, respectively;

the VH and VL regions of the antibody or fragment comprise the amino acid sequences of SEQ ID NOs: 12 and 91, respectively, or sequences having at least or at least about 90%, 91%, 92%, 93%, 94%, 95%, 96%, 97%, 98%, or 99% amino acid sequence identity thereto, respectively; or the VH and VL regions of the antibody or fragment comprise the amino acid sequences of SEQ ID NOs: 63 and 90, respectively, or sequences having at least or at least about 90%, 91%, 92%, 93%, 94%, 95%, 96%, 97%, 98%, or 99% amino acid sequence identity thereto, respectively.

In some embodiments, the VH region comprises SEQ ID NO: 11 and the VL region comprises SEQ ID NO: 13; in some embodiments, the VH region comprises SEQ ID NO: 11 and the VL region comprises SEQ ID NO: 14; in some embodiments, the VH region comprises SEQ ID NO: 11 and the VL region comprises SEQ ID NO: 15; in some embodiments, the VH region comprises SEQ ID NO: 11 and the VL region comprises SEQ ID NO: 16, or sequences having at least or at least about 90%, 91%, 92%, 93%, 94%, 95%, 96%, 97%, 98%, or 99% amino acid sequence identity thereto; in some embodiments, the VH region comprises SEQ ID NO: 11 and the VL region comprises SEQ ID NO: 17, or sequences having at least or at least about 90%, 91%, 92%, 93%, 94%, 95%, 96%, 97%, 98%, or 99% amino acid sequence identity thereto.

In some embodiments, the VH region comprises SEQ ID NO: 12 and the VL region comprises SEQ ID NO: 13; in some embodiments, the VH region comprises SEQ ID NO: 12 and the VL region comprises SEQ ID NO: 14; in some embodiments, the VH region comprises SEQ ID NO: 12 and the VL region comprises SEQ ID NO: 15; in some embodiments, the VH region comprises SEQ ID NO: 12 and the VL region comprises SEQ ID NO: 16, or sequences having at least or at least about 90%, 91%, 92%, 93%, 94%, 95%, 96%, 97%, 98%, or 99% amino acid sequence identity thereto; in some embodiments, the VH region comprises SEQ ID NO: 12 and the VL region comprises SEQ ID NO: 16, or sequences having at least or at least about 90%, 91%, 92%, 93%, 94%, 95%, 96%, 97%, 98%, or 99% amino acid sequence identity thereto.

In some embodiments, the antibody is a single chain fragment, such as one with two or more variable regions joined by one or more flexible immunoglobulin linker. In some embodiments, the antibody is an scFv. In some embodiments, the scFv comprises a linker that is rich in serine and/or glycine, such as a linker comprising GGGS (SEQ ID NO: 122) or GGGGS (SEQ ID NO:123) repeats, such as one comprising the sequence set forth SEQ ID NO: 34. In some embodiments the linker comprises a sequence of SEQ ID NO: 43.

In some embodiments, the antibody fragment, e.g., scFv, contains a VH region or portion thereof, followed by a linker, followed by a VL or portions thereof. In some embodiments, the antibody fragment, e.g., scFv, contains a VL region or portion thereof followed by a linker, followed by a VH region or portion thereof.

In some embodiments, the scFv comprises the amino acid sequence set forth in SEQ ID NO: 2, 4, 6, 8, or 10, or a sequence having at least or at least about 90%, 91%, 92%, 93%, 94%, 95%, 96%, 97%, 98%, or 99% amino acid sequence identity thereto.

In some embodiments, the scFv comprises the amino acid sequence set forth in SEQ ID NO: 2, 4, 6, 8, 10, 45, 47, 49, 51, 53, 55, 57, 59, 87, or 89, or has a sequence at least at or about 90, 91, 92, 93, 94, 95, 96, 97, 98, or 99% identical to such a sequence.

In some embodiments, the antibody or fragment specifically binds to the same, similar, and/or an overlapping epitope of CD19 as the epitope specifically bound by a reference antibody, and/or the antibody competes for binding to CD19 with the reference antibody. In some aspects, the reference antibody is a murine or chimeric or human or humanized anti-CD19 antibody, FMC63, SJ25C1, an antibody having a variable region sequence of SEQ ID NO: 39 and/or 40, or an antibody having a variable region sequence of SEQ ID NO: 41 and/or 42. In some aspect, the reference antibody is an antibody including a sequence as described herein, including sequence(s) of any of the aforementioned embodiments. For example, in some embodiments, the reference antibody can be an scFv that contains the amino acid sequence set forth in SEQ ID NO: 2, 4, 6, 8, 10, 45, 47, 49, 51, 53, 55, 57, 59, 87, or 89. In some embodiments, the provided antibody or fragment contains one or more or all CDRs that are distinct from those in the reference antibody. For example, in some embodiments, the provided antibody or fragment contains one or more or all CDRs that are distinct from the corresponding CDRs in the antibody designated FMC63 or SJ25C1.

For example, provided are human antibody and antigen-binding fragments that specifically bind to the same or an overlapping epitope of CD19 as the epitope specifically bound by the reference antibody, such as FMC63, SJ25C1, an antibody having a variable region sequence of SEQ ID NO: 39 and/or 40, or an antibody having a variable region sequence of SEQ ID NO: 41 and/or 42, and comprising heavy and light chain CDRs that are distinct from the CDRs present in the reference antibody.

In some embodiments, the antibody competes for binding with the reference antibody to at least the same degree as the reference antibody competes for binding with itself to CD19, or a degree of competition that is no more than 1.5-fold or 2-fold lower, 3-fold lower, 4-fold lower, 5-fold lower, or 10-fold lower than the competition by the reference antibody, and/or a measured IC50 that is no more than 1.5-fold or 2-fold or 3-fold or 4-fold or 5-fold or 10-fold higher than the IC50 of the reference antibody competing for binding with itself, for example, as measured in the same assay.

In some embodiments, the antibody has a binding affinity that is at least as high or substantially as high as the binding affinity for CD19 of the reference antibody. In some aspects, the antibody has a binding affinity of an EC50 that is about the same or lower than the EC50 reference antibody or no more than about 1.5-fold or no more than about 2-fold greater, no more than 3-fold greater, and/or no more than 10-fold greater, than the EC50 of the reference antibody. In some embodiments, binding affinity of the antibody is compared to the corresponding form of the reference antibody. Comparison is generally by the same or a similar assay.

In some of any such embodiments, CD19 is a human CD19. In some of any such embodiments, the antibody or fragment specifically binds, exhibits binding affinity and/or competes for binding to human CD19.

In some embodiments, the antibody is human. In some embodiments, the antibody is recombinant. In some embodiments, the antibody is monoclonal. In some embodiments, the antibody is isolated.

In some embodiments, the antibody or fragment further includes at least a portion of an immunoglobulin constant region. The constant region may include any one or more of CH1, CH2, CH3, and/or CH4, and/or CL, of a human or other antibody, and be of any class, including IgG, IgM, IgA, IgE, and IgD, for example, including human IgG, e.g., IgG1 or IgG4, constant region domains. In some embodiments, the constant region comprises or is an Fc region, such as a human IgG Fc region.

Also provided are molecules such as chimeric and/or fusion molecules, including receptors, such as recombinant receptors, that include the antibody of any of the embodiments (e.g., contained in or part of an extracellular domain) and additional domains, such as intracellular signaling domains, spacers, linkers, and/or transmembrane domains. In some embodiments, the receptor is a chimeric antigen receptor, comprising an extracellular portion comprising the antibody or fragment of any of the embodiments and an intracellular signaling domain.

In some embodiments, the antibody or fragment comprises an scFv. In some embodiments, the intracellular signaling domain comprises an ITAM and/or signaling domain capable of delivering a signal approximating that of natural ligation of an ITAM-containing molecule or receptor complex such as a TCR receptor complex. In some aspects, the intracellular signaling domain comprises a signaling domain of a zeta chain of a CD3-zeta (CD3) chain.

In some embodiments, the receptor further includes one or more domains, such as a transmembrane domain, linking the antibody transmembrane domain linking the extracellular domain and the intracellular signaling domain. In some aspects, the transmembrane domain comprises a transmembrane portion of a costimulatory molecule, such as a T cell costimulatory molecule, e.g., CD28 and/or 41BB. In some embodiments, the T cell costimulatory molecule is selected from the group consisting of CD28 and 41BB, and in some embodiments, the receptor includes signaling domains from CD28 and 41BB.

Also provided are nucleic acids encoding the antibody (including fragments) of any of embodiments or the receptor, e.g., chimeric antigen receptor of any of the embodiments, vectors including such nucleic acids, and cells containing the vectors and/or nucleic acids, for example, for expression of the antibodies and/or molecules.

Thus, also provided are cells and vectors for producing and expressing the molecules, including the antibodies and molecules such as receptors, e.g., chimeric antigen receptors (CARs). For example, provided are engineered cells expressing the chimeric antigen receptor of any of the embodiments. In some aspects, the cell is a T cell. In some aspects, the cell is an NK cell. In some aspects, the cell is a stem cell.

Also provided are compositions comprising the antibodies, receptors, molecules, and/or cells, including pharmaceutical compositions, e.g., further including pharmaceutically acceptable substances such as carriers.

Also provided are methods of administration, including methods of treatment, carried out by administering the cell, antibody, receptor, composition, or other molecule, of any of the embodiments, to a subject, for example, in an effective, e.g., therapeutically effective, amount. In some embodiments, the subject has or is suspected of having a disease or disorder associated with CD19, such as a B cell malignancy, such as B cell chronic lymphocytic leukemia (CLL), acute lymphocytic leukemia (ALL), pro-lymphocytic leukemias, hairy cell leukemias, common acute lymphocytic leukemias, Null-acute lymphoblastic leukemias, non-Hodgkin lymphomas, diffuse large B cell lymphomas (DLBCLs), multiple myelomas, follicular lymphoma, splenic, marginal zone lymphoma, mantle cell lymphoma, indolent B cell lymphoma, or Hodgkin lymphoma, or an autoimmune or inflammatory disease in which B cells are implicated.

In some embodiments, administration of the antibody or receptor is associated with a lower degree of immunogenicity as compared to administration of a reference antibody (or receptor containing the reference antibody) that competes for binding with the antibody or binds to an overlapping epitope. In some aspects, the reference antibody is a humanized, chimeric, or non-human antibody.

BRIEF DESCRIPTION OF THE DRAWINGS

FIGS. 14A and 14B show cytokine secretion of primary human CD8+ T cells expressing various anti-CD19 specific CARs after co-culture with CD19-expressing cells. C is EGFRt alone (negative control); FM is FMC63 scFv CAR, 18 is Clone 18 scFv CAR, 17 is Clone 17 scFv CAR, 76 is Clone 76 scFv CAR, 5 is Clone 5 scFv CAR and 18B is Clone 18B scFv CAR.

FIGS. 16A and 16B show proliferation of primary human CD8+ T cells or CD4+ T cells, respectively, expressing various anti-CD19 specific CARs against CD19-expressing cells after co-culture with CD19-expressing cells.

DETAILED DESCRIPTION

Figure 1A:
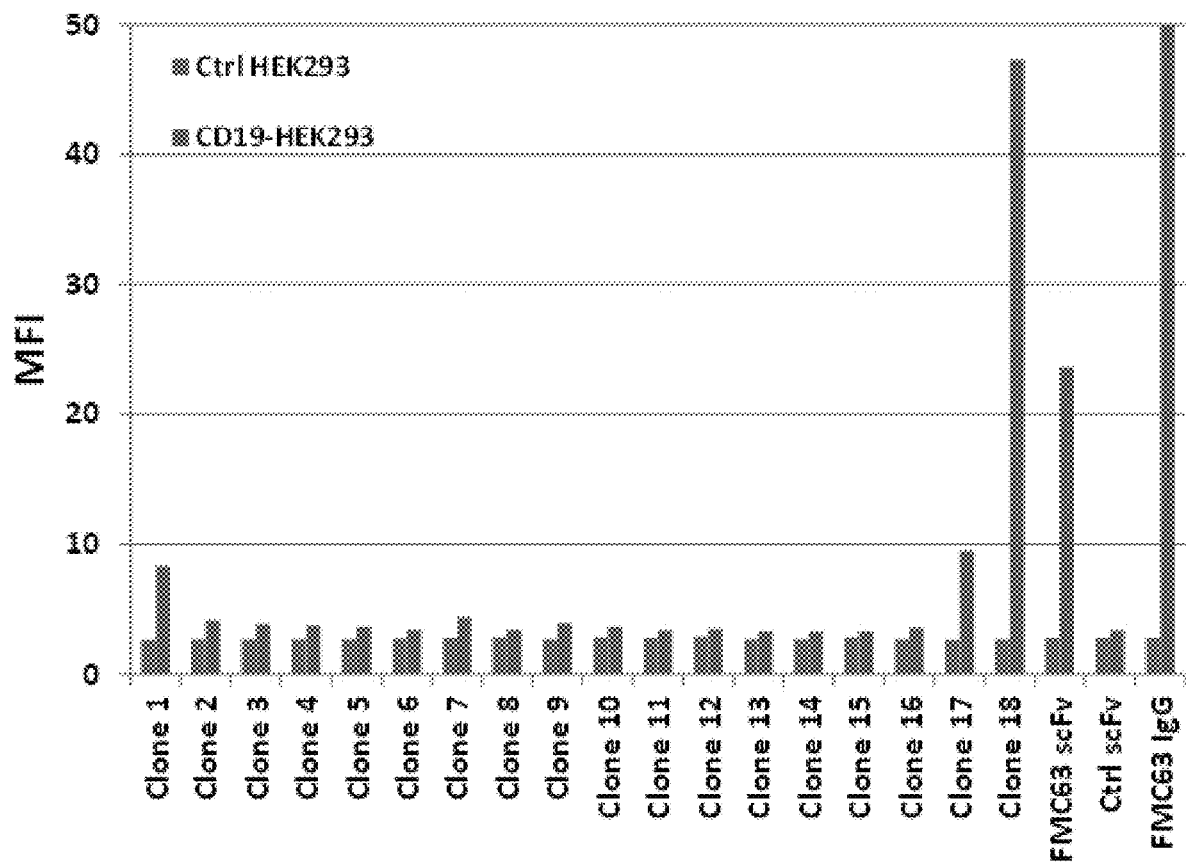
FIGS. 1A and 1B show results from a binding assay comparing binding of exemplary human scFvs to CD19-expressing HEK293 cells as compared to binding to non-CD19-expressing HEK293 cells. MFI=mean fluorescence intensity.

Provided are CD19-binding molecules, including antibodies (including antigen-binding antibody fragments, such as single chain fragments, including scFvs) and recombinant receptors, including chimeric receptors containing such antibodies and fragments, nucleic acids encoding such antibodies and fragments, and cells, such as recombinant cells, expressing and for production of these antibodies and fragments. Also provided are methods of making and using the antibodies and fragments as well as cells expressing or containing the antibodies and fragments.

I. CD19 BINDING MOLECULES

Provided in some aspects are CD19 binding molecules, such as CD19-binding polypeptides. Such binding molecules include antibodies that specifically bind to CD19, such as a human CD19 molecule, including antigen-binding fragments thereof. Also among the binding molecules are recombinant receptors such as chimeric antigen receptors containing such antibodies.

A. CD19 Antibodies

Provided are anti-CD19 antibodies, including functional antibody fragments, including those comprising a variable heavy chain and a variable light chain, such as scFvs. Also provided are molecules containing such antibodies, e.g., fusion proteins and/or recombinant receptors such as chimeric receptors, including antigen receptors. Among the provided anti-CD19 antibodies are human antibodies. In some embodiments, the antibodies, such as the human antibodies, specifically bind to a particular epitope or region of CD19, generally an extracellular epitope or region. In some embodiments, the antibodies bind to the same or a similar epitope or region of CD19 as bound by another antibody, such as one or more of the mouse antibodies, FMC63 or SJ25C1. In some embodiments, the antibodies bind to an overlapping epitope of CD19 as bound by one of these known antibodies and/or compete for binding with such an antibody. The antibodies include isolated antibodies. The molecules include isolated molecules.

The term "antibody" herein is used in the broadest sense and includes polyclonal and monoclonal antibodies, including intact antibodies and functional (antigen-binding) antibody fragments, including fragment antigen binding (Fab) fragments, F(ab')$_2$ fragments, Fab' fragments, Fv fragments, recombinant IgG (rIgG) fragments, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD.

The terms "complementarity determining region," and "CDR," synonymous with "hypervariable region" or "HVR," are known in the art to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4).

The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273, 927-948 ("Chothia" numbering scheme), MacCallum et al., J. Mol. Biol. 262: 732-745 (1996), "Antibody-antigen interactions: Contact analysis and binding site topography," J. Mol. Biol. 262, 732-745." ("Contact" numbering scheme), Lefranc M P et al., "IMGT unique numbering for immunoglobulin and T cell receptor variable domains and Ig superfamily V-like domains," Dev Comp Immunol, 2003 January; 27(1):55-77 ("IMGT" numbering scheme), and Honegger A and Pluckthun A, "Yet another numbering scheme for immunoglobulin variable domains: an automatic modeling and analysis tool," J Mol Biol, 2001 Jun. 8; 309(3):657-70, ("Aho" numbering scheme).

The boundaries of a given CDR or FR may vary depending on the scheme used for identification. For example, the Kabat scheme is based structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme.

Table 1, below, lists exemplary position boundaries of CDR-L1, CDR-L2, CDR-L3 and CDR-H1, CDR-H2, CDR-H3 as identified by Kabat, Chothia, and Contact schemes, respectively. For CDR-H1, residue numbering is listed using both the Kabat and Chothia numbering schemes. FRs are located between CDRs, for example, with FR-L1 located between CDR-L1 and CDR-L2, and so forth. It is noted that because the shown Kabat numbering scheme places insertions at H35A and H35B, the end of the Chothia CDR-H1 loop when numbered using the shown Kabat numbering convention varies between H32 and H34, depending on the length of the loop.

TABLE 1

| CDR | Kabat | Chothia | Contact |
| --- | --- | --- | --- |
| CDR-L1 | L24--L34 | L24--L34 | L30--L36 |
| CDR-L2 | L50--L56 | L50--L56 | L46--L55 |
| CDR-L3 | L89--L97 | L89--L97 | L89--L96 |
| CDR-H1 (Kabat Numbering[1]) | H31--H35B | H26--H32 . . . 34 | H30--H35B |
| CDR-H1 (Chothia Numbering[2]) | H31--H35 | H26--H32 | H30--H35 |
| CDR-H2 | H50--H65 | H52--H56 | H47--H58 |
| CDR-H3 | H95--H102 | H95--H102 | H93--H101 |

[1]Kabat et al. (1991), "Sequences of Proteins of Immunological Interest," 5th Ed. Public Health Service, National Institutes of Health, Bethesda, MD
[2]Al-Lazikani et al., (1997) JMB 273, 927-948

Thus, unless otherwise specified, a "CDR" or "complementary determining region," or individual specified CDRs (e.g., "CDR-H1, CDR-H2), of a given antibody or region thereof, such as a variable region thereof, should be understood to encompass a (or the specific) complementary determining region as defined by any of the aforementioned schemes. For example, where it is stated that a particular CDR (e.g., a CDR-H3) contains the amino acid sequence of a corresponding CDR in a given VH or VL amino acid sequence, it is understood that such a CDR has a sequence of the corresponding CDR (e.g., CDR-H3) within the variable region, as defined by any of the aforementioned schemes. In some embodiments, specified CDR sequences are specified.

Likewise, unless otherwise specified, a FR or individual specified FR(s) (e.g., FR-H1, FR-H2), of a given antibody or region thereof, such as a variable region thereof, should be understood to encompass a (or the specific) framework region as defined by any of the known schemes. In some instances, the scheme for identification of a particular CDR, FR, or FRs or CDRs is specified, such as the CDR as defined by the Kabat, Chothia, or Contact method. In other cases, the particular amino acid sequence of a CDR or FR is given.

The term "variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., J. Immunol. 150: 880-887 (1993); Clarkson et al., Nature 352:624-628 (1991).

Among the provided antibodies are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments. In particular embodiments, the antibodies are single-chain antibody fragments comprising a variable heavy chain region and/or a variable light chain region, such as scFvs.

Single-domain antibodies are antibody fragments comprising all or a portion of the heavy chain variable domain or all or a portion of the light chain variable domain of an antibody. In certain embodiments, a single-domain antibody is a human single-domain antibody.

Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, e.g., peptide linkers, and/or that are may not be produced by enzyme digestion of a naturally-occurring intact antibody. In some aspects, the antibody fragments are scFvs.

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody, refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

Among the provided anti-CD19 antibodies are human antibodies. A "human antibody" is an antibody with an amino acid sequence corresponding to that of an antibody produced by a human or a human cell, or non-human source that utilizes human antibody repertoires or other human antibody-encoding sequences, including human antibody libraries. The term excludes humanized forms of non-human antibodies comprising non-human antigen-binding regions, such as those in which all or substantially all CDRs are non-human.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic animals, the endogenous immunoglobulin loci have generally been inactivated. Human antibodies also may be derived from human antibody libraries, including phage display and cell-free libraries, containing antibody-encoding sequences derived from a human repertoire.

Among the provided antibodies are monoclonal antibodies, including monoclonal antibody fragments. The term "monoclonal antibody" as used herein refers to an antibody obtained from or within a population of substantially homogeneous antibodies, i.e., the individual antibodies comprising the population are identical, except for possible variants containing naturally occurring mutations or arising during production of a monoclonal antibody preparation, such variants generally being present in minor amounts. In contrast to polyclonal antibody preparations, which typically include different antibodies directed against different epitopes, each monoclonal antibody of a monoclonal antibody preparation is directed against a single epitope on an antigen. The term is not to be construed as requiring production of the antibody by any particular method. A monoclonal antibody may be made by a variety of techniques, including but not limited to generation from a hybridoma, recombinant DNA methods, phage-display and other antibody display methods.

The terms "polypeptide" and "protein" are used interchangeably to refer to a polymer of amino acid residues, and are not limited to a minimum length. Polypeptides, including the provided antibodies and antibody chains and other peptides, e.g., linkers and CD19-binding peptides, may include amino acid residues including natural and/or non-natural amino acid residues. The terms also include post-expression modifications of the polypeptide, for example, glycosylation, sialylation, acetylation, phosphorylation, and the like. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

Exemplary Anti-CD19 Antibodies

In some embodiments, the anti-CD19 antibody, e.g., antigen-binding antibody fragment, contains particular heavy and/or light chain CDR sequences and/or heavy and/or light chain variable ($V_H$ or $V_L$) region sequences. Also among the provided antibodies are those having sequences at least at or about 90, 91, 92, 93, 94, 95, 96, 97, 98, or 99% identical to such a sequence.

In some embodiments, the antibody, e.g., antigen-binding fragment thereof, includes a heavy chain complementarity determining region 3 (CDR-H3) comprising an amino acid sequence of a CDR-H3 present in a reference antibody, such as one present in a reference antibody having a VH region with the amino acid sequence set forth in set forth in SEQ ID NO: 11, 12, 60, 61, 63 62, 167 or 185, such as set forth in SEQ ID NO: 11, 12, 60, 61, 63, or 62. In some embodiments, the CDR-H3 comprises SEQ ID NO: 20. In some embodiments, the antibody, e.g., antigen-binding fragment thereof, has a VH region having at least 90, 91, 92, 93, 94, 95, 96, 97, 98, or 99% sequence identity to (or 100% identity thereto) the VH region amino acid sequence of the reference antibody, such as to the VH region amino acid sequence set forth in SEQ ID NO: 11, 12, 60, 61, 63 62, 167 or 185, such as set forth in SEQ ID NO: 11, 12, 60, 61, 63, or 62.

In some embodiments, the CDR-H1 contains the amino acid sequence DYAMH (SEQ ID NO: 18), the CDR-H2 contains the amino acid sequence GISWNSGRIG (SEQ ID NO: 81), GISWNSGSIG (SEQ ID NO: 82), the amino acid sequence set forth in SEQ ID NO: 19 (GISWNSGRIG-YADSVKG), or the amino acid sequence set forth in SEQ ID NO: 72 (GISWNSGSIGYADSVKG), and/or the CDR-H3 contains the amino acid sequence of SEQ ID NO: 20.

In some embodiments, the provided antibody contains a CDR-H3 having the amino acid sequence of SEQ ID NO: 20.

In some embodiments, the antibody contains a $V_H$ having the amino acid sequence set forth in SEQ ID NO: 11 or 12, or has a sequence at least at or about 90, 91, 92, 93, 94, 95, 96, 97, 98, or 99% identical to such a sequence. In some embodiments, the antibody, e.g., antigen-binding fragment thereof, contains a VH region having the amino acid sequence set forth in SEQ ID NO: 11, 12, 60, 61, 63, or 62, or a sequence at least at or about 90, 91, 92, 93, 94, 95, 96, 97, 98, or 99% identical to such a sequence. In some embodiments, the antibody, e.g., antigen-binding fragment thereof, contains a VH region having the amino acid sequence set forth in SEQ ID NO: 11, 12, 60, 61, 63, 62, 167 or 185, or a sequence at least at or about 90, 91, 92, 93, 94, 95, 96, 97, 98, or 99% identical to such a sequence.

In some embodiments, the antibody contains the sequence of residues 1-119 of SEQ ID NO: 11, 12, 60, 61, 63, 62, 167 or 185 or a sequence comprising the portion of SEQ ID NO: 11, 12, 60, 61, 63, 62, 167 or 185 including the first three framework regions and the three heavy chain CDRs. In some embodiments, the antibody contains the sequence of residues 1-119 of SEQ ID NO: 11, 12, 60, 61, 63 or 62 or a sequence comprising the portion of SEQ ID NO: 11, 12, 60, 61, 63, or 62 including the first three framework regions and the three heavy chain CDRs.

In some embodiments, the anti-CD19 antibody includes light chain complementarity determining regions 1, 2, and/or 3 (CDR-L1, CDR-L2, and/or CDR-L3), respectively, having the amino acid sequences of CDR 1, 2, and/or 3 sequences contained within the light chain variable (VL) region amino acid sequence set forth in SEQ ID NO: 13, 14, 15, 16, 17, 71, 65, 64, 66, 70, 69, 67, 90, 91 or 187-205, such as set forth in SEQ ID NO: 13, 14, 15, 16, or 17, or in SEQ ID NO: 13, 14, 15, 16, 17, 71, 90, 91, 68, 65, 64, 66, 70, 69, or 67.

In some embodiments, the anti-CD19 antibody includes a CDR-L1, CDR-L2, and/or CDR-L3 in which:

In some embodiments, the CDR-L1 contains the amino acid sequence: $X_1X_2X_3X_4X_5X_6X_7X_8X_9X_{10}X_{11}X_{12}X_{13}X_{14}$ (SEQ ID NO: 110), wherein $X_1$ is T, W, S or R; $X_2$ is G or A; $X_3$ is I, T, D or S; $X_4$ is S, R, T or Q; $X_5$ is null or S; $X_6$ is null, D, N or G; $X_7$ is null, V or L; $X_8$ is X or null; $X_9$ is X or null; $X_{10}$ is X; $X_{11}$ is X; $X_{12}$ is Y, F, D or W; $X_{13}$ is V, A or L and $X_{14}$ is S, N or A. For example, in some embodiments, the CDR-L1 contains the amino acid sequence of $X_1X_2X_3X_4X_5X_6X_7X_8X_9X_{10}X_{11}X_{12}X_{13}X_{14}$ (SEQ ID NO: 226), wherein $X_1$ is T, Q, S, or R; $X_2$ is G, A or E; $X_3$ is I, T, A, D, or S; $X_4$ is S, R, T Q, G or I; $X_5$ is null, S, R or T; $X_6$ is G, D, N, or null; $X_7$ is null, V, L or I; $X_8$ is D, G, I, L, S, or null; $X_9$ is S, G, A, I, D, R, or null; $X_{10}$ is H, Y, F, S, or N; $X_{11}$ is R, N, D, H, Y or T; $X_{12}$ is Y, F, D, W, H, T or S; $X_{13}$ is V, A, or L; and $X_{14}$ is S, N, or A. In some embodiments, the CDR-L1 contains the amino acid sequence $X_1X_2X_3X_4X_5X_6X_7X_8X_9X_{10}X_{11}X_{12}X_{13}X_{14}$ (SEQ ID NO: 111), wherein $X_1$ is T, Q, S, or R; $X_2$ is G or A; $X_3$ is I, T, D, or S; $X_4$ is S, R, T, or Q; $X_5$ is null or S; $X_6$ is G, D, N, or null; $X_7$ is null, V, or L; $X_8$ is D, G, I, L, S, or null; $X_9$ is S, G, A, I, R, or null; $X_{10}$ is H, Y, F, S, or N; $X_{11}$ is R, N, D, H, or Y; $X_{12}$ is Y, F, D, or W; $X_{13}$ is V, A, or L; and $X_{14}$ is S, N, or A.

In some embodiments, the CDR-L2 contains the amino acid sequence of $X_1X_2X_3X_4X_5X_6X_7$ (SEQ ID NO: 227), wherein $X_1$ is D, S or G; $X_2$ is F, V, N, K, or A; $X_3$ is S, T, D, or N; $X_4$ is K, V, N, Q, or R; $X_5$ is R, V, or L; $X_6$ is P, K, A, or E; and $X_7$ is S, P, A, or T. In some embodiments, the CDR-L2 contains the amino acid sequence of $X_1X_2X_3X_4X_5X_6X_7$ (SEQ ID NO: 112), wherein $X_1$ is D or S; $X_2$ is F, V, N, K, or A; $X_3$ is S, T, D, or N; $X_4$ is K, V, N, Q, or R; $X_5$ is R, V, or L; $X_6$ is P, K, A, or E; and $X_7$ is S, P, A, or T.

In some embodiments, the CDR-L3 contains the amino acid sequence of $X_1X_2X_3X_4X_5X_6X_7X_8X_9X_{10}X_{11}X_{12}$ (SEQ ID NO: 228), wherein $X_1$ is S, G, T, A, Q, C, or N; $X_2$ is S, Q, A, or T; $X_3$ is Y, S, W, R; $X_4$ is A, D, R, T, or Y; $X_5$ is A, S, P, G, N, or D; $X_6$ is S, G, T, A, L, H, R, or N; $X_7$ is S, P, L, Y, G; $X_8$ is P, T, S, Q, M, R, N or null; $X_9$ is S, L, N, A, M, R or null; $X_{10}$ is L, D or null; $X_{11}$ is Y, W, F, V, A, or L; and $X_{12}$ is V, T, P or L. In some embodiments, the CDR-L3 contains the amino acid sequence of $X_1X_2X_3X_4X_5X_6X_7X_8X_9X_{10}X_{11}X_{12}$ (SEQ ID NO: 115), wherein $X_1$ is X; $X_2$ is S, Q, A, or T; $X_3$ is Y, S, W, R; $X_4$ is A, D, R, T, or Y; $X_5$ is X; $X_6$ is X; $X_7$ is S, P, L, Y, G; $X_8$ is X or null; $X_9$ is X or null; $X_{10}$ is L or null; $X_{11}$ is X; and $X_{12}$ is V, T, or L. For example, in some embodiments, the antibody has a CDR-L3 comprising the amino acid sequence $X_1X_2X_3X_4X_5X_6X_7X_8X_9X_{10}X_{11}X_{12}$ (SEQ ID NO: 114), wherein $X_1$ is S, G, T, A, Q, C or N; $X_2$ is S, Q, A, or T; $X_3$ is Y, S, W, R; $X_4$ is A, D, R, T, or Y; $X_5$ is A, S, P, G, N or D; $X_6$ is I, S, G, T, A, L, H, R, N; $X_7$ is S, P, L, Y, G; $X_8$ is P, T, S, Q, M, R, N or null; $X_9$ is S, L, N, A, M or null; $X_{10}$ is L or null; $X_{11}$ is Y, W, F, V, A or L; and $X_{12}$ is V, T, or L In some embodiments, in the CDR-L1, such as set forth in SEQ ID NO:110, 226 or 111, $X_3$ is I, T, or S; $X_4$ is S, T, or Q; $X_5$ is D, G, I, S, or null; $X_9$ is S, G, I, or null; $X_{10}$ is H, Y, S, or N; $X_{11}$ is R, N, D, or H; $X_{12}$ is Y or D; and $X_{13}$ is V or L; and/or in the CDR-L2, such as set forth in SEQ ID NO:227 or 112, $X_1$ is D; $X_4$ is K, V, N, Q, or R; $X_6$ is P, K, or A; and $X_7$ is S, A, or T; and/or in the CDR-L3, such as set forth in SEQ ID NO:228, 114 or 115, $X_1$ is S, G, T, A, Q, C, or N; $X_5$ is A, S, P, G, N, or D; $X_6$ is I, S, G, T, A, L, H, R, or N; $X_8$ is P, T, S, Q, M, R, N or null; $X_9$ is S, L, N, A, M or null; and $X_{11}$ is Y, W, F, V, A, or L. In some embodiments, in the CDR-L3, $X_1$ is S, G, Q, or N; $X_2$ is S, Q, or T; $X_4$ is A, D, T, or Y; $X_5$ is A, S, or G; and $X_6$ is I, S, N, R, A, H, or T.

In some embodiments, the antibody includes a sequence of amino acids that contains a CDR-L1 set forth in SEQ ID NO:83, a CDR-L2 set forth in SEQ ID NO:84 and/or a CDR-L3 set forth in SEQ ID NO:85.

In some embodiments, the antibody, e.g., the antibody fragment contains a CDR-L1 that contains the amino acid sequence set forth in SEQ ID NO: 21, 25, 28, or 31. In some embodiments, the antibody or fragment contains a CDR-L1 that contains the amino acid sequence set forth in SEQ ID NO: 80, 77, 74, 73, 75, 79, 78, 76, 21, 25, 28, 31 or 146 to 152, such as contains the amino acid sequence set forth in SEQ ID NO: 80, 77, 74, 73, 75, 79, 78, 76, 21, 25, 28, or 31.

In some embodiments, the antibody or fragment contains a CDR-L1 that contains the amino acid sequence set forth in SEQ ID NO: 80, 77, 74, 73, 78, 21, or 28.

In some embodiments, the antibody or fragment contains a CDR-L2 that contains the amino acid sequence set forth in SEQ ID NO: 22, 26, 29, or 32. In some embodiments, the antibody or fragment contains a CDR-L2 that contains the amino acid sequence SEQ ID NO: 100, 97, 94, 93, 95, 99, 98, 96, 22, 26, 29, 32 or 153 to 157, such as contains the amino acid sequence set forth in SEQ ID NO: 100, 97, 94, 93, 95, 99, 98, 96, 22, 26, 29, or 32. In some embodiments, the antibody or fragment contains a CDR-L2 that contains the amino acid sequence set forth in SEQ ID NO: 100, 97, 94, 93, 98, 22, or 29.

In some embodiments, the antibody or fragment contains a CDR-L3 that includes the sequence set forth in SEQ ID NO: 23, 24, 27, 30, or 33. In some embodiments, the antibody or fragment contains a CDR-L3 that includes the sequence set forth in SEQ ID NO: 109, 106, 103, 101, 104, 108, 107, 105, 102, 23, 24, 27, 30, 33, 158 or 159, such as contains the amino acid sequence set forth in SEQ ID NO: 109, 106, 103, 101, 104, 108, 107, 105, 102, 23, 24, 27, 30, or 33. In some embodiments, the antibody or fragment contains a CDR-L3 that includes the sequence set forth in SEQ ID NO: 109, 106, 103, 101, 107, 24 or 30.

In some embodiments, the CDR-L1, CDR-L2, and CDR-L3 contain the sequences of SEQ ID NOs: 21, 22, and 23, respectively; the CDR-L1, CDR-L2, and CDR-L3 include the sequences of SEQ ID NOs: 21, 22, and 24, respectively; the CDR-L1, CDR-L2, and CDR-L3 include the sequences of SEQ ID NOs: 25, 26, and 27, respectively; the CDR-L1, CDR-L2, and CDR-L3 contain the sequences of SEQ ID NOs: 28, 29, and 30, respectively; or the CDR-L1, CDR-L2, and CDR-L3 contain the sequences of SEQ ID NOs: 31, 32, and 33, respectively.

In some embodiments, the CDR-L1, CDR-L2, and CDR-L3 comprise the sequences of SEQ ID NOs: 21, 22, and 23, respectively; the CDR-L1, CDR-L2, and CDR-L3 comprise the sequences of SEQ ID NOs: 21, 22, and 24, respectively; the CDR-L1, CDR-L2, and CDR-L3 comprise the sequences of SEQ ID NOs: 25, 26, and 27, respectively; the CDR-L1, CDR-L2, and CDR-L3 comprise the sequences of SEQ ID NOs: 28, 29, and 30, respectively; the CDR-L1, CDR-L2, and CDR-L3 comprise the sequences of SEQ ID NOs: 31, 32, and 33, respectively; the CDR-L1, CDR-L2, and CDR-L3 comprise the sequences of SEQ ID NOs: 80, 100, and 109, respectively; the CDR-L1, CDR-L2, and CDR-L3 comprise the sequences of SEQ ID NOs:77, 97, and 106, respectively; the CDR-L1, CDR-L2, and CDR-L3 comprise the sequences of SEQ ID NOs: 74, 94, and 103, respectively; the CDR-L1, CDR-L2, and CDR-L3 comprise the sequences of SEQ ID NOs: 73, 93, and 101, respectively; the CDR-L1, CDR-L2, and CDR-L3 comprise the sequences of SEQ ID NOs:75, 95, and 104, respectively; the CDR-L1, CDR-L2, and CDR-L3 comprise the sequences of SEQ ID NOs: 79, 99, and 108, respectively; the CDR-L1, CDR-L2, and CDR-L3 comprise the sequences of SEQ ID NOs: 78, 98, and 107, respectively; the CDR-L1, CDR-L2, and CDR-L3 comprise the sequences of SEQ ID NOs: 76, 96, and 105, respectively; the CDR-L1, CDR-L2, and CDR-L3 comprise the sequences of SEQ ID NOs: 73, 93, and 102, respectively; the CDR-L1, CDR-L2, and CDR-L3 comprise the sequences of SEQ ID NOs: 77, 97, and 106, respectively; the CDR-L1, CDR-L2, and CDR-L3 comprise the sequences of SEQ ID NOs: 163, 164, and 165, respectively; the CDR-L1, CDR-L2, and CDR-L3 comprise the sequences of SEQ ID NOs: 80, 100, and 109, respectively; the CDR-L1, CDR-L2, and CDR-L3 comprise the sequences of SEQ ID NOs: 146, 97, and 106, respectively; the CDR-L1, CDR-L2, and CDR-L3 comprise the sequences of SEQ ID NOs: 28, 153 and 158, respectively; the CDR-L1, CDR-L2, and CDR-L3 comprise the sequences of SEQ ID NOs: 74, 94, and 103, respectively; the CDR-L1, CDR-L2, and CDR-L3 comprise the sequences of SEQ ID NOs: 147, 154 and 121, respectively; the CDR-L1, CDR-L2, and CDR-L3 comprise the sequences of SEQ ID NOs: 148, 94 and 103, respectively; the CDR-L1, CDR-L2, and CDR-L3 comprise the sequences of SEQ ID NOs: 75, 95 and 104, respectively; the CDR-L1, CDR-L2, and CDR-L3 comprise the sequences of SEQ ID NOs: 149, 155 and 119, respectively; the CDR-L1, CDR-L2, and CDR-L3 comprise the sequences of SEQ ID NOs: 150, 22, and 120, respectively; the CDR-L1, CDR-L2, and CDR-L3 comprise the sequences of SEQ ID NOs: 21, 22 and 159, respectively; the CDR-L1, CDR-L2, and CDR-L3 comprise the sequences of SEQ ID NOs: 151, 26 and 118, respectively; the CDR-L1, CDR-L2, and CDR-L3 comprise the sequences of SEQ ID NOs: 28, 156 and 116, respectively; or the CDR-L1, CDR-L2, and CDR-L3 comprise the sequences of SEQ ID NOs: 152, 157 and 117, respectively.

Also provided are antibodies having sequences at least at or about 90, 91, 92, 93, 94, 95, 96, 97, 98, or 99% identical to such sequences.

In some embodiments, the CDR-H1, CDR-H2, and CDR-H3 comprise the sequences of SEQ ID NOs: 18, 81, and 20, respectively; the CDR-H1, CDR-H2, and CDR-H3 comprise the sequences of SEQ ID NOs: 18, 19, and 20, respectively; the CDR-H1, CDR-H2, and CDR-H3 comprise the sequences of SEQ ID NOs: 18, 82, and 20, respectively; or the CDR-H1, CDR-H2, and CDR-H3 comprise the sequences of SEQ ID NOs: 18, 72, and 20, respectively.

Also provided are antibodies having sequences at least at or about 90, 91, 92, 93, 94, 95, 96, 97, 98, or 99% identical to such sequences.

In some embodiments, the VH region of the antibody or fragment comprises the amino acid sequence of SEQ ID NO: 11, 12, 60, 61, 6362, 167 or 185, such as SEQ ID NO: 11, 12, 60, 61, 63, or 62; and/or the VL region of the antibody or fragment comprises the amino acid sequence of SEQ ID NO: 13, 14, 15, 16, 17, 71, 90, 91, 68, 65, 64, 66, 70, 69, 67 or 187 to 205, such as SEQ ID NO: 13, 14, 15, 16, 17, 71, 90, 91, 68, 65, 64, 66, 70, 69, or 67. In some embodiments, the VH region of the antibody or fragment comprises the amino acid sequence of SEQ ID NO: 11, 60, 63, or 62; and/or the VL region of the antibody or fragment comprises the amino acid sequence of SEQ ID NO: 14, 16, 71, 90, 65, 64, or 69.

Also provided are antibodies having sequences at least at or about 90, 91, 92, 93, 94, 95, 96, 97, 98, or 99% identical to such sequences.

In some embodiments, the VH and VL regions of the antibody or fragment comprise the amino acid sequences of SEQ ID NOs: 12 and 17, respectively; the VH and VL regions of the antibody or fragment comprise the amino acid sequences of SEQ ID NOs: 12 and 15, respectively; the VH and VL regions of the antibody or fragment comprise the amino acid sequences of SEQ ID NOs: 11 and 13, respectively; the VH and VL regions of the antibody or fragment comprise the amino acid sequences of SEQ ID NOs: 11 and 14, respectively; the VH and VL regions of the antibody or fragment comprise the amino acid sequences of SEQ ID NOs: 11 and 16, respectively; the VH and VL regions of the antibody or fragment comprise the amino acid sequences of SEQ ID NOs: 63 and 71, respectively; the VH and VL regions of the antibody or fragment comprise the amino acid sequences of SEQ ID NOs: 62 and 68, respectively; the VH and VL regions of the antibody or fragment comprise the amino acid sequences of SEQ ID NOs: 11 and 65, respectively; the VH and VL regions of the antibody or fragment comprise the amino acid sequences of SEQ ID NOs: 60 and 64, respectively; the VH and VL regions of the antibody or fragment comprise the amino acid sequences of SEQ ID NOs: 61 and 66, respectively; the VH and VL regions of the antibody or fragment comprise the amino acid sequences of SEQ ID NOs: 63 and 70, respectively; the VH and VL regions of the antibody or fragment comprise the amino acid sequences of SEQ ID NOs: 62 and 69, respectively; the VH and VL regions of the antibody or fragment comprise the amino acid sequences of SEQ ID NOs: 12 and 67, respectively; the VH and VL regions of the antibody or fragment comprise the amino acid sequences of SEQ ID NOs: 12 and 91, respectively; or the VH and VL regions of the antibody or fragment comprise the amino acid sequences of SEQ ID NOs: 63 and 90, respectively. In some embodiments, the VH and VL regions of the antibody or fragment comprise the amino acid sequences of SEQ ID NOs: 11 and 14, respectively; the VH and VL regions of the antibody or fragment comprise the amino acid sequences of SEQ ID NOs: 11 and 16, respectively; the VH and VL regions of the antibody or fragment comprise the amino acid sequences of SEQ ID NOs: 63 and 71, respectively; the VH and VL regions of the antibody or fragment comprise the amino acid sequences of SEQ ID NOs: 11 and 65, respectively; the VH and VL regions of the antibody or fragment comprise the amino acid sequences of SEQ ID NOs: 60 and 64, respectively; the VH and VL regions of the antibody or fragment comprise the amino acid sequences of SEQ ID NOs: 62 and 69, respectively; the VH and VL regions of the antibody or fragment comprise the amino acid sequences of SEQ ID NOs: 63 and 90, respectively; the VH and VL regions of the antibody or fragment comprise the amino acid sequences of SEQ ID NOs: 167 and 207, respectively; the VH and VL regions of the antibody or fragment comprise the amino acid sequences of SEQ ID NOs: 168 or 63 and 208, respectively; the VH and VL regions of the antibody or fragment comprise the amino acid sequences of SEQ ID NOs: 169 or 11 and 209, respectively; the VH and VL regions of the antibody or fragment comprise the amino acid sequences of SEQ ID NOs: 170 or 61 and 210, respectively; the VH and VL regions of the antibody or fragment comprise the amino acid sequences of SEQ ID NOs: 171 or 61 and 211, respectively; the VH and VL regions of the antibody or fragment comprise the amino acid sequences of SEQ ID NOs: 172 and 212, respectively; the VH and VL regions of the antibody or fragment comprise the amino acid sequences of SEQ ID NOs: 173 or 11 and 213, respectively; the VH and VL regions of the antibody or fragment comprise the amino acid sequences of SEQ ID NOs: 174 or 11 and 214, respectively; the VH and VL regions of the antibody or fragment comprise the amino acid sequences of SEQ ID NOs: 175 or 11 and 215, respectively; the VH and VL regions of the antibody or fragment comprise the amino acid sequences of SEQ ID NOs: 176 or 61 and 216, respectively; the VH and VL regions of the antibody or fragment comprise the amino acid sequences of SEQ ID NOs: 177 or 61 and 217, respectively; the VH and VL regions of the antibody or fragment comprise the amino acid sequences of SEQ ID NOs: 178 or 61 and 218, respectively; the VH and VL regions of the antibody or fragment comprise the amino acid sequences of SEQ ID NOs: 179 or 61 and 219, respectively; the VH and VL regions of the antibody or fragment comprise the amino acid sequences of SEQ ID NOs: 180 or 12 and 220, respectively; the VH and VL regions of the antibody or fragment comprise the amino acid sequences of SEQ ID NOs: 181 or 12 and 221, respectively; the VH and VL regions of the antibody or fragment comprise the amino acid sequences of SEQ ID NOs: 182 or 11 and 222, respectively; the VH and VL regions of the antibody or fragment comprise the amino acid sequences of SEQ ID NOs: 183 or 60 and 223, respectively; the VH and VL regions of the antibody or fragment comprise the amino acid sequences of SEQ ID NOs: 184 or 11 and 224, respectively; or the VH and VL regions of the antibody or fragment comprise the amino acid sequences of SEQ ID NOs: 185 and 225, respectively.

Also provided are antibodies having sequences at least at or about 90, 91, 92, 93, 94, 95, 96, 97, 98, or 99% identical to such sequences.

In some embodiments, the antibody or fragment contains a $V_H$ region including the amino acid sequence of SEQ ID NO: 11 or 12 or residues 1-119 of such a sequence or a sequence having at least at or about 90, 91, 92, 93, 94, 95, 96, 97, 98, or 99% identical to such a sequence.

In some embodiments, the antibodies include or further include a $V_L$ region including the amino acid sequence of SEQ ID NO: 13, 14, 15, 16, 17, or a sequence having at least at or about 90, 91, 92, 93, 94, 95, 96, 97, 98, or 99% identical to such a sequence.

In some embodiments, the antibody is a single-chain antibody fragment, such as an scFv or diabody. In some embodiments, the single-chain antibody includes one or more linkers joining two antibody domains or regions, such as a variable heavy chain ($V_H$) region and a variable light chain ($V_L$). The linker typically is a peptide linker, e.g., a flexible and/or soluble peptide linker. Among the linkers are those rich in glycine and serine and/or in some cases threonine. In some embodiments, the linkers further include charged residues such as lysine and/or glutamate, which can improve solubility. In some embodiments, the linkers further include one or more proline.

Accordingly, also provided are single-chain antibody fragments, such as scFvs and diabodies, particularly human single-chain fragments, typically comprising linker(s) joining two antibody domains or regions, such VH and VL domains. The linker typically is a peptide linker, e.g., a flexible and/or soluble peptide linker, such as one rich in glycine and serine.

In some aspects, the linkers rich in glycine and serine (and/or threonine) include at least 80, 85, 90, 91, 92, 93, 94, 95, 96, 97, 98, or 99% such amino acid(s). In some embodiments, they include at least at or about 50%, 55%, 60%, 70%, or 75%, glycine, serine, and/or threonine. In some embodiments, the linker is comprised substantially entirely of glycine, serine, and/or threonine. The linkers generally are between about 5 and about 50 amino acids in length, typically between at or about 10 and at or about 30, e.g., 10, 11, 12, 13, 14, 15, 16, 17, 18, 19, 20, 21, 22, 23, 24, 25, 26, 27, 28, 29, or 30, and in some examples between 10 and 25 amino acids in length. Exemplary linkers include linkers having various numbers of repeats of the sequence GGGGS (4GS; SEQ ID NO:123) or GGGS (3GS; SEQ ID NO:122), such as between 2, 3, 4, and 5 repeats of such a sequence. Exemplary linkers include those having or consisting of a sequence set forth in SEQ ID NO: 34 (GGGGSGGGGSGGGGS). Exemplary linkers further include those having or consisting of the sequence set forth in SEQ ID NO: 43 (GSTSGSGKPGSGEGSTKG).

Accordingly, in some embodiments, also provided are single-chain fragments, e.g., scFvs, comprising one or more of the aforementioned linkers, such as glycine/serine rich linkers, including linkers having repeats of GGGS (SEQ ID NO:122) or GGGGS (SEQ ID NO:123), such as the linker set forth as SEQ ID NO: 34. In some embodiments, the linker has an amino acid sequence containing the sequence set forth SEQ ID NO: 34.

The fragment, e.g., scFv, may include a $V_H$ region or portion thereof, followed by the linker, followed by a $V_L$ or portions thereof. The fragment, e.g., the scFv, may include the $V_L$, followed by the linker, followed by the VH.

In some aspects, the scFv has the amino acid sequence set forth in SEQ ID NO: 2, 4, 6, 8, or 10, or has a sequence at least at or about 90, 91, 92, 93, 94, 95, 96, 97, 98, or 99% identical to such a sequence.

In some aspects, the scFv has the amino acid sequence set forth set forth in SEQ ID NO: 2, 4, 6, 8, 10, 45, 47, 49, 51, 53, 55, 57, 59, 87, or 89, or has a sequence at least at or about 90, 91, 92, 93, 94, 95, 96, 97, 98, or 99% identical to such a sequence.

In some aspects, the scFv has the amino acid sequence set forth in SEQ ID NO: 2, 4, 6, 8, 10, 45, 47, 49, 51, 53, 55, 57, 59, 87, 89, or 207 to 225 or has a sequence at least at or about 90, 91, 92, 93, 94, 95, 96, 97, 98, or 99% identical to such a sequence.

In some aspects, the scFv contains the VH, linker and VL as set forth in SEQ ID NO: 2, 4, 6, 8, 10, 45, 47, 49, 51, 53, 55, 57, 59, 87 89 or 207 to 225, or a sequence at least at or about 90, 91, 92, 93, 94, 95, 96, 97, 98, or 99% identical to such a sequence, but in which the VH and VL are configured in the opposite orientation, i.e. VL-VH, as compared to such sequence.

The antibody, e.g., antibody fragment, may contain at least a portion of an immunoglobulin constant region, such as one or more constant region domain. In some embodiments, the constant regions include a light chain constant region and/or a heavy chain constant region 1 (CH1). In some embodiments, the antibody includes a CH2 and/or CH3 domain, such as an Fc region. In some embodiments, the Fc region is an Fc region of a human IgG, such as an IgG1 or IgG4.

In some embodiments, any of the above antibodies, e.g., antibody fragments is human. For example, provided herein are human anti-CD19 antibodies that specifically bind CD19, such as specifically bind human CD19.

In some embodiments of a provided human anti-CD19 antibody, the human antibody contains a VH region that contains a portion having at least 95%, 96%, 97%, 98%, 99%, or 100% sequence identity to an amino acid sequence encoded by a germline nucleotide human heavy chain V segment, a portion with at least 95%, 96%, 97%, 98%, 99%, or 100% identity to an amino acid sequence encoded by a germline nucleotide human heavy chain D segment, and/or a portion having at least 95%, 96%, 97%, 98%, 99%, or 100% identity to an amino acid sequence encoded by a germline nucleotide human heavy chain J segment; and/or contains a VL region that contains a portion with at least 95%, 96%, 97%, 98%, 99%, or 100% identity to an amino acid sequence encoded by a germline nucleotide human kappa or lambda chain V segment, and/or a portion with at least 95%, 96%, 97%, 98%, 99%, or 100% identity to an amino acid sequence encoded by a germline nucleotide human kappa or lambda chain J segment. In some embodiments, the portion of the VH region corresponds to the CDR-H1, CDR-H2 and/or CDR-H3. In some embodiments, the portion of the VH region corresponds to the framework region 1 (FR1), FR2, FR2 and/or FR4. In some embodiments, the portion of the VL region corresponds to the CDR-L1, CDR-L2 and/or CDR-L3. In some embodiments, the portion of the VL region corresponds to the FR1, FR2, FR2 and/or FR4.

In some embodiments, the human antibody contains a CDR-H1 having at least 95%, 96%, 97%, 98%, 99%, or 100% sequence identity to an amino acid sequence of the corresponding CDR-H1 region within a sequence encoded by a germline nucleotide human heavy chain V segment. For example, the human antibody in some embodiments contains a CDR-H1 having a sequence that is 100% identical or with no more than one, two or three amino acid differences as compared to the corresponding CDR-H1 region within a sequence encoded by a germline nucleotide human heavy chain V segment.

In some embodiments, the human antibody contains a CDR-H2 having at least 95%, 96%, 97%, 98%, 99%, or 100% sequence identity to an amino acid sequence of the corresponding CDR-H2 region within a sequence encoded by a germline nucleotide human heavy chain V segment. For example, the human antibody in some embodiments contains a CDR-H2 having a sequence that is 100% identical or with no more than one, two or three amino acid difference as compared to the corresponding CDR-H2 region within a sequence encoded by a germline nucleotide human heavy chain V segment.

In some embodiments, the human antibody contains a CDR-H3 having at least 95%, 96%, 97%, 98%, 99%, or 100% sequence identity to an amino acid sequence of the corresponding CDR-H3 region within a sequence encoded by a germline nucleotide human heavy chain V segment, D segment and J segment. For example, the human antibody in some embodiments contains a CDR-H3 having a sequence that is 100% identical or with no more than one, two or three amino acid differences as compared to the corresponding CDR-H3 region within a sequence encoded by a germline nucleotide human heavy chain V segment, D segment and J segment.

In some embodiments, the human antibody contains a CDR-L1 having at least 95%, 96%, 97%, 98%, 99%, or 100% sequence identity to an amino acid sequence of the corresponding CDR-L1 region within a sequence encoded by a germline nucleotide human light chain V segment. For example, the human antibody in some embodiments contains a CDR-L1 having a sequence that is 100% identical or with no more than one, two or three amino acid differences as compared to the corresponding CDR-L1 region within a sequence encoded by a germline nucleotide human light chain V segment.

In some embodiments, the human antibody contains a CDR-L2 having at least 95%, 96%, 97%, 98%, 99%, or 100% sequence identity to an amino acid sequence of the corresponding CDR-L2 region within a sequence encoded by a germline nucleotide human light chain V segment. For example, the human antibody in some embodiments contains a CDR-L2 having a sequence that is 100% identical or with no more than one, two or three amino acid difference as compared to the corresponding CDR-L2 region within a sequence encoded by a germline nucleotide human light chain V segment.

In some embodiments, the human antibody contains a CDR-L3 having at least 95%, 96%, 97%, 98%, 99%, or 100% sequence identity to an amino acid sequence of the corresponding CDR-L3 region within a sequence encoded by a germline nucleotide human light chain V segment and J segment. For example, the human antibody in some embodiments contains a CDR-L3 having a sequence that is 100% identical or with no more than one, two or three amino acid differences as compared to the corresponding CDR-L3 region within a sequence encoded by a germline nucleotide human light chain V segment and J segment.

In some embodiments, the human antibody contains a framework region that contains human germline gene segment sequences. For example, in some embodiments, the human antibody contains a $V_H$ region in which the framework region, e.g. FR1, FR2, FR3 and FR4, has at least 95%, 96%, 97%, 98%, 99%, or 100% sequence identity to a framework region encoded by a human germline antibody segment, such as a V and/or J segment. In some embodiments, the human antibody contains a $V_L$ region in which the framework region e.g. FR1, FR2, FR3 and FR4, has at least 95%, 96%, 97%, 98%, 99%, or 100% sequence identity to a framework region encoded by a human germline antibody segment, such as a V and/or segment. For example, in some such embodiments, the framework sequence of the VH and/or VL sequence differs by no more than 10 amino acids, such as no more than 9, 8, 7, 6, 5, 4, 3, 2 or 1 amino acid, compared to the framework region encoded by a human germline antibody segment.

The antibody, e.g., antibody fragment, may contain at least a portion of an immunoglobulin constant region, such as one or more constant region domain. In some embodiments, the constant regions include a light chain constant region and/or a heavy chain constant region 1 (CH1). In some embodiments, the antibody includes a CH2 and/or CH3 domain, such as an Fc region. In some embodiments, the Fc region is an Fc region of a human IgG, such as an IgG1 or IgG4.

Also provided are nucleic acids encoding the antibodies and/or portions, e.g., chains, thereof. Among the provided nucleic acids are those encoding the anti-CD19 antibodies described herein. The nucleic acids may include those encompassing natural and/or non-naturally occurring nucleotides and bases, e.g., including those with backbone modifications. The terms "nucleic acid molecule", "nucleic acid" and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides that comprise the nucleic acid molecule or polynucleotide. Exemplary nucleic acids and vectors are those having the sequences set forth as SEQ ID NOs: 1, 3, 5, 7, 9, 44, 46, 48, 50, 52, 54, 56, 58, 86, and 88, and CDR-encoding portions thereof, as well as sequences containing at least at or about 90, 91, 92, 93, 94, 95, 96, 97, 98, or 99% identity thereto. The nucleic acid may encode an amino acid sequence comprising the VL and/or an amino acid sequence comprising the VH of the antibody (e.g., the light and/or heavy chains of the antibody).

Also provided are vectors containing the nucleic acids, host cells containing the vectors, e.g., for producing the antibodies. Also provided are methods for producing the antibodies. In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In some embodiments, a method of making the anti-CD19 antibody is provided, wherein the method comprises culturing a host cell comprising a nucleic acid encoding the antibody, as provided above, under conditions suitable for expression of the antibody, and optionally recovering the antibody from the host cell (or host cell culture medium).

Also provided are methods of making the anti-CD19 antibodies (including antigen-binding fragments). For recombinant production of the anti-CD19 antibody, nucleic acid encoding an antibody, e.g., as described above, may be isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

In addition to prokaryotes, eukaryotic microbes such as filamentous fungi or yeast are suitable cloning or expression hosts for antibody-encoding vectors, including fungi and yeast strains whose glycosylation pathways have been modified to mimic or approximate those in human cells, resulting in the production of an antibody with a partially or fully human glycosylation pattern. See Gerngross, Nat. Biotech. 22:1409-1414 (2004), and Li et al., Nat. Biotech. 24:210-215 (2006).

Exemplary eukaryotic cells that may be used to express polypeptides include, but are not limited to, COS cells, including COS 7 cells; 293 cells, including 293-6E cells; CHO cells, including CHO-S, DG44. Lec13 CHO cells, and FUT8 CHO cells; PER.C6® cells; and NSO cells. In some embodiments, the antibody heavy chains and/or light chains may be expressed in yeast. See, e.g., U.S. Publication No. US 2006/0270045 A1. In some embodiments, a particular eukaryotic host cell is selected based on its ability to make desired post-translational modifications to the heavy chains and/or light chains. For example, in some embodiments, CHO cells produce polypeptides that have a higher level of sialylation than the same polypeptide produced in 293 cells.

In some embodiments, the antibody is produced in a cell-free system. Exemplary cell-free systems are described, e.g., in Sitaraman et al., *Methods Mol. Biol.* 498: 229-44 (2009); Spirin, *Trends Biotechnol.* 22: 538-45 (2004); Endo et al., *Biotechnol. Adv.* 21: 695-713 (2003).

The provided embodiments further include vectors and host cells and other expression systems for expressing and producing the antibodies and other binding proteins, including eukaryotic and prokaryotic host cells, including bacteria, filamentous fungi, and yeast, as well as mammalian cells such as human cells, as well as cell-free expression systems.

Exemplary Features

In some aspects, the provided antibodies, including antigen-binding fragments, have one or more specified functional features, such as binding properties, including binding to particular epitopes, such as epitopes that are similar to or overlap with those of other antibodies, the ability to compete for binding with other antibodies, and/or particular binding affinities.

In some embodiments, the antibodies specifically bind to CD19 protein. In some aspects of any of the embodiments herein, CD19 refers to human CD19. Generally, the observation that an antibody or other binding molecule binds to CD19 or specifically binds to CD19 does not necessarily mean that it binds to CD19 of every species. For example, in some embodiments, features of binding to CD19, such as the ability to specifically bind thereto and/or to compete for binding thereto with a reference antibody, and/or to bind with a particular affinity or compete to a particular degree, in some embodiments, refers to the ability with respect to human CD19 protein and the antibody many not have this feature with respect to a CD19 of another species, such as monkey or mouse.

In some embodiments, the provided antibodies, including antigen-binding fragments, bind to human CD19, such as to an epitope or region of human CD19, such as to human CD19 set forth in 92 (Accession No. P15391), or an allelic variant or splice variant thereof. In certain embodiments, the anti-CD19 antibody binds to an epitope of CD19 that is conserved among CD19 from different species. In some embodiments, the anti-CD19 antibody binds to an epitope of CD19 that is not conserved or not entirely conserved among CD19 from different species, such as among human and *Macaca mulatta* (rhesus macaque (rhesus)) CD19.

In some embodiments, the antibody binds to an epitope containing one or more amino acids within (or is entirely within) an extracellular domain of a CD19 and/or within (or is entirely within) a membrane-proximal region of the extracellular portion of CD19. In some embodiments, the antibody binds to an epitope containing one or more amino acids within, or is entirely within, the Ig-like domain 2 of CD19, a portion encoded by the fourth exon of the CD19, a portion corresponding to positions 176-277 of the human CD19 sequence set forth in SEQ ID NO: 92, and/or the membrane-proximal-most 100, 90, 80, 75, 70, 65, 60, 55, 50, 45, 44, 43, 43, 41, or 40 amino acid portion of the extracellular portion of the CD19. In some embodiments, such a portion or domain is required for binding of the antibody to CD19. In some embodiments, the epitope contains (or further contains) one or more amino acids that is within, or is entirely within, the Ig-like domain 1 of CD19, a portion encoded by the second exon of the CD19 and/or a portion corresponding to positions 20-117 of the human CD19 sequence set forth in SEQ ID NO: 92. In some embodiments, such a portion or domain is required for binding of the antibody to CD19. In some embodiments, the antibody specifically binds to a peptide comprising or consisting of or consisting essentially of the sequence of such a portion, and not containing the entire sequence of full-length CD19.

In some embodiments, the epitope contains one or more amino acids within, is within, or includes a portion of CD19 corresponding to residues 218-249 of the human CD19 sequence set forth in SEQ ID NO: 92, such as a portion having the sequence set forth in SEQ ID NO: 143.

In some embodiments, the epitope includes an amino acid at a position corresponding to one or more of the positions of CD19 corresponding to the following amino acids at the following positions of the human CD19 sequence set forth in SEQ ID NO: 92: the histidine (H) at position 218, the alanine (A) at position 236, the methionine (M) at position 242, the glutamate (E) at position 243, the proline (P) at position 249, and/or the lysine (K) and/or serine (S) at positions 223 and 224. In some embodiments, an amino acid at one or more such a position is important or necessary for binding of the antibody to CD19. In some embodiments, the amino acid in the epitope at such one or more position corresponds to the amino acid at the respective position in the human CD19 sequence set forth in SEQ ID NO: 92.

In some embodiments, the epitope includes an amino acid (such as a histidine) at a position of CD19 corresponding to the histidine at position 218 of the human CD19 sequence set forth in SEQ ID NO: 92; in some embodiments, such amino acid is important for binding of the antibody to CD19.

In some embodiments, the epitope includes an amino acid (such as an alanine) at a position of CD19 corresponding to the alanine at position 236 of the human CD19 sequence set forth in SEQ ID NO: 92; in some embodiments, such amino acid is important for binding of the antibody to CD19.

In some embodiments, the epitope includes an amino acid (such as a methionine) at a position of CD19 corresponding to the methionine at position 242 of the human CD19 sequence set forth in SEQ ID NO: 92; in some embodiments, such amino acid is important for binding of the antibody to CD19.

In some embodiments, the epitope includes an amino acid (such as a glutamate) at a position of CD19 corresponding to the glutamate at position 243 of the human CD19 sequence set forth in SEQ ID NO: 92; in some embodiments, such amino acid is important for binding of the antibody to CD19.

In some embodiments, the epitope includes an amino acid (such as a proline) at a position of CD19 corresponding to the proline at position 249 of the human CD19 sequence set forth in SEQ ID NO: 92; in some embodiments, such amino acid is important for binding of the antibody to CD19.

In some embodiments, the epitope contains amino acid(s) (such as lysine and/or serine) at one or two positions corresponding to the lysine and/or serine at positions 223 and 224 of the human CD19 sequence set forth in SEQ ID NO: 92; in some embodiments, such amino acid(s) are important for binding of the antibody to CD19.

In some embodiments, the epitope is the same as, similar to, overlapping with, or contains one or more of the same amino acids as an epitope that is specifically bound to by a reference antibody, such as FMC63 or SJ25C1. In some embodiments, the same one or more amino acids is important for the binding of the provided antibody and the reference antibody.

In some embodiments, the extent of binding of an anti-CD19 antibody to an unrelated, non-CD19 protein, such as non-human CD19 or other non-CD19 protein, is less than about 40% of the binding of the antibody to human CD19 as measured, for example, by a radioimmunoassay (MA). In some embodiments, among provided antibodies are antibodies in which binding to a non-human CD19 or other non-CD19 protein is less than or about 30%, less than or about 20% or less than or about 10% of the binding of the antibody to human CD19.

In some embodiments, such properties of provided antibodies, including antigen-binding fragments, are described in relation to properties observed for another antibody, e.g., a reference antibody. In some embodiments, the reference antibody is a non-human anti-CD19 antibody, such as a murine or chimeric or humanized anti-CD19 antibody. In some aspects, the reference antibody is the antibody designated FMC63 or the antibody designated SJ25C1 (see, e.g., Zola H et al., *Immunol Cell Biol.* 1991 December; 69 (Pt 6):411-22; U.S. Pat. No. 7,446,190), and/or a fragment derived therefrom such as an scFv fragment thereof, and/or an antibody containing the VH and VL sequences of such an antibody and/or the heavy and light chain CDRs of such an antibody.

For example, in some embodiments, the reference antibody has a VH region containing the sequence set forth in SEQ ID NO: 39 or 41, or comprises CDR1, CDR2, and/or CDR3 within such a sequence, and/or has a VL containing the sequence set forth in SEQ ID NO: 40 or 42, or comprises CDR1, CDR2, and/or CDR3 within such a sequence. Thus, in some embodiments, the antibody competes for binding with, and/or binds to the same or an overlapping epitope of CD19 as, FMC63 or SJ25C1 or an antigen-binding fragment thereof.

In some embodiments, the reference antibody has a sequence present in an antibody or portion thereof as described herein. For example, in some embodiments, the reference antibody has a light chain variable (VL) region amino acid sequence set forth in SEQ ID NO: 13, 14, 15, 16, or 17 and/or set forth in SEQ ID NO: 13, 14, 15, 16, 17, 71, 90, 91, 68, 65, 64, 66, 70, 69, or 67, and/or has a heavy chain variable (VH) region set forth in SEQ ID NO: 11, 12, 60, 61, 63, or 62. In some embodiments, the antibody has heavy and/or light chain CDRs 1, 2, and/or 3 as present in such an antibody. In some embodiments, the reference antibody can be an scFv that contains the amino acid sequence set forth in SEQ ID NO: 2, 4, 6, 8, 10, 45, 47, 49, 51, 53, 55, 57, 59, 87 or 89.

In some embodiments, the antibody nonetheless contains heavy and light chain CDRs that are distinct from the CDRs present in the reference antibody or antibodies, such as FMC63 and SJ25C1. For example, among the provided antibodies are those that compete for binding with and/or bind to the same or overlapping epitopes of CD19 as those bound by a reference antibody or antibody, but nonetheless contain distinct CDRs, e.g., distinct heavy and/or light chain CDR1, CDR2, and CDR3. In some embodiments, the provided antibody contains heavy and light chain CDRs that are distinct from the CDRs present in the antibody designated FMC63, such as present in the VH region set forth in SEQ ID NO:39 and/or the VL region set forth in SEQ ID NO:40. In some embodiments, the provided antibody contains heavy and light chain CDRs that are distinct from the CDRs present in the antibody designated SJ25C1, such as present in the VH region set forth in SEQ ID NO:41 and/or the VL region set forth in SEQ ID NO:42.

For example, in some embodiments, the antibody specifically binds to an epitope that overlaps with the epitope of CD19 bound by a reference antibody, such as antibodies that bind to the same or a similar epitope as the reference antibody. In some embodiments, the antibody competes for binding to CD19 with the reference antibody.

In some embodiments, the antibodies display a binding preference for CD19-expressing cells as compared to CD19-negative cells, such as particular cells known in the art and/or described herein. In some embodiments, the binding preference is observed where a significantly greater degree of binding is measured to the CD19-expressing, as compared to the non-expressing, cells. In some embodiments, the fold change in degree of binding detected, for example, as measured by mean fluorescence intensity in a flow cytometry-based assay and/or dissociation constant or EC50, to the CD19-expressing cells as compared to the non-CD19-expressing cells, is at least at or about 1.5, 2, 3, 4, 5, 6, or more, and/or is about as great, about the same, at least as great or at least about as great, or greater, than the fold change observed for the reference antibody, such as the corresponding form of the reference antibody. In some cases, the total degree of observed binding to CD19 or to the CD19-expressing cells is approximately the same, at least as great, or greater than that observed for the reference antibody. In any of the provided embodiments, comparison of binding properties, such as affinities or competition, may be via measurement by the same or similar assay.

An antibody "competes for binding" to CD19 with a reference antibody if it competitively inhibits binding of the reference antibody to CD19, and/or if the reference antibody competitively inhibits binding of the antibody to CD19. An antibody competitively inhibits binding of a reference antibody to an antigen if the presence of the antibody in excess detectably inhibits (blocks) binding of the other antibody to its antigen. A particular degree of inhibition may be specified.

In some embodiments, addition of the provided antibody in excess, e.g., 1-, 2-, 5-, 10-, 50- or 100-fold excess, as compared to the amount or concentration of the reference antibody, inhibits binding to the antigen by the reference antibody (or vice versa). In some embodiments, the inhibition of binding is by at least 50%, and in some embodiments by at least 75%, 90% or 99%. In some aspects, the competitive inhibition is as measured in a competitive binding assay (see, e.g., Junghans et al., Cancer Res. 1990:50:1495-1502).

In some embodiments, where the reference antibody is present at a concentration of 10 nM, the provided antibody inhibits binding of the reference antibody with an IC50 of less than at or about 100, 50, 40, 30, 25, 20, 19, 18, 17, 16, 15, 14, 13, 12, 11, or 10 nM, or less than at or about 9, 8, 7, 6, or 5 nM. In some embodiments, where the provided antibody is present at a concentration of 10 nM, the reference antibody inhibits binding of the provided antibody with an IC50 of less than at or about 100, 50, 40, 30, 25, 20, 19, 18, 17, 16, 15, 14, 13, 12, 11, or 10 nM, or less than at or about 9, 8, 7, 6, or 5 nM.

In some embodiments, competitive inhibition of the reference antibody's binding by the provided antibody (or vice versa) is at or about or least at or about the same degree as the degree of competitive inhibition of the reference antibody's binding by the reference antibody itself, e.g., unlabeled reference antibody. In some embodiments, the provided antibody inhibits binding of the reference antibody, such as binding of FMC63 or SJ25C1, to human CD19 by at least 70%, 75%, 80%, 85%, 90%, 91%, 92%, 93%, 94%, 95%, 96%, 97%, 98%, or 99%. Competitive inhibition assays are known and include ELISA-based, flow cytometry-based assays, and RIA-based assays. In some aspects, competitive inhibition assays are carried out by incorporating an excess of an unlabeled form of one of the antibodies and assessing its ability to block binding of the other antibody, which is labeled with a detectable marker, such that degree of binding and reduction thereof can be assessed by detection of the label or marker.

In some embodiments, two antibodies specifically bind to the same epitope if all or essentially all amino acid mutations in the antigen that reduce or eliminate binding of one antibody reduce or eliminate binding of the other antibody. In some embodiments, two antibodies specifically bind to an overlapping epitope if at least some of the amino acid mutations in the antigen that reduce binding or eliminate binding to the antigen by one antibody also reduce or eliminate binding to the antigen by the other antibody.

In some embodiments, the provided antibodies are capable of binding CD19, such as human CD19, with at least a certain affinity, as measured by any of a number of known methods. In some embodiments, the affinity is represented by a dissociation constant (Kd); in some embodiments, the affinity is represented by EC50. In certain embodiments, the binding affinity (EC50) and/or the dissociation constant of the antibody to CD19 is at or about or less than at or about 100 nM, 50 nM, 40 nM, 30 nM, 25 nM, 20 nM, 19, 18, 17, 16, 15, 14, 13, 12, 11, 10, 9, 8, 7, 6, 5, 4, 3, 2, or 1 nM, such as between at or about 1 nM and at or about 15 nM, e.g., between at or about 5 and at or about 10 nM. In one embodiment, the extent of binding of an anti-CD19 antibody to an unrelated, non-CD19 protein is less than at or about 10% of the binding of the antibody to CD19 as measured, e.g., by a radioimmunoassay (RIA).

In some aspects, the affinity is at or about the same degree or substantially the same degree of affinity compared to the reference antibody, such as murine CD19 antibody, for example FMC63 or SJ25C1. In some aspects, the affinity is at least 80, 85, 90, 95, or 99% the same as that of the reference antibody. In some embodiments, binding affinity is compared with respect to the corresponding form of the reference antibody.

In some embodiments, the antibody has an affinity, e.g., EC50 or Kd, about the same as or lower than that of the reference antibody, such as of the corresponding form of the reference antibody, e.g., no more than about 1.5-fold or no more than about 2-fold greater, no more than 3-fold greater, and/or no more than 10-fold greater, than the EC50 of the reference antibody, e.g., as measured in the same or similar assay.

Anti-CD19 antibodies provided herein may be identified, screened for, or characterized for their physical/chemical properties and/or biological activities by various known assays. In one aspect, the antibody is tested for its antigen binding activity, e.g., by known methods such as ELISA, Western blotting, and/or flow cytometric assays, including cell-based binding assays, for example, assessing binding of the antibody (e.g., conjugated to a fluorescent marker or tagged) to a cell expressing the target antigen, e.g., CD19, in some cases compared to results using cells that do not express the target antigen, e.g., CD19. Binding affinity may be measured as Kd or EC50.

Competition assays may be used to identify an antibody that competes with any of the antibodies described herein. Assays for mapping epitopes bound by the antibodies and reference antibodies also may be used and are known.

Immunoconjugates

In some embodiments, the antibody is or is part of an immunoconjugate, in which the antibody is conjugated to one or more heterologous molecule(s), such as, but not limited to, a cytotoxic agent, an imaging agent, a detectable moiety a multimerization domain or other heterologous molecule. Cytotoxic agents include, but are not limited to, radioactive isotopes (e.g., At211, I131, I125, Y90, Re186, Re188, Sm153, Bi212, P32, Pb212 and radioactive isotopes of Lu); chemotherapeutic agents (e.g., methotrexate, adriamicin, *vinca* alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins. In some embodiments, the antibody is conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

Among the immunoconjugates are antibody-drug conjugates (ADCs), in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

Also among the immunoconjugates are those in which the antibody is conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

Also among the immunoconjugates are those in which the antibody is conjugated to a radioactive atom to form a radioconjugate. Exemplary radioactive isotopes include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu.

Conjugates of an antibody and cytotoxic agent may be made using any of a number of known protein coupling agents, e.g., linkers, (see Vitetta et al., *Science* 238:1098 (1987)), WO94/11026. The linker may be a "cleavable linker" facilitating release of a cytotoxic drug in the cell, such as acid-labile linkers, peptidase-sensitive linkers, photolabile linkers, dimethyl linkers, and disulfide-containing linkers (Chari et al., *Cancer Res.* 52:127-131 (1992); U.S. Pat. No. 5,208,020).

Conjugates may also include fusion proteins such as Fc-fusions and chimeric molecules.

Multispecific Antibodies

In certain embodiments, the CD19-binding molecules, e.g., antibodies are multispecific. Among the multispecific binding molecules are multispecific antibodies, including, e.g. bispecific. Multi specific binding partners, e.g., antibodies, have binding specificities for at least two different sites, which may be in the same or different antigens. In certain embodiments, one of the binding specificities is for CD19 and the other is for another antigen. In certain embodiments, bispecific antibodies may bind to two different epitopes of CD19. Bispecific antibodies may also be used to localize cytotoxic agents to cells which express CD19. Bispecific antibodies can be prepared as full length antibodies or antibody fragments. Among the bispecific antibodies are multispecific single-chain antibodies, e.g., diabodies, triabodies, and tetrabodies, tandem di-scFvs, and tandem tri-scFvs. Also provided are multispecific chimeric receptors, such as multispecific CARs, containing the antibodies.

Exemplary additional antigens include other B cell specific antigens and antigens expressed on T cells. Exemplary antigens include CD4, CD5, CD8, CD14, CD15, CD20, CD21, CD22, CD23, CD25, CD33, CD37, CD38, CD40, CD40L, CD46, CD52, CD54, CD74, CD80, CD126, CD138, B7, MUC-1, Ia, HM1.24, HLA-DR, tenascin, an angiogenesis factor, VEGF, PIGF, ED-B fibronectin, an oncogene, an oncogene product, CD66a-d, necrosis antigens, Ii, IL-2, T101, TAC, IL-6, TRAIL-R1 (DR4) and TRAIL-R2 (DR5).

Variants

In certain embodiments, the antibodies include one or more amino acid variations, e.g., substitutions, deletions, insertions, and/or mutations, compared to the sequence of an antibody described herein. Exemplary variants include those designed to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In certain embodiments, the antibodies include one or more amino acid substitutions, e.g., as compared to an antibody sequence described herein and/or compared to a sequence of a natural repertoire, e.g., human repertoire. Sites of interest for substitutional mutagenesis include the CDRs and FRs. Amino acid substitutions may be introduced into an antibody of interest and the products screened for a desired activity, e.g., retained/improved antigen binding, decreased immunogenicity, improved half-life, and/or improved effector function, such as the ability to promote antibody-dependent cellular cytotoxicity (ADCC) or complement-dependent cytotoxicity (CDC). In some embodiments, the variant antibody exhibits retained or improved binding to CD19.

In some embodiments, one or more residues within a CDR of a parent antibody (e.g. a humanized or human antibody) is/are substituted. In some embodiments, the substitution is made to revert a sequence or position in the sequence to a germline sequence, such as an antibody sequence found in the germline (e.g., human germline), for example, to reduce the likelihood of immunogenicity, e.g., upon administration to a human subject.

In some embodiments, alterations are made in CDR "hotspots," residues encoded by codons that undergo mutation at high frequency during the somatic maturation process (see, e.g., Chowdhury, Methods Mol. Biol. 207:179-196 (2008)), and/or residues that contact antigen, with the resulting variant $V_H$ or $V_L$ being tested for binding affinity. Affinity maturation by constructing and reselecting from secondary libraries has been described, e.g., in Hoogenboom et al. in Methods in Molecular Biology 178:1-37 (O'Brien et al., ed., Human Press, Totowa, N.J., (2001)). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves CDR-directed approaches, in which several CDR residues (e.g., 4-6 residues at a time) are randomized. CDR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in CDRs. Such alterations may, for example, be outside of antigen contacting residues in the CDRs. In certain embodiments of the variant VH and VL sequences provided above, each CDR either is unaltered, or contains no more than one, two or three amino acid substitutions.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme or a polypeptide which increases the serum half-life of the antibody.

Modifications

In certain embodiments, the antibody is altered to increase or decrease the extent to which the antibody is glycosylated, for example, by removing or inserting one or more glycosylation sites by altering the amino acid sequence and/or by modifying the oligosaccharide(s) attached to the glycosylation sites, e.g., using certain cell lines. Glycosylation sites include asparagine 297 of the heavy chain (according to Kabat numbering).

Exemplary modifications, variants, and cell lines are described, e.g., in Patent Publication Nos. US 2003/0157108, US 2004/0093621, US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336:1239-1249 (2004); Yamane-Ohnuki et al. Biotech. Bioeng. 87: 614 (2004). Ripka et al. Arch. Biochem. Biophys. 249:533-545 (1986); US Pat Appl No US 2003/0157108 A1, Presta, L; and WO 2004/056312 A1, Yamane-Ohnuki et al. Biotech. Bioeng. 87: 614 (2004); Kanda, Y. et al., Biotechnol. Bioeng., 94(4):680-688 (2006); and WO2003/085107); WO 2003/011878 (Jean-Mairet et al.); U.S. Pat. No. 6,602,684 (Umana et al.); and US 2005/0123546 (Umana et al.); WO 1997/30087 (Patel et al.); WO 1998/58964 (Raju, S.); and WO 1999/22764 (Raju, S.).

Among the modified antibodies are those having one or more amino acid modifications in the Fc region, such as those having a human Fc region sequence or other portion of a constant region (e.g., a human IgG1, IgG2, IgG3 or IgG4 Fc region) comprising an amino acid modification (e.g. a substitution) at one or more amino acid positions.

Such modifications can be made, e.g., to improve half-life, alter binding to one or more types of Fc receptors, and/or alter effector functions.

Also among the variants are cysteine engineered antibodies such as "thioMAbs" and other cysteine engineered variants, in which one or more residues of an antibody are substituted with cysteine residues, in order to generate reactive thiol groups at accessible sites, e.g., for use in conjugation of agents and linker-agents, to produce immunoconjugates. Cysteine engineered antibodies are described, e.g., in U.S. Pat. Nos. 7,855,275 and 7,521,541.

In some embodiments, the antibodies are modified to contain additional nonproteinaceous moieties, including water soluble polymers. Exemplary polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

B. Recombinant Receptors

Among the provided CD19 binding molecules are recombinant receptors, such as antigen receptors and other chimeric receptors, that specifically bind to CD19, such as receptors containing the provided anti-CD19 antibodies, e.g., antibody fragments. Among the antigen receptors are functional non-TCR antigen receptors, such as chimeric antigen receptors (CARs). Also provided are cells expressing the recombinant receptors and uses thereof in adoptive cell therapy, such as treatment of diseases and disorders associated with CD19 expression.

Exemplary antigen receptors, including CARs, and methods for engineering and introducing such receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April; 3(4): 388-398; Davila et al. (2013) PLoS ONE 8(4): e61338; Turtle et al., Curr. Opin. Immunol., 2012 October; 24(5): 633-39; Wu et al., Cancer, 2012 March 18(2): 160-75. In some aspects, the antigen receptors include a CAR as described in U.S. Pat. No. 7,446,190, and those described in International Patent Application Publication No.: WO/2014055668 A1. Exemplary of the CARs include CARs as disclosed in any of the aforementioned publications, such as WO2014031687, U.S. Pat. Nos. 8,339,645, 7,446,179, US 2013/0149337, U.S. Pat. Nos. 7,446,190, 8,389,282, e.g., and in which the antigen-binding portion, e.g., scFv, is replaced by an antibody, e.g., as provided herein.

Among the chimeric receptors are chimeric antigen receptors (CARs). The chimeric receptors, such as CARs, generally include an extracellular antigen binding domain that includes, is, or is comprised within, one of the provided anti-CD19 antibodies. Thus, the chimeric receptors, e.g., CARs, typically include in their extracellular portions one or more CD19-binding molecules, such as one or more antigen-binding fragment, domain, or portion, or one or more antibody variable domains, and/or antibody molecules, such as those described herein. In some embodiments, the CAR includes a CD19-binding portion or portions of the antibody molecule, such as a variable heavy ($V_H$) chain region and/or variable light ($V_L$) chain region of the antibody, e.g., an scFv antibody fragment.

CD19-targeting CARs are described, for example, by Kochenderfer et al., 2013, Nature Reviews Clinical Oncology, 10, 267-276 (2013); Wang et al. (2012) J. Immunother. 35(9): 689-701; and Brentjens et al., Sci Transl Med. 2013 5(177). See also WO2014031687, U.S. Pat. Nos. 8,339,645, 7,446,179, US 2013/0149337, U.S. Pat. Nos. 7,446,190, and 8,389,282.

In some embodiments, the recombinant receptor, such as a CAR, such as the antibody portion thereof, further includes a spacer, which may be or include at least a portion of an immunoglobulin constant region or variant or modified version thereof, such as a hinge region, e.g., an IgG4 hinge region, and/or a CH1/CL and/or Fc region. In some aspects, the portion of the constant region serves as a spacer region between the antigen-recognition component, e.g., scFv, and transmembrane domain. The spacer can be of a length that provides for increased responsiveness of the cell following antigen binding, as compared to in the absence of the spacer. In some examples, the spacer is at or about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. Exemplary spacers include IgG4 hinge alone, IgG4 hinge linked to CH2 and CH3 domains, or IgG4 hinge linked to the CH3 domain. Exemplary spacers include, but are not limited to, those described in Hudecek et al. (2013) Clin. Cancer Res., 19:3153, international patent application publication number WO2014031687, U.S. Pat. No. 8,822,647 or published app. No. US2014/0271635.

In some embodiments, the constant region or portion is of a human IgG, such as IgG4 or IgG1. In some embodiments, the spacer has the sequence ESKYGPPCPPCP (set forth in SEQ ID NO: 124), and is encoded by the sequence set forth in SEQ ID NO: 125. In some embodiments, the spacer has the sequence set forth in SEQ ID NO: 126. In some embodiments, the spacer has the sequence set forth in SEQ ID NO: 127. In some embodiments, the constant region or portion is of IgD. In some embodiments, the spacer has the sequence set forth in SEQ ID NO:128. In some embodiments, the spacer has a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOS: 124, 126, 127 or 128.

The antigen recognition domain generally is linked to one or more intracellular signaling components, such as signaling components that mimic activation through an antigen receptor complex, such as a TCR complex, in the case of a CAR, and/or signal via another cell surface receptor. Thus, in some embodiments, the CD19-specific binding component (e.g., antibody) is linked to one or more transmembrane and intracellular signaling domains. In some embodiments, the transmembrane domain is fused to the extracellular domain. In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CD8, CD9, CD 16, CD22, CD33, CD37, CD64, CD80, CD86, CD 134, CD137, CD 154, and/or transmembrane regions containing functional variants thereof such as those retaining a substantial portion of the structural, e.g., transmembrane, properties thereof. In some embodiments, the transmembrane domain is a transmembrane domain derived from CD4, CD28, or CD8, e.g., CD8alpha, or functional variant thereof. In some embodiments the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s).

Among the intracellular signaling domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

The receptor, e.g., the CAR, generally includes at least one intracellular signaling component or components. In some embodiments, the receptor includes an intracellular component of a TCR complex, such as a TCR CD3 chain that mediates T-cell activation and cytotoxicity, e.g., CD3 zeta chain. Thus, in some aspects, the CD19-binding antibody is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor γ, CD8, CD4, CD25, or CD16. For example, in some aspects, the CAR includes a chimeric molecule between CD3-zeta (CD3-ζ) or Fc receptor γ and CD8, CD4, CD25 or CD16.

In some embodiments, upon ligation of the CAR, the cytoplasmic domain or intracellular signaling domain of the CAR activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptor to initiate signal transduction following antigen receptor engagement, and/or any derivative or variant of such molecules, and/or any synthetic sequence that has the same functional capability.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

In some aspects, the CAR includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from TCR zeta, FcR gamma, FcR beta, CD3 gamma, CD3 delta, CD3 epsilon, CD8, CD22, CD79a, CD79b, and CD66d. In some embodiments, cytoplasmic signaling molecule(s) in the CAR contain(s) a cytoplasmic signaling domain, portion thereof, or sequence derived from CD3 zeta.

In some embodiments, the CAR includes a signaling domain and/or transmembrane portion of a costimulatory receptor, such as CD28, 4-1BB, OX40, DAP10, or ICOS, or CD27. In some aspects, the same CAR includes both the activating and costimulatory components.

In some embodiments, the activating domain (e.g. CD3 zeta) is included within one CAR, whereas the costimulatory component (e.g. CD28 or 4-1BB) is provided by another CAR recognizing another antigen. In some embodiments, the CARs include activating or stimulatory CARs, costimulatory CARs, both expressed on the same cell (see WO2014/055668). In some aspects, the CD19-targeting CAR is the stimulatory or activating CAR; in other aspects, it is the costimulatory CAR. In some embodiments, the cells further include inhibitory CARs (iCARs, see Fedorov et al., Sci. Transl. Medicine, 5(215) (December, 2013), such as a CAR recognizing an antigen other than CD19, whereby an activating signal delivered through the CD19-targeting CAR is diminished or inhibited by binding of the inhibitory CAR to its ligand, e.g., to reduce off-target effects.

In some embodiments, the intracellular signaling component of the recombinant receptor, such as CAR, comprises a CD3 zeta intracellular domain and a costimulatory signaling region. In certain embodiments, the intracellular signaling domain comprises a CD28 transmembrane and signaling domain linked to a CD3 (e.g., CD3-zeta) intracellular domain. In some embodiments, the intracellular signaling domain comprises a chimeric CD28 and/or CD137 (4-1BB, TNFRSF9) co-stimulatory domains, linked to a CD3 zeta intracellular domain.

In some embodiments, the CAR encompasses one or more, e.g., two or more, costimulatory domains and an activation domain, e.g., primary activation domain, in the cytoplasmic portion. Exemplary CARs include intracellular components of CD3-zeta, CD28, and 4-1BB.

In some embodiments, the CAR or other antigen receptor further includes a marker, such as a cell surface marker, which may be used to confirm transduction or engineering of the cell to express the receptor, such as a truncated version of a cell surface receptor, such as truncated EGFR (tEGFR). In some aspects, the marker includes all or part (e.g., truncated form) of CD34, a NGFR, or epidermal growth factor receptor (e.g., tEGFR) or a functional variant thereof. In some embodiments, the nucleic acid encoding the marker is operably linked to a polynucleotide encoding for a linker sequence, such as a cleavable linker sequence, e.g., T2A. For example, a marker, and optionally a linker sequence, can be any as disclosed in published patent application No. WO2014031687. For example, the marker can be a truncated EGFR (tEGFR) that is, optionally, linked to a linker sequence, such as a T2A cleavable linker sequence. An exemplary polypeptide for a truncated EGFR (e.g. tEGFR) comprises the sequence of amino acids set forth in SEQ ID NO: 138 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO:138. An exemplary T2A linker sequence comprises the sequence of amino acids set forth in SEQ ID NO:137 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO:137.

In some embodiments, the marker is a molecule, e.g., cell surface protein, not naturally found on T cells or not naturally found on the surface of T cells, or a portion thereof.

In some embodiments, the molecule is a non-self molecule, e.g., non-self protein, i.e., one that is not recognized as "self" by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

In some cases, CARs are referred to as first, second, and/or third generation CARs. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR in some aspects is one that includes multiple costimulatory domains of different costimulatory receptors.

In some embodiments, the chimeric antigen receptor includes an extracellular portion containing the antibody or fragment described herein. In some aspects, the chimeric antigen receptor includes an extracellular portion containing the antibody or fragment described herein and an intracellular signaling domain. In some embodiments, the antibody or fragment includes an scFv and the intracellular domain contains an ITAM. In some aspects, the intracellular signaling domain includes a signaling domain of a zeta chain of a CD3-zeta (CD3) chain. In some embodiments, the chimeric antigen receptor includes a transmembrane domain linking the extracellular domain and the intracellular signaling domain. In some aspects, the transmembrane domain contains a transmembrane portion of CD28. The extracellular domain and transmembrane domain can be linked directly or indirectly. In some embodiments, the extracellular domain and transmembrane are linked by a spacer, such as any described herein. In some embodiments, the receptor contains extracellular portion of the molecule from which the transmembrane domain is derived, such as a CD28 extracellular portion. In some embodiments, the chimeric antigen receptor contains an intracellular domain derived from a T cell costimulatory molecule or a functional variant thereof, such as between the transmembrane domain and intracellular signaling domain. In some aspects, the T cell costimulatory molecule is CD28 or 41BB.

For example, in some embodiments, the CAR contains an antibody, e.g., an antibody fragment, as provided herein, a transmembrane domain that is or contains a transmembrane portion of CD28 or a functional variant thereof, and an intracellular signaling domain containing a signaling portion of CD28 or functional variant thereof and a signaling portion of CD3 zeta or functional variant thereof. In some embodiments, the CAR contains an antibody, e.g., antibody fragment, as provided herein, a transmembrane domain that is or contains a transmembrane portion of CD28 or a functional variant thereof, and an intracellular signaling domain containing a signaling portion of a 4-1BB or functional variant thereof and a signaling portion of CD3 zeta or functional variant thereof. In some such embodiments, the receptor further includes a spacer containing a portion of an Ig molecule, such as a human Ig molecule, such as an Ig hinge, e.g. an IgG4 hinge, such as a hinge-only spacer.

In some embodiments, the transmembrane domain of the recombinant receptor, e.g., the CAR, is or includes a transmembrane domain of human CD28 (e.g. Accession No. P01747.1) or variant thereof, such as a transmembrane domain that comprises the sequence of amino acids set forth in SEQ ID NO: 129 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO:129; in some embodiments, the transmembrane-domain containing portion of the recombinant receptor comprises the sequence of amino acids set forth in SEQ ID NO: 130 or a sequence of amino acids having at least at or about 85%, 86%, 87%, 88%, 89%, 90%, 91%, 92%, 93%, 94%, 95%, 96%, 97%, 98%, 99% or more sequence identity thereto.

In some embodiments, the intracellular signaling component(s) of the recombinant receptor, e.g. the CAR, contains an intracellular costimulatory signaling domain of human CD28 or a functional variant or portion thereof, such as a domain with an LL to GG substitution at positions 186-187 of a native CD28 protein. For example, the intracellular signaling domain can comprise the sequence of amino acids set forth in SEQ ID NO:131 or 132 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO:131 or 132. In some embodiments, the intracellular domain comprises an intracellular costimulatory signaling domain of 4-1BB (e.g. (Accession No. Q07011.1) or functional variant or portion thereof, such as the sequence of amino acids set forth in SEQ ID NO:133 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 133.

In some embodiments, the intracellular signaling domain of the recombinant receptor, e.g. the CAR, comprises a human CD3 zeta stimulatory signaling domain or functional variant thereof, such as an 112 AA cytoplasmic domain of isoform 3 of human CD3 (Accession No.: P20963.2) or a CD3 zeta signaling domain as described in U.S. Pat. No.

7,446,190 or 8,911,993. For example, in some embodiments, the intracellular signaling domain comprises the sequence of amino acids 134, 135 or 136 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO:134, 135 or 136.

In some aspects, the spacer contains only a hinge region of an IgG, such as only a hinge of IgG4 or IgG1, such as the hinge only spacer set forth in SEQ ID NO:124. In other embodiments, the spacer is or contains an Ig hinge, e.g., an IgG4-derived hinge, optionally linked to a CH2 and/or CH3 domains. In some embodiments, the spacer is an Ig hinge, e.g., an IgG4 hinge, linked to CH2 and CH3 domains, such as set forth in SEQ ID NO:127. In some embodiments, the spacer is an Ig hinge, e.g., an IgG4 hinge, linked to a CH3 domain only, such as set forth in SEQ ID NO:126. In some embodiments, the spacer is or comprises a glycine-serine rich sequence or other flexible linker such as known flexible linkers.

For example, in some embodiments, the CAR includes an anti-CD19 antibody such as an anti-CD19 antibody fragment, such as any of the provided human anti-CD19 antibodies, e.g., single-chain antibodies including scFvs, described herein, a spacer, such as a spacer containing a portion of an immunoglobulin molecule, such as a hinge region and/or one or more constant regions of a heavy chain molecule, such as an Ig-hinge containing spacer, a transmembrane domain containing all or a portion of a CD28-derived transmembrane domain, a CD28-derived intracellular signaling domain, and a CD3 zeta signaling domain. In some embodiments, the CAR includes an anti-CD19 antibody or fragment, such as any of the human anti-CD19 antibodies, including scFvs described herein, a spacer such as any of the Ig-hinge containing spacers, a CD28-derived transmembrane domain, a 4-1BB-derived intracellular signaling domain, and a CD3 zeta-derived signaling domain.

In some embodiments, such CAR constructs further includes a T2A ribosomal skip element and/or a tEGFR sequence, e.g., downstream of the CAR, such as set forth in SEQ ID NO:137 and/or 138, respectively, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 137 or 138

C. Engineered Cells

Also provided are cells, cell populations, and compositions containing the cells, e.g., the engineered cells, e.g. that contain an engineered antigen receptor, e.g., that contains an extracellular domain including the anti-CD19 antibody or fragment, described herein. Among the compositions are pharmaceutical compositions and formulations for administration, such as for adoptive cell therapy. Also provided are therapeutic methods for administering the cells and compositions to subjects, e.g., patients.

Thus also provided are genetically engineered cells expressing the recombinant receptors containing the antibodies, e.g., cells containing the CARs. The cells generally are eukaryotic cells, such as mammalian cells, and typically are human cells. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). The cells typically are primary cells, such as those isolated directly from a subject and/or isolated from a subject and frozen. In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, as described herein, and re-introducing them into the same patient, before or after cryopreservation.

Among the sub-types and subpopulations of T cells and/or of CD4+ and/or of CD8+ T cells are naïve T ($T_N$) cells, effector T cells ($T_{EFF}$), memory T cells and sub-types thereof, such as stem cell memory T ($T_{SCM}$), central memory T ($T_{CM}$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MATT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

In some embodiments, the cells include one or more nucleic acids introduced via genetic engineering, and thereby express recombinant or genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

Vectors and Methods for Genetic Engineering

Also provided are methods, nucleic acids, compositions, and kits, for expressing the binding molecules, including receptors comprising the antibodies, and for producing the genetically engineered cells expressing such binding molecules. The genetic engineering generally involves introduction of a nucleic acid encoding the recombinant or engineered component into the cell, such as by retroviral transduction, transfection, or transformation.

In some embodiments, gene transfer is accomplished by first stimulating the cell, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

In some contexts, overexpression of a stimulatory factor (for example, a lymphokine or a cytokine) may be toxic to a subject. Thus, in some contexts, the engineered cells include gene segments that cause the cells to be susceptible to negative selection in vivo, such as upon administration in adoptive immunotherapy. For example in some aspects, the cells are engineered so that they can be eliminated as a result of a change in the in vivo condition of the patient to which they are administered. The negative selectable phenotype may result from the insertion of a gene that confers sensitivity to an administered agent, for example, a compound. Negative selectable genes include the Herpes simplex virus type I thymidine kinase (HSV-I TK) gene (Wigler et al., Cell II:223, 1977) which confers ganciclovir sensitivity; the cellular hypoxanthine phosphribosyltransferase (HPRT) gene, the cellular adenine phosphoribosyltransferase (APRT) gene, bacterial cytosine deaminase, (Mullen et al., Proc. Natl. Acad. Sci. USA. 89:33 (1992)).

In some aspects, the cells further are engineered to promote expression of cytokines or other factors. Various methods for the introduction of genetically engineered components, e.g., antigen receptors, e.g., CARs, are well known and may be used with the provided methods and compositions. Exemplary methods include those for transfer of nucleic acids encoding the receptors, including via viral, e.g., retroviral or lentiviral, transduction, transposons, and electroporation.

In some embodiments, recombinant nucleic acids are transferred into cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 November 29(11): 550-557.

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207, 453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

Methods of lentiviral transduction are known. Exemplary methods are described in, e.g., Wang et al. (2012) *J. Immunother.* 35(9): 689-701; Cooper et al. (2003) *Blood.* 101: 1637-1644; Verhoeyen et al. (2009) *Methods Mol Biol.* 506: 97-114; and Cavalieri et al. (2003) *Blood.* 102(2): 497-505.

In some embodiments, recombinant nucleic acids are transferred into T cells via electroporation (see, e.g., Chicaybam et al. (2013) *PLoS ONE* 8(3): e60298 and Van Tedeloo et al. (2000) *Gene Therapy* 7(16): 1431-1437). In some embodiments, recombinant nucleic acids are transferred into T cells via transposition (see, e.g., Manuri et al. (2010) Hum Gene Ther 21(4): 427-437; Sharma et al. (2013) *Molec Ther Nucl* Acids 2, e74; and Huang et al. (2009) *Methods Mol Biol* 506: 115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346: 776-777 (1990)); and strontium phosphate DNA co-precipitation (Brash et al., *Mol. Cell Biol.,* 7: 2031-2034 (1987)).

Other approaches and vectors for transfer of the nucleic acids encoding the recombinant products are those described, e.g., in international patent application, Publication No.: WO2014055668, and U.S. Pat. No. 7,446,190.

Among additional nucleic acids, e.g., genes for introduction are those to improve the efficacy of therapy, such as by promoting viability and/or function of transferred cells; genes to provide a genetic marker for selection and/or evaluation of the cells, such as to assess in vivo survival or localization; genes to improve safety, for example, by making the cell susceptible to negative selection in vivo as described by Lupton S. D. et al., *Mol. and Cell Biol.,* 11:6 (1991); and Riddell et al., *Human Gene Therapy* 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

Preparation of Cells for Engineering

In some embodiments, preparation of the engineered cells includes one or more culture and/or preparation steps. The cells for introduction of the CD19-binding molecule, e.g., CAR, may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, and pig.

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., $CD28^+$, $CD62L^+$, $CCR7^+$, $CD27^+$, $CD127^+$, $CD4^+$, $CD8^+$, $CD45RA^+$, and/or $CD45RO^+$ T cells, are isolated by positive or negative selection techniques.

For example, CD3+, CD28+ T cells can be positively selected using CD3/CD28 conjugated magnetic beads (e.g., DYNABEADS® M-450 CD3/CD28 T Cell Expander).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed (marker$^+$) at a relatively higher level (marker$^{high}$) on the positively or negatively selected cells, respectively.

In some embodiments, T cells are separated from a PBMC sample by negative selection of markers expressed on non-T cells, such as B cells, monocytes, or other white blood cells, such as CD14. In some aspects, a $CD4^+$ or $CD8^+$ selection step is used to separate $CD4^+$ helper and $CD8^+$ cytotoxic T cells. Such $CD4^+$ and $CD8^+$ populations can be further sorted into sub-populations by positive or negative selection for markers expressed or expressed to a relatively higher degree on one or more naive, memory, and/or effector T cell subpopulations.

In some embodiments, $CD8^+$ cells are further enriched for or depleted of naive, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such subpopulations. See Terakura et al. (2012) Blood. 1:72-82; Wang et al. (2012) *J Immunother.* 35(9):689-701. In some embodiments, combining $T_{CM}$-enriched CD8$^+$ T cells and CD4$^+$ T cells further enhances efficacy.

In embodiments, memory T cells are present in both CD62L$^+$ and CD62L$^-$ subsets of CD8$^+$ peripheral blood lymphocytes. PBMC can be enriched for or depleted of CD62L$^-$ CD8$^+$ and/or CD62L$^+$ CD8$^+$ fractions, such as using anti-CD8 and anti-CD62L antibodies.

In some embodiments, the enrichment for central memory T ($T_{CM}$) cells is based on positive or high surface expression of CD45RO, CD62L, CCR7, CD28, CD3, and/or CD 127; in some aspects, it is based on negative selection for cells expressing or highly expressing CD45RA and/or granzyme B. In some aspects, isolation of a CD8$^+$ population enriched for $T_{CM}$ cells is carried out by depletion of cells expressing CD4, CD14, CD45RA, and positive selection or enrichment for cells expressing CD62L. In one aspect, enrichment for central memory T ($T_{CM}$) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the CD8$^+$ cell population or subpopulation, also is used to generate the CD4$^+$ cell population or sub-population, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of CD4$^+$ cells, where both the negative and positive fractions are retained. The negative fraction then is subjected to negative selection based on expression of CD14 and CD45RA or CD19, and positive selection based on a marker characteristic of central memory T cells, such as CD62L or CCR7, where the positive and negative selections are carried out in either order.

CD4$^+$ T helper cells are sorted into naïve, central memory, and effector cells by identifying cell populations that have cell surface antigens. CD4$^+$ lymphocytes can be obtained by standard methods. In some embodiments, naive CD4$^+$ T lymphocytes are CD45RO$^-$, CD45RA$^+$, CD62L$^+$, CD4$^+$ T cells. In some embodiments, central memory CD4$^+$ cells are CD62L$^+$ and CD45RO$^+$. In some embodiments, effector CD4$^+$ cells are CD62L$^-$ and CD45RO$^-$.

In one example, to enrich for CD4$^+$ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher© Humana Press Inc., Totowa, N.J.).

In some aspects, the sample or composition of cells to be separated is incubated with small, magnetizable or magnetically responsive material, such as magnetically responsive particles or microparticles, such as paramagnetic beads (e.g., such as Dynalbeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, magnetizable particles or antibodies conjugated to cleavable linkers, etc. In some embodiments, the magnetizable particles are biodegradable.

In some embodiments, the affinity-based selection is via magnetic-activated cell sorting (MACS) (Miltenyi Biotech, Auburn, Calif.). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International Patent Application, Publication Number WO2009/072003, or US 20110003380 A1.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS system (Miltenyi Biotic), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some aspects is equipped with a cell processing unity that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood is automatically separated into erythrocytes, white blood cells and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. (2012) *J Immunother.* 35(9): 651-660, Terakura et al. (2012) Blood. 1:72-82, and Wang et al. (2012) *J Immunother* 35(9):689-701.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) *Lab Chip* 10, 1567-1573; and Godin et al. (2008) *J Biophoton.* 1(5):355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are then frozen to −80° C. at a rate of 1° per minute and stored in the vapor phase of a liquid nitrogen storage tank.

In some embodiments, the provided methods include cultivation, incubation, culture, and/or genetic engineering steps. For example, in some embodiments, provided are methods for incubating and/or engineering the depleted cell populations and culture-initiating compositions.

Thus, in some embodiments, the cell populations are incubated in a culture-initiating composition. The incubation and/or engineering may be carried out in a culture vessel, such as a unit, chamber, well, column, tube, tubing set, valve, vial, culture dish, bag, or other container for culture or cultivating cells.

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR component and/or costimulatory receptor, e.g., anti-CD3, anti-CD28, for example, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2 and/or IL-15, for example, an IL-2 concentration of at least about 10 units/mL.

In some aspects, incubation is carried out in accordance with techniques such as those described in U.S. Pat. No. 6,040,177 to Riddell et al., Klebanoff et al. (2012) J Immunother. 35(9): 651-660, Terakura et al. (2012) Blood. 1:72-82, and/or Wang et al. (2012) J Immunother. 35(9):689-701.

In some embodiments, the T cells are expanded by adding to the culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In embodiments, antigen-specific T cells, such as antigen-specific CD4+ and/or CD8+ T cells, are obtained by stimulating naive or antigen specific T lymphocytes with antigen. For example, antigen-specific T cell lines or clones can be generated to cytomegalovirus antigens by isolating T cells from infected subjects and stimulating the cells in vitro with the same antigen.

II. COMPOSITIONS, METHODS AND USES

Also provided are compositions including the CD19 binding molecules and engineered cells, including pharmaceutical compositions and formulations, and methods of using and uses of the molecules and compositions, such as in the treatment of diseases, conditions, and disorders in which CD19 is expressed, and/or detection, diagnostic, and prognostic methods.

A. Pharmaceutical Compositions and Formulations

Provided are pharmaceutical formulations including the CD19-binding molecule, e.g., antibody or chimeric receptor, and/or the engineered cells expressing the molecules. The pharmaceutical compositions and formulations generally include one or more optional pharmaceutically acceptable carrier or excipient. In some embodiments, the composition includes at least one additional therapeutic agent.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell, binding molecule, and/or antibody, and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

Formulations of the antibodies can include lyophilized formulations and aqueous solutions.

The formulation or composition may also contain more than one active ingredients useful for the particular indication, disease, or condition being treated with the binding molecules or cells, preferably those with activities complementary to the binding molecule or cell, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In some embodiments, the cells or antibodies are administered in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

Active ingredients may be entrapped in microcapsules, in colloidal drug delivery systems (for example, liposomes, albumin microspheres, microemulsions, nano-particles and nanocapsules) or in macroemulsions. In certain embodiments, the pharmaceutical composition is formulated as an inclusion complex, such as cyclodextrin inclusion complex, or as a liposome. Liposomes can serve to target the host cells (e.g., T-cells or NK cells) to a particular tissue. Many methods are available for preparing liposomes, such as those described in, for example, Szoka et al., Ann. Rev. Biophys. Bioeng., 9: 467 (1980), and U.S. Pat. Nos. 4,235,871, 4,501,728, 4,837,028, and 5,019,369.

The pharmaceutical composition in some aspects can employ time-released, delayed release, and sustained release delivery systems such that the delivery of the composition occurs prior to, and with sufficient time to cause, sensitization of the site to be treated. Many types of release delivery systems are available and known. Such systems can avoid repeated administrations of the composition, thereby increasing convenience to the subject and the physician.

The pharmaceutical composition in some embodiments contains the binding molecules and/or cells in amounts effective to treat or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

In certain embodiments, in the context of genetically engineered cells containing the binding molecules, a subject is administered the range of about one million to about 100 billion cells, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges, and/or such a number of cells per kilogram of body weight of the subject.

The may be administered using standard administration techniques, formulations, and/or devices. Provided are formulations and devices, such as syringes and vials, for storage and administration of the compositions. Administration of the cells can be autologous or heterologous. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, and intraperitoneal administration. In some embodiments, the cell populations are administered to a subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyoi (for example, glycerol, propylene glycol, liquid polyethylene glycol) and suitable mixtures thereof.

Sterile injectable solutions can be prepared by incorporating the binding molecule in a solvent, such as in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin.

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

B. Therapeutic and Prophylactic Methods and Uses

Also provided are methods for using and uses of the CD19 binding molecules, including the anti-CD19 antibodies, e.g., antibody fragments, and/or engineered cells expressing the recombinant receptors. Such methods and uses include therapeutic methods and uses, for example, involving administration of the molecules, cells, or compositions containing the same, to a subject having a disease, condition, or disorder expressing or associated with CD19 expression, and/or in which cells or tissues express CD19. In some embodiments, the molecule, cell, and/or composition is administered in an effective amount to effect treatment of the disease or disorder. Uses include uses of the antibodies and cells in such methods and treatments, and in the preparation of a medicament in order to carry out such therapeutic methods. In some embodiments, the methods are carried out by administering the antibodies or cells, or compositions comprising the same, to the subject having or suspected of having the disease or condition. In some embodiments, the methods thereby treat the disease or condition or disorder in the subject.

As used herein, "treatment" (and grammatical variations thereof such as "treat" or "treating") refers to complete or partial amelioration or reduction of a disease or condition or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms do not imply complete curing of a disease or complete elimination of any symptom or effect(s) on all symptoms or outcomes.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. In some embodiments, the provided molecules and compositions are used to delay development of a disease or to slow the progression of a disease.

As used herein, to "suppress" a function or activity is to reduce the function or activity when compared to otherwise same conditions except for a condition or parameter of interest, or alternatively, as compared to another condition. For example, an antibody or composition or cell which suppresses tumor growth reduces the rate of growth of the tumor compared to the rate of growth of the tumor in the absence of the antibody or composition or cell.

An "effective amount" of an agent, e.g., a pharmaceutical formulation, binding molecule, antibody, or cells, or composition, in the context of administration, refers to an amount effective, at dosages/amounts and for periods of time necessary, to achieve a desired result, such as a therapeutic or prophylactic result.

A "therapeutically effective amount" of an agent, e.g., a pharmaceutical formulation, antibody, or cells, refers to an amount effective, at dosages and for periods of time necessary, to achieve a desired therapeutic result, such as for treatment of a disease, condition, or disorder, and/or pharmacokinetic or pharmacodynamic effect of the treatment. The therapeutically effective amount may vary according to factors such as the disease state, age, sex, and weight of the subject, and the populations of cells administered. In some embodiments, the provided methods involve administering the molecules, cells, and/or compositions at effective amounts, e.g., therapeutically effective amounts.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

As used herein, a "subject" is a mammal, such as a human or other animal, and typically is human. The diseases and disorders include B cell malignancies, such as B cell leukemias and lymphomas, including B cell chronic lymphocytic leukemia (CLL), acute lymphocytic leukemia (ALL), pro-lymphocytic leukemias, hairy cell leukemias, common acute lymphocytic leukemias, Null-acute lymphoblastic leukemias, non-Hodgkin lymphomas, diffuse large B cell lymphomas (DLBCLs), multiple myelomas, follicular lymphoma, splenic, marginal zone lymphoma, mantle cell lymphoma, indolent B cell lymphoma, Hodgkin lymphoma. Also among the diseases and conditions are autoimmune and inflammatory diseases, including those associated with inappropriate or enhanced B cell numbers and/or activation. Exemplary diseases and conditions include multiple sclerosis, rheumatoid arthritis, and systemic lupus erythematosus (SLE).

In some embodiments, the subject has persistent or relapsed disease, e.g., following treatment with another CD19-specific antibody and/or cells expressing a CD19- targeting chimeric receptor and/or other therapy, including chemotherapy, radiation, and/or hematopoietic stem cell transplantation (HSCT), e.g., allogenic HSCT. In some embodiments, the administration effectively treats the subject despite the subject having become resistant to another CD19-targetetd therapy. In some embodiments, the subject has not relapsed but is determined to be at risk for relapse, such as at a high risk of relapse, and thus the compound or composition is administered prophylactically, e.g., to reduce the likelihood of or prevent relapse.

In some embodiments, the treatment does not induce an immune response by the subject to the therapy, and/or does not induce such a response to a degree that prevents effective treatment of the disease or condition. In some aspects, the degree of immunogenicity and/or graft versus host response is less than that observed with a different but comparable treatment. For example, in the case of adoptive cell therapy using cells expressing CARs including the provided anti-CD19 antibodies, the degree of immunogenicity is reduced compared to CARs including a different antibody that binds to a similar, e.g., overlapping epitope and/or that competes for binding to CD19 with the provided antibody, such as a mouse antibody.

In some embodiments, the methods include adoptive cell therapy, whereby genetically engineered cells expressing the provided anti-CD19-containing receptors (e.g., CD19-targeted CARs) are administered to subjects. Such administration can promote activation of the cells (e.g., T cell activation) in a CD19-targeted manner, such that the cells of the disease or disorder are targeted for destruction.

Thus, the provided methods and uses include methods and uses for adoptive cell therapy. In some embodiments, the methods include administration of the cells or a composition containing the cells to a subject, tissue, or cell, such as one having, at risk for, or suspected of having the disease, condition or disorder. In some embodiments, the cells, populations, and compositions are administered to a subject having the particular disease or condition to be treated, e.g., via adoptive cell therapy, such as adoptive T cell therapy. In some embodiments, the cells or compositions are administered to the subject, such as a subject having or at risk for the disease or condition. In some aspects, the methods thereby treat, e.g., ameliorate one or more symptom of the disease or condition, such as by lessening tumor burden in a CD19-expressing cancer.

Methods for administration of cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338.

In some embodiments, the cell therapy, e.g., adoptive cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

In some embodiments, the subject, to whom the cells, cell populations, or compositions are administered is a primate, such as a human. In some embodiments, the primate is a monkey or an ape. The subject can be male or female and can be any suitable age, including infant, juvenile, adolescent, adult, and geriatric subjects. In some embodiments, the subject is a non-primate mammal, such as a rodent. In some examples, the patient or subject is a validated animal model for disease, adoptive cell therapy, and/or for assessing toxic outcomes such as cytokine release syndrome (CRS).

The CD19-binding molecules, such as antibodies and chimeric receptors containing the antibodies and cells expressing the same, can be administered by any suitable means, for example, by injection, e.g., intravenous or subcutaneous injections, intraocular injection, periocular injection, subretinal injection, intravitreal injection, trans-septal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, or subcutaneous administration. Dosing and administration may depend in part on whether the administration is brief or chronic. Various dosing schedules include but are not limited to single or multiple administrations over various time-points, bolus administration, and pulse infusion.

For the prevention or treatment of disease, the appropriate dosage of the binding molecule or cell may depend on the type of disease to be treated, the type of binding molecule, the severity and course of the disease, whether the binding molecule is administered for preventive or therapeutic purposes, previous therapy, the patient's clinical history and response to the binding molecule, and the discretion of the attending physician. The compositions and molecules and cells are in some embodiments suitably administered to the patient at one time or over a series of treatments.

Depending on the type and severity of the disease, dosages of antibodies may include about 1 μg/kg to 15 mg/kg (e.g. 0.1 mg/kg-10 mg/kg), about 1 μg/kg to 100 mg/kg or more, about 0.05 mg/kg to about 10 mg/kg, 0.5 mg/kg, 2.0 mg/kg, 4.0 mg/kg or 10 mg/kg. Multiple doses may be administered intermittently, e.g. every week or every three weeks. An initial higher loading dose, followed by one or more lower doses may be administered.

In certain embodiments, in the context of genetically engineered cells containing the binding molecules, a subject is administered the range of about one million to about 100 billion cells and/or that amount of cells per kilogram of body weight, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges and/or per kilogram of body weight. Again, dosages may vary depending on attributes particular to the disease or disorder and/or patient and/or other treatments.

In some embodiments, the cells or antibodies are administered as part of a combination treatment, such as simultaneously with or sequentially with, in any order, another therapeutic intervention, such as another antibody or engineered cell or receptor or agent, such as a cytotoxic or therapeutic agent.

The cells or antibodies in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells or antibodies are administered prior to the one or more additional therapeutic agents. In some embodiments, the cells or antibodies are administered after to the one or more additional therapeutic agents.

Once the cells are administered to a mammal (e.g., a human), the biological activity of the engineered cell populations and/or antibodies in some aspects is measured by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285 (1): 25-40 (2004). In certain embodiments, the biological activity of the cells also can be measured by assaying expression and/or secretion of certain cytokines, such as CD 107a, IFNγ, IL-2, and TNF. In some aspects the biological activity is measured by assessing clinical outcome, such as reduction in tumor burden or load.

In certain embodiments, engineered cells are modified in any number of ways, such that their therapeutic or prophylactic efficacy is increased. For example, the engineered CAR or TCR expressed by the population can be conjugated either directly or indirectly through a linker to a targeting moiety. The practice of conjugating compounds, e.g., the CAR or TCR, to targeting moieties is known in the art. See, for instance, Wadwa et al., J. Drug Targeting 3:111 (1995), and U.S. Pat. No. 5,087,616.

C. Diagnostic and Detection Methods

Also provided are methods involving use of the provided binding molecules, e.g., antibodies, including antibody fragments, and molecules (such as conjugates and complexes) containing one or more of such antibodies, for detection, prognosis, diagnosis, staging, determining binding of a particular treatment to one or more tissues or cell types, and/or informing treatment decisions in a subject, such as by the detection of CD19 and/or the presence of an epitope thereof recognized by the antibody. In some embodiments, the methods are diagnostic and/or prognostic methods in association with a CD19-expressing disease or condition. The methods in some embodiments include incubating and/or probing a biological sample with the antibody and/or administering the antibody to a subject. In certain embodiments, a biological sample includes a cell or tissue or portion thereof, such as tumor or cancer tissue or biopsy or section thereof. In certain embodiments, the contacting is under conditions permissive for binding of the anti-CD19 antibody to CD19 present in the sample. In some embodiments, the methods further include detecting whether a complex is formed between the anti-CD19 antibody and CD19 in the sample, such as detecting the presence or absence or level of such binding. Such a method may be an in vitro or in vivo method. In one embodiment, an anti-CD19 antibody is used to select subjects eligible for therapy with an anti-CD19 antibody or engineered antigen receptor, e.g. where CD19 is a biomarker for selection of patients.

In some embodiments, a sample, such as a cell, tissue sample, lysate, composition, or other sample derived therefrom is contacted with the anti-CD19 antibody and binding or formation of a complex between the antibody and the sample (e.g., CD19 in the sample) is determined or detected. When binding in the test sample is demonstrated or detected as compared to a reference cell of the same tissue type, it may indicate the presence of an associated disease or condition, and/or that a therapeutic containing the antibody (e.g., antibody fragment) will specifically bind to a tissue or cell that is the same as or is of the same type as the tissue or cell or other biological material from which the sample is derived. In some embodiments, the sample is from human tissues and may be from diseased and/or normal tissue, e.g., from a subject having the disease or condition to be treated and/or from a subject of the same species as such subject but that does not have the disease or condition to be treated. In some cases, the normal tissue or cell is from a subject having the disease or condition to be treated but is not itself a diseased cell or tissue, such as a normal tissue from the same or a different organ than a cancer that is present in a given subject.

Various methods known in the art for detecting specific antibody-antigen binding can be used. Exemplary immunoassays include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (MA). An indicator moiety, or label group, can be attached to the subject antibodies and is selected so as to meet the needs of various uses of the method which are often dictated by the availability of assay equipment and compatible immunoassay procedures. Exemplary labels include radionuclides (e.g. $^{125}I$, $^{131}I$, $^{35}S$, $^{3}H$, or $^{32}P$ and/or chromium ($^{51}Cr$), cobalt ($^{57}Co$), fluorine ($^{18}F$), gadolinium ($^{153}Gd$, $^{159}Gd$), germanium ($^{68}Ge$), holmium ($^{166}Ho$), indium ($^{115}In$, $^{113}In$, $^{112}In$, $^{111}In$) iodine ($^{125}I$, $^{123}I$, $^{121}I$), lanthanium ($^{140}La$) lutetium ($^{177}Lu$), manganese ($^{54}Mn$), molybdenum ($^{99}Mo$), palladium ($^{103}Pd$), phosphorous ($^{32}P$), praseodymium ($^{142}Pr$), promethium ($^{149}Pm$), rhenium ($^{186}Re$, $^{188}Re$), rhodium ($^{105}Rh$), rutheroium ($^{97}Ru$), samarium ($^{153}Sm$), scandium ($^{47}Sc$), selenium ($^{75}Se$), ($^{85}Sr$), sulphur ($^{35}S$), technetium ($^{99}Tc$), thallium ($^{201}Ti$) tin ($^{113}Sn$, $^{117}Sn$), tritium (3H), xenon ($^{133}Xe$), ytterbium ($^{169}Yb$, $^{175}Yb$), yttrium ($^{90}Y$),), enzymes (e.g., alkaline phosphatase, horseradish peroxidase, luciferase, or β-glactosidase), fluorescent moieties or proteins (e.g., fluorescein, rhodamine, phycoerythrin, GFP, or BFP), or luminescent moieties (e.g., Qdot™ nanoparticles supplied by the Quantum Dot Corporation, Palo Alto, Calif.). Various general techniques to be used in performing the various immunoassays noted above are known.

For purposes of diagnosis, the antibodies can be labeled with a detectable moiety including but not limited to radioisotopes, fluorescent labels, and various enzyme-substrate labels know in the art. Methods of conjugating labels to an antibody are known in the art.

In some embodiments, antibodies need not be labeled, and the presence thereof can be detected using a labeled antibody which binds to any of the antibodies.

The antibodies provided herein can be employed in any known assay method, such as competitive binding assays, direct and indirect sandwich assays, and immunoprecipitation assays. Zola, Monoclonal Antibodies: A Manual of Techniques, pp. 147-158 (CRC Press, Inc. 1987).

The antibodies and polypeptides can also be used for in vivo diagnostic assays, such as in vivo imaging. Generally, the antibody is labeled with a radionuclide (such as $^{111}$In, $^{99}$Tc, $^{14}$C, $^{131}$I, $^{125}$I, or $^{3}$H) so that the cells or tissue of interest can be localized in vivo following administration to a subject.

The antibody may also be used as staining reagent in pathology, e.g., using known techniques.

III. ARTICLES OF MANUFACTURE

Also provided are articles of manufacture containing the provided binding molecules, e.g., antibodies and CARs and/or genetically engineered cells, and/or compositions. The articles of manufacture may include a container and a label or package insert on or associated with the container. Suitable containers include, for example, bottles, vials, syringes, IV solution bags, etc. The containers may be formed from a variety of materials such as glass or plastic. The container in some embodiments holds a composition which is by itself or combined with another composition effective for treating, preventing and/or diagnosing the condition. In some embodiments, the container has a sterile access port. Exemplary containers include an intravenous solution bags, vials, including those with stoppers pierceable by a needle for injection. The label or package insert may indicate that the composition is used for treating the CD19-expressing or -associated disease or condition. The article of manufacture may include (a) a first container with a composition contained therein, wherein the composition includes the antibody or engineered antigen receptor; and (b) a second container with a composition contained therein, wherein the composition includes a further agent, such as a cytotoxic or otherwise therapeutic agent. The article of manufacture may further include a package insert indicating that the compositions can be used to treat a particular condition. Alternatively, or additionally, the article of manufacture may further include another or the same container comprising a pharmaceutically-acceptable buffer. It may further include other materials such as other buffers, diluents, filters, needles, and/or syringes.

As used herein, reference to a "corresponding form" of an antibody means that when comparing a property or activity of two antibodies, the property is compared using the same form of the antibody. For example, if it is stated that an antibody has greater activity compared to the activity of the corresponding form of a first antibody, that means that a particular form, such as a scFv of that antibody, has greater activity compared to the scFv form of the first antibody.

As used herein, recitation that nucleotides or amino acid positions "correspond to" nucleotides or amino acid positions in a disclosed sequence, such as set forth in the Sequence listing, refers to nucleotides or amino acid positions identified upon alignment with the disclosed sequence to maximize identity using a standard alignment algorithm, such as the GAP algorithm. For example, in some embodiments, exemplary corresponding residues of a CD19 protein, such as a human CD19 protein, can be identified by alignment of a sequence with an exemplary Vpx sequence set forth in SEQ ID NO:92. By aligning the sequences, one skilled in the art can identify corresponding residues, for example, using conserved and identical amino acid residues as guides. In general, to identify corresponding positions, the sequences of amino acids are aligned so that the highest order match is obtained (see, e.g.: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; Carrillo et al. (1988) SIAM J Applied Math 48: 1073).

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

The terms "full length antibody," "intact antibody," and "whole antibody" are used herein interchangeably to refer to an antibody having a structure substantially similar to a native antibody structure or having heavy chains that contain an Fc region as defined herein.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., J. Chromatogr. B 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-CD19 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

As used herein, "percent (%) amino acid sequence identity" and "percent identity" when used with respect to an amino acid sequence (reference polypeptide sequence) is defined as the percentage of amino acid residues in a candidate sequence (e.g., the subject antibody or fragment) that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

An amino acid substitution may include replacement of one amino acid in a polypeptide with another amino acid. Exemplary substitutions are shown in Table 1. Amino acid substitutions may be introduced into a binding molecule, e.g., antibody, of interest and the products screened for a desired activity, e.g., retained/improved antigen binding, decreased immunogenicity, or improved ADCC or CDC.

Amino acids generally can be grouped according to the following common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative amino acid substitutions will involve exchanging a member of one of these classes for another class.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "package insert" is used to refer to instructions customarily included in commercial packages of therapeutic products, that contain information about the indications, usage, dosage, administration, combination therapy, contraindications and/or warnings concerning the use of such therapeutic products.

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

As used herein, a composition refers to any mixture of two or more products, substances, or compounds, including cells. It may be a solution, a suspension, liquid, powder, a paste, aqueous, non-aqueous or any combination thereof.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

IV. EXEMPLARY EMBODIMENTS

Among the embodiments provided herein are:

1. An anti-CD19 antibody or antigen-binding fragment thereof, said antibody or antigen-binding fragment comprising a heavy chain variable (VH) region and a light chain variable (VL) region, wherein:
said VH region comprises a heavy chain complementarity determining region 3 (CDR-H3) comprising the amino acid sequence set forth as SEQ ID NO: 20 or
said VH region comprises at least 90% sequence identity to the VH region amino acid sequence set forth in SEQ ID NO: 11, 12, 60, 61, 63, or 62.

2. An antibody or antigen-binding fragment thereof comprising:
a CDR-H1, a CDR-H2, and a CDR-H3, respectively comprising the amino acid sequences of CDR-H1, CDR-H2, and CDR-H3 sequences contained within the VH region amino acid sequence set forth in SEQ ID NO: 11, 12, 60, 61, 63, or 62; and/or
light chain complementarity determining regions 1, 2, and 3 (CDR-L1, CDR-L2, and CDR-L3), respectively comprising the amino acid sequences of CDR-L1, CDR-L2, and CDR-L3 sequences contained within the light chain variable (VL) region amino acid sequence set forth in SEQ ID NO: 13, 14, 15, 16, 17, 71, 65, 64, 66, 70, 69, 67, 90 or 91.

3. An antibody or antigen-binding fragment thereof comprising:
a CDR-H1 comprising the amino acid sequence of SEQ ID NO: 18, a CDR-H2 comprising the amino acid sequence of SEQ ID NO: 81 or 82, and a CDR-H3 comprising the amino acid sequence set forth as SEQ ID NO: 20; and/or
a CDR-L1 comprising the amino acid sequence of $X_1X_2X_3X_4X_5X_6X_7X_8X_9X_{10}X_{11}X_{12}X_{13}X_{14}$ (SEQ ID NO: 111), wherein $X_1$ is T, Q, S, or R; $X_2$ is G or A; $X_3$ is I, T, D, or S; $X_4$ is S, R, T, or Q; $X_5$ is null or S; $X_6$ is G, D, N, or null; $X_7$ is null, V, or L; $X_8$ is D, G, I, L, S, or null; $X_9$ is S, G, A, I, R, or null; $X_{10}$ is H, Y, F, S, or N; $X_{11}$ is R, N, D, H, or Y; $X_{12}$ is Y, F, D, or W; $X_{13}$ is V, A, or L; and $X_{14}$ is S, N, or A;

a CDR-L2 comprising the amino acid sequence of $X_1X_2X_3X_4X_5X_6X_7$ (SEQ ID NO: 112), wherein $X_1$ is D or S; $X_2$ is F, V, N, K, or A; $X_3$ is S, T, D, or N; $X_4$ is K, V, N, Q, or R; $X_5$ is R, V, or L; $X_6$ is P, K, A, or E; and $X_7$ is S, P, A, or T, and a CDR-L3 comprising the amino acid sequence of $X_1X_2X_3X_4X_5X_6X_7X_8X_9X_{10}X_{11}X_{12}$ (SEQ ID NO: 115), wherein $X_1$ is X; $X_2$ is S, Q, A, or T; $X_3$ is Y, S, W, R; $X_4$ is A, D, R, T, or Y; $X_5$ is X; $X_6$ is X; $X_7$ is S, P, L, Y, G; $X_8$ is X or null; $X_9$ is X or null; $X_{10}$ is L or null; $X_{11}$ is X; and $X_{12}$ is V, T, or L.

4. The antibody or antigen-binding fragment thereof of embodiment 3, wherein:
in said CDR-L1, $X_3$ is I, T, or S; $X_4$ is S, T, or Q; $X_5$ is D, G, I, S, or null; $X_9$ is S, G, I, or null; $X_{10}$ is H, Y, S, or N; $X_{11}$ is R, N, D, or H; $X_{12}$ is Y or D; and $X_{13}$ is V or L; and/or
in said CDR-L2, $X_1$ is D; $X_4$ is K, V, N, Q, or R; $X_6$ is P, K, or A; and $X_7$ is S, A, or T; and/or
in said CDR-L3, $X_1$ is S, G, T, A, Q, C, or N; $X_5$ is A, S, P, G, N, or D; $X_6$ is I, S, G, T, A, L, H, R, or N; $X_8$ is P, T, S, Q, M, R, N or null; $X_9$ is S, L, N, A, M or null; and $X_{11}$ is Y, W, F, V, A, or L.

5. The antibody or antigen binding fragment of embodiment 3 or embodiment 4, wherein, in said CDR-L3, $X_1$ is S, G, Q, or N; $X_2$ is S, Q, or T; $X_4$ is A, D, T, or Y; $X_5$ is A, S, or G; and $X_6$ is I, S, N, R, A, H, or T.

6. The antibody or fragment of any of embodiments 1-5, wherein:
the CDR-H2 comprises the amino acid sequence set forth in SEQ ID NO: 19 (GISWNSGRIGYADSVKG); or
the CDR-H2 comprises the amino acid sequence set forth in SEQ ID NO: 72 (GISWNSGSIGYADSVKG).

7. The antibody or fragment of any of embodiments 1-6, wherein the CDR-L1 comprises the amino acid sequence set forth in SEQ ID NO: 80, 77, 74, 73, 75, 79, 78, 76, 21, 25, 28, or 31.

8. The antibody or fragment of embodiment 7, wherein said CDR-L1 comprises the amino acid sequence set forth in SEQ ID NO: 80, 77, 74, 73, 78, 21, or 28.

9. The antibody or fragment of any of embodiments 1-8, wherein the CDR-L2 comprises the amino acid sequence set forth in SEQ ID NO: 100, 97, 94, 93, 95, 99, 98, 96, 22, 26, 29, or 32.

10. The antibody or fragment of embodiment 9, wherein the CDR-L2 comprises the amino acid sequence set forth in SEQ ID NO: 100, 97, 94, 93, 98, 22, or 29.

11. The antibody or fragment of any of embodiments 1-10, wherein the CDR-L3 comprises the amino acid sequence set forth in SEQ ID NO: 109, 106, 103, 101, 104, 108, 107, 105, 102, 23, 24, 27, 30, or 33.

12. The antibody or fragment of embodiment 11, wherein the CDR-L3 comprises the amino acid sequence set forth in SEQ ID NO: 109, 106, 103, 101, 107, 24 or 30.

13. The antibody or fragment of any of embodiments 1-12, wherein:
the CDR-L1, CDR-L2, and CDR-L3 comprise the sequences of SEQ ID NOs: 21, 22, and 23, respectively;
the CDR-L1, CDR-L2, and CDR-L3 comprise the sequences of SEQ ID NOs: 21, 22, and 24, respectively;
the CDR-L1, CDR-L2, and CDR-L3 comprise the sequences of SEQ ID NOs: 25, 26, and 27, respectively;
the CDR-L1, CDR-L2, and CDR-L3 comprise the sequences of SEQ ID NOs: 28, 29, and 30, respectively;
the CDR-L1, CDR-L2, and CDR-L3 comprise the sequences of SEQ ID NOs: 31, 32, and 33, respectively;
the CDR-L1, CDR-L2, and CDR-L3 comprise the sequences of SEQ ID NOs: 80, 100, and 109, respectively;

the CDR-L1, CDR-L2, and CDR-L3 comprise the sequences of SEQ ID NOs:77, 97, and 106, respectively;

the CDR-L1, CDR-L2, and CDR-L3 comprise the sequences of SEQ ID NOs: 74, 94, and 103, respectively;

the CDR-L1, CDR-L2, and CDR-L3 comprise the sequences of SEQ ID NOs: 73, 93, and 101, respectively;

the CDR-L1, CDR-L2, and CDR-L3 comprise the sequences of SEQ ID NOs:75, 95, and 104, respectively;

the CDR-L1, CDR-L2, and CDR-L3 comprise the sequences of SEQ ID NOs: 79, 99, and 108, respectively;

the CDR-L1, CDR-L2, and CDR-L3 comprise the sequences of SEQ ID NOs: 78, 98, and 107, respectively;

the CDR-L1, CDR-L2, and CDR-L3 comprise the sequences of SEQ ID NOs: 76, 96, and 105, respectively;

the CDR-L1, CDR-L2, and CDR-L3 comprise the sequences of SEQ ID NOs: 73, 93, and 102, respectively; or the CDR-L1, CDR-L2, and CDR-L3 comprise the sequences of SEQ ID NOs: 77, 97, and 106, respectively.

14. The antibody or antigen-binding fragment thereof of any of embodiments 1-13, wherein:

the CDR-H1, CDR-H2, and CDR-H3 comprise the sequences of SEQ ID NOs: 18, 81, and 20, respectively;

the CDR-H1, CDR-H2, and CDR-H3 comprise the sequences of SEQ ID NOs: 18, 19, and 20, respectively;

the CDR-H1, CDR-H2, and CDR-H3 comprise the sequences of SEQ ID NOs: 18, 82, and 20, respectively; or the CDR-H1, CDR-H2, and CDR-H3 comprise the sequences of SEQ ID NOs: 18, 72, and 20, respectively.

15. The antibody or fragment of any of embodiments 1-14, wherein:

the VH region of the antibody or fragment comprises the amino acid sequence of SEQ ID NO: 11, 12, 60, 61, 63, or 62; and/or the VL region of the antibody or fragment comprises the amino acid sequence of SEQ ID NO: 13, 14, 15, 16, 17, 71, 90, 91, 68, 65, 64, 66, 70, 69, or 67.

16. The antibody or fragment of embodiment 15, wherein:

the VH region of the antibody or fragment comprises the amino acid sequence of SEQ ID NO: 11, 60, 63, or 62; and/or the VL region of the antibody or fragment comprises the amino acid sequence of SEQ ID NO: 14, 16, 71, 90, 65, 64, or 69.

17. The antibody or fragment of any of embodiments 1-16, wherein:

the VH and VL regions of the antibody or fragment comprise the amino acid sequences of SEQ ID NOs: 12 and 17, respectively;

the VH and VL regions of the antibody or fragment comprise the amino acid sequences of SEQ ID NOs: 12 and 15, respectively;

the VH and VL regions of the antibody or fragment comprise the amino acid sequences of SEQ ID NOs: 11 and 13, respectively;

the VH and VL regions of the antibody or fragment comprise the amino acid sequences of SEQ ID NOs: 11 and 14, respectively;

the VH and VL regions of the antibody or fragment comprise the amino acid sequences of SEQ ID NOs: 11 and 16, respectively;

the VH and VL regions of the antibody or fragment comprise the amino acid sequences of SEQ ID NOs: 63 and 71, respectively;

the VH and VL regions of the antibody or fragment comprise the amino acid sequences of SEQ ID NOs: 62 and 68, respectively;

the VH and VL regions of the antibody or fragment comprise the amino acid sequences of SEQ ID NOs: 11 and 65, respectively;

the VH and VL regions of the antibody or fragment comprise the amino acid sequences of SEQ ID NOs: 60 and 64, respectively;

the VH and VL regions of the antibody or fragment comprise the amino acid sequences of SEQ ID NOs: 61 and 66, respectively;

the VH and VL regions of the antibody or fragment comprise the amino acid sequences of SEQ ID NOs: 63 and 70, respectively;

the VH and VL regions of the antibody or fragment comprise the amino acid sequences of SEQ ID NOs: 62 and 69, respectively;

the VH and VL regions of the antibody or fragment comprise the amino acid sequences of SEQ ID NOs: 12 and 67, respectively;

the VH and VL regions of the antibody or fragment comprise the amino acid sequences of SEQ ID NOs: 12 and 91, respectively; or the VH and VL regions of the antibody or fragment comprise the amino acid sequences of SEQ ID NOs: 63 and 90, respectively.

18. The antibody or fragment of embodiment 17, wherein:

the VH and VL regions of the antibody or fragment comprise the amino acid sequences of SEQ ID NOs: 11 and 14, respectively;

the VH and VL regions of the antibody or fragment comprise the amino acid sequences of SEQ ID NOs: 11 and 16, respectively;

the VH and VL regions of the antibody or fragment comprise the amino acid sequences of SEQ ID NOs: 63 and 71, respectively;

the VH and VL regions of the antibody or fragment comprise the amino acid sequences of SEQ ID NOs: 11 and 65, respectively;

the VH and VL regions of the antibody or fragment comprise the amino acid sequences of SEQ ID NOs: 60 and 64, respectively;

the VH and VL regions of the antibody or fragment comprise the amino acid sequences of SEQ ID NOs: 62 and 69, respectively; or the VH and VL regions of the antibody or fragment comprise the amino acid sequences of SEQ ID NOs: 63 and 90, respectively.

19. The antibody or fragment of any of embodiments 1-18, wherein the antibody specifically binds to CD19.

20. The antibody or fragment of embodiment 19, wherein the antibody specifically binds to the same or an overlapping epitope of CD19 as the epitope specifically bound by a reference anti-CD19 antibody selected from the group consisting of FMC63 and SJ25C1.

21. The antibody or fragment of embodiment 19, wherein the antibody competes for binding to CD19 with an anti-CD19 antibody selected from the group consisting of FMC63 and SJ25C1.

22. A human antibody fragment that specifically binds to the same or an overlapping epitope of CD19 as the epitope specifically bound by a reference antibody, which is the antibody or fragment thereof of any of embodiments 1-21 or is an anti-CD19 antibody selected from the group consisting of FMC63 and SJ25C1, said human antibody fragment comprising heavy and light chain CDRs that are distinct from the CDRs present in FMC63 and SJ25C1.

23. A human antibody fragment that specifically binds to CD19 and competes for binding to CD19 with a reference antibody, which is the antibody or fragment of any of embodiments 1-21 or is an anti-CD19 antibody selected from the group consisting of FMC63 and SJ25C1, said antibody fragment comprising heavy and light chain CDRs that are distinct from the CDRs present in FMC63 and SJ25C1.

24. The antibody or fragment of embodiment 21 or 23, which competes for binding with the reference antibody to at least the same degree as the reference antibody competes for binding with itself to CD19, or a degree of competition that is no more than 1.5-fold or 2-fold lower than the competition by the reference antibody.

25. The antibody or fragment of any of embodiment 1-24, wherein the antibody has a binding affinity that is at least as high or substantially as high as the binding affinity for CD19 of a reference antibody selected from the group consisting of FMC63 and SJ25C1.

26. The antibody or fragment of embodiment 25, which has a binding affinity of an EC50 that is about the same or lower than the EC50 of the reference antibody or no more than about 1.5-fold or no more than about 2-fold greater, no more than 3-fold greater, and/or no more than 10-fold greater, than the EC50 of the reference antibody.

27. The antibody or fragment of any of embodiments 1-26, wherein the antibody or fragment is human.

28. The antibody or fragment of any of embodiments 1-27, wherein the antibody or fragment is recombinant.

29. The antibody or fragment of any of embodiments 1-28, which is monoclonal. 30. The antibody or fragment of any of any of embodiments 1-29, which is a single chain fragment.

31. The antibody or fragment of any of embodiments 1-30, which is a fragment comprising antibody variable regions joined by a flexible immunoglobulin linker.

32. The antibody or fragment of embodiment 30 or 31, wherein the fragment comprises an scFv.

33. The antibody or fragment of embodiment 32, wherein the scFv comprises a linker comprising the sequence set forth SEQ ID NO: 34.

34. The antibody or fragment of embodiment 32, wherein the scFv comprises the amino acid sequence set forth in SEQ ID NO: 2, 4, 6, 8, 10, 45, 47, 49, 51, 53, 55, 57, 59, 87, or 89.

35. The antibody or fragment of any of embodiments 1-34, which further comprises at least a portion of an immunoglobulin constant region.

36. The antibody or fragment of embodiment 35, wherein the at least a portion of an immunoglobulin constant region comprises an Fc region.

37. The antibody or fragment of embodiment 36, wherein the Fc region is an Fc region of a human IgG.

38. The antibody or fragment of any of embodiments 1-37, wherein CD19 is human CD19.

39. A chimeric antigen receptor (CAR) comprising an extracellular portion comprising the antibody or fragment of any of embodiments 1-38 and an intracellular signaling domain.

40. The chimeric antigen receptor of embodiment 38, wherein the antibody or fragment comprises an scFv and the intracellular signaling domain comprises an ITAM.

41. The chimeric antigen receptor of embodiment 39 or 40, wherein the intracellular signaling domain comprises a signaling domain of a zeta chain of a CD3-zeta (CD3) chain.

42. The chimeric antigen receptor of any of embodiments 39-41, further comprising a transmembrane domain linking the extracellular domain and the intracellular signaling domain.

43. The chimeric antigen receptor of embodiment 42, wherein the transmembrane domain comprises a transmembrane portion of CD28.

44. The chimeric antigen receptor of any of embodiments 39-43, further comprising an intracellular signaling domain of a T cell costimulatory molecule.

45. The chimeric antigen receptor of embodiment 44, wherein the T cell costimulatory molecule is selected from the group consisting of CD28 and 41BB.

46. An engineered cell expressing the chimeric antigen receptor of any of embodiments 39-45.

47. The engineered cell of embodiment 46, which is a T cell. 48. A method of treatment, comprising administering the cell of embodiment 46 or 47 to a subject having a disease or disorder associated with CD19.

49. A method of treatment, comprising administering the antibody of any of embodiments 1-38 to a subject having a disease or disorder associated with CD19.

50. The method of embodiment 48 or 49, wherein the disease or disorder is a B cell malignancy.

51. The method of embodiment 50, wherein the B cell malignancy is selected from the group consisting of B cell chronic lymphocytic leukemia (CLL), acute lymphocytic leukemia (ALL), pro-lymphocytic leukemias, hairy cell leukemias, common acute lymphocytic leukemias, Null-acute lymphoblastic leukemias, non-Hodgkin lymphomas, diffuse large B cell lymphomas (DLBCLs), multiple myelomas, follicular lymphoma, splenic, marginal zone lymphoma, mantle cell lymphoma, indolent B cell lymphoma, and Hodgkin lymphoma.

52. A nucleic acid encoding the antibody or fragment thereof of any of embodiments 1-38 or the chimeric antigen receptor of any of embodiments 39-45.

53. A composition comprising the antibody or fragment thereof of any of embodiments 1-38, the CAR of any of embodiments 39-45, or the cell of embodiment 46 or 47.

54. A method of treatment, comprising administering the composition of embodiment 53 to a subject having a disease or disorder associated with CD19.

55. An antibody or antigen-binding fragment thereof comprising:

heavy chain complementarity determining regions 1, 2, and 3 (CDR-H1, CDR-H2, and CDR-H3), respectively comprising the amino acid sequences of CDR 1, 2, and 3 sequences contained within the heavy chain variable (VH) region amino acid sequence set forth in SEQ ID NO: 11 or 12; and light chain complementarity determining regions 1, 2, and 3 (CDR-L1, CDR-L2, and CDR-L3), respectively comprising the amino acid sequences of CDR 1, 2, and 3 sequences contained within the light chain variable (VL) region amino acid sequence set forth in SEQ ID NO: 13, 14, 15, 16, or 17.

56. The antibody or fragment of embodiment 55, wherein:

the CDR-H1 comprises the amino acid sequence of DYAMH (SEQ ID NO: 18);

the CDR-H2 comprises the amino acid sequence GISWNSGRIGY (SEQ ID NO: 35);

the CDR-H3 comprises the amino acid sequence of SEQ ID NO: 20;

the CDR-L1 comprises the amino acid sequence $X_1GX_3X_4X_5X_6X_7X_8X_9X_{10}X_{11}X_{12}X_{13}S$ (SEQ ID NO: 36), wherein $X_1$ is T, S, or Q, $X_3$ is T, S, or D, $X_4$ is T or S, $X_5$ is null or S, $X_6$ is null, D, or N, $X_7$ is null or V, $X_8$ is null, G, or I, $X_9$ is null, G, or R, $X_{10}$ is S, Y, or N, $X_{11}$ is D or N, $X_{12}$ is D or Y, $X_{13}$ is V or A;

the CDR-L2 comprises the amino acid sequence $X_1X_2X_3X_4RPS$ (SEQ ID NO: 37), wherein $X_1$ is D or S, $X_2$ is V, N, or K, $X_3$ is S, N, or D, and $X_4$ is K, Q, or N; and the CDR-L3 comprises the amino acid sequence $X_1X_2X_3X_4X_5X_6X_7X_8X_9X_{10}X_{11}X_{12}$ (SEQ ID NO: 38), wherein $X_1$ is C, S, A, G, or N, $X_2$ is S, A, or T, $X_3$ is Y, W, or R, $X_4$ is A or D, $X_5$ is G, D, or S, $X_6$ is R, S, or N, $X_7$ is Y, L, or G, $X_8$ is N or S, $X_9$ is S or null, $X_{10}$ is V, A, or N, $X_{11}$ is W or null, and $X_{12}$ is L or V.

57. The antibody or fragment of embodiment 56, wherein: in the CDR-L1, $X_1$ is T or S, $X_3$ is T or S, $X_{11}$ is D or N, and $X_{13}$ is V; in the CDR-L2, $X_2$ is V or N and $X_4$ is K or Q; and/or in the CDR-L3, $X_1$ is C, S, A, or G, $X_3$ is Y or W, $X_5$ is G or D, $X_7$ is Y or L, $X_{10}$ is V or A, and $X_{11}$ is null.

58. The antibody or fragment of any of embodiments 55-57, wherein the CDR-H2 comprises the amino acid sequence set forth in SEQ ID NO: 19 (GISWNSGRIG-YADSVKG).

59. The antibody or fragment of any of embodiments 55-58, wherein the CDR-L1 comprises the sequence set forth in SEQ ID NO: 21, 25, 28, or 31.

60. The antibody or fragment of any of embodiments 55-59, wherein the CDR-L2 comprises the sequence set forth in SEQ ID NO: 22, 26, 29, or 32.

61. The antibody or fragment of any of embodiments 55-60, wherein the CDR-L3 comprises the sequence set forth in SEQ ID NO: 23, 24, 27, 30, or 33.

62. The antibody or fragment of any of embodiments 55-61, wherein:

the CDRL1, CDR-L2, and CDR-L3 comprise the sequences of SEQ ID NOs: 21, 22, and 23, respectively;

the CDRL1, CDR-L2, and CDR-L3 comprise the sequences of SEQ ID NOs: 21, 22, and 24, respectively;

the CDRL1, CDR-L2, and CDR-L3 comprise the sequences of SEQ ID NOs: 25, 26, and 27, respectively;

the CDRL1, CDR-L2, and CDR-L3 comprise the sequences of SEQ ID NOs: 28, 29, and 30, respectively; or the CDRL1, CDR-L2, and CDR-L3 comprise the sequences of SEQ ID NOs: 31, 32, and 33, respectively.

63. The antibody or fragment of any of embodiments 55-62, wherein the antibody or fragment comprises:

a VH region comprising the amino acid sequence of SEQ ID NO: 11 or 12; and a VL region comprising the amino acid sequence of SEQ ID NO: 13, 14, 15, 16, or 17.

64. The antibody or fragment of embodiment 63, wherein the VH region comprises the amino acid sequence of SEQ ID NO: 11.

65. The antibody or fragment of embodiment 63, wherein the VH region comprises the amino acid sequence of SEQ ID NO: 12.

66. The antibody or fragment of any of embodiments 55-65, wherein the antibody specifically binds to CD19.

67. The antibody or fragment of embodiment 66, wherein the antibody specifically binds to the same or an overlapping epitope of CD19 as the epitope specifically bound by a reference anti-CD19 antibody selected from the group consisting of FMC63 and SJ25C1.

68. The antibody or fragment of embodiment 66, wherein the antibody competes for binding to CD19 with an anti-CD19 antibody selected from the group consisting of FMC63 and SJ25C1.

69. A human antibody fragment that specifically binds to the same or an overlapping epitope of CD19 as the epitope specifically bound by a reference antibody, which is the antibody or fragment thereof of any of embodiments 55-68 or by an anti-CD19 antibody selected from the group consisting of FMC63 and SJ25C1, said human antibody fragment comprising heavy and light chain CDRs that are distinct from the CDRs present in FMC63 and SJ25C1.

70. A human antibody fragment that specifically binds to CD19 and competes for binding to CD19 with a reference antibody, which is the antibody or fragment of any of embodiments 55-68 or an anti-CD19 antibody selected from the group consisting of FMC63 and SJ25C1, said antibody fragment comprising heavy and light chain CDRs that are distinct from the CDRs present in FMC63 and SJ25C1.

71. The antibody of embodiment 68 or 70, which competes for binding with the reference antibody to at least the same degree as the reference antibody competes for binding with itself to CD19, or a degree of competition that is no more than 1.5-fold or 2-fold lower than the competition by the reference antibody.

72. The antibody of any of embodiments 55-71, wherein the antibody has a binding affinity that is at least as high or substantially as high as the binding affinity for CD19 of a reference antibody selected from the group consisting of FMC63 and SJ25C1.

73. The antibody of embodiment 72, which has a binding affinity of an $EC_{50}$ that is about the same or lower than the $EC_{50}$ reference antibody or no more than about 1.5-fold or no more than about 2-fold greater, no more than 3-fold greater, and/or no more than 10-fold greater, than the $EC_{50}$ of the reference antibody.

74. The antibody or fragment of any of embodiments 55-73, wherein the antibody is human.

75. The antibody or fragment of any of embodiments 55-74, wherein the antibody is recombinant.

76. The antibody or fragment of any of embodiments 55-75, which is monoclonal.

77. The antibody or fragment of any of any of embodiments 55-76, which is a single chain fragment.

78. The antibody or fragment of any of embodiments 55-77, which is a fragment comprising antibody variable regions joined by a flexible immunoglobulin linker.

79. The antibody or fragment of embodiment 77 or 78, wherein the fragment comprises an scFv.

80. The antibody or fragment of embodiment 79, wherein the scFv comprises a linker comprising the sequence set forth SEQ ID NO: 34.

81. The antibody or fragment of embodiment 80, wherein the scFv comprises the amino acid sequence set forth in SEQ ID NO: 2, 4, 6, 8, or 10.

82. The antibody or fragment of any of embodiments 55-81, which further comprises at least a portion of an immunoglobulin constant region.

83. The antibody or fragment of embodiment 82, wherein the at least a portion of an immunoglobulin constant region comprises an Fc region.

84. The antibody or fragment of embodiment 83, wherein the Fc region is an Fc region of a human IgG.

85. The antibody or fragment of any of embodiments 55-84, wherein the CD19 is a human CD19.

86. A chimeric antigen receptor comprising an extracellular portion comprising the antibody or fragment of any of embodiments 55-85 and an intracellular signaling domain.

87. The chimeric antigen receptor of embodiment 86, wherein the antibody or fragment comprises an scFv and the intracellular signaling domain comprises an ITAM.

88. The chimeric antigen receptor of embodiment 87, wherein the intracellular signaling domain comprises a signaling domain of a zeta chain of a CD3-zeta (CD3) chain.

89. The chimeric antigen receptor of any of embodiments 86-88, further comprising a transmembrane domain linking the extracellular domain and the intracellular signaling domain.

90. The chimeric antigen receptor of embodiment 89, wherein the transmembrane domain comprises a transmembrane portion of CD28.

91. The chimeric antigen receptor of any of embodiments 86-90, further comprising an intracellular signaling domain of a T cell costimulatory molecule.

92. The chimeric antigen receptor of embodiment 91, wherein the T cell costimulatory molecule is selected from the group consisting of CD28 and 41BB.

93. An engineered cell expressing the chimeric antigen receptor of any of embodiments 86-92.

94. The engineered cell of embodiment 93, which is a T cell.

95. A method of treatment, comprising administering the cell of embodiment 93 or 94 to a subject having a disease or disorder associated with CD19.

96. A method of treatment, comprising administering the antibody of any of embodiments 55-85 to a subject having a disease or disorder associated with CD19.

97. The method of embodiment 95 or 96, wherein the disease or disorder is a B cell malignancy.

98. The method of embodiment 97, wherein the B cell malignancy is selected from the group consisting of B cell chronic lymphocytic leukemia (CLL), acute lymphocytic leukemia (ALL), pro-lymphocytic leukemias, hairy cell leukemias, common acute lymphocytic leukemias, Null-acute lymphoblastic leukemias, non-Hodgkin lymphomas, diffuse large B cell lymphomas (DLBCLs), multiple myelomas, follicular lymphoma, splenic, marginal zone lymphoma, mantle cell lymphoma, indolent B cell lymphoma, and Hodgkin lymphoma.

99. A nucleic acid encoding the antibody of any of embodiments 55-85 or the chimeric antigen receptor of any of embodiments 86-92.

100. A composition comprising the antibody of any of embodiments 55-85, the CAR of any of embodiments 86-92, or the cell of embodiment 93 or 94.

101. A method of treatment, comprising administering the composition of embodiment 100 to a subject having a disease or disorder associated with CD19.

102. The antibody or fragment of any of embodiments 1-38 or 55-85, the CAR of any of embodiments 39-45 or 86-92, the cell of any of embodiments 46, 47, 93, and 94, the method of any of embodiments 48-51, 54, 95-98, and 101, the nucleic acid of embodiment 52 or 99, or the composition of any of embodiments 53 and 100, wherein the antibody or fragment specifically binds to an epitope containing one or more amino acids within a region of the extracellular portion of a CD19.

103. The antibody or fragment of any of embodiments 1-38 or 55-85, the CAR of any of embodiments 39-45 or 86-92, the cell of any of embodiments 46, 47, 93, and 94, the method of any of embodiments 48-51, 54, 95-98, and 101, the nucleic acid of embodiment 52 or 99, or the composition of any of embodiments 53 and 100, wherein the antibody or fragment specifically binds to an epitope that is within a region of the extracellular portion of a CD19.

103. The antibody or fragment of any of embodiments 1-38 or 55-85, the CAR of any of embodiments 39-45 or 86-92, the cell of any of embodiments 46, 47, 93, and 94, the method of any of embodiments 48-51, 54, 95-98, and 101, the nucleic acid of embodiment 52 or 99, or the composition of any of embodiments 53 and 100, wherein the antibody or fragment specifically binds to a polypeptide consisting or consisting essentially of region of the extracellular portion of a CD19, or that comprises the region of the extracellular portion of the CD19 but not any, or substantially no, other portion of CD19.

104. The antibody, fragment, cell, method, nucleic acid, or composition of any of embodiments 102-103, wherein the region of the extracellular portion of the CD19 is a membrane-proximal region.

105. The antibody, fragment, cell, method, nucleic acid, or composition of any of embodiments 102-104, wherein the region of the extracellular portion of the CD19 is a portion encoded by the fourth exon of the CD19 or a portion corresponding to positions 176-277 of the human CD19 sequence set forth in SEQ ID NO: 92.

106. The antibody, fragment, cell, method, nucleic acid, or composition of any of embodiments 102-105, wherein the region of the extracellular portion of the CD19 consists of or comprises the membrane-proximal-most 100, 90, 80, 75, 70, 65, 60, 55, 50, 45, 44, 43, 43, 41, or 40 amino acid portion of the extracellular portion of the CD19.

107. The antibody, fragment, cell, method, nucleic acid, or composition of any of embodiments 102-106, wherein the region of the extracellular portion consists of or comprises the Ig-like domain 1 of CD19, a portion encoded by the second exon of the CD19 and/or a portion corresponding to positions 20-117 of the human CD19 sequence set forth in SEQ ID NO: 92

108. The antibody, fragment, cell, method, nucleic acid, or composition of any of embodiments 102-106, which optionally is any of the portions of the extracellular region described in any of embodiments 105-107.

109. The antibody or fragment of any of embodiments 1-38 or 55-85, the CAR of any of embodiments 39-45 or 86-92, the cell of any of embodiments 46, 47, 93, and 94, the method of any of embodiments 48-51, 54, 95-98, and 101, the nucleic acid of embodiment 52 or 99, or the composition of any of embodiments 53 and 100, wherein the antibody or fragment specifically binds to an epitope of CD19 that contains one or more amino acids within, is within, or includes a portion of CD19 corresponding to residues 218-249 of the human CD19 sequence set forth in SEQ ID NO: 92.

110. The antibody, fragment, cell, method, nucleic acid, or composition of embodiment 109, wherein the portion comprises the sequence set forth in SEQ ID NO: 143.

111. The antibody or fragment of any of embodiments 1-38 or 55-85, the CAR of any of embodiments 39-45 or 86-92, the cell of any of embodiments 46, 47, 93, and 94, the method of any of embodiments 48-51, 54, 95-98, and 101, the nucleic acid of embodiment 52 or 99, or the composition of any of embodiments 53 and 100, wherein the antibody or fragment specifically binds to an epitope of CD19 that contains an amino acid at a position corresponding to a position of the human CD19 sequence set forth in SEQ ID NO: 92 selected from the group consisting of: the histidine (H) at position 218, the alanine (A) at position 236, the methionine (M) at position 242, the glutamate (E) at position 243, the proline (P) at position 249, and/or the lysine (K) and/or serine (S) at positions 223 and 224, and combinations thereof.

112. The antibody or fragment of any of embodiments 1-38 or 55-85, the CAR of any of embodiments 39-45 or 86-92, the cell of any of embodiments 46, 47, 93, and 94, the method of any of embodiments 48-51, 54, 95-98, and 101, the nucleic acid of embodiment 52 or 99, or the composition of any of embodiments 53 and 100, wherein an amino acid at a position corresponding to a position of the human CD19 sequence set forth in SEQ ID NO: 92 selected from the group consisting of: the histidine (H) at position 218, the alanine (A) at position 236, the methionine (M) at position 242, the glutamate (E) at position 243, the proline (P) at position 249, and/or the lysine (K) and/or serine (S) at positions 223 and 224, and combinations thereof is necessary or important for binding of the antibody to human CD19.

113. The antibody, fragment, cell, method, nucleic acid, or composition of embodiment 111 or 112, wherein the amino acid is identical to the amino acid present at the corresponding position in SEQ ID NO: 92.

114. The antibody, fragment, cell, method, nucleic acid, or composition of any of embodiments 111-113, wherein the amino acid is or comprises an amino acid at the position corresponding to the histidine at position 218 of the human CD19, optionally wherein the amino acid at said position is a histidine.

115. The antibody, fragment, cell, method, nucleic acid, or composition of any of embodiments 111-114, wherein the amino acid is or comprises an amino acid at the position corresponding to the alanine at position 236 of the human CD19 sequence, optionally wherein the amino acid at said position is an alanine.

116. The antibody, fragment, cell, method, nucleic acid, or composition of any of embodiments 111-115, wherein the amino acid is or comprises an amino acid at the position corresponding to the methionine at position 242 of the human CD19, optionally wherein the amino acid at said position is a methionine.

117. The antibody, fragment, cell, method, nucleic acid, or composition of any of embodiments 111-116, wherein the amino acid is or comprises an amino acid at the position corresponding to the glutamate at position 243 of the human CD19, optionally wherein the amino acid at said position is a glutamate.

118. The antibody, fragment, cell, method, nucleic acid, or composition of any of embodiments 111-117, wherein the amino acid is or comprises an amino acid at the position corresponding to the proline at position 249 of the human CD19, optionally wherein the amino acid at said position is a proline.

119. The antibody, fragment, cell, method, nucleic acid, or composition of any of embodiments 111-118, wherein the amino acid is or comprises an amino acid(s) at one or both of the positions corresponding to the lysine and/or serine at positions 223 and 224 of the human CD19.

120. The antibody or fragment of any of embodiments 1-38 or 55-85, the CAR of any of embodiments 39-45 or 86-92, the cell of any of embodiments 46, 47, 93, and 94, the method of any of embodiments 48-51, 54, 95-98, and 101, the nucleic acid of embodiment 52 or 99, or the composition of any of embodiments 53 and 100, wherein the antibody or fragment specifically binds to an epitope that overlaps with or is identical to or comprises an epitope specifically bound by a reference antibody, wherein the overlapping portion comprises or is within a portion of CD19 (a) comprising SEQ ID NO: 143, (b) corresponding to residues 218-249 of the human CD19 sequence set forth in SEQ ID NO: 92, or (c) corresponding to a region of CD19 encoded by exon 4 of human CD19, or (d) within a portion corresponding to the 75-most or 80-most membrane proximal residues of human CD19.

121. The antibody, fragment, cell, method, nucleic acid, or composition of embodiment 120, wherein the reference antibody is FMC63, or is wherein the reference antibody is SJ25C1.

V. EXAMPLES

The following examples are included for illustrative purposes only and are not intended to limit the scope of the invention.

Example 1: Generation and Assessment of Anti-CD19 Antibodies

Exemplary anti-CD19 antibodies that specifically bind to CD19-expressing cells with similar binding properties to murine anti-CD19 reference antibodies, and/or compete for binding with murine anti-CD19 reference antibodies were generated and assessed.

1A. Library Selection, Antibody Generation

Exemplary anti-CD19 antibodies (scFvs) were generated through a series of selection steps carried out on dsDNA-encoded human naïve antibody libraries displayed in a cell-free system. Members of a $V_H$ library were selected for binding to live cells through three successive rounds, enriching for members that bind specifically to stably-transfected CD19-expressing HEK293 cells, but not parental HEK293 cells and/or to CHOK1 cells that did not expresses CD19. At the end of each selection round, three separate elution pools were generated by (a) surface stripping to recover binders from target cells, (b) competitive elution using a murine anti-CD19 antibody, FMC63 IgG, and (c) competitive elution using another murine anti-CD19 antibody, SJ25C1 ((b) and (c) carried out to enrich for binders that compete with FMC63 and/or SJ25C1 for binding to CD19).

At end of 3 rounds of selections, these enriched $V_H$ libraries were then converted to scFv libraries by shuffling $V_H$ members of these respective pools and a naïve human $V_L$ library in $V_H$-(G4S)$_3$—$V_L$ format. The resulting scFv libraries were subjected to a fourth round, enriching for members that bound specifically to CD19-expressing HEK293 cells and not to parental cells, followed by surface stripping.

A fifth round was carried out to further enrich for members that bound to other CD19-expressing cells (CD19/K562). Selections were followed by the generation of separate elution pools using either (a) surface stripping, (b) FMC63 competitive elution, or (c) SJ25C1 competitive elution. In a sixth round, these three pools were individually further enriched by negative selection for members that did not bind parental cells (HEK293, twice, K562), followed by positive selection for members that bound CD19-expressing HEK293 cells and immunoprecipitation with an anti-Myc antibody that recognized a C-terminal tag on CD19 expressed on HEK293 cells.

In one study, forty-eight (48) clones from each of the three R6 scFv resulting pools were sequenced using forward and reverse primers to determine amino acid sequences. 130 of the determined scFv sequences showed full length reading. Convergence was observed among the sequences. Eighteen (18) replicates were identified among the 130 scFv sequences (representing forty-six (46) of the 130 clones). In this study, one $V_H$ portion sequence containing CDRs 1-3 and FRs 1-3 was detected fourteen (14) times in two of the different pools (10 copies from one and 4 copies from another), paired with 5 different $V_L$s. Other replicates were identified between 2 and 5 times in different pools; others were single-copy sequences. In another study, additional CD19-binding clones were identified and sequenced. The same VH portion appeared among them, with different $V_L$ sequences.

1B. Specific Binding to CD19-Expressing Cells

Figure 1B:
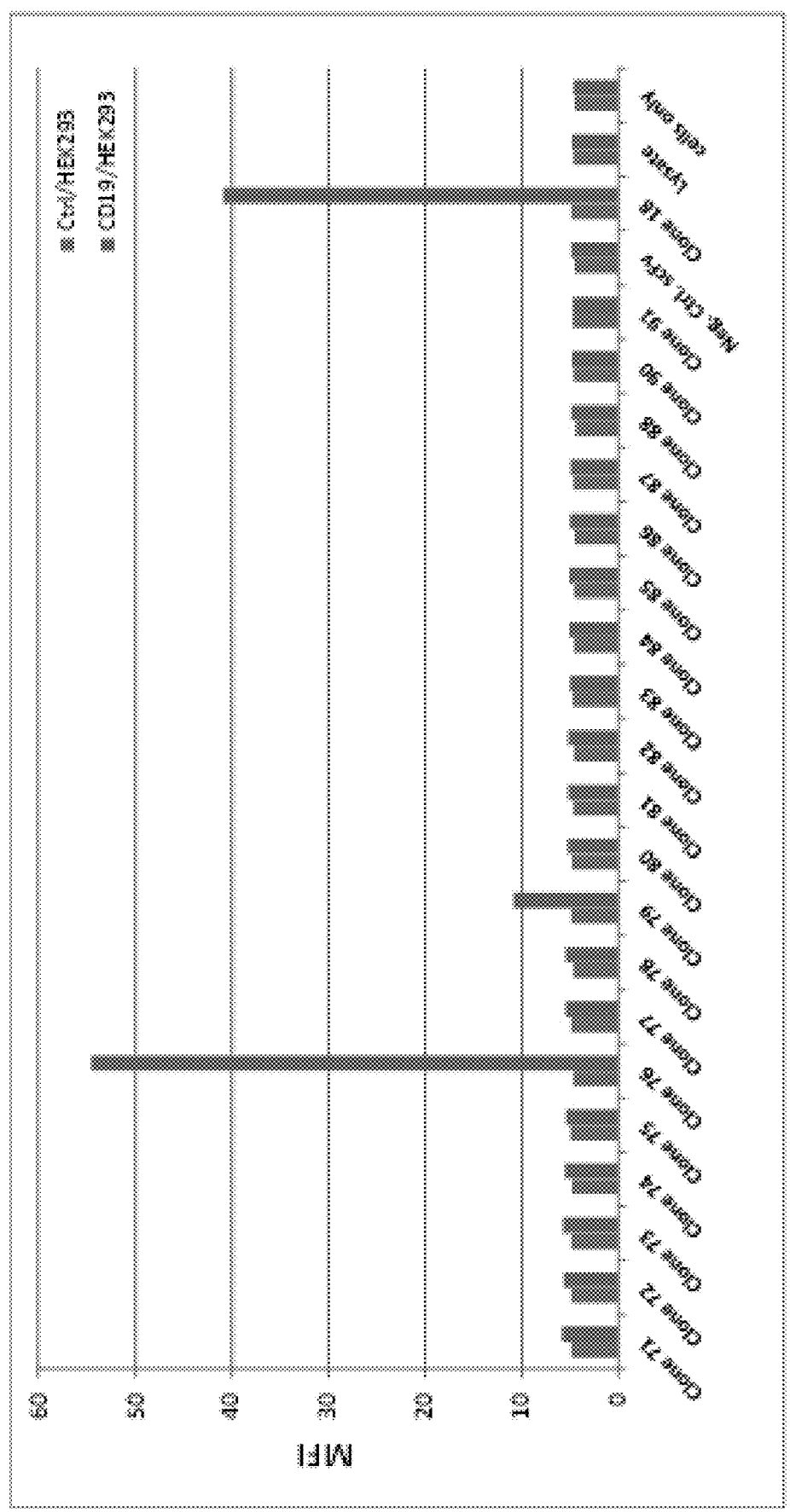

Binding of the sequenced clones to CD19-expressing and control HEK293 cells, as compared to cells that did not express CD19, was assessed by flow cytometry either with in vitro translated crude cell lysate or with bacterially-produced supernatant. Briefly, RNA of each clone was normalized and in vitro translated as crude scFv with a C-terminal FLAG tag. CD19-expressing HEK293 and control (mock transfected) HEK293 cells were used in the assay. Binding of the individual scFvs to CD19 and control cells was measured with a secondary anti-FLAG-Alexa647 conjugate. Alternatively, scFv binding pools were cloned into E. coli expression vectors and were produced as HIS-tagged scFvs which were detected with anti-HIS-Alexa647 conjugate in flow-cytometric assays. Murine anti-CD19 antibodies (FMC63 scFv and FMC63 IgG) were used as positive controls; a control scFv also was used. Mean fluorescence intensity (MFI) was assessed by flow cytometry. The results are shown in FIGS. 1A and 1B, demonstrating binding of identified clones to CD19-expressing cells. Among the clones assessed were scFvs, including clones 5, 17, 18 (identified with in vitro translated lysates), and 76 (identified with bacterial supernatant), that displayed clear binding preference for CD19-expressing cells as compared to CD19-negative cells.

As shown in FIGS. 1A and 1B, for some clones, the fold change in degree of binding detected, in this case as measured by mean fluorescence intensity, to the CD19-expressing cells as compared to the non-CD19-expressing cells, was about as great, at least as great, or greater than the fold change observed for the positive control reference antibodies, murine anti-CD19 antibodies FMC63 scFv and/or FMC63 IgG. In some cases, the total degree of observed binding to the CD19-expressing cells was approximately the same, at least as great, or greater than that observed for one or more of the positive control reference antibody.

Four (4) scFv clones that displayed clear binding preference for CD19-expressing cells compared to non-CD19-expressing cells ("clone 18," "clone 17," "clone 5," and "clone 76") were further analyzed. Sequencing revealed that the clones shared common CDR sequences within their VH sequences, with different VL sequences and different CDR-Ls. Sequence identifiers corresponding to sequences, including exemplary scFv, $V_H$, $V_L$, and CDR (Kabat) amino acid sequences and encoding nucleotide scFv sequences, for the four clones are listed Table 2. A germline variant of clone 18 (deemed "clone 18B") was generated by a cysteine (C) to serine (S) substitution at Kabat position 89; sequences for this clone also are listed in Table 2. Each of the clones had a $V_H3$ chain sequence. Clone 18 included a light chain framework derived from a Vλ2 sequence (with clone 18B having the Vλ2 germline framework sequence); clones 17 and 76 had Vλ1 sequences, and clone 5 included a Vλ3 sequence. Clones 18 and 17 were derived from multiple branches and libraries, including $V_H$-$V_L$ shuffling and scFv. Clone 76 was derived from $V_H$-$V_L$ SJ25C1 competitive elution (Round 6); clone 5 was derived from $V_H$-$V_L$ FMC63 competitive elution (Round 6).

TABLE 2

Sequences for Exemplary Clones (SEQ ID NO.)

| Clone # | Heavy Chain Variable (VH) Region (Amino Acid) | Light Chain Variable (VL) Region (Amino Acid) | ScFv Sequence (Amino Acid, Nucleotide) | CDR-H (1, 2, 3) (Kabat) (Amino Acid) | CDR-L (1, 2, 3) (Kabat) (Amino Acid) |
|---|---|---|---|---|---|
| 5 | 12 | 17 | 10 | 18, 19, 20 | 31, 32, 33 |
| 17 | 12 | 15 | 6 | 18, 19, 20 | 25, 26, 27 |
| 18 | 11 | 13 | 2 | 18, 19, 20 | 21, 22, 23 |
| 18B | 11 | 14 | 4 | 18, 19, 20 | 21, 22, 24 |
| 76 | 11 | 16 | 8 | 18, 19, 20 | 28, 29, 30 |

1C. Binding Affinities, Competition with Reference Antibodies

Figure 2:
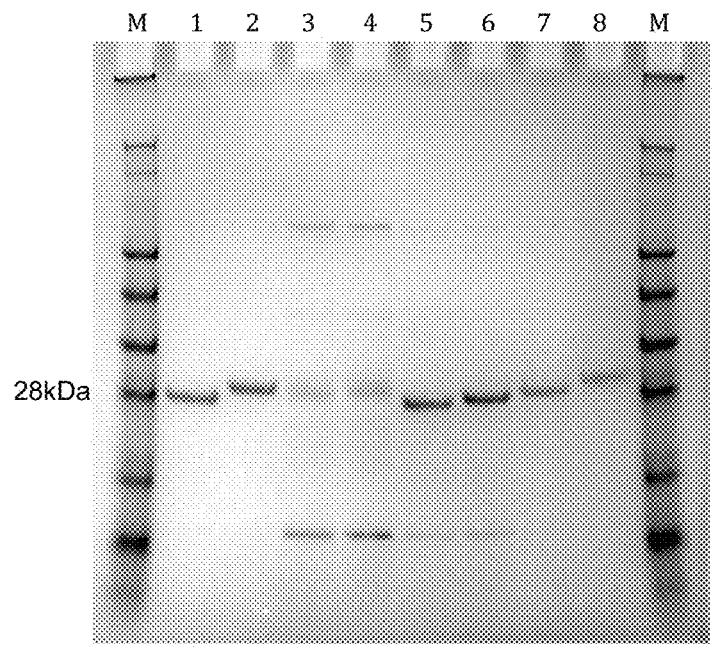
FIG. 2 shows an SDS gel assessing purification of exemplary anti-CD19 antibodies (scFv fragments).

Clones 5, 17, 18, 18B, and 76, were purified by single-step purification and purification assessed via SDS gel. A gel from an exemplary study is shown in FIG. 2 (lanes 1 and 2=clone 5, non-reduced, reduced; lanes 3 and 4=clone 17, non-reduced, reduced; lanes 5 and 6=clone 18, non-reduced and reduced; lanes 7 and 8=clone 76, non-reduced and reduced). In this study, isoelectric points were measured as 5.36, 5.32, 7.11, and 5.32, respectively for clones 5, 17, 18, and 76.

Melting temperature (Tm) measurements were made using BioTad CFX96 instrument to analyze sypro orange protein incorporation at incremental temperatures, revealing similar $T_m$ values as those observed for the reference antibody FMC63 scFv. The results are presented in Table 3.

TABLE 3

Assessment of $T_m$

| Clone, Condition | $T_m$ (° C.) |
|---|---|
| 5, Imidazole | 53 |
| 5, pH 6 | 61 |
| 5, pH 7 | 57 |
| 5, pH 8 | 57 |
| 17 | 51 |
| 18 | 59 |
| 18B | 59 |
| FMC63 scFv | 56 |

Clones were titrated, and their binding affinities ($EC_{50}$) to CD19-expressing K562 cells assessed by flow cytometry, with a reference murine CD19 antibody, FMC63 scFv, used as a positive control. Results from three separate assays, each including and comparing other binding affinities to that for clone 18, are shown in FIGS. 3A-3C.

Figure 3A:
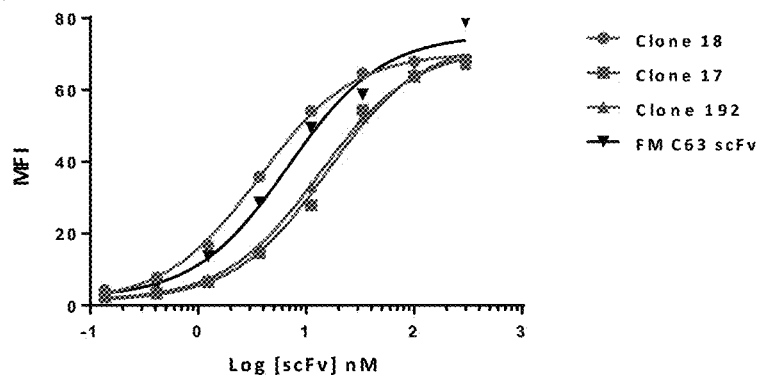
FIGS. 3A, 3B, and 3C show results from studies assessing binding affinities of various exemplary scFv antibodies (scFv fragments), including anti-CD19 antibodies. MFI=mean fluorescence intensity.
Figure 3B:
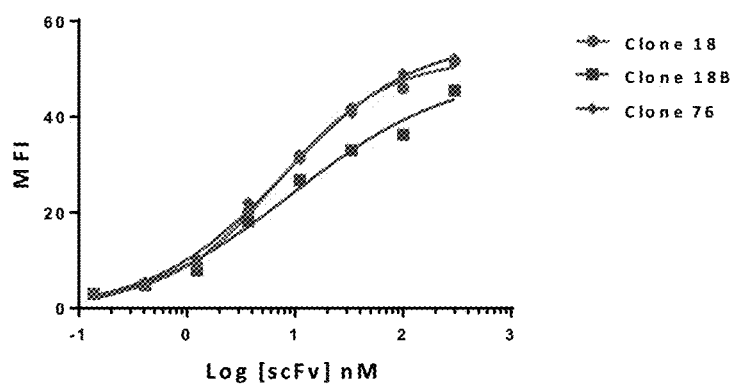
Figure 3C:
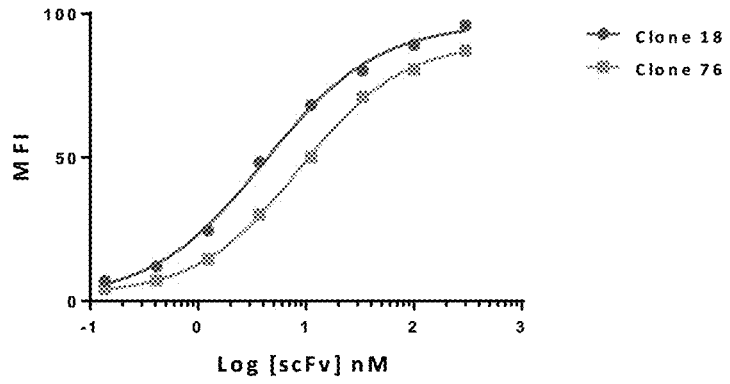

In the assay the results of which are shown in FIG. 3A, $EC_{50}$ values for clone 18, clone 17, another clone identified by the study (deemed clone 192; see sequences in Table 6), and the reference antibody (FMC63 scFv) were measured as 3.79 nM, 14.86 nM, 12.80 nM, and 7.37 nM, respectively. In the assay the results of which are shown in FIG. 3B, $EC_{50}$ values for clone 18, clone 18B, and clone 76 were measured as 7.1 nM and 9.3 nM, and 7.9 nM, respectively. In the assay the results of which are shown in FIG. 3C, $EC_{50}$ values for clone 18 and clone 76 were measured as 4.1 nM and 8.8 nM respectively.

Thus, each of the clones assayed specifically bound to the CD19-expressing cells with affinities similar to that of the reference antibody, e.g., having $EC_{50}$s about the same as or lower than that of the reference antibody, or no more than about 1.5-fold or no more than about 2-fold, or no more than about 3-fold greater than the $EC_{50}$ of the reference antibody.

Figure 4:
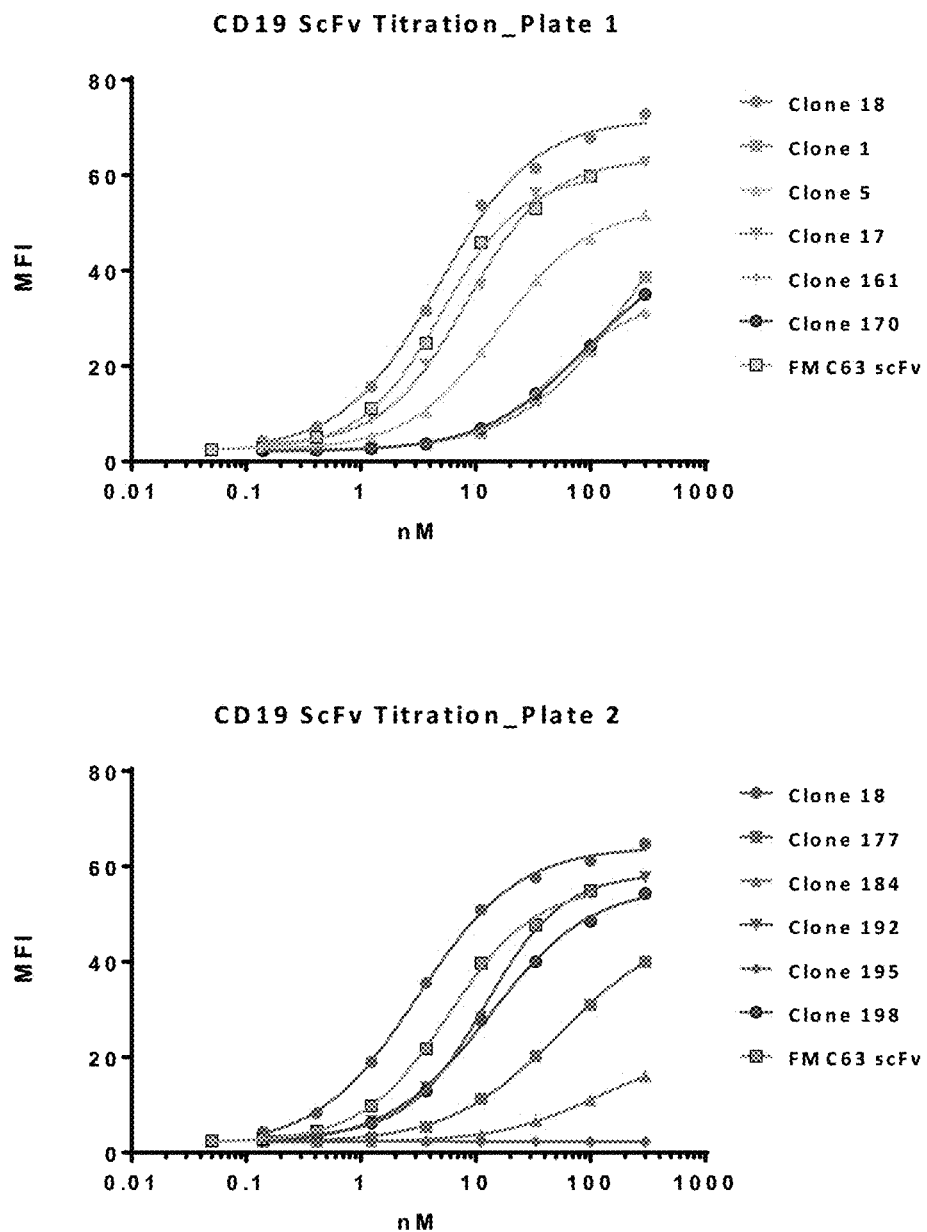
FIG. 4 show results from studies assessing binding affinities of various exemplary scFv antibodies, including anti-CD19 scFv antibody fragments. MFI=mean fluorescence intensity.

In another assay, clones 18, 5, 17, other clones identified (161, 170, 1 (see sequence information in Table 6)), and the positive control reference antibody FMC63 scFv (one plate) and clone 18, other clones identified (177, 184, 192, 198), and the positive control reference antibody FMC63 scFv (another plate) were assessed by the same assay. Results are presented in FIG. 4. $EC_{50}$ values observed for the two plates are presented in Tables 4A and 4B. As shown, clones were observed to have comparable binding affinities with that of the reference antibody.

TABLE 4A

|  | Clone 18 | Clone 5 | Clone 17 | Exemplary AdditionalClones (clones 161, 170, 1) | FMC63 scFv |
|---|---|---|---|---|---|
| $EC_{50}$(nM) | 4.79 | 15.84 | 8.32 | 52.26, 96.68, 213.80 | 5.06 |

TABLE 4B

|  | Clone 18 | Exemplary Additional Clones (clones 177, 184, 192, 198) | FMC63 scFv |
|---|---|---|---|
| $EC_{50}$(nM) | 3.11 | 53.33, 113.90, 12.02, 13.21 | 5.83 |

Figure 5A:
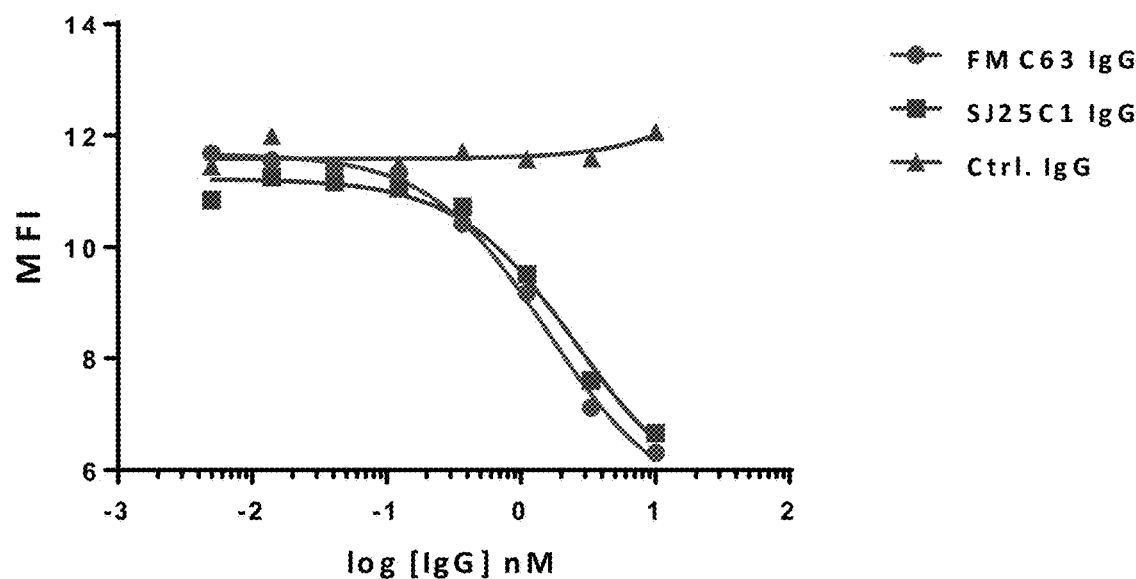
FIGS. 5A and 5B show results from competitive binding assays, assessing binding of respective labeled antibody in the presence of varying concentrations of competing antibodies. MFI=mean fluorescence intensity.
Figure 5B:
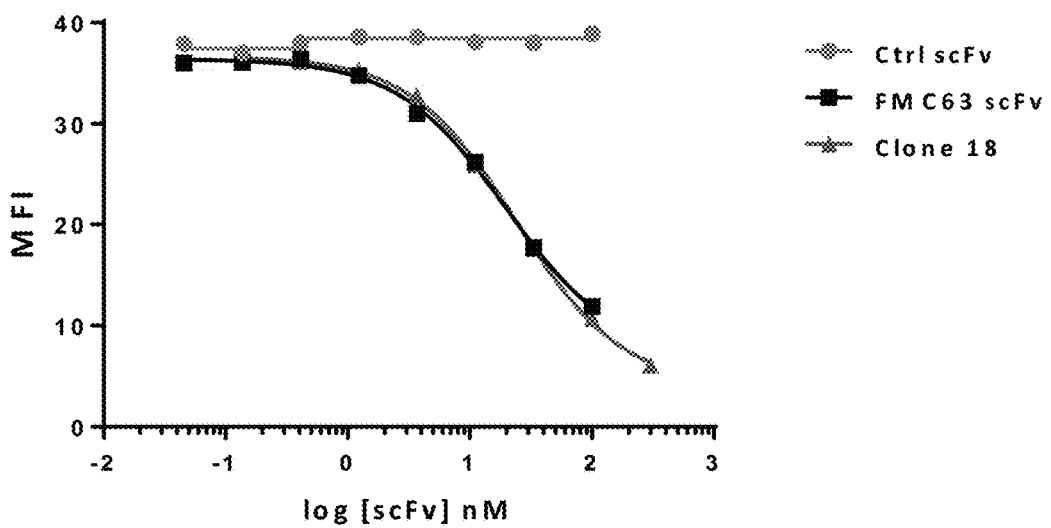

Competition binding assays were performed to assess competition of various antibodies for binding to CD19-expressing cells. In one assay, binding of 0.5 nM (~$EC_{50}$) FITC-labeled SJ25C1 to Ramos cells was assessed in the presence or absence of various concentrations of unconjugated competitor FMC63 IgG or a control IgG; binding was assessed by flow cytometry (mean fluorescence intensity). The results are shown in FIG. 5A, indicating that FMC63 IgG competed for binding to CD19 with SJ25C1 IgG1 in this study, suggesting that SJ25C1 and FMC63 bound to overlapping epitopes e.g., a common epitope, of CD19. In another assay, CD19-expressing cells were incubated with labeled FMC63 IgG in the presence of various concentrations of (or absence of) clone 18 scFv, FMC63 scFv (positive control) and a control scFv (negative control). Results are shown in FIG. 5B. As shown, both the clone 18 scFv and FMC63 scFv (but not the negative control scFv) were observed to compete with the FMC63 IgG for binding to CD19-expressing cells, with comparable IC50 values (24.0 nM and 19.8 nM, respectively), indicating that clone 18 bound to an epitope of CD19 that overlaps with the epitope recognized by FMC63, and competed for binding with the reference antibody to a similar degree.

Figure 6:
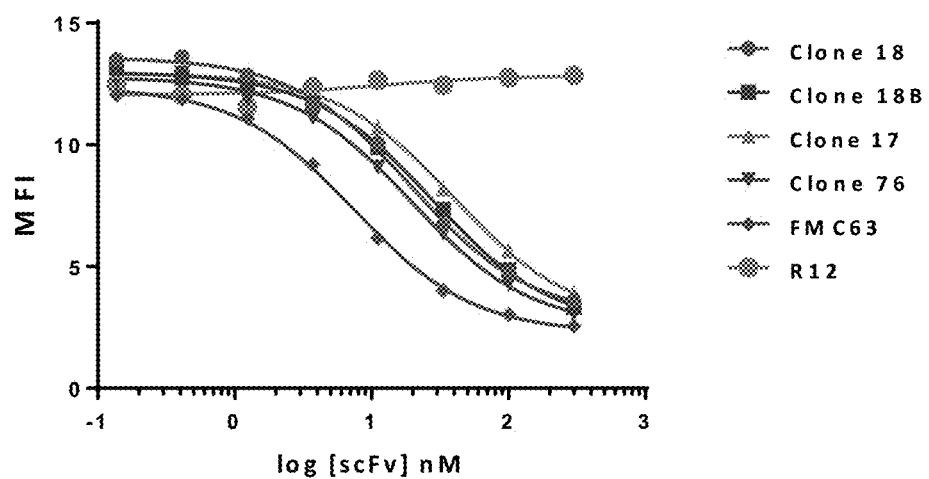
FIG. 6 shows results from competitive binding assays, assessing binding of a labeled reference scFv antibody in the presence of varying concentrations of competing scFv antibodies. MFI=mean fluorescence intensity.

In another assay, 10 nM ($EC_{50}$) Alexa647-labeled FMC63 scFv was incubated with CD19-expressing K562 cells in the presence or absence of varying concentrations of clone 18 scFv, clone 18B scFv, clone 17 scFv, clone 76 scFv, a reference antibody (FMC63 scFv) and a negative control antibody (R12). Results are presented in FIG. 6. The clones and reference antibody, but not the negative control antibody, displayed competition for binding to CD19 with the FMC63 scFv, and competition by the reference antibody with itself was similar to competition observed for the tested clones.

Collectively, in a number of studies, the following $EC_{50}$ (binding affinity) and $IC_{50}$ (competition) values were observed for the various clones, as listed in Table 5. As shown, among the identified human CD19 antibodies were those having similar degrees of binding affinity for CD19 and similar degrees of competitive inhibition for a murine anti-CD19 reference antibody, as compared to the reference antibody itself, for example, about the same, less than, or no more than 1.5-fold, 2-fold, or 3-fold greater $EC_{50}$ and/or IC50.

TABLE 5

Summary of Data from Exemplary Binding Studies

| Clone/Antibody | $EC_{50}$ (CD19-Expressing Cells) (nM) | $IC_{50}$ (nM) (competition for binding with FMC63) |
|---|---|---|
| Clone 18 | 4.1 ± .57 (n = 7) | 20.1 ± 9.8 (n = 3) |
| Clone 18B | 5.4 ± 1.3 (n = 5) | 28 (n = 1) |
| Clone 76 | 8.04 ± 0.3 | 18.2 ± 1.5 (n = 2) |
| Clone 17 | 11.7 ± 1.9 | 35.4 ± 3.9 (n = 2) |
| Clone 5 | 15.8 (n = 1) | 50 (n = 1) |
| FMC63 | 6.1 ± 1.2 (n = 6) | 20.5 ± 6.7 (n = 3) |

1D. Size Exclusion Chromatography

Figure 7A:
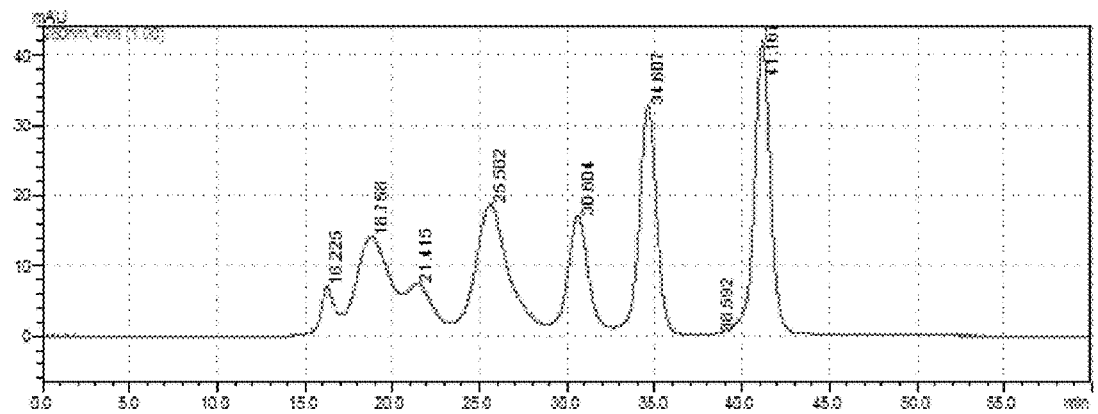
FIG. 7A shows results from size-exclusion chromatography; a column was calibrated, standard proteins injected, and fractions collected to generate references.
Figure 7B:
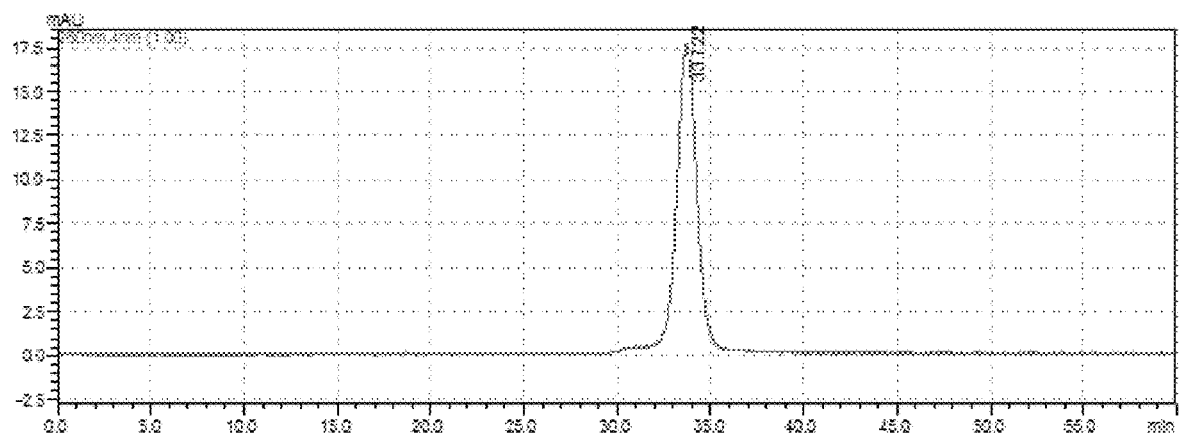
FIG. 7B shows results following injection of an anti-CD19 scFv (clone 18B) into the same column and collection of fraction under the same conditions.

Biophysical properties of clone 18B were assessed via size-exclusion chromatography. A HiLoad 16/600 Superdex 200 column was calibrated and Bio-Rad gel filtration standard 150-1901 kDa proteins were injected, and fractions collected at 1.5 mL/min to generate references. 770 ug of clone 18B scFv was injected into the column and fraction collected under the same conditions. The results are shown in FIGS. 7A and 7B (FIG. 7A=standard; FIG. 7B=Clone 18B). The results for clone 18B scFv revealed a single peak, with minimal large size aggregates observed.

Example 2: Generation and Assessment of Additional Anti-CD19 Antibodies

Additional exemplary anti-CD19 antibodies (scFv fragments) having similar binding properties to (and/or that compete for binding with) murine anti-CD19 reference antibodies were generated and assessed.

2A. Library Selection, Antibody Generation

Additional exemplary anti-CD19 scFvs were generated by two different selection approaches, each involving a series of selection steps carried out on dsDNA-encoded human antibody libraries displayed in a cell-free system.

In one approach (deemed "clone 18 CDR3 grafting"), a heavy chain CDR3 (CDR-H3) sequence present in clones identified in Example 1 (SEQ ID NO: 20, DQGYHYYD-SAEHAFDI) was grafted into human naïve $V_H$ library frameworks. Members of the resulting CDR3-grafted $V_H$ library were shuffled with members of a naïve human $V_L$ library to generate an scFv library as $V_H$-(G4S)3-$V_L$ format. The resulting scFv library was subjected to three rounds of selection, to enrich for members that bound specifically to CD19-expressing HEK293 cells and not to parental cells, followed by surface stripping for round (R1), immunoprecipitation and off-rate for round 2 (R2).

In another approach (deemed "FMC63 guided selection"), two initial scFv libraries were generated, respectively, by (a) shuffling members of a naïve $V_H$ library with the $V_L$ region of FMC63 and (b) shuffling members of a naïve $V_L$ library with the $V_H$ region of FMC63. After two and three rounds of selection, respectively, to enrich the library members from (a) and (b) for CD19-binding with the guidance of the parental FMC63 $V_H$ or $V_L$. The binding molecules were eluted off by surface stripping from CD19/HEK293 cells (R1) and FMC63 elution from CD19/K562 cells (R2 and R3). A third scFv library was generated by shuffling the VH sequences from the selection in (a) with the VL sequences resulting from the selection in (b). Three further rounds of selection were carried out on CD19/HEK293 cells with surface stripping (R1), followed by CD19/K562 cells with FMC63 elution (R2) and CD19/HEK293 cells with immunoprecipitation (R3). Binding by the selected scFv clones to CD19-expressing cells was confirmed by flow cytometry using bacterially-produced supernatant. The selected scFv pools were cloned into E. coli expression vectors and produced as HIS-tagged scFvs. Binding of individual clones to CD19-transfected HEK293 cells was detected with anti-HIS-Alexa647 conjugate by flow cytometry. Clone 18 or Clone 18B were used as positive controls, along with various negative controls. The results are shown in FIGS. 8A-C (MFI=mean fluorescence intensity).

Figure 8A:
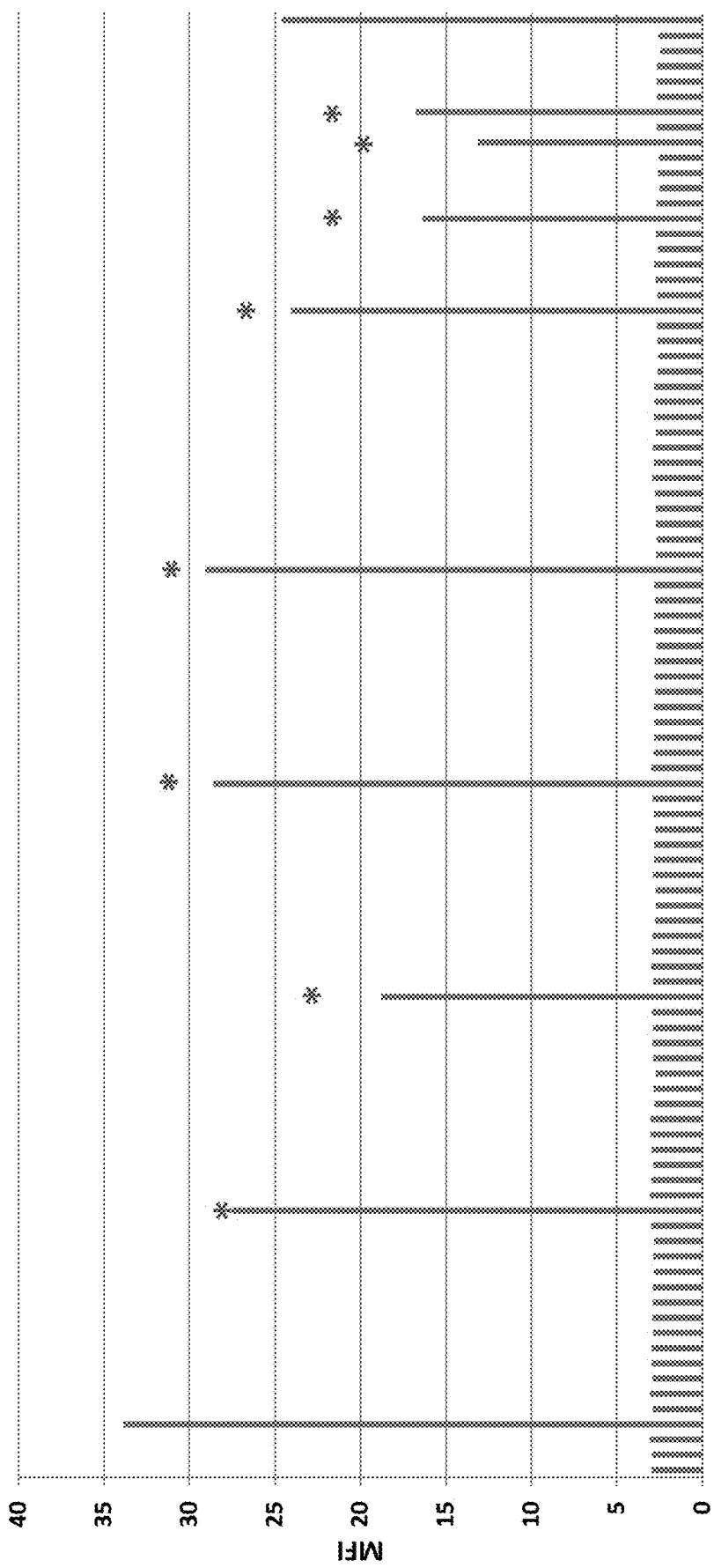
FIG. 8A show results from a binding assay assessing binding of exemplary human scFv clones to CD19-expressing cells in order from left to right as follows: cells only, mock supernatant (Moc. Supe.) negative control antibody (Neg. Ctrl.), Clone 18, Clones 200 to 287, cells only, Moc. Supe, Neg. Ctrl. and Clone 18. Exemplary hits that show CD19-specific binding (indicated by an asterisk) are (in order from left to right): Clone 213, Clone 227, Clone 241, Clone 255, Clone 272, Clone 278, Clone 283 and Clone 285. MFI=mean fluorescence intensity.
Figure 8B:
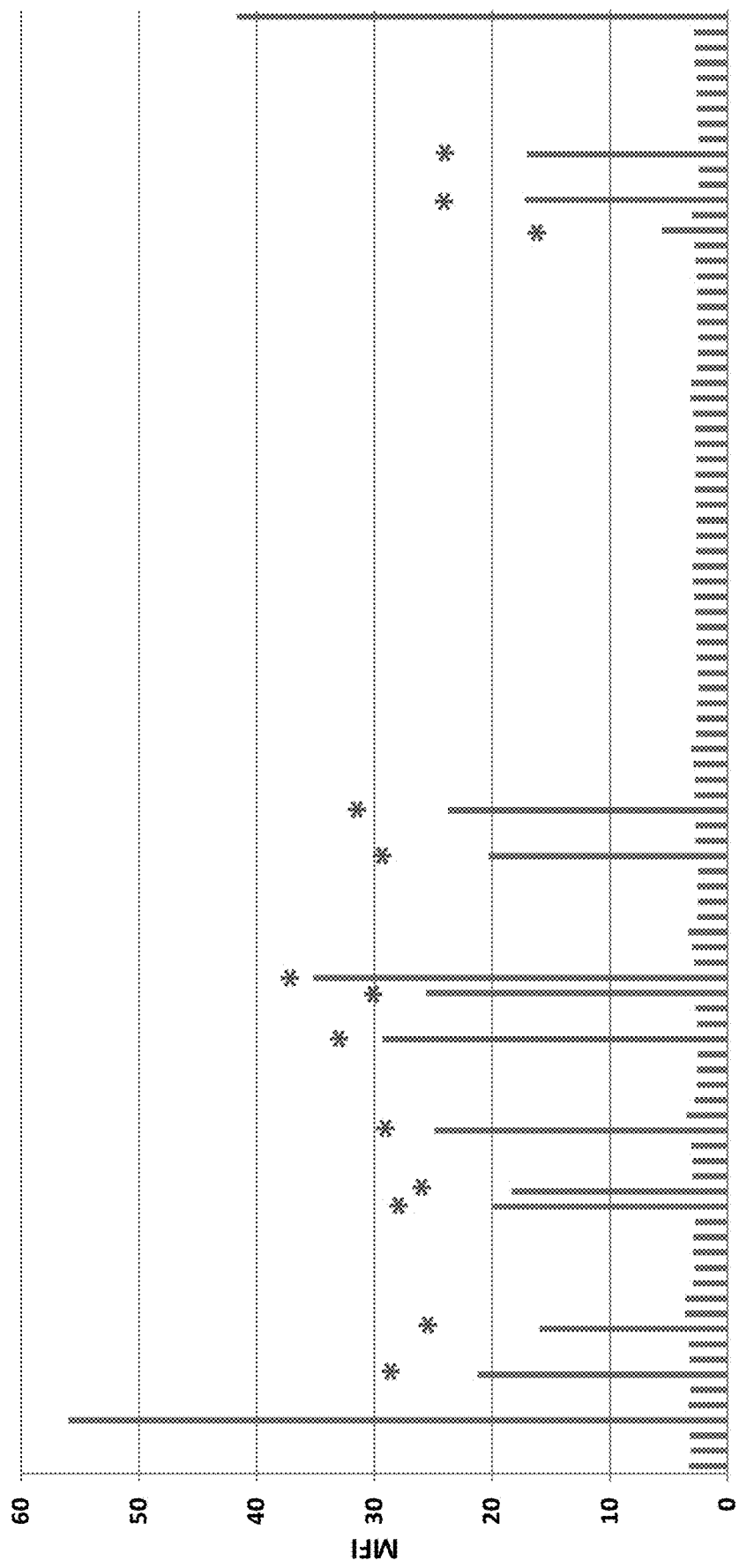
FIG. 8B shows results from a binding assay assessing binding of exemplary human scFv clones to CD19-expressing cells in order from left to right as follows: cells only, mock supernatant (Moc. Supe.) negative control antibody (Neg. Ctrl.), Clone 18B, Clones 300-387, cells only, Moc. Supe., Neg. Ctrl. and Clone 18B. Exemplary hits that show CD19-specific binding (indicated by an asterisk) are (in order from left to right): Clone 302, Clone 305, Clone 313, Clone 314, Clone 318, Clone 324, Clone 327, Clone 328, Clone 336, Clone 339, Clone 377, Clone 379 and Clone 382. MFI=mean fluorescence intensity.
Figure 8C:
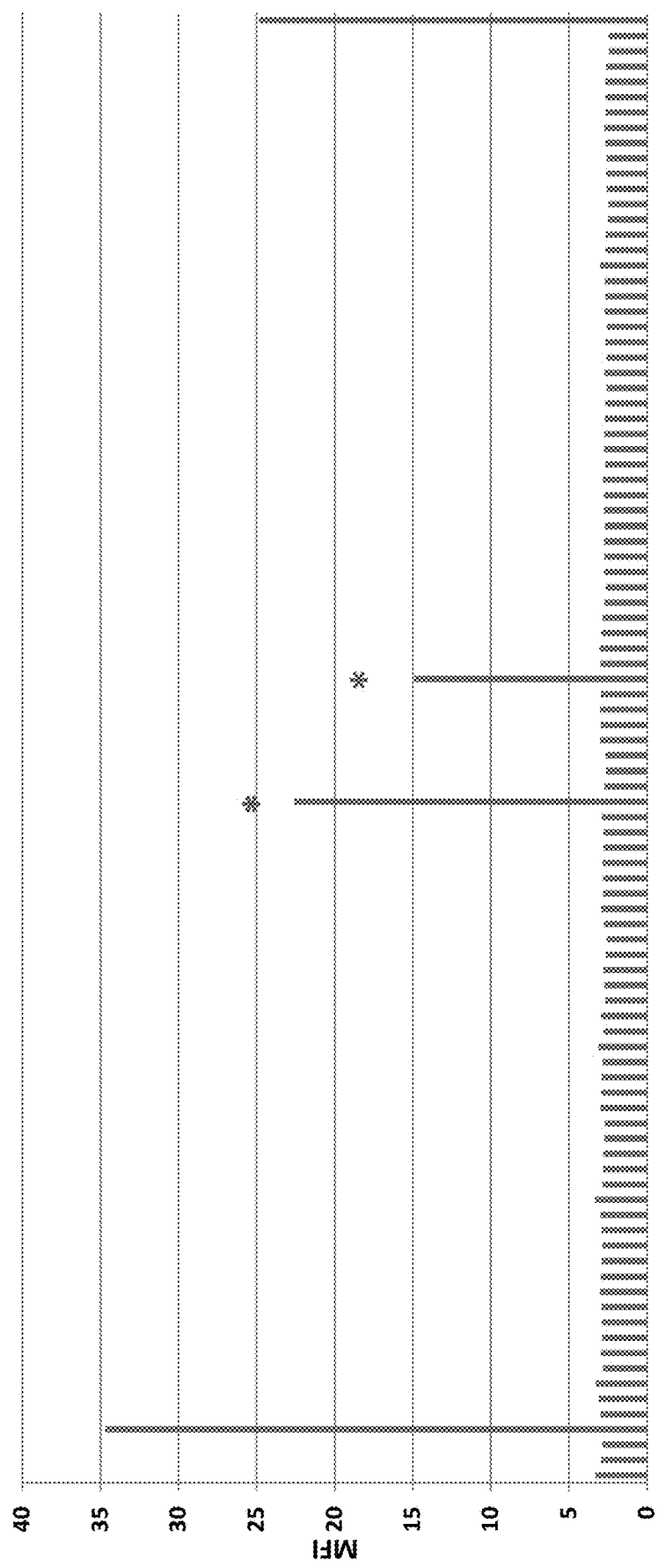
FIG. 8C shows results from a binding assay assessing binding of exemplary human scFv clones to CD19-expressing cells in order from left to right as follows: cells only, mock supernatant (Moc. Supe.) negative control antibody (Neg. Ctrl.), Clone 18B, Clones 400-487, cells only, Moc. Supe., Neg. Ctrl. and Clone 18B. Exemplary hits that show CD19-specific binding (indicated by an asterisk) are (in order from left to right): Clone 440 and Clone 448.
Figure 8D:
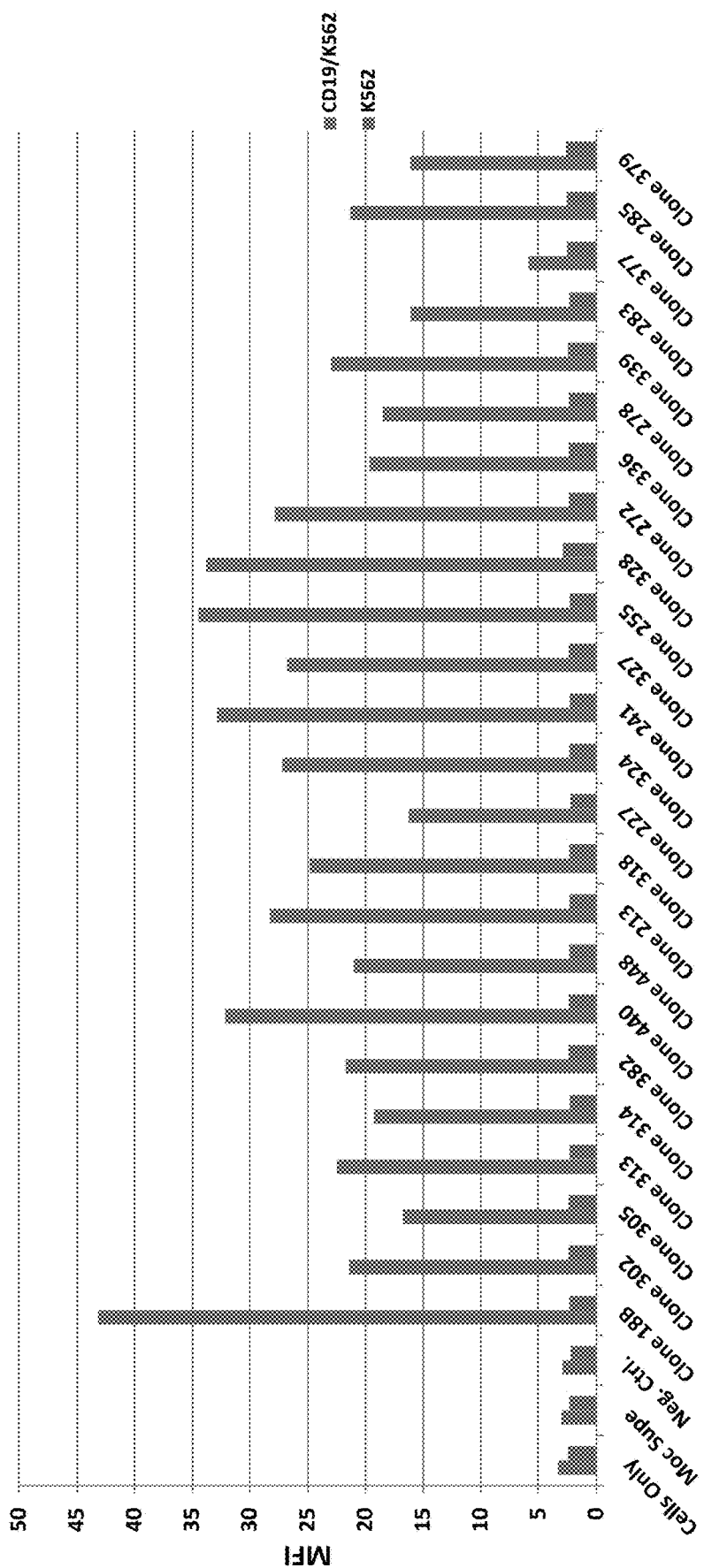
FIG. 8D shows results from a binding assay comparing binding of exemplary human scFvs to CD19-expressing K562 cells as compared to non-CD19-expressing K562 cells. MFI=mean fluorescence intensity.

The results shown in FIG. 8D confirm CD19-specific binding by an exemplary twenty-three (23) of the hits (marked with asterisks in FIGS. 8A-C, representing 4 hits identified via the CDR3 grafting approach and 19 via FMC63-guided selection). Binding of in vitro-translated FLAG-tagged scFvs to CD19-expressing K562 cells, as compared to control (mock transfected) K562 cells, was assessed by flow cytometry as described in Example 1. As shown, the clones specifically bound to CD19-expressing cells.

These and additional CD19-specific scFv clones generated by the selection approaches in Examples 1 and 2 were further assessed. Sequencing revealed several CD19-specific binding antibodies (scFvs) with various different light chain sequences and sharing a common CDR-H3 sequence (SEQ ID NO: 20) also present in scFvs described in Example 1. Sequence identifiers corresponding to various sequences of additional CD19-binding scFvs are listed in Table 6, including for scFv, VH, VL, and CDR (Kabat) amino acid sequences (and the encoding scFv nucleotide sequences). Among the CD19-specific scFv clones were those having several different light chain variable and CDR sequences, some of which had CDR-H1, CDR-H2, and/or CDR-H3 present in SEQ ID NO: 11, CDR-H1, CDR-H2, and/or CDR-H3 having sequences of SEQ ID NOs: 18,19, and/or 20, and/or CDR-H1, CDR-H2, and/or CDR-H3 having sequences of 18, 72, and 20. Each of the clones listed in Table 6 was derived from a human $V_H3$ framework (with kappa and lambda gene V segments from which the clones are derived indicated).

TABLE 6

Sequences for Exemplary Clones (SEQ ID NO.)

| Clone # | Heavy Chain Variable ($V_H$) Region (Amino Acid) | Light Chain Variable ($V_L$) Region (Amino Acid) | ScFv Sequence (Amino Acid, Nucleotide) | CDR-H (1, 2, 3) (Kabat) (Amino Acid) | CDR-L (1, 2, 3) (Kabat) (Amino Acid) | Light Chain Framework Derived From |
|---|---|---|---|---|---|---|
| 488 | 63 | 71 | 45, 44 | 18, 72, 20 | 80, 100, 109 | Vκ3 |
| 1304 | 62 | 68 | 47, 46 | 18, 72, 20 | 77, 97, 106 | Vκ1 |
| 285 | 11 | 65 | 49, 48 | 18, 19, 20 | 74, 94, 103 | Vλ2 |
| 192B | 60 | 64 | 51, 50 | 18, 19, 20 | 73, 93, 101 | Vλ2 |
| 328 | 61 | 66 | 53, 52 | 18, 19, 20 | 75, 95, 104 | Vλ2 |
| 227 | 63 | 70 | 55, 54 | 18, 72, 20 | 79, 99, 108 | Vκ1 |
| 1300 | 62 | 69 | 57, 56 | 18, 72, 20 | 78, 98, 107 | Vκ1 |
| 1 | 12 | 67 | 59, 58 | 18, 19, 20 | 76, 96, 105 | Vλ1 |
| 192 | 12 | 91 | 87, 86 | 18, 19, 20 | 73, 93, 102 | Vλ2 |
| 241 | 63 | 90 | 89, 88 | 18, 72, 20 | 77, 97, 106 | Vκ1 |

2B. Purification and Assessment

Figure 9:
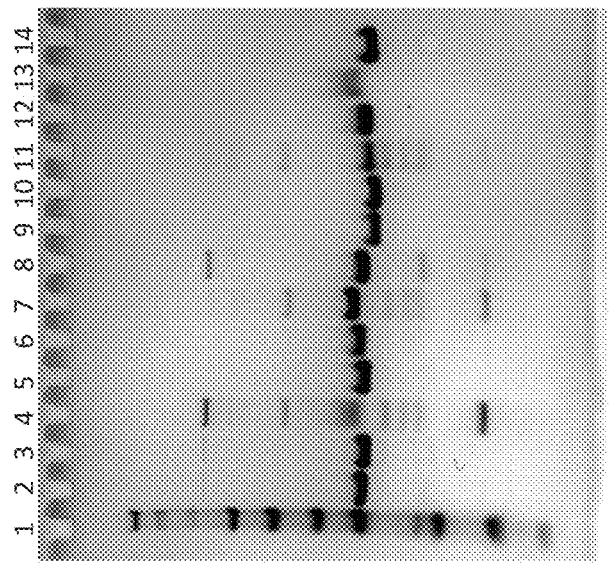
FIG. 9 shows an SDS gel assessing purification of exemplary anti-CD19 antibodies (scFv fragments).
Figure 10A:
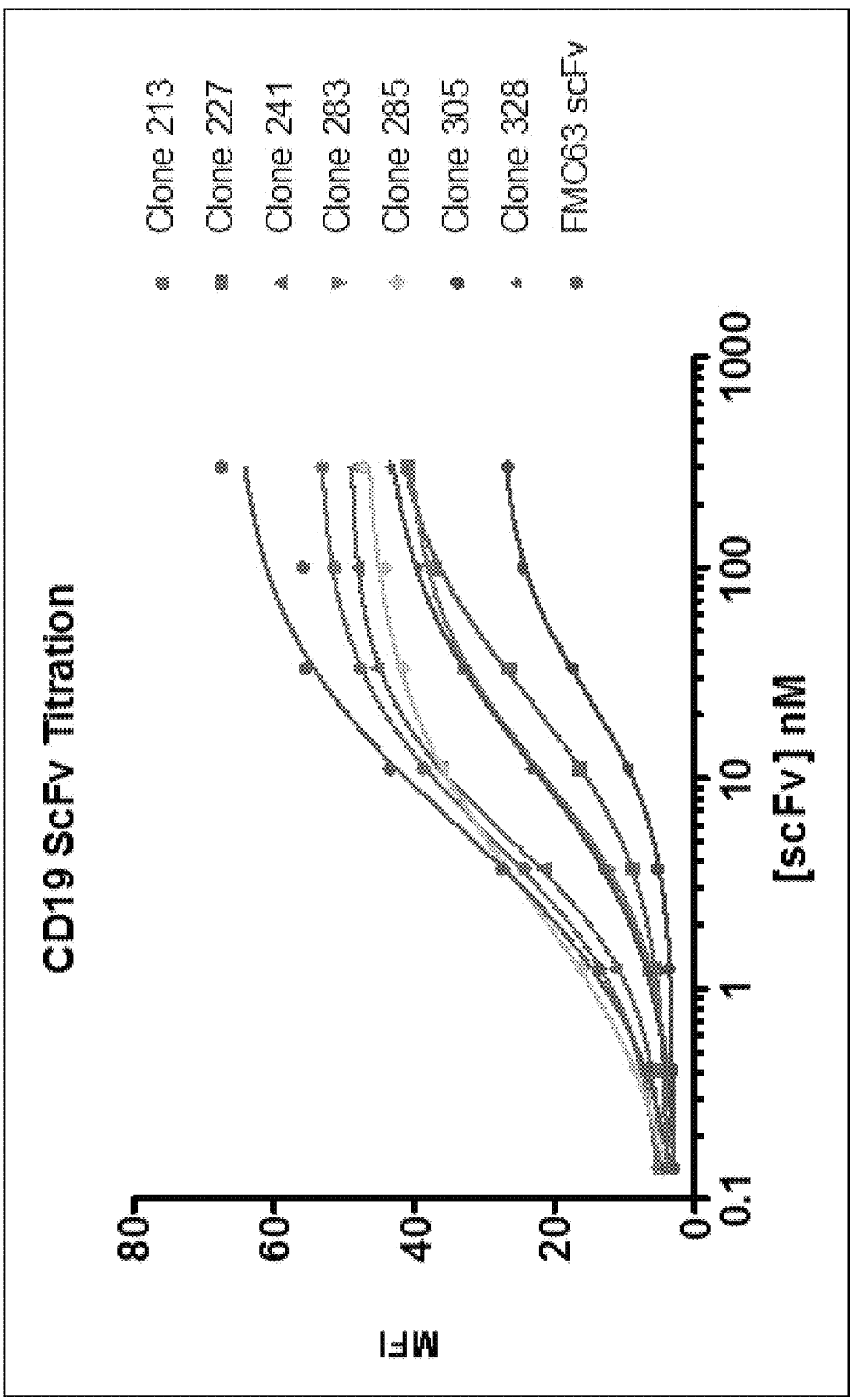
FIGS. 10A-E show results from separate binding assays assessing binding affinities of various exemplary scFv antibodies, including anti-CD19 scFv antibody fragments. MFI=mean fluorescence intensity.
Figure 10B:
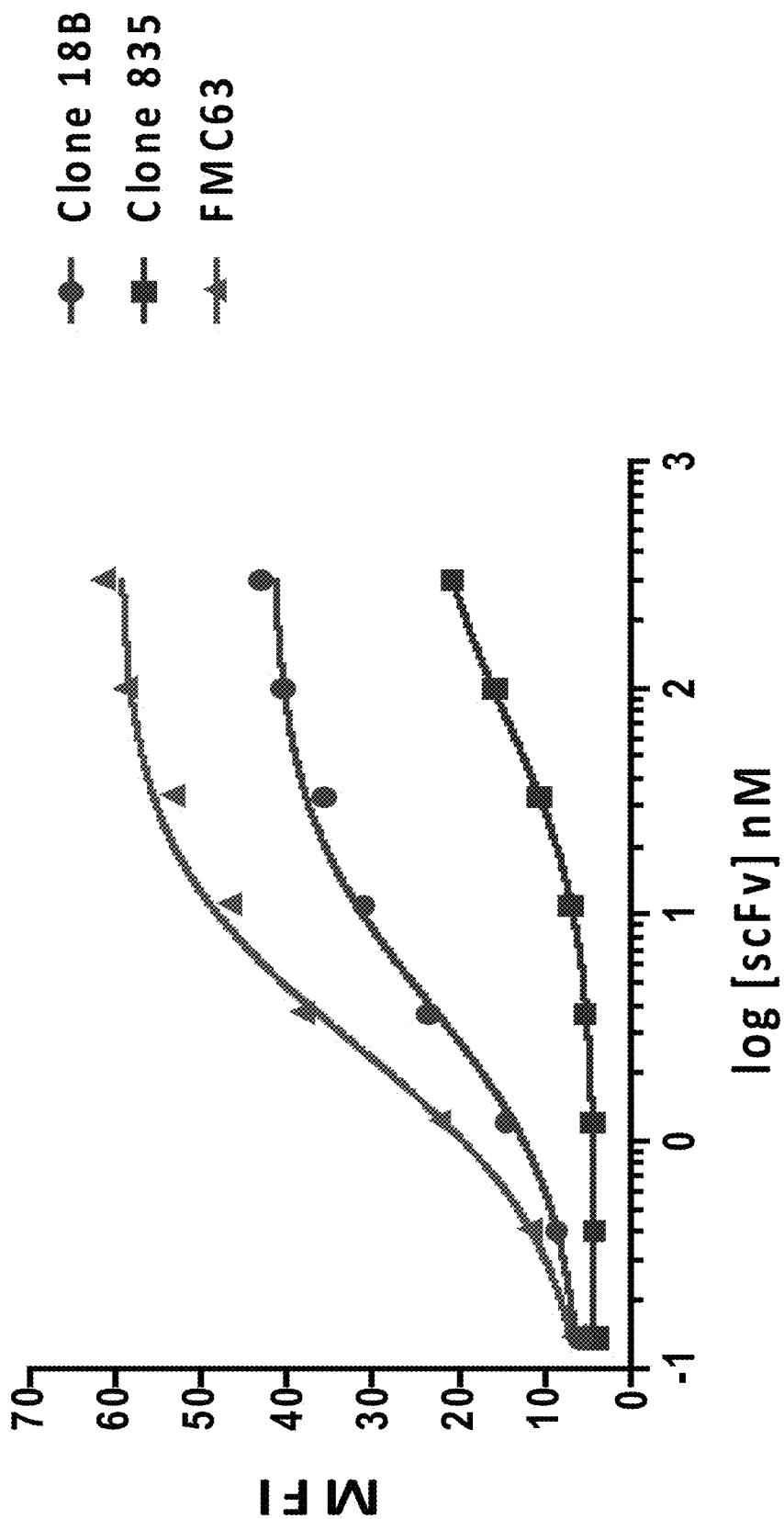
Figure 10C:
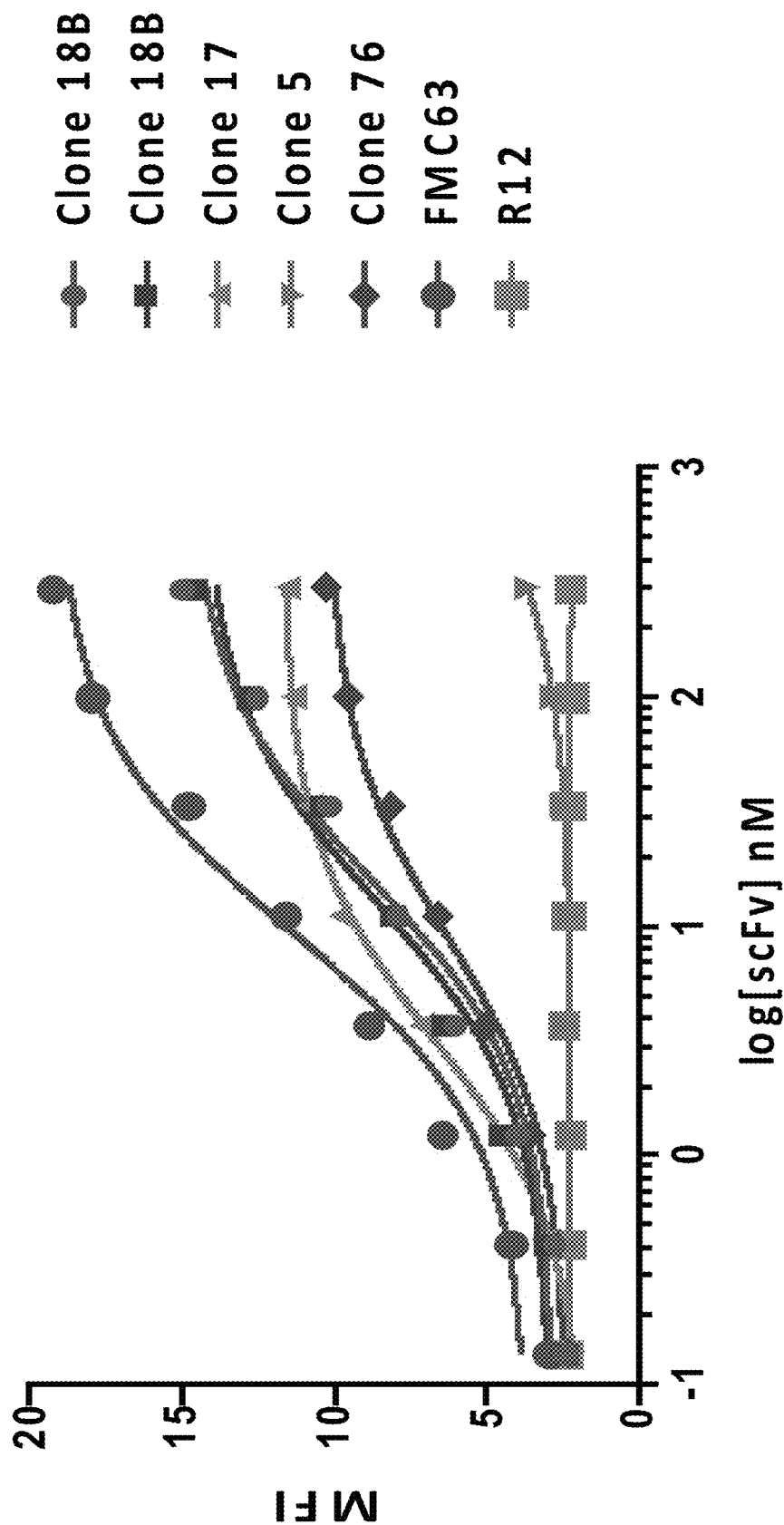
Figure 10D:
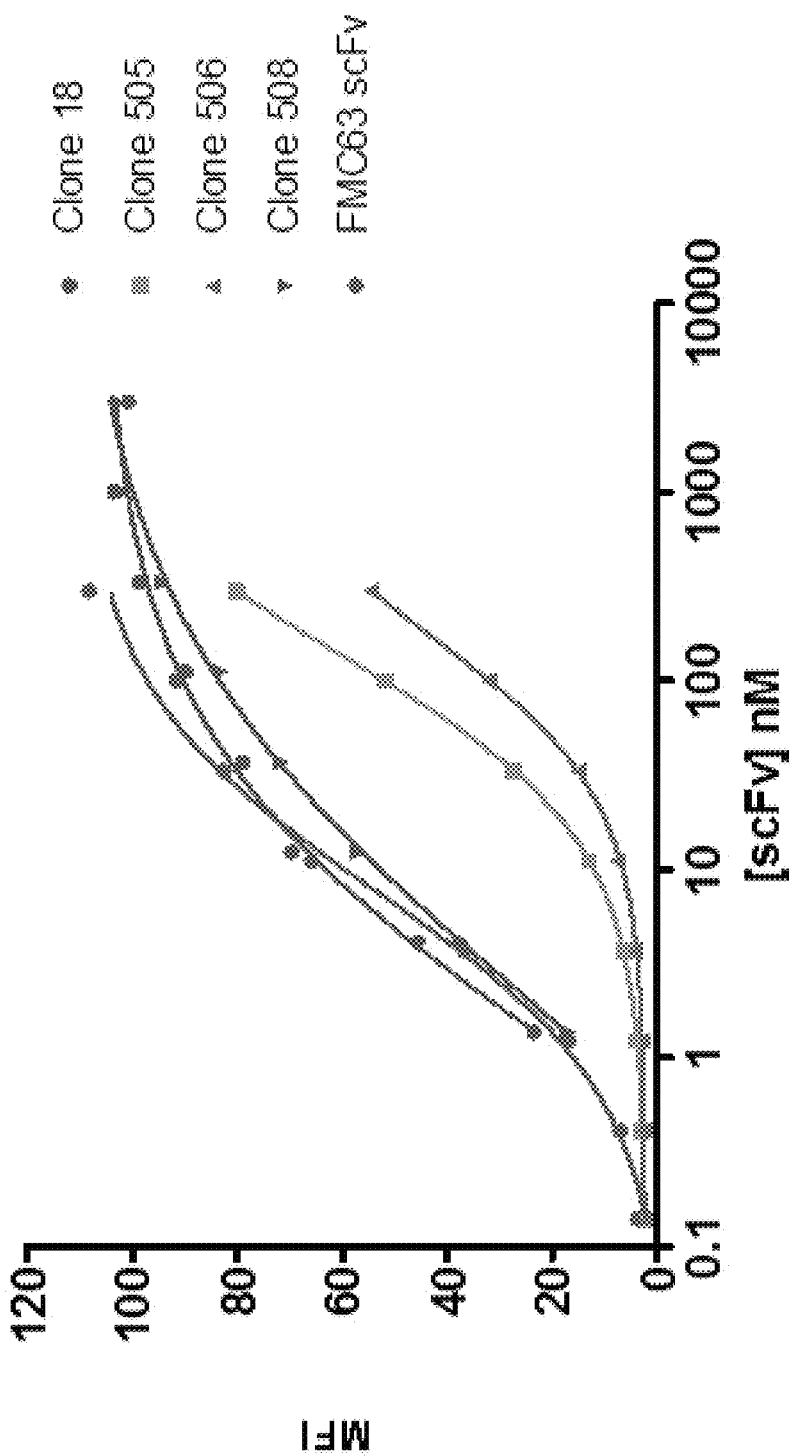
Figure 10E:
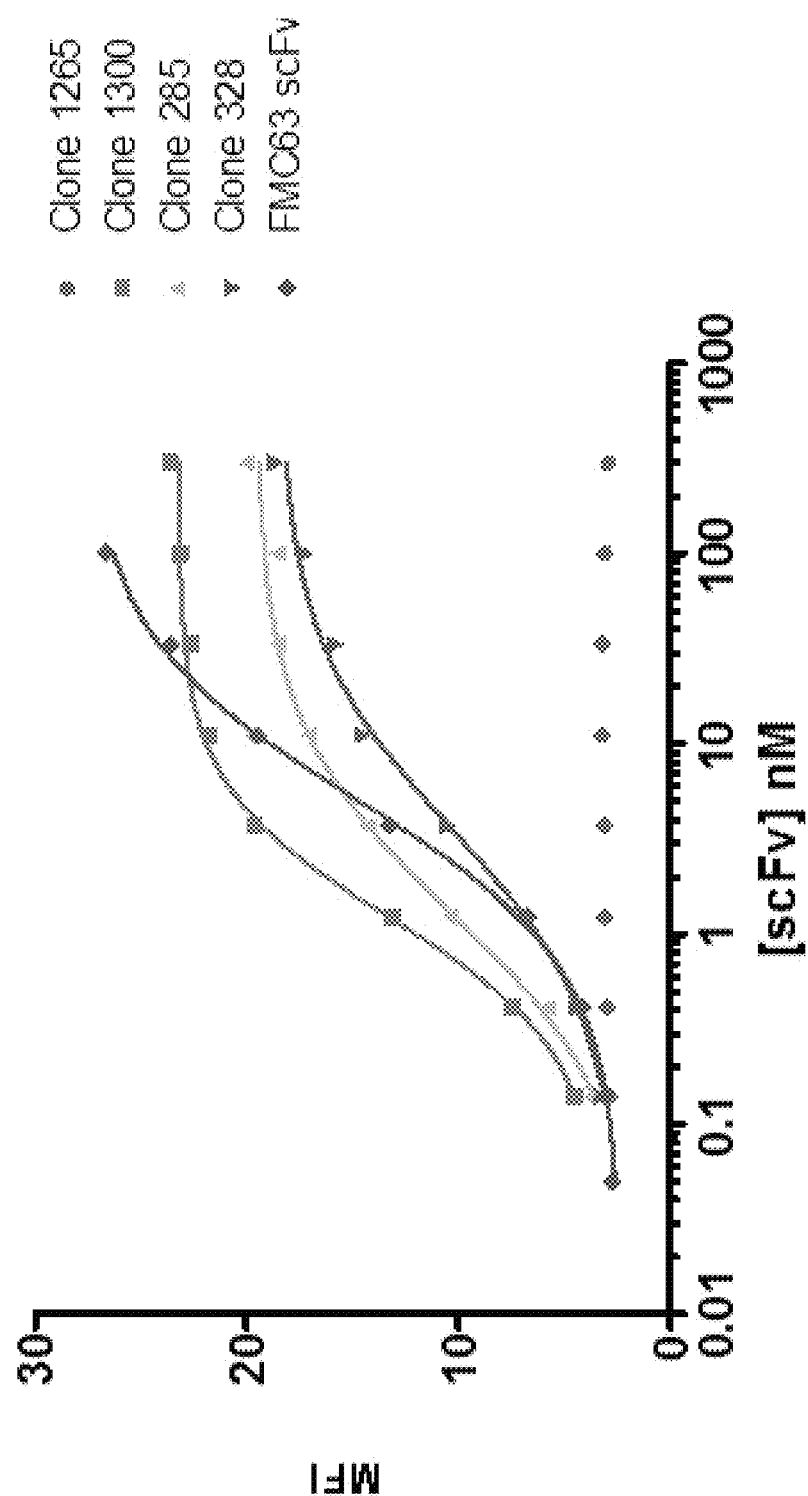

Clones described above, including clones listed in Table 6 and/or described in Example 1, were purified by single-step purification and purification assessed via SDS gel. The results are presented in FIG. 9 (lane 1=MW marker; lanes 2, 9, and 10=clone 5 (1530, 2880, 1130 µg/mL); lane 3=clone 18B (660 µg/mL); lanes 4, 11, 12, and 13=clone 17 (300, 1060, 180, 1440 µg/mL); lane 5=clone 192B (1580 µg/mL); lanes 6 and 14=clone 76 (1340, 3220 µg/mL); lane 7=clone 835 (470 µg/mL); lane 8=clone 488 (340 µg/mL)). Melting temperature (Tm) measurements were made as described in Example 1, revealing similar Tm values as those observed for the reference antibody and clones in Example 1 (Table 7).

TABLE 7

Assessment of $T_m$

| Clone | $T_m$ (° C.) |
|---|---|
| 5 | 58 |
| 18B | 57 |
| 17 | 52 |
| 192B | 64 |
| 76 | 51/59 |
| 488 | 63 |
| 285 | 68 |
| 227 | 60 |

Various clones were titrated and their binding affinity ($EC_{50}$) to various CD19-expressing cells assessed by flow cytometry. The FMC63 scFv reference antibody was used as a positive control. The results from five separate assays assessing binding affinities for various CD19-specific scFv clones are shown in FIGS. 10A-10E. As shown, the selections resulted in several CD19-specific scFv clones with various binding affinities and a range of saturatable binding activity.

Figure 11:
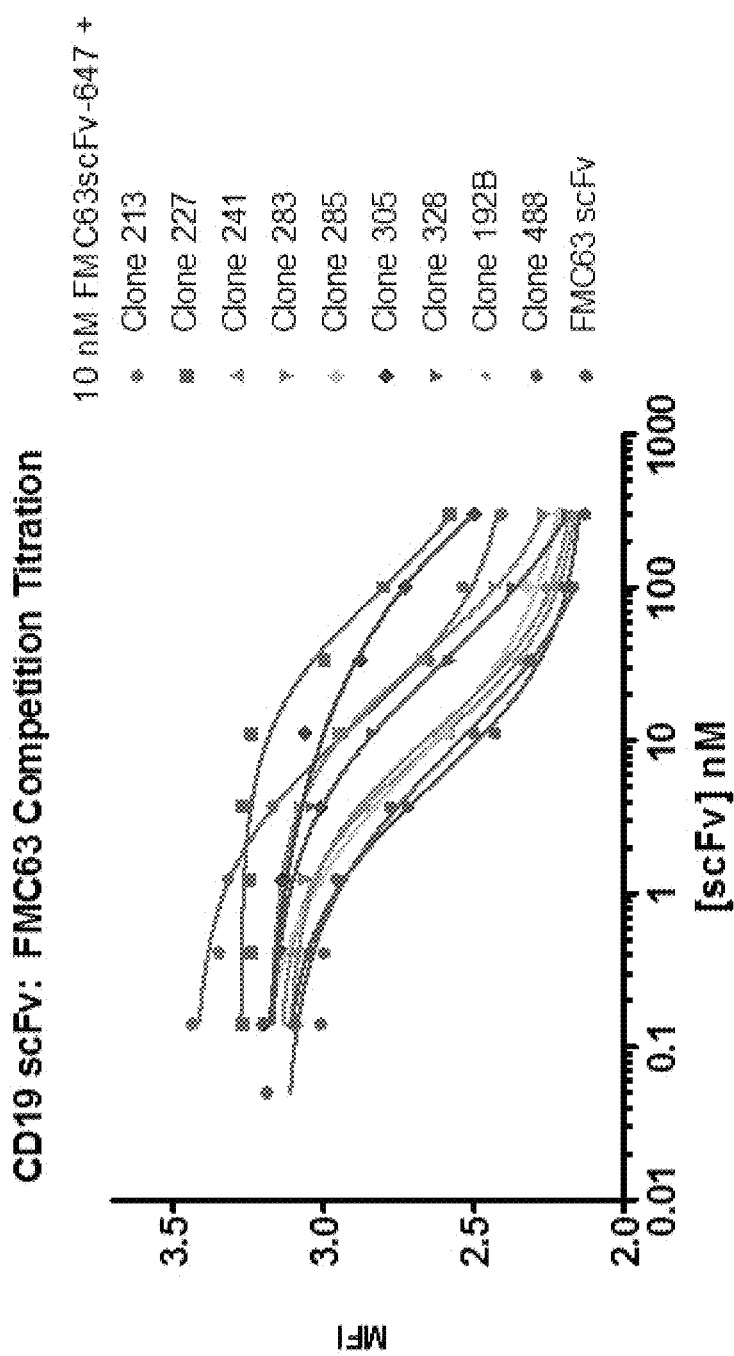
FIG. 11 shows results from competitive binding assays, assessing binding of a labeled reference scFv antibody in the presence of varying concentrations of competing scFv antibodies. MFI=mean fluorescence intensity.

Competition binding assays were performed as described in Example 1 to assess the ability of various identified antibodies (scFv clones) to compete for binding with a murine reference antibody for binding to CD19-expressing cells. In one example, CD19-expressing cells were incubated with 10 nM labeled FMC63 scFv in the presence of various concentrations of the indicated scFv clones having different light chain sequences and sharing a common heavy chain CDR3 (or FMC63 scFv (positive control)). The results, shown in FIG. 11, demonstrated that the clones competed with FMC63 scFv for binding to CD19-expressing cells, with various $IC_{50}$ values. Similar studies were carried out to assess properties of other clones identified in the screening approaches described in Examples 1 and 2. $EC_{50}$ (binding affinity) and $IC_{50}$ (competition) values observed for various CD19-binding antibodies (scFvs) are listed in Table 8. CDR-L3 sequences for clones 79, 835, 184, 505, 506, and 305 are set forth as SEQ ID NOs: 116, 117, 118, 119, 120, 121, and respectively.

TABLE 8

Results from Various Binding and Competition Assays

| Clone/ Antibody | $EC_{50}$ (CD19-Expressing Cells) (nM) | $IC_{50}$ (nM) (competition for binding with FMC63) |
| --- | --- | --- |
| Clone 18B | 4.9 ± 0.8 (n = 7) | 32.9 ± 3.2 (n = 3) |
| Clone 17 | 11.6 ± 1.1 (n = 5) | 35.4 ± 3.9 (n = 2) |
| Clone 76 | 7.0 ± 1.4 (n = 5) | 18.2 ± 1.5 (n = 2) |
| Clone 5 | 15.8 (n = 1) | 50 (n = 1) |
| Clone 192B | 7.7 ± 1.4 (n = 3) | 15.7 ± 2.5 (n = 3) |
| Clone 488 | 2.9 ± 0.4 (n = 4) | 6.1 ± 0.7 (n = 6) |
| Clone 79 | 65.7 (n = 1) | 102.5 (n = 1) |
| Clone 835 | 71.8 (n = 1) | >200 |
| Clone 184 | 113.9 (n = 1) | N/A |
| Clone 505 | 138.9 (n = 1) | N/A |
| Clone 506 | 179.3 (n = 1) | N/A |
| Clone 1 | 213.8 (n = 1) | N/A |
| Clone 241 | 5.2 ± 0.1 (n = 2) | 14.6 ± 2.7 (n = 3) |
| 1300 | 1.3 ± 0.1 (n = 3) | 3.9 ± 0.5 (n = 2) |
| 227 | 31.8 ± 5.3 (n = 3) | 56.1 ± 3.9 (n = 2) |
| 285 | 2.5 ± 0.5 (n = 4) | 9.4 ± 1.4 (n = 3) |
| 305 | 32.2 ± 6.9 (n = 2) | >500 (n = 2) |
| 328 | 10.9 ± 4.6 (n = 4) | 32.9 (n = 1) |
| FMC63 | 6.0 ± 0.8 (n = 9) | 15.0 ± 2.8 (n = 10) |

Among the identified human CD19 antibodies (scFv fragments), many demonstrated similar or greater degrees of binding affinity (e.g., similar or lower $EC_{50}$ values) for CD19 as compared to a murine anti-CD19 reference antibody, FMC63. Many also demonstrated similar or greater degrees of competition (e.g., similar or lower $IC_{50}$ values) with a murine anti-CD19 reference antibody for CD19 binding, as compared to the reference antibody's ability to compete with itself.

For example, clones were observed with $EC_{50}$ values that were less than, about the same as, or no more than at or about 1.5-fold greater, 2-fold greater, or 3-fold greater than those for the reference antibody. Likewise, several of the identified anti-CD19 antibodies (scFvs) were observed to compete with labeled FMC63 scFv for binding to CD19-expressing cells with $IC_{50}$ values that were lower than the $IC_{50}$ values observed for FMC63 scFv, about the same as the $IC_{50}$ values observed for FMC63, or no more than 1.5-fold or 2-fold or 3-fold higher (e.g., a degree of competition that is no more than 1.5-fold or 2-fold lower than the competition by the reference antibody). The results indicated that these studies identified a plurality of antibodies that bind to an epitope of CD19 that overlaps with the epitope specifically bound by FMC63.

Example 3: Generation of Chimeric Antigen Receptors (CARs) Against CD19 and Engineering of Cells Expressing Such CARs Various exemplary chimeric antigen receptors (CARs) were generated, with antigen-binding regions containing human anti-CD19 scFvs as described in Example 1. Specifically, nucleic acid molecules were generated that encoded CARs with scFvs (in the VH-VL format) derived from the following clones and having the amino acid sequences set forth in the indicated sequence identifiers: Clone 18 (SEQ ID NO:2), Clone 18B (SEQ ID NO:4), Clone 17 (SEQ ID NO:6), Clone 76 (SEQ ID NO: 8), and Clone 5 (SEQ ID NO:10). Additionally, for each clone, constructs encoding a CAR having the same VH and VL sequences, but present in the reverse orientation (VL-VH), also were generated. A CAR containing a murine anti-CD19 scFv derived from FMC63 (in the VH-VL orientation) was used as a control. Each CAR further contained an Ig-derived spacer; a human CD28-derived transmembrane domain; a human 4-1BB-derived intracellular signaling domain; and a human CD3 zeta-derived signaling domain, a truncated EGFR (EGFRt) sequence, for use as a transduction marker, separated from the CAR sequence by a self-cleaving T2A sequence.

Primary human T cell populations expressing the various CARs were generated. Nucleic acid molecules encoding each CAR were individually cloned into a lentiviral vector, which was used to transduce CD4+ and CD8+ T cells in populations isolated from human PBMC samples obtained from healthy donors (essentially as described by Yam et al. (2002) Mol. Ther. 5:479; WO2015/095895).

Figure 12A:
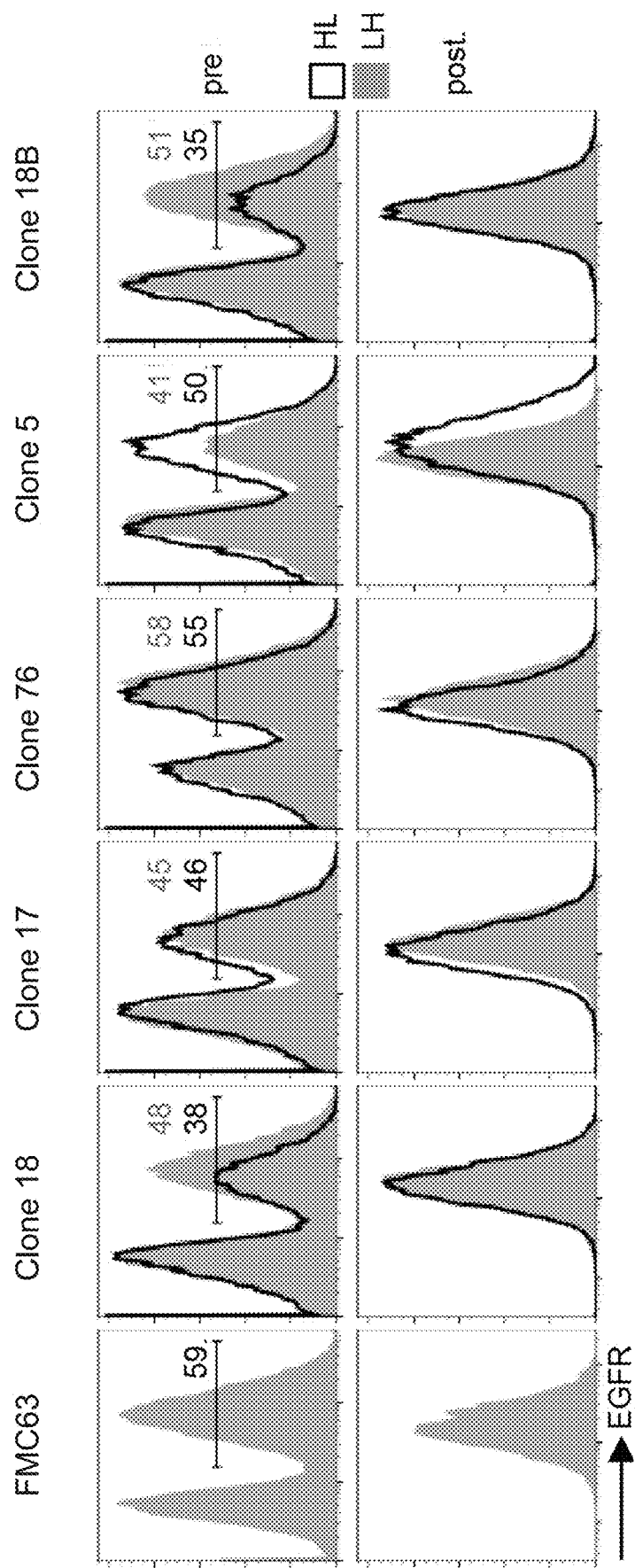
FIG. 12A shows cell surface expression of the various CARs, in either VH-VL (HL) orientation HL; dark line) or VL-VH orientation (LH; grey line), in transduced CD8+ T cells as measured by expression of EGFRt for cells before enrichment (pre) and after enrichment following sorting with an anti-EGFR antibody and expansion by stimulation with CD19+ B-LCL (post).
Figure 12B:
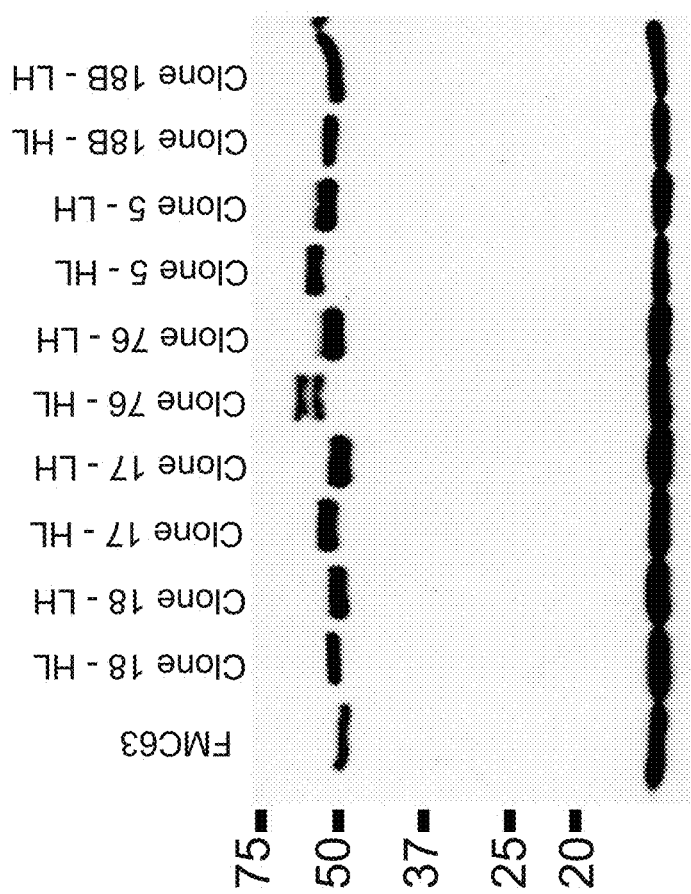
FIG. 12B shows an SDS gel assessing expression of exemplary human anti-CD19 CARs in transduced primary human T cells.

After transduction and expansion, staining with anti-EGFR antibody was used to verify expression of the EGFRt transduction marker on the surface of CD4+ and CD8+ T cells by flow cytometry. FIG. 12A provides representative results for expression of the various CARs in CD8+ cells; similar results were observed for CD4+ cells. CAR protein expression was confirmed by western blotting using an anti-CD247 (CD3 zeta) antibody (which in each case detected a band at approximately 50 kD, representing the CAR, and a band at approximately 18 kDa, representing the endogenous CD3 zeta chain present in the cells) (FIG. 12B). The results demonstrated comparable degrees of transduction and CAR protein expression for each of the various human scFv-containing CAR constructs (including VH-VL and VL-VH orientations) and control (murine, FMC63-derived) CAR constructs in primary T cell populations. No EGFRt expression was detected in cells not subjected to transduction. Results from western blotting confirmed that the CAR derived from clone 76, in the VH-VL orientation, was present in different glycosylation forms.

As shown in FIG. 12A, T cell populations were successfully enriched for transduced cells (at or close to 100% EGFRt+ as confirmed by flow cytometry) by staining with an anti-EGFR antibody, sorting on a flow cytometer, and stimulation in the presence of irradiated (8,000 rad) cells from a CD19+ B-lymphoblastoid cell line (B-LCL) essentially as described by Yam et al. (2002) Mol. Ther. 5:479; WO2015/095895.

Example 4: Assessing Effector Functions of T Cells Engineered to Express Anti-CD19 Chimeric Antigen Receptor (CAR) In Vitro Genetically engineered human T cells (either CD8+ or CD4+) expressing various CARs containing human anti-CD19 scFvs, produced as described in Example 3, were assessed for various responses following co-culture with CD19-expressing cells.

A. Cytolytic Activity

CD19-expressing target cells were incubated with CD8+ T cells expressing the various CARs and separately with cells transduced with EGFRt alone (negative control). Following incubation, lysis of target cells was monitored. Specifically, lysis of CD19-transduced K562 cells (K562/CD19), Raji (CD19+ B cell lymphoma line) cells, and non-transduced K562 control cells (negative control) (FIG. 13A) and primary human chronic lymphocytic leukemia cells (CLL; FIG. 13B) were tested.

The target cells (K562/CD19 Raji non-transduced K562 control cells or CLL) were labeled overnight with $^{51}$Cr. Labeled cells were washed and incubated in triplicate with effector T cells (CAR-expressing and negative control CD8+ cells) at an effector to target (E:T) ratio of 30:1. To measure spontaneous lysis, target cells were incubated with an equal volume of media but without effector cells and maximum lysis was determined following incubation of target cells with detergent to completely lyse the target cells. Supernatants were harvested for γ-counting after a 4 hour incubation. The percent specific lysis for the experimental conditions was calculated as:

[(Experimental Release−Spontaneous Release)/ (Maximum Release−Spontaneous Release)]× 100.

Figure 13A:
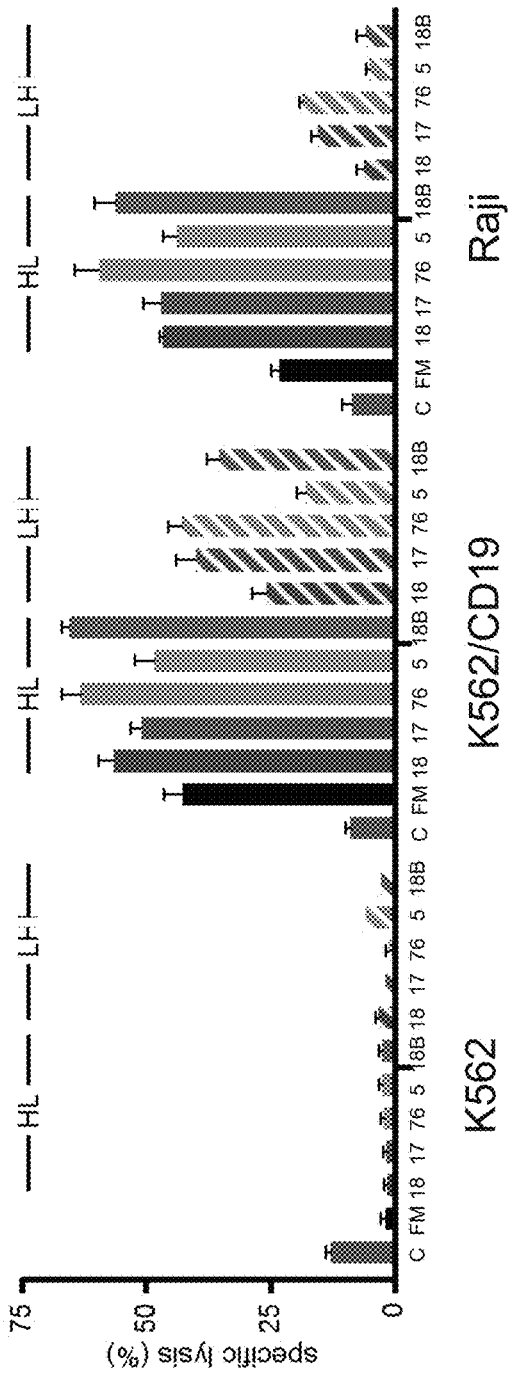
FIGS. 13A and 13B show cytolytic activity of primary human CD8+ T cells expressing various anti-CD19 specific CARs against CD19-expressing cells. C is EGFRt alone (negative control); FM is FMC63 scFv CAR, 18 is Clone 18 scFv CAR, 17 is Clone 17 scFv CAR, 76 is Clone 76 scFv CAR, 5 is Clone 5 scFv CAR and 18B is Clone 18B scFv CAR.
Figure 13B:
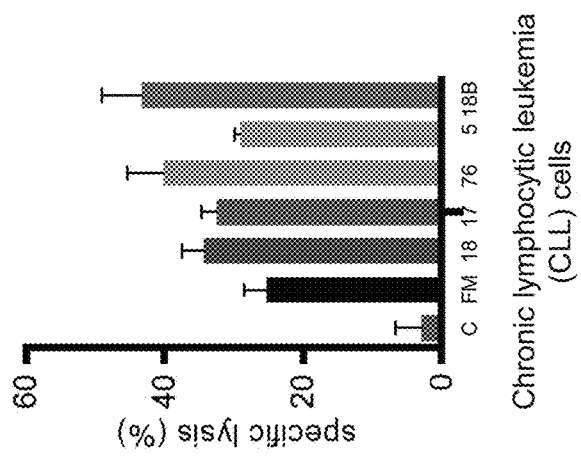

The results are set forth in FIGS. 13A and 13B. As shown in FIG. 13A, engineered CD8+ T cells expressing the various human anti-CD19 scFv-containing CARs exhibited antigen-specific cytolytic activity against CD19+ cells, to a comparable degree as cells expressing CARs containing the murine anti-CD19 (FMC63) scFv. This cytotoxic activity was not observed against control K562 cells not expressing CD19. The degree of cytolytic activity observed for cells expressing CARs with the human scFvs in the VH-VL orientation (HL) was observed to be comparable or greater than that observed for cells expressing the murine scFv-containing CAR. The degree of cytolytic activity observed for cells expressing a CAR with a given human scFv in the VH-VL (HL) orientation was generally greater than that observed for cells expressing a CAR with the corresponding scFv in the reverse VL-VH orientation (LH). As shown in FIG. 13B, the results also demonstrated antigen-specific cytolytic activity against the primary human CLL cells by the engineered CD8+ cells expressing the various human anti-CD19 scFv-containing CARs (VH-VL orientation) also was observed.

B. Cytokine Release

Cytokine release was assessed following incubation of the CAR-expressing cells with antigen-expressing and control target cells. Transduced CD8+ and CD4+ T cells were co-cultured in triplicate with target cells (K562, K562/CD19, Raji) at an effector to target (E:T) ratio of 2:1. Cytokine secretion following co-culture of transduced CD8+ cells with primary human chronic lymphocytic leukemia cells (CLL) also was similarly tested. The co-cultured cells were incubated for about 24 hours, and then supernatants were collected for measurement of IFN-γ (CD8+ cells) or IFN-γ, TNF-α, or IL-2 (CD4+ cells) using a multiplex cytokine immunoassay (Luminex®).

The results for CD8+ cells are set forth in FIGS. 14A and 14B. Engineered CD8+ T cells expressing the various human anti-CD19 scFv-containing CARs were observed to secrete IFN-γ in an antigen-specific manner following incubation with CD19+ cells, to a comparable degree as that observed for cells expressing CARs containing the murine anti-CD19 (FMC63) scFv. The cytokine secretion was not observed following incubation control K562 cells not expressing CD19. The levels of cytokine secretion observed for cells expressing CARs with the tested human anti-CD19 scFvs in the VH-VL orientation were comparable and in some cases greater than that observed for cells expressing the murine anti-CD19 scFv-containing CAR. The degree of IFNγ secretion observed for cells expressing a CAR with a given human scFv in the VH-VL orientation was generally greater that observed for cells expressing a CAR with the corresponding scFv in the reverse (VL-VH) orientation. As shown in FIG. 14B, antigen-specific cytokine secretion by CD8+ engineered T cells expressing the various human anti-CD19 scFv-containing CARs (VH-VL orientation) also was observed following co-culture with the CLL cells.

Figure 15:
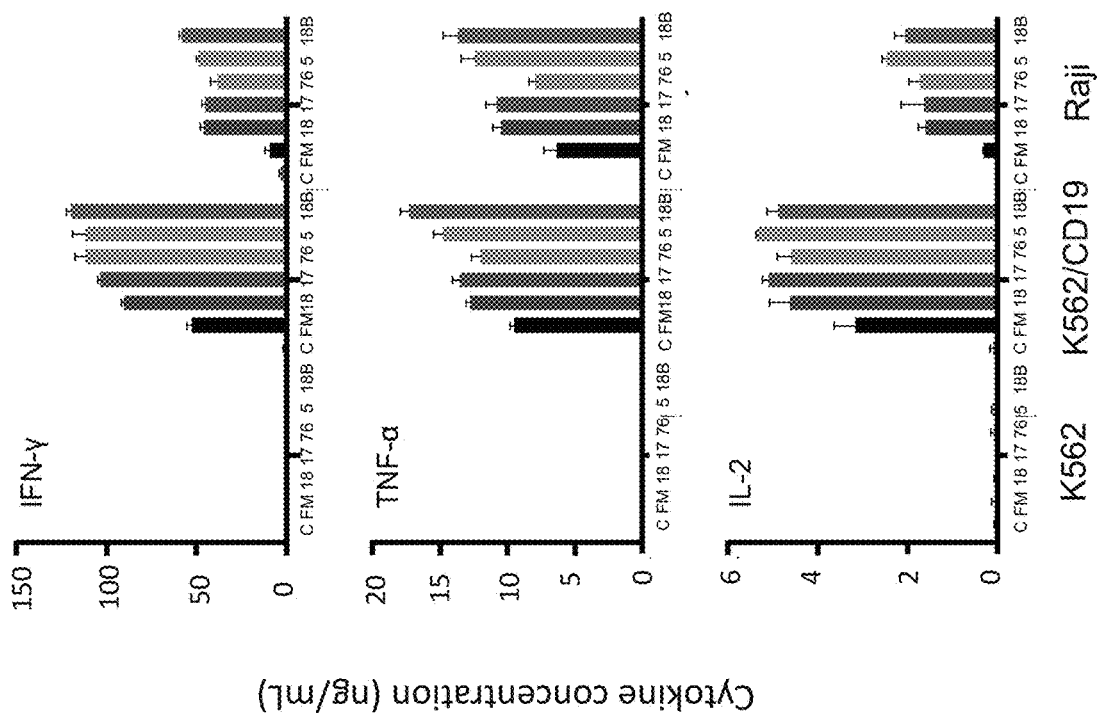
FIG. 15 shows cytokine secretion of primary human CD4+ T cells expressing various anti-CD19 specific CARs after co-culture with CD19-expressing cells. C is EGFRt alone (negative control); FM is FMC63 scFv CAR, 18 is Clone 18 scFv CAR, 17 is Clone 17 scFv CAR, 76 is Clone 76 scFv CAR, 5 is Clone 5 scFv CAR and 18B is Clone 18B scFv CAR.

The results for CD4+ CAR-expressing T cells are set forth in FIG. 15. Engineered CD4+ T cells expressing the various human anti-CD19 scFv-containing CARs (VH-VL orientation) were observed to secrete cytokines in an antigen-specific manner following incubation with CD19+ target cells, at levels comparable to and in general greater than those observed for cells expressing the murine-scFv (FMC63)-containing CAR. The cytokine secretion was not observed following CD19-negative control cells.

C. T Cell Proliferation

Proliferation of the various CAR-expressing T cells following incubation with CD19-expressing target cells was assessed by flow cytometry. CD8+ or CD4+ CAR-expressing T cells were labeled with 0.2 μM carboxyfluorescein succinmidyl ester (CFSE). Cells were washed and incubated for 72 hours in triplicate with target cells (K562, K562/CD19 or Raji) in serum-containing medium without exogenous cytokines. Division of live T cells was indicated by CFSE dilution, as assessed by flow cytometry.

The results are set forth in FIGS. 16A and 16B for CD8+ CAR-expressing T cells and CD4+ CAR-expressing T cells, respectively. As shown in FIG. 16A, CD8+ T cells expressing each of the tested human anti-CD19 scFv-containing CAR constructs proliferated after co-culture with CD19-expressing K562/CD19 or Raji target cells, but generally not with K562 control cells.

The degree of proliferation observed for T cells expressing CARs with the tested human anti-CD19 scFv was comparable to that observed for cells expressing the murine anti-CD19 scFv-containing CAR. The degree of proliferation of cells expressing a CAR with a given human scFv in the VH-VL orientation was generally observed to be greater than observed for cells expressing a CAR with the corresponding scFv in the reverse (VL-VH) orientation.

Antigen-specific proliferation of CAR-expressing T cells also was observed for CD4+ cells. As shown in FIG. 16B, CD4+ T cell expressing each of the tested human anti-CD19 scFv-containing CAR constructs proliferated after co-culture with CD19-expressing K562/CD19 or Raji target cells. The degree of proliferation observed for CD4+ T cells expressing CARs with the tested human anti-CD19 scFv was comparable to that observed for cells expressing the murine anti-CD19 scFv-containing CAR.

Example 5: Anti-Tumor Effect of CAR-Expressing T Cells after Adoptive Transfer In Vivo The anti-tumor effects of CAR-expressing engineered primary human T cells was assessed by monitoring tumors following adoptive transfer of cells to patient-derived xenograft (PDX) tumor model animal subjects. Six- to eight-week old female NOD.Cg.Prkdc$^{scid}$IL2rg$^{tm1Wjl}$/SzJ (NSG) mice were injected intravenously (i.v.) with 0.5×10$^6$ Raji lymphoma tumor cells transfected with firefly luciferase (Raji-ffluc). Tumor engraftment was allowed to occur for 6 days and verified using bioluminescence imaging. On day 7, mice received a single intravenous (i.v.) injection of a sub-optimal dose (1×10$^6$ CAR-expressing T cells in this study) of the various engineered primary human T cells (CD8+ cells alone (FIG. 17A) or combined CD4+ and CD8+ cells at a 1:1 ratio (FIG. 17B)) described in Example 3. As a control, mice were administered cells that were transduced with EGFRt alone (negative control). The sub-optimal dose was used in order to better visualize differences in anti-tumor effects.

Anti-tumor activity of the adoptively transferred CAR-expressing cells was monitored by bioluminescence imaging on days 6, 9, 13, 20 27 and 34. For bioluminescence imaging, mice received intraperitoneal (i.p.) injections of luciferin substrate (CaliperLife Sciences, Hopkinton, Mass.) resuspended in PBS (15 µg/g body weight). Mice were anesthetized and imaged essentially as described in WO2015/095895. The average radiance (p/s/cm$^2$/sr) was determined.

Figure 17B:
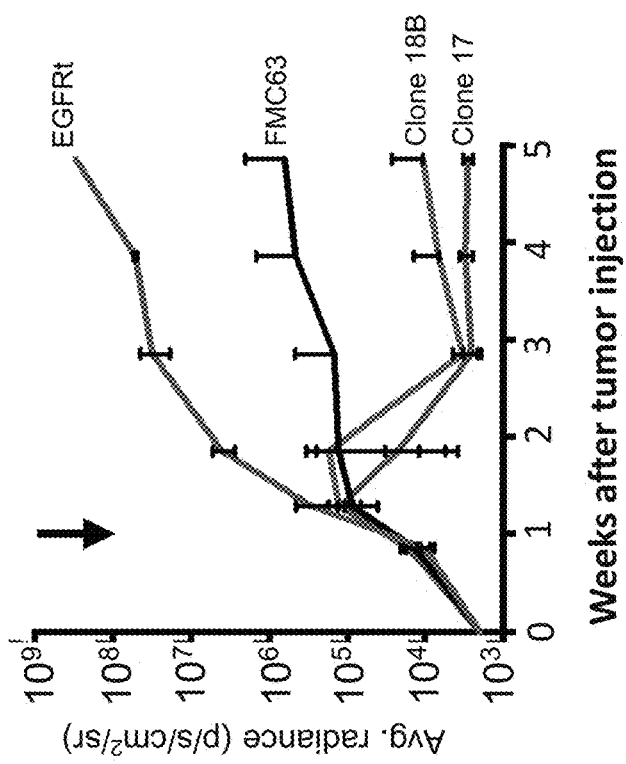
FIG. 17B shows antitumor activity of primary human CD4+ and CD8+ T cells expressing various anti-CD19 specific CARs and administered at a 1:1 ratio to NSG mice engrafted with Raji cells.
Figure 17A:
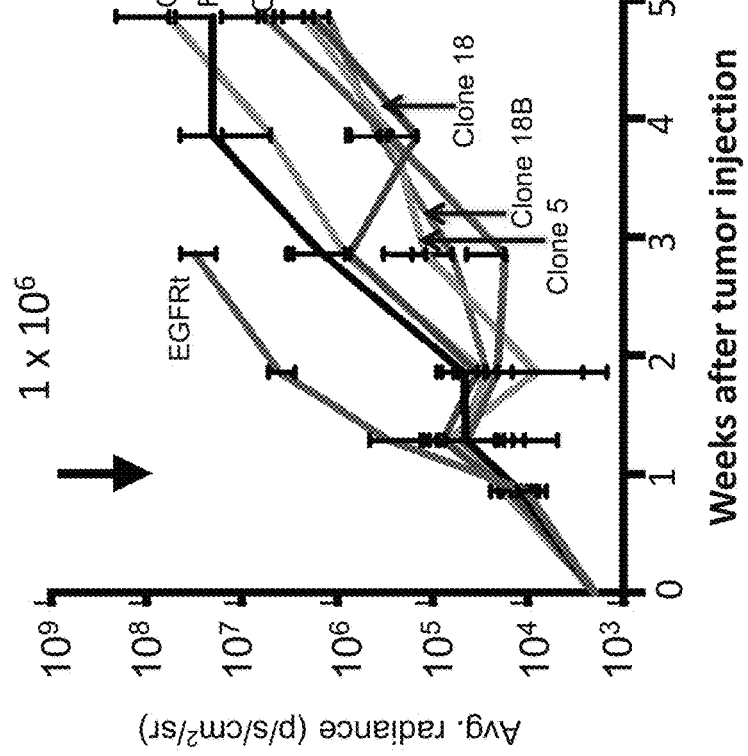
FIG. 17A shows the antitumor activity of primary human CD8+ T cells expressing various anti-CD19 specific CARs following administration to NSG mice engrafted with Raji cells that express firefly luciferase.

As shown in FIGS. 17A and 17B, tumors in control mice continued to grow over the course of the study following adoptive transfer of control T cells (CD8+ cells alone (FIG. 17A) or combination of CD4+ and CD8+ cells (FIG. 17B) transduced with EGFRt alone). Compared to the control mice, mice having been administered adoptive transfer of engineered T cells expressing each of the various tested anti-CD19 scFv-containing CARs were observed to have a lower degree of bioluminescence signal, indicating a reduction in tumor size over time and/or a lower degree of tumor growth in the treated animals. In general, as shown in FIG. 17A, adoptive transfer of CD8+ T cells expressing the tested human anti-CD19 scFv CARs alone led to a comparative reduction in tumor size to at least the same degree as adoptive transfer of cells expressing a CAR containing the mouse anti-CD19 scFv (FMC63). As shown in FIG. 17B, adoptive transfer of the combination of CD8+ and CD4+ T cells expressing the tested human anti-CD19 CARs was observed to reduce tumor size over time. Tumor size (as indicated by bioluminescence signal) following adoptive transfer of such human anti-CD19 CAR-expressing cells was observed to be comparatively lower than that detected following adoptive transfer of the mouse-scFv-derived CAR-expressing cells.

Example 6: Identification of Region in Human CD19 Recognized by Anti-CD19 Antibodies CARs containing certain anti-CD19 antibodies (scFvs) described in Example 1, or the murine anti-CD19 (FMC63) scFv, were assessed for binding to various CD19 molecules. K562 cells were engineered to express (a) a human CD19 (having the amino acid sequence set forth in SEQ ID NO:92), (b) a *Macaca mulatta* (rhesus macaque (rhesus)) CD19 (having the amino acid sequence set forth in SEQ ID NO:139; Accession No. F7F486), or (c) one the three different human/rhesus chimeric CD19 molecules, V1, V2, and V3, which contained membrane-proximal regions having the sequences depicted in FIG. 18A. Aside from the region depicted in FIG. 18A, the remaining regions of each chimeric molecule were identical in sequence to the corresponding regions of the rhesus CD19.

Figures 18A, 18B:
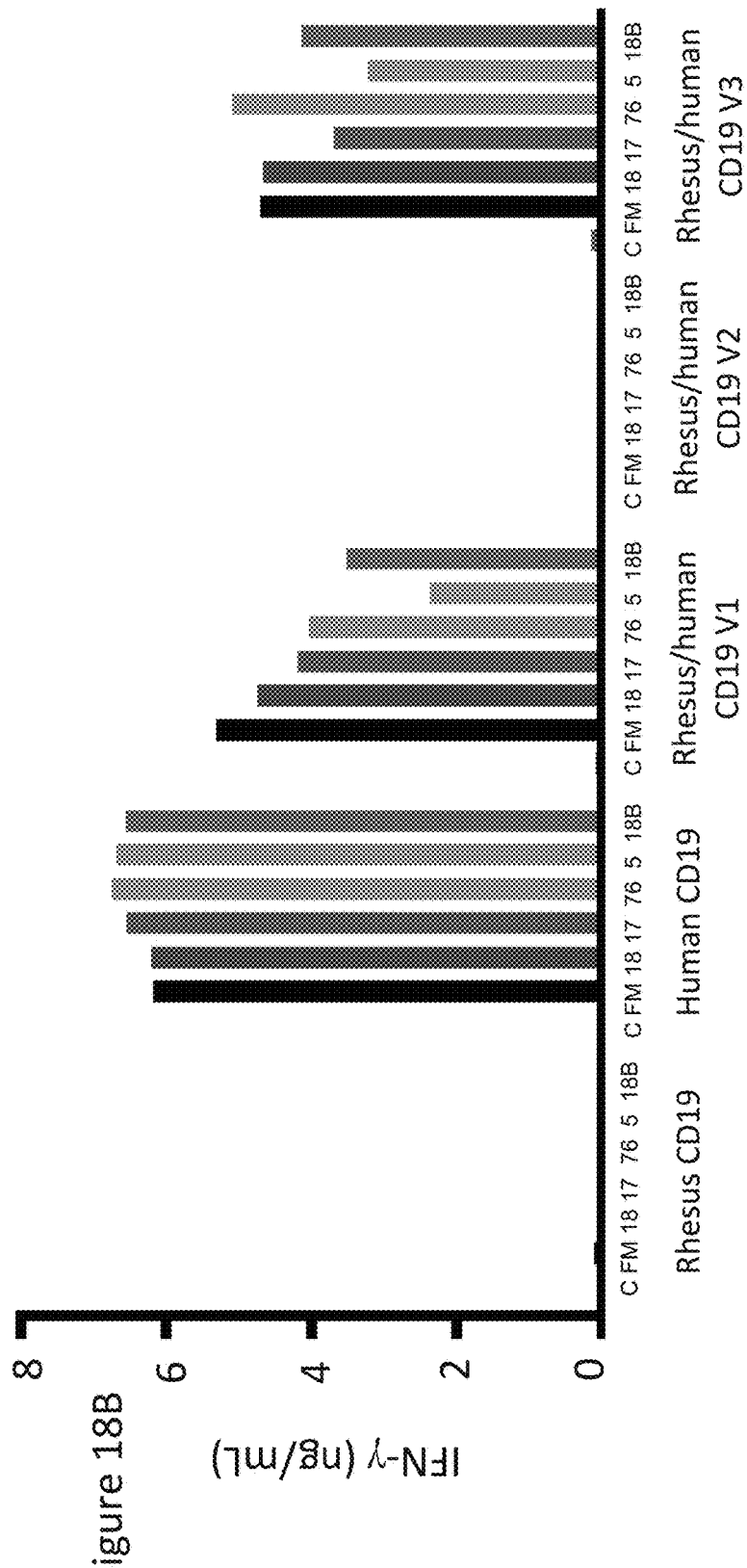
FIG. 18A shows the amino acid sequence of a 74-residue or 75-residue membrane-proximal region for each of the three different chimeric CD19 molecules. Below all three sequences shown in FIG. 18A, each aligned position of the depicted region at which the human and rhesus sequences contain an identical amino acid is marked with an asterisk ("*"). Positions at which the rhesus sequence contains a non-identical but conservative amino acid substitution compared to the human sequence are marked with a ":". Positions at which the rhesus sequence contains a non-identical but semi-conservative amino acid substitution compared to the human sequences are marked with a ".". Positions at which the rhesus sequence contains an insertion or a non-identical, non-conservative/semi-conservative substitution compared with the human sequence are not marked with a symbol.
FIG. 18B show cytokine secretion of primary human CD8+ T cells expressing various anti-CD19 specific CARs after co-culture with cells expressing human CD19, rhesus CD19 or chimeric rhesus/human CD19 molecules (V1, V2 or V3). C is EGFRt alone (negative control); FM is FMC63 scFv CAR, 18 is Clone 18 scFv CAR, 17 is Clone 17 scFv CAR, 76 is Clone 76 scFv CAR, 5 is Clone 5 scFv CAR and 18B is Clone 18B scFv CAR.

Chimeric CD19 V1:

The 74-amino acid membrane-proximal region depicted in FIG. 18A of the chimeric molecule designated V1 had the amino acid sequence set forth in SEQ ID NO: 140, which was identical to the sequence of the corresponding region (residues 218 to 291) of the human CD19 molecule having the sequence set forth in SEQ ID NO: 92.

Chimeric CD19 V2:

The 75-amino acid membrane-proximal region depicted in FIG. 18A of the chimeric CD19 molecule designated V2 had the amino acid sequence set forth in SEQ ID NO: 141. Within this region, the 27-amino acid membrane-proximal portion was identical in sequence to the corresponding portion (residues 265 to 291) of human CD19. The remaining portion of the shown region was identical in sequence to the corresponding portion of the rhesus CD19 sequence set forth in SEQ ID NO: 139. Positions in this remaining portion having a substitution or an insertion compared to the corresponding human sequence are underlined.

Chimeric CD19 V3:

The 74-amino acid region depicted in FIG. 18A of the chimeric CD19 molecule designated V3 had the amino acid sequence set forth in SEQ ID NO: 142. Within this depicted region, a 47-amino acid portion was identical in sequence to the corresponding portion (residues 218-264) of the human CD19 sequence set forth in SEQ ID NO: 92. The remaining 27-amino acid membrane-proximal portion was identical in sequence to the corresponding portion of rhesus CD19 sequence set forth in SEQ ID NO: 139. Positions in this remaining 27-amino acid portion having a substitution compared to the corresponding human sequence are underlined.

Primary human T cells expressing various human anti-CD19 scFv-containing CARs or a murine anti-CD19 scFv (FMC63)-containing CAR were generated as described in Example 3 and co-cultured with the various K562 target cells transfected with nucleic acid molecules encoding the various CD19 molecules, at an effector to target (E:T) ratio of 2:1. The cells were incubated for 24 hours, and supernatants were collected for measurement of IFN-γ, using a cytokine immunoassay, as an indicator of functional binding by the anti-CD19 scFv-containing CARs to the respective CD19 molecules on the surface of the target cells. The results are shown in FIG. 18B.

Each of the tested anti-CD19 CARs exhibited detectable levels of cytokine following co-culture with cells expressing the human CD19 molecule (indicating functional binding thereto), but not following co-culture with cells expressing the rhesus CD19. For each of the tested anti-CD19 CARs, detectable levels of secretion were observed following co-culture with cells expressing the rhesus/human chimeric molecules designated V1 (entire membrane-proximal 74-amino acid region human-derived) and V3 (27-amino acid membrane-proximal portion rhesus-derived), but not to cells expressing the rhesus/human chimeric molecule designated V2 (27-amino acid membrane-proximal portion human-derived).

These results indicated that at least part of a 32-amino acid portion (SEQ ID NO: 143 (HPKGPKSLLSLELKDDR-PARDMWVMETGLLLP) of the human CD19 molecule (corresponding to residues 218-249 of SEQ ID NO: 92), was important for functional binding to CD19 by each of the tested anti-CD19 CARs. Specifically, whereas each of V1 and V3 contained this 32-amino acid sequence (set forth in bold in FIG. 18A), the corresponding portion of V2 contained the 33-residue amino acid sequence set forth in SEQ ID NO: 144 (RPKGPKSSLLSLELKDDRPDRDMWVVDTGLLLT), which was identical in sequence to the corresponding portion of the rhesus CD19 molecule, but contained five amino acid substitutions (at positions 218, 236, 242, 243, and 249 of the human CD19 sequence of SEQ ID NO: 92) and one insertion (between positions 223 and 224 of the human CD19 sequence of SEQ ID NO: 92) compared with the corresponding human sequence, each underlined in FIG. 18A. Thus, the results indicate that the amino acid(s) present at at least one of these position(s) in the human sequence (positions 218, 236, 242, 243, 249 and/or 223-224 of SEQ ID NO: 92) was important for the ability of each CAR tested to specifically bind to human CD19. Thus, the results support a conclusion that each of the tested human scFv-containing CARs bound to a similar and/or overlapping epitope as compared to the CAR containing the mouse scFv, FMC63.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

TABLE 9

SEQUENCES

| SEQ ID NO. | Sequence | Description |
|---|---|---|
| 1 | GAAGTGCAGCTGGTGGAGTCTGGGGGAGGCTTGGTACAGCCTGGCAGGTC<br>CCTGAGACTCTCCTGTGCAGCCTCTGGATTCACCTTTGATGATTATGCCAT<br>GCACTGGGTCCGGCAAGCTCCAGGGAAGGGCCTGGAGTGGGTCTCAGGTA<br>TTAGTTGGAATAGTGGTAGGATAGGCTATGCGGACTCTGTAAAGGGCCGA<br>TTCACCATCTCCAGAGACAACGCCAAGAACTCCCTGTTTCTGCAAATGAA<br>CAGTCTGAGAGCTGAGGACACGGCCGTGTATTACTGTGCGAGAGATCAGG<br>GGTATCATTACTATGATAGTGCCGAACATGCTTTTGATATCTGGGGCCAAG<br>GGACAGTGGTCACCGTCTCCTCAGGTGGAGGCGGTTCAGGCGGAGGTGGC<br>TCTGGCGGTGGCGGATCGCAGTCTGCCCTGACTCAGCCTCGCTCAGTGTCC<br>GGCTTTCCTGGACAATCAGTCACCATCTCCTGCACTGGAACCACCAGTGAT<br>GATGTCTCCTGGTACCAACAACACCCAGGCAAAGCCCCCCAACTTATGCT<br>TTATGATGTCAGTAAGCGGCCCTCCGGGGTCCCTCATCGCTTCTCTGGCTC<br>CAGGTCTGGCAGAGCGGCCTCCCTGATCATCTCTGGGCTCCAGACTGAGG<br>ATGAGGCTGATTATTTCTGCTGCTCATATGCAGGCCGATACAACTCTGTCC<br>TTTTCGGCGGAGGGACCAAGCTGACCGTCCTA | Clone 18 scFv (nt) |
| 2 | EVQLVESGGGLVQPGRSLRLSCAASGFTFDDYAMHWVRQAPGKGLEWVSGI<br>SWNSGRIGYADSVKGRFTISRDNAKNSLFLQMNSLRAEDTAVYYCARDQGY<br>HYYDSAEHAFDIWGQGTVVTVSSGGGGSGGGGSGGGGSQSALTQPRSVSGFP<br>GQSVTISCTGTTSDDVSWYQQHPGKAPQLMLYDVSKRPSGVPHRFSGSRSGR<br>AASLIISGLQTEDEADYFCCSYAGRYNSVLFGGGTKLTVL | Clone 18 scFv (aa) |
| 3 | GAAGTGCAGCTGGTGGAGTCTGGGGGAGGCTTGGTACAGCCTGGCAGGTC<br>CCTGAGACTCTCCTGTGCAGCCTCTGGATTCACCTTTGATGATTATGCCAT<br>GCACTGGGTCCGGCAAGCTCCAGGGAAGGGCCTGGAGTGGGTCTCAGGTA<br>TTAGTTGGAATAGTGGTAGGATAGGCTATGCGGACTCTGTAAAGGGCCGA<br>TTCACCATCTCCAGAGACAACGCCAAGAACTCCCTGTTTCTGCAAATGAA<br>CAGTCTGAGAGCTGAGGACACGGCCGTGTATTACTGTGCGAGAGATCAGG<br>GGTATCATTACTATGATAGTGCCGAACATGCTTITGATATCTGGGGCCAAG<br>GGACAGTGGTCACCGTCTCCTCAGGTGGAGGCGGTTCAGGCGGAGGTGGC<br>TCTGGCGGTGGCGGATCGCAGTCTGCCCTGACTCAGCCTCGCTCAGTGTCC<br>GGCTTTCCTGGACAATCAGTCACCATCTCCTGCACTGGAACCACCAGTGAT<br>GATGTCTCCTGGTACCAACAACACCCAGGCAAAGCCCCCCAACTTATGCT<br>TTATGATGTCAGTAAGCGGCCCTCCGGGGTCCCTCATCGCTTCTCTGGCTC<br>CAGGTCTGGCAGAGCGGCCTCCCTGATCATCTCTGGGCTCCAGACTGAGG<br>ATGAGGCTGATTATTTCTGCAGCTCATATGCAGGCCGATACAACTCTGTCC<br>TTTTCGGCGGAGGGACCAAGCTGACCGTCCTA | Clone 18B scFv (nt) |
| 4 | EVQLVESGGGLVQPGRSLRLSCAASGFTFDDYAMHWVRQAPGKGLEWVSGI<br>SWNSGRIGYADSVKGRFTISRDNAKNSLFLQMNSLRAEDTAVYYCARDQGY<br>HYYDSAEHAFDIWGQGTVVTVSSGGGGSGGGGSGGGGSQSALTQPRSVSGFP<br>GQSVTISCTGTTSDDVSWYQQHPGKAPQLMLYDVSKRPSGVPHRFSGSRSGR<br>AASLIISGLQTEDEADYFCSSYAGRYNSVLFGGGTKLTVL | Clone 18B scFv (aa) |
| 5 | GAAGTGCAGCTGGTGGAGTCTGGGGGAGGCTTGGTACAGCCTGGCAGGTC<br>CCTGAGACTCTCCTGTGCAGCCTCTGGATTCACCTTTGATGATTATGCCAT<br>GCACTGGGTCCGGCAAGCTCCAGGGAAGGGCCTGGAGTGGGTCTCAGGTA<br>TTAGTTGGAATAGTGGTAGGATAGGCTATGCGGACTCTGTAAAGGGCCGA<br>TTCACCATCTCCAGAGACAACGCCAAGAACTCCCTGTTTCTGCAAATGAA<br>CAGTCTGAGAGCTGAGGACACGGCCGTGTATTACTGTGCGAGAGATCAGG<br>GGTATCATTACTATGATAGTGCCGAACATGCTTTTGATATCTGGGGCCAAG<br>GGACAATGGTCACCGTCTCCTCAGGTGGAGGCGGTTCAGGCGGAGGTGGC | Clone 17 scFv (nt) |

TABLE 9-continued

SEQUENCES

| SEQ ID NO. | Sequence | Description |
|---|---|---|
| | TCTGGCGGTGGCGGATCGCAGTCTGCCCTGACTCAGCCTGCCTCCGTGTCT GGGTCTCCTGGACAGTCGATCACCATCTTCTGCACTGGAACCAGCAGTGA CGTTGGTGGTTATAACTATGTCTCCTGGTACCAGCAGCTCCCAGGAACGGC CCCCAAACTCCTCATCTATAGTAATAATCAGCGGCCCTCAGGGGTCCCTG ACCGATTCTCTGGCTCCAAGTCTGGCACCTCAGCCTCCCTGGCCATCAGTG GGCTCCGGTCCGAGGATGAGGCTGATTATTACTGTGCAGCATGGGATGAC AGCCTGAGTGTGGTATTCGGCGGAGGGACCAAGCTGACCGTCCTC | |
| 6 | EVQLVESGGGLVQPGRSLRLSCAASGFTFDDYAMHWVRQAPGKGLEWVSGI SWNSGRIGYADSVKGRFTISRDNAKNSLFLQMNSLRAEDTAVYYCARDQGY HYYDSAEHAFDIWGQGTMVTVSSGGGGSGGGGSGGGGSQSALTQPASVSGS PGQSITIFCTGTSSDVGGYNYVSWYQQLPGTAPKLLIYSNNQRPSGVPDRF SGSKSGTSASLAISGLRSEDEADYYCAAWDDSLSVVFGGGTKLTVL | Clone 17 scFv (aa) |
| 7 | GAAGTGCAGCTGGTGGAGTCTGGGGGAGGCTTGGTACAGCCTGGCAGGTC CCTGAGACTCTCCTGTGCAGCCTCTGGATTCACCTTTGATGATTATGCCAT GCACTGGGTCCGGCAAGCTCCAGGGAAGGGCCTGGAGTGGGTCTCAGGTA TTAGTTGGAATAGTGGTAGGATAGGCTATGCGGACTCTGTAAAGGGCCGA TTCACCATCTCCAGAGACAACGCCAAGAACTCCCTGTTTCTGCAAATGAA CAGTCTGAGAGCTGAGGACACGGCCGTGTATTACTGTGCGAGAGATCAGG GGTATCATTACTATGATAGTGCCGAACATGCTTTTGATATCTGGGGCCAAG GGACAGTGGTCACCGTCTCCTCAGGTGGAGGCGGTTCAGGCGGAGGTGGC TCTGGCGGTGGCGGATCGCAGTCTGTGCTGACGCAGCCGCCCTCAGTGTC TGCGGCCCCAGGACAGGAGGTCACCATCTCCTGCTCTGGAAGCAGCTCCA ACATTGGGAATAATTATGTATCCTGGTACCAGCAACTCCCAGGAACAGCC CCCAAACTCCTCATTTATGACAATGATAAGCGACCCTCAGGGATTCCTGA CCGATTCTCTGGCTCCAAGTCTGGCACGTCAGCCACCCTGGGCATCACCG GACTCCAGACTGGGGACGAGGCCGATTATTACTGCGGAACATGGGATGGC AATCTGAGTGCTGTATTCGGCGGAGGGACCAAGGTGACCGTCCTA | Clone 76 scFv (nt) |
| 8 | EVQLVESGGGLVQPGRSLRLSCAASGFTFDDYAMHWVRQAPGKGLEWVSGI SWNSGRIGYADSVKGRFTISRDNAKNSLFLQMNSLRAEDTAVYYCARDQGY HYYDSAEHAFDIWGQGTVVTVSSGGGGSGGGGSGGGGSQSVLTQPPSVSAA PGQEVTISCSGSSSNIGNNYVSWYQQLPGTAPKLLIYDNDKRPSGIPDRFS GSKSGTSATLGITGLQTGDEADYYCGTWDGNLSAVFGGGTKVTVL | Clone 76 scFv (aa) |
| 9 | GAAGTGCAGCTGGTGGAGTCTGGGGGAGGCTTGGTACAGCCTGGCAGGTC CCTGAGACTCTCCTGTGCAGCCTCTGGATTCACCTTTGATGATTATGCCAT GCACTGGGTCCGGCAAGCTCCAGGGAAGGGCCTGGAGTGGGTCTCAGGTA TTAGTTGGAATAGTGGTAGGATAGGCTATGCGGACTCTGTAAAGGGCCGA TTCACCATCTCCAGAGACAACGCCAAGAACTCCCTGTTTCTGCAAATGAA CAGTCTGAGAGCTGAGGACACGGCCGTGTATTACTGTGCGAGAGATCAGG GGTATCATTACTATGATAGTGCCGAACATGCTTTTGATATCTGGGGCCAAG GGACAATGGTCACCGTCTCCTCAGGTGGAGGCGGTTCAGGCGGAGGTGGC TCTGGCGGTGGCGGATCGTCCTATGAGCTGACTCAGGACCCTGCTGTGTCT GTGGCCTTGGGACAGACAGTCAGGATCACATGCCAAGGAGACAGCCTCAG AAGCTATTATGCAAGCTGGTACCAGCAGAAGCCAGGACAGGCCCCTGTAC TTGTCATCTATGATAAAAACAACCGGCCCTCAGGGATCCCAGACCGATTC TCTGGCTCCAGCTCAGGAAACACAGCTTCCTTGACCATCACTGGGGCTCA GGCGGAAGATGAGGCTGACTACTACTGCAACTCCCGGGACAGCAGTGGTA ACAATTGGGTGTTCGGCGGAGGGACCAAGCTGACCGTCCTA | Clone 5 scFv (nt) |
| 10 | EVQLVESGGGLVQPGRSLRLSCAASGFTFDDYAMHWVRQAPGKGLEWVSGI SWNSGRIGYADSVKGRFTISRDNAKNSLFLQMNSLRAEDTAVYYCARDQGY HYYDSAEHAFDIWGQGTMVTVSSGGGGSGGGGSGGGGSSYELTQDPAVSVA LGQTVRITCQGDSLRSYYASWYQQKPGQAPVLVIYDKNNRPSGIPDRFSGS SSGNTASLTITGAQAEDEADYYCNSRDSSGNNWVFGGGTKLTVL | Clone 5 scFv (aa) |
| 11 | EVQLVESGGGLVQPGRSLRLSCAASGFTFDDYAMHWVRQAPGKGLEWVSGI SWNSGRIGYADSVKGRFTISRDNAKNSLFLQMNSLRAEDTAVYYCARDQGY HYYDSAEHAFDIWGQGTVVTVSS | VH (clones 18, 18B reversion, 76, 285) (aa) |
| 12 | EVQLVESGGGLVQPGRSLRLSCAASGFTFDDYAMHWVRQAPGKGLEWVSGI SWNSGRIGYADSVKGRFTISRDNAKNSLFLQMNSLRAEDTAVYYCARDQGY HYYDSAEHAFDIWGQGTMVTVSS | VH (clones 17, 5, 1, 192) (aa) |
| 13 | QSALTQPRSVSGFPGQSVTISCTGTTSDDVSWYQQHPGKAPQLMLYDVSKRP SGVPHRFSGSRSGRAASLIISGLQTEDEADYYCCSYAGRYNSVLFGGGTKLT VL | VL Clone 18 (aa) |
| 14 | QSALTQPRSVSGFPGQSVTISCTGTTSDDVSWYQQHPGKAPQLMLYDVSKRP SGVPHRFSGSRSGRAASLIISGLQTEDEADYFCCSYAGRYNSVLFGGGTKLT VL | VL, Clone 18B (aa) |

TABLE 9-continued

SEQUENCES

| SEQ ID NO. | Sequence | Description |
|---|---|---|
| 15 | QSALTQPASVSGSPGQSITIFCTGTSSDVGGYNYVSWYQQLPGTAPKWYSNNQRPSGVPDRFSGSKSGTSASLAISGLRSEDEADYYCAAWDDSLSVVFGGGTKLTVL | VL, Clone 17 (aa) |
| 16 | QSVLTQPPSVSAAPGQEVTISCSGSSSNIGNNYVSWYQQLPGTAPKLLIYDNDKRPSGIPDRFSGSKSGTSATLGITGLQTGDEADYYCGTWDGNLSAVFGGGTKVTVL | VL, Clone 76 (aa) |
| 17 | SYELTQDPAVSVALGQTVRITCQGDSLRSYYASWYQQKPGQAPVLVIYDKNNRPSGIPDRFSGSSSGNTASLTITGAQAEDEADYYCNSRDSSGNNWVFGGGTKLTVL | VL, Clone 5 (aa) |
| 18 | DYAMH | CDR-H1 (aa) |
| 19 | GISWNSGRIGYADSVKG | CDR-H2 (aa) |
| 20 | DQGYHYYDSAEHAFDI | CDR-H3 (aa) |
| 21 | TGTTSDDVS | Clones 18, 18B CDR-L1 (aa) |
| 22 | DVSKRPS | Clones 18, 18B CDR-L2 (aa) |
| 23 | CSYAGRYNSVL | Clone 18 CDR-L3 (aa) |
| 24 | SSYAGRYNSVL | Clone 18B CDR-L3 (aa) |
| 25 | TGTSSDVGGYNYVS | Clone 17 CDR-L1 (aa) |
| 26 | SNNQRPS | Clone 17 CDR-L2 (aa) |
| 27 | AAWDDSLSVV | Clone 17 CDR-L3 (aa) |
| 28 | SGSSSNIGNNYVS | Clone 76 CDR-L1 (aa) |
| 29 | DNDKRPS | Clone 76 CDR-L2 (aa) |
| 30 | GTWDGNLSAV | Clone 76 CDR-L3 (aa) |
| 31 | QGDSLRSYYAS | Clone 5 CDR-L1 (aa) |
| 32 | DKNNRPS | Clone 5 CDR-L2 (aa) |
| 33 | NSRDSSGNNWV | Clone 5 CDR-L3 (aa) |
| 34 | GGGGSGGGGSGGGGS | Linker (aa) |
| 35 | GISWNSGRIGY | CDR-H2 |
| 36 | $X_1GX_3X_4X_5X_6X_7X_8X_9X_{10}X_{11}X_{12}X_{13}S$<br>$X_1$ = T, S, or Q; $X_3$ = T, S, or D; $X_4$ = T or S; $X_5$ = null or S; $X_6$ = null, D, or N; $X_7$ = null or V; $X_8$ = null, G, or I; $X_9$ = null, G, or R; $X_{10}$ = S, Y, or N; $X_{11}$ = D or N; $X_{12}$ = D or Y; $X_{13}$ = V or A | CDR-L1 consensus |
| 37 | $X_1X_2X_3X_4RPS$<br>$X_1$ = D or S; $X_2$ = V, N, or K; $X_3$ = S, N, or D; $X_4$ = K, Q, or N | CDR-L2 consensus |
| 38 | $X_1X_2X_3X_4X_5X_6X_7X_8X_9X_{10}X_{11}X_{12}$<br>$X_1$ = C, S, A, G, or N; $X_2$ = S, A, or T; $X_3$ = Y, W, or | CDR-L3 |

TABLE 9-continued

SEQUENCES

| SEQ ID NO. | Sequence | Description |
|---|---|---|
| | R; $X_4$ = A or D; $X_5$ = G, D, or S; $X_6$ = R, S, or N; $X_7$ = Y, L, or G; $X_8$ = N or S; $X_9$ = S or null; $X_{10}$ = V, A, or N; $X_{11}$ = W or null; $X_{12}$ = L or V. | |
| 39 | EVKLQESGPGLVAPSQSLSVTCTVSGVSLPDYGVSWIRQPPRKGLEWLGVIW GSETTYYNSALKSRLTIIKDNSKSQVFLKMNSLQTDDTAIYYCAKHYYYGGS YAMDYWGQGTSVTVSS | FMC63 VH |
| 40 | DIQMTQTTSSLSASLGDRVTISCRASQDISKYLNWYQQKPDGTVKLLIYHTSR LHSGVPSRFSGSGSGTDYSLTISNLEQEDIATYFCQQGNTLPYTFGGGTKLEIT | FMC63VL |
| 41 | EVKLQQSGAELVRPGSSVKISCKASGYAFSSYWMNWVKQRPGQGLEWIGQI YPGDGDTNYNGKFKGQATLTADKSSSTAYMQLSGLTSEDSAVYFCARKTISS VVDFYFDYWGQGTTVTVSS | SJ25C1VH |
| 42 | DIELTQSPKFMSTSVGDRVSVTCKASQNVGTNVAWYQQKPGQSPKPLIYSAT YRNSGVPDRFTGSGSGTDFTLTITNVQSKDLADYFCQQYNRYPYTSGGGTKL EI | SJ25C1 VL |
| 43 | GSTSGSGKPGSGEGSTKG | Linker |
| 44 | GAAGTGCAGCTGGTGCAGTCTGGGGGAGGCTTGGTACAGCCTGGCAGGTC CCTGAGACTCTCCTGTGCAGCCTCTGGATTCACCTTTGATGATTATGCCAT GCACTGGGTCCGGCAAGCTCCAGGGAAGGGCCTGGAGTGGGTCTCAGGTA TTAGTTGGAATAGTGGTAGCATAGGCTATGCGGACTCTGTGAAGGGCCGA TTCACCATCTCCAGAGACAACGCCAAGAACTCCCTGTATCTGCAAATGAA CAGTCTGAGAGCTGAGGACACCGCCGTGTATTACTGTGCGAGAGATCAGG GGTATCATTACTATGATAGTGCCGAACATGCTTTTGATATCTGGGGCCAAG GGACAGTGGTCACCGTCTCCTCAGGTGGAGGCGGTTCAGGCGGAGGTGGC TCTGGCGGTGGCGGATCGGAAATTGTGTTGACGCAGTCTCCAGCCACCCT GTCTTTGTCTCCAGGGGAGACCGCCACCCTCTCCTGCAGGGCCAGTCAGA GTATTAACCACTACTTAGCCTGGTACCAACAGAAACCTGGCCAGGCTCCC CGGCTCCTCATCTATGATGCCTCCAACAGGGCCACTGGCATCCCAGCCAG GTTCAGTGGCAGTGGGTCTGGGACAGACTTCACTCTCACCATCAGCAGCC TAGAGCCTGAAGATTTTGCAACTTACTACTGTCAACAGAGTTACAGTCACC CTCGAATGTACACTTTTGGCCAGGGGACCAAACTGGATATCAAA | Clone 488 scFv (nt) |
| 45 | EVQLVQSGGGLVQPGRSLRLSCAASGFTFDDYAMHWVRQAPGKGLEWVSGI SWNSGSIGYADSVKGRFTISRDNAKNSLYLQMNSLRAEDTAVYYCARDQGY HYYDSAEHAFDIWGQGTVVTVSSGGGGSGGGGSGGGGSEIVLTQSPATLSL SPGETATLSCRASQSINHYLAWYQQKPGQAPRLLIYDASNRATGIPARFSG SGSGTDFTLTISSLEPEDFATYYCQQSYSHPRMYTFGQGTKLDIK | Clone 488 scFv (aa) |
| 46 | CAGATGCAGCTGGTGCAGTCTGGGGGAGGCTTGGTACAGCCTGGCAGGTC CCTGAGACTCTCCTGTGCAGCCTCTGGATTCACCTTTGATGATTATGCCAT GCACTGGGTCCGGCAAGCTCCAGGGAAGGGCCTGGAGTGGGTCTCAGGTA TTAGTTGGAATAGTGGTAGCATAGGCTATGCGGACTCTGTGAAGGGCCGA TTCACCATCTCCAGAGACAACGCCAAGAACTCCCTGTATCTGCAAATGAA CAGTCTGAGAGCTGAGGACACGGCCGTGTATTACTGTGCGAGAGATCAGG GGTATCATTACTATGATAGTGCCGAACATGCTTTTGATATCTGGGGCCAAG GGACAGTGGTCACCGTCTCCTCAGGTGGAGGCGGTTCAGGCGGAGGTGGC TCTGGCGGTGGCGGATCGGCCATCCGGATGACCCAGTCTCCATCCTCCCTG TCTGCATCTGTAGGAGACAGAGTCACCGTCACTTGCCAGGCGAGTCAGGA CATTAGCAACTATTTAAATTGGTATCAGCAGAAACCAGGAAGAGCCCCTA AGCTCCTGATCTACGATGCATCCAATGTGAAAGCAGGGGTCCCATCAAGG TTCAGTGGGGGTGGATCTGGGACAGATTTCACTCTCACCATCAGCAGTCTG CAACCTGAAGATTTTGCAACTTACTACTGTCAACAGAGTTACAGTACCCCT CAGGCGTACACTTTTGGCCAGGGGACCAAGCTGGAGATCAAA | Clone 1304 scFv (nt) |
| 47 | QMQLVQSGGGLVQPGRSLRLSCAASGFTFDDYAMHWVRQAPGKGLEWVSG ISWNSGSIGYADSVKGRFTISRDNAKNSLYLQMNSLRAEDTAVYYCARDQGY HYYDSAEHAFDIWGQGTVVTVSSGGGGSGGGGSGGGGSAIRMTQSPSSLSAS VGDRVTVTCQASQDISNYLNWYQQKPGRAPKWYDASNVKAGVPSRFSGG GSGTDFTLTISSLQPEDFATYYCQQSYSTPQAYTFGQGTKLEIK | Clone 1304 scFv (aa) |
| 48 | GAGGTGCAGCTGGTGGAGTCTGGGGGAGGCTTGGTACAGCCTGGCAGGTC CCTGAGACTCTCCTGTGCAGCCTCTGGATTCACCTTTGATGATTATGCCAT GCACTGGGTCCGGCAAGCTCCAGGGAAGGGCCTGGAGTGGGTCTCAGGTA TTAGTTGGAATAGTGGTAGGATAGGCTATGCGGACTCTGTAAAGGGCCGA TTCACCATCTCCAGAGACAACGCCAAGAACTCCCTGTTTCTGCAAATGAA CAGTCTGAGAGCTGAGGACACGGCCGTGTATTACTGTGCGAGAGATCAGG GGTATCATTACTATGATAGTGCCGAACATGCTTTTGATATCTGGGGCCAAG GGACAGTGGTCACCGTCTCCTCAGGTGGAGGCGGTTCAGGCGGAGGTGGC TCTGGCGGTGGCGGATCGCAGTCTGCCCTGACTCAGCCTGCCTCCGTGTCT | Clone 285 scFv (nt) |

TABLE 9-continued

SEQUENCES

| SEQ ID NO. | Sequence | Description |
|---|---|---|
| | GGGTCTCCTGGACAGTCGATCACCATCTCCTGCACTGGAACCAGCAGTGA CCTTGGTGGTTACAATTATGTCTCCTGGTATCAACACCGCCCAGGCAAAGC CCCCAAACTCATCATTTATGATGTCACTGTTCGGCCCTCAGGGGTTTCTGA TCGCTTCTCTGGCTCCAAGTCTGGCAACACGGCCTCCCTGACCATCTCTGG GCTCCAGGCTGAGGACGAGGCTGATTATTACTGCGGCTCATATACAAGCA GTAGCACTCTTCTTTGGGTGTTCGGCGGAGGGACCAAGCTCACCGTCCTA | |
| 49 | EVQLVESGGGLVQPGRSLRLSCAASGFTFDDYAMHWVRQAPGKGLEWVSGI SWNSGRIGYADSVKGRFTISRDNAKNSLFLQMNSLRAEDTAVYYCARDQGY HYYDSAEHAFDIWGQGTVVTVSSGGGGSGGGGSGGGGSQSALTQPASVSGS PGQSITISCTGTSSDLGGYNYVSWYQHRPGKAPKLIIYDVTVRPSGVSDRF SGSKSGNTASLTISGLQAEDEADYYCGSYTSSSTLLWVFGGGTKLTVL | Clone 285 scFv (aa) |
| 50 | CAGGTGCAGCTGGTGGAGTCTGGGGGAGGCTTGGTACAGCCTGGCAGGTC CCTGAGACTCTCCTGTGCAGCCTCTGGATTCACCTTTGATGATTATGCCAT GCACTGGGTCCGGCAAGCTCCAGGGAAGGGCCTGGAGTGGGTCTCAGGTA TTAGTTGGAATAGTGGTAGGATAGGCTATGCGGACTCTGTAAAGGGCCGA TTCACCATCTCCAGAGACAACGCCAAGAACTCCCTGTTTCTGCAAATGAA CAGTCTGAGAGCTGAGGACACGGCCGTGTATTACTGTGCGAGAGATCAGG GGTATCATTACTATGATAGTGCCGAACATGCTTTTGATATCTGGGGCCAAG GGACAATGGTCACCGTCTCCTCAGGTGGAGGCGGTTCAGGCGGAGGTGGC TCTGGCGGTGGCGGATCGCAGGCTGTGCTGACTCAGCCTCGCTCAGTGTC CGGGTCTCCTGGACAGTCAGTCACCATCTCCTGCACTGGAATCAGCAGTG GTGTTGATAGTCATAGGTATGTCTCCTGGTACCAACACCACCCAGGCAAA GCCCCCAAACTCATGATTTATGATTTCAGTAAGCGGCCCTCAGGGGTCCCT GATCGTTTCTCTGGCTCCAAGTCTGGCAACACGGCCTCCCTGACCATCTCT GGGCTCCAGGCTGAGGATGAGGCTGATTACTATTGCAGCTCATATGCAGC CATCTCCCCTAATTATGTCTTCGGAACTGGGACCAAGCTCACCGTCCTA | Clone 192B scFv (nt) |
| 51 | QVQLVESGGGLVQPGRSLRLSCAASGFTFDDYAMHWVRQAPGKGLEWVSGI SWNSGRIGYADSVKGRFTISRDNAKNSLFLQMNSLRAEDTAVYYCARDQGY HYYDSAEHAFDIWGQGTMVTVSSGGGGSGGGGSGGGGSQAVLTQPRSVSGS PGQSVTISCTGISSGVDSHRYVSWYWHPGKAPKLMIYDFSKRPSGVPDRFS GSKSGNTASLTISGLQAEDEADYYCSSYAAISPNYVFGTGTKLTVL | Clone 192B scFv (aa) |
| 52 | CAGGTGCAGCTGGTGGAGTCTGGGGGAGGCTTGGTACAGCCTGGCAGGTC CCTGAGACTCTCCTGTGCAGCCTCTGGATTCACCTTTGATGATTATGCCAT GCACTGGGTCCGGCAAGCTCCAGGGAAGGGCCTGGAGTGGGTCTCAGGTA TTAGTTGGAATAGTGGTAGGATAGGCTATGCGGACTCTGTAAAGGGCCGA TTCACCATCTCCAGAGACAACGCCAAGAACTCCCTGTTTCTGCAAATGAA CAGTCTGAGAGCTGAGGACACGGCCGTGTATTACTGTGCGAGAGATCAGG GGTATCATTACTATGATAGTGCCGAACATGCTTTTGATATCTGGGGCCAAG GGACAGTGGTCACCGTCTCCTCAGGTGGAGGCGGTTCAGGCGGAGGTGGC TCTGGCGGTGGCGGATCGCAGTCTGCCCTGACTCAGCCTGCCTCCGTGTCT GGGTCTCCTGGACATTCGATCACCATCTCCTGCACTGGAACCAGAAGTGA CGTCGGTGGTTTTGATTATGTCTCCTGGTACCAGCATAACCCAGGCAAAGC CCCCAAACTCATAATTTATGATGTCACTAAGCGGCCCTCAGGGGTCTCTAA TCGCTTCTCTGGCGCCAAGTCTGGCATCACGGCCTCCCTGACCATCTCTGG GCTCCAGGCTGAGGACGAGGCTGATTATTACTGCACCTCATATAGACCCG GTCCAACATTTGTCTTCGGCACCGGGACCAAGCTCACCGTCCTA | Clone 328 scFv (nt) |
| 53 | QVQLVESGGGLVQPGRSLRLSCAASGFTFDDYAMHWVRQAPGKGLEWVSGI SWNSGRIGYADSVKGRFTISRDNAKNSLFLQMNSLRAEDTAVYYCARDQGY HYYDSAEHAFDIWGQGTVVTVSSGGGGSGGGGSGGGGSQSALTQPASVSGS PGHSITISCTGTRSDVGGFDYVSWYQHNPGKAPKLIIYDVTKRPSGVSNRF SGAKSGITASLTISGLQAEDEADYYCTSYRPGPTFVFGTGTKLTVL | Clone 328 scFv (aa) |
| 54 | GAAGTGCAGCTGGTGCAGTCTGGGGGAGGCTTGGTACAGCCTGGCAGGTC CCTGAGACTCTCCTGTGCAGCCTCTGGATTCACCTTTGATGATTATGCCAT GCACTGGGTCCGGCAAGCTCCAGGGAAGGGCCTGGAGTGGGTCTCAGGTA TTAGTTGGAATAGTGGTAGCATAGGCTATGCGGACTCTGTGAAGGGCCGA TTCACCATCTCCAGAGACAACGCCAAGAACTCCCTGTATCTGCAAATGAA CAGTCTGAGAGCTGAGGACACGGCCGTGTATTACTGTGCGAGAGATCAGG GGTATCATTACTATGATAGTGCCGAACATGCTTTTGATATCTGGGGCCAAG GGACAGTGGTCACCGTCTCCTCAGGTGGAGGCGGTTCAGGCGGAGGTGGC TCTGGCGGTGGCGGATCGGACATCCAGTTGACCCAGTCTCCTTCCACCCTG TCTGCATCTGTAGGAGACAGAGTCACCATCACTTGCCGGGCCAGTCAGAG TATTAGTAGGTGGTTGGCCTGGTATCAGCAGAAACCAGGGAAAGCCCCTA AGCTCCTGATCTACGATGCATCCAATTTGGAAACAGGGGTCCCATCCAGG TTCAGTGGAAGTGGATCTGGGACAGATTTACTTTCACCATCAGCAGCCTG CAGCCTGAAGATATTGCAACATATTACTGTCAACAGTATGATAATCTCCCT CTCACTTTCGGCGGAGGGACCAAGGTGGAGATCAAA | Clone 227 scFv (nt) |

TABLE 9-continued

SEQUENCES

| SEQ ID NO. | Sequence | Description |
|---|---|---|
| 55 | EVQLVQSGGGLVQPGRSLRLSCAASGFTFDDYAMHWVRQAPGKGLEWVSGI SWNSGSIGYADSVKGRFTISRDNAKNSLYLQMNSLRAEDTAVYYCARDQGY HYYDSAEHAFDIWGQGTVVTVSSGGGGSGGGGSGGGGSDIQLTQSPSTLSA SVGDRVTITCRASQSISRWLAWYQQKPGKAPKLLIYDASNLETGVPSRFSG SGSGTDFTFTISSLQPEDIATYYCQQYDNLPLTFGGGTKVEIK | Clone 227 scFv (aa) |
| 56 | CAGATGCAGCTGGTGCAGTCTGGGGGAGGCTTGGTACAGCCTGGCAGGTC CCTGAGACTCTCCTGTGCAGCCTCTGGATTCACCTTTGATGATTATGCCAT GCACTGGGTCCGGCAAGCTCCAGGGAAGGGCCTGGAGTGGGTCTCAGGTA TTAGTTGGAATAGTGGTAGCATAGGCTATGCGGACTCTGTGAAGGGCCGA TTCACCATCTCCAGAGACAACGCCAAGAACTCCCTGTATCTGCAAATGAA CAGTCTGAGAGCTGAGGACACGGCCGTGTATTACTGTGCGAGAGATCAGG GGTATCATTACTATGATAGTGCCGAACATGCTTTTGATATCTGGGGCCAAG GGACAGTGGTCACCGTCTCCTCAGGTGGAGGCGGTTCAGGCGGAGGTGGC TCTGGCGGTGGCGGATCGGCCATCCGGATGACCCAGTCTCCTTCCACCCTG TCTGCATCTGTGGGAGACAGAGTCACCATCACTTGCCGGGCCAGTCAGAG CATTAGTCACTACTTGGCCTGGTATCAACAGAAACCAGGGAAAGCCCCTA AGCTCCTGATCTTTGATGCCTCCCGITTGGCAAGTGGGGTCCCATCAAGGT TCAGTGGCAGTGGATCTGGGACAGATTTCACTCTCACCATCAGCAGTCTGC AACCTGAAGATTTTGCGACATACTACTGTCAACAGAGTTACGGTGCCCCT ATGTTCACTTTCGGCCCTGGGACCAGAGTGGATCTCAAA | Clone 1300 scFv (nt) |
| 57 | QMQLVQSGGGLVQPGRSLRLSCAASGFTFDDYAMHWVRQAPGKGLEWVSG ISWNSGSIGYADSVKGRFTISRDNAKNSLYLQMNSLRAEDTAVYYCARDQGY HYYDSAEHAFDIWGQGTVVTVSSGGGGSGGGGSGGGGSAIRMTQSPSTLSAS VGDRVTITCRASQSISHYLAWYQQKPGKAPKLLIFDASRLASGVPSRFSGSG SGTDFTLTISSLQPEDFATYYCQQSYGAPMFTFGPGTRVDLK | Clone 1300 scFv (aa) |
| 58 | GAAGTGCAGCTGGTGGAGTCTGGGGGAGGCTTGGTACAGCCTGGCAGGTC CCTGAGACTCTCCTGTGCAGCCTCTGGATTCACCTTTGATGATTATGCCAT GCACTGGGTCCGGCAAGCTCCAGGGAAGGGCCTGGAGTGGGTCTCAGGTA TTAGTTGGAATAGTGGTAGGATAGGCTATGCGGACTCTGTAAAGGGCCGA TTCACCATCTCCAGAGACAACGCCAAGAACTCCCTGTTTCTGCAAATGAA CAGTCTGAGAGCTGAGGACACGGCCGTGTATTACTGTGCGAGAGATCAGG GGTATCATTACTATGATAGTGCCGAACATGCTTTGATATCTGGGGCCAAG GGACAATGGTCACAGTCTCCTCAGGTGGAGGCGGTTCAGGCGGAGGTGGC TCTGGCGGTGGCGGATCGCAGTCTGCCCTGACTCAGCCCGCCTCCGTGTCT GGGTCTCCTGGACAGTCGATCACCATCTCCTGCACTGGGACCAGCAGTGA CGTTGGTGCTTATAACTTTGTCTCCTGGTACCAGCAGCTCCCAGGAACAGC CCCCAAATTCCTCATTTATGACAATAATAAAGACCCCCAGGGATTCCTG ACCGATTCTCTGGCTCAAGTCTGGCACGTCAGCCACCCTGGGCATCACC GGACTCCAGACTGGGACGAGGCCGATTATTACTGCGCAACATGGGATAG CGGCCTGAGTGCTGTGGTATTCGGCGGAGGGACCAAGCTGACCGTCCTA | Clone 1 scFv (nt) |
| 59 | EVQLVESGGGLVQPGRSLRLSCAASGFTFDDYAMHWVRQAPGKGLEWVSGI SWNSGRIGYADSVKGRFTISRDNAKNSLFLQMNSLRAEDTAVYYCARDQGY HYYDSAEHAFDIWGQGTMVTVSSGGGGSGGGGSGGGGSQSALTQPASVSGS PGQSITISCTGTSSDVGAYNFVSWYQQLPGTAPKFLIYDNNKRPPGIPDRF SGSKSGTSATLGITGLQTGDEADYYCATWDSLSAVVFGGGTKLTVL | Clone 1 scFv (aa) |
| 60 | QVQLVESGGGLVQPGRSLRLSCAASGFTFDDYAMHWVRQAPGKGLEWVSGI SWNSGRIGYADSVKGRFTISRDNAKNSLFLQMNSLRAEDTAVYYCARDQGY HYYDSAEHAFDIWGQGTMVTVSS | VH Clone 192B (aa) |
| 61 | QVQLVESGGGLVQPGRSLRLSCAASGFTFDDYAMHWVRQAPGKGLEWVSGI SWNSGRIGYADSVKGRFTISRDNAKNSLFLQMNSLRAEDTAVYYCARDQGY HYYDSAEHAFDIWGQGTVVTVSS | VH Clone 328 (aa) |
| 62 | QMQLVQSGGGLVQPGRSLRLSCAASGFTFDDYAMHWVRQAPGKGLEWVSG ISWNSGSIGYADSVKGRFTISRDNAKNSLYLQMNSLRAEDTAVYYCARDQG YHYYDSAEHAFDIWGQGTVVTVSS | VH Clone 1304 Clone 1300 (aa) |
| 63 | EVQLVQSGGGLVQPGRSLRLSCAASGFTFDDYAMHWVRQAPGKGLEWVSGI SWNSGSIGYADSVKGRFTISRDNAKNSLYLQMNSLRAEDTAVYYCARDQGY HYYDSAEHAFDIWGQGTVVTVSS | VH Clones 227, 488, 241 (aa) |
| 64 | QAVLTQPRSVSGSPGQSVTISCTGISSGVDSHRYVSWYWHPGKAPKLMIYDF SKRPSGVPDRFSGSKSGNTASLTISGLQAEDEADYYCSSYAAISPNYVFGTGT KLTVL | VL Clone 192B (aa) |

TABLE 9-continued

SEQUENCES

| SEQ ID NO. | Sequence | Description |
|---|---|---|
| 65 | QSALTQPASVSGSPGQSITISCTGTSSDLGGYNYVSWYQHRPGKAPKLIIYDV TVRPSGVSDRFSGSKSGNTASLTISGLQAEDEADYYCGSYTSSSTLLWVFGGG TKLTVL | VL Clone 285 (aa) |
| 66 | QSALTQPASVSGSPGHSITISCTGTRSDVGGFDYVSWYQHNPGKAPKLIIYDV TKRPSGVSNRFSGAKSGITASLTISGLQAEDEADYYCTSYRPGPTFVFGTGTK LTVL | VL Clone 328 (aa) |
| 67 | QSALTQPASVSGSPGQSITISCTGTSSDVGAYNFVSWYQQLPGTAPKFLIYDN NKRPPGIPDRFSGSKSGTSATLGITGLQTGDEADYYCATWDSGLSAVVFGGGT KLTVL | VL Clone 1 (aa) |
| 68 | AIRMTQSPSSLSASVGDRVTVTCQASQDISNYLNWYQQKPGRAPKLLIYDAS NVKAGVPSRFSGGGSGTDFTLTISSLQPEDFATYYCQQSYSTPQAYTFGQGT KLEIK | VL Clone 1304 (aa) |
| 69 | AIRMTQSPSTLSASVGDRVTITCRASQSISHYLAWYQQKPGKAPKLLIFDASR LASGVPSRFSGSGSGTDFTLTISSLQPEDFATYYCQQSYGAPMFTFGPGTRVDL K | VL Clone 1300 (aa) |
| 70 | DIQLTQSPSTLSASVGDRVTITCRASQSISRWLAWYQQKPGKAPKLLIYDASN LETGVPSRFSGSGSGTDFTFTISSLQPEDIATYYCQQYDNLPLTFGGGTKVEIK | VL Clone 227 (aa) |
| 71 | EIVLTQSPATLSLSPGETATLSCRASQSINHYLAWYQQKPGQAPRLLIYDASNR ATGIPARFSGSGSGTDFTLTISSLEPEDFATYYCQQSYSHPRMYTFGQGTKLDI K | VL Clone 488 (aa) |
| 72 | GISWNSGSIGYADSVKG | CDR-H2 Clone 1304 Clone 1300 Clone 227 Clone 488 Clone 241 (aa) |
| 73 | TGISSGVDSHRYVS | CDR-L1 Clone 192B Clone 192 (aa) |
| 74 | TGTSSDLGGYNYVS | CDR-L1 Clone 285 (aa) |
| 75 | TGTRSDVGGFDYVS | CDR-L1 Clone 328 (aa) |
| 76 | TGTSSDVGAYNFVS | CDR-L1 Clone 1 (aa) |
| 77 | QASQDISNYLN | CDR-L1 Clone 1304 Clone 241 (aa) |
| 78 | RASQSISHYLA | CDR-L1 Clone 1300 (aa) |
| 79 | RASQSISRWLA | CDR-L1 Clone 227 (aa) |
| 80 | RASQSINHYLA | CDR-L1 Clone 488 (aa) |
| 81 | GISWNSGRIG | CDR-H2 |
| 82 | GISWNSGSIG | CDR-H2 |

TABLE 9-continued

SEQUENCES

| SEQ ID NO. | Sequence | Description |
|---|---|---|
| 83 | $X_1X_2X_3X_4X_5X_6X_7X_8X_9X_{10}X_{11}X_{12}X_{13}X_{14}$<br>$X_1$ = T, Q, or R; $X_2$ = G or A; $X_3$ = I, T, or S; $X_4$ = S, R, or Q; $X_5$ = null or S; $X_6$ = null, D, or G; $X_7$ = null, V, or L; $X_8$ = D, G, or S; $X_9$ = S, G, A, or I; $X_{10}$ = H, Y, F, S, or N; $X_{11}$ = R, N, D, or H; $X_{12}$ = Y, F, or W; $X_{13}$ = V or L; $X_{14}$ = S, N, or A | CDR-L1 Consensus |
| 84 | $DX_2X_3X_4X_5X_6X_7$<br>$X_2$ = F, V, N, or A; $X_3$ = S, T, or N; $X_4$ = K, V, N, or R; $X_5$ = R, V, or L; $X_6$ = P, K, A, or E; $X_7$ = S, P, A, or T | CDR-L2 Consensus |
| 85 | $X_1X_2X_3X_4X_5X_6X_7X_8X_9X_{10}X_{11}X_{12}X_{13}X_{14}$<br>$X_1$ = S, G, T, A, or Q; $X_2$ = S, T, or Q; $X_3$ = Y, W, or S; $X_4$ = A, T, R, D, or Y; $X_5$ = A, S, P, G, or N; $X_6$ = I, S, G, T, L, A, or H; $X_7$ = S, P, or L; $X_8$ = P, T, S, Q, M, R, or null; $X_9$ = N, L, A, M, or null; $X_{10}$ = L or null; $X_{11}$ = Y, W, F, V, or L; $X_{12}$ = V or T | CDR-L3 Consensus |
| 86 | GAAGTGCAGCTGGTGGAGTCTGGGGGAGGCTTGGTACAGCCTGGCAGGTC<br>CCTGAGACTCTCCTGTGCAGCCTCTGGATTCACCTTTGATGATTATGCCAT<br>GCACTGGGTCCGGCAAGCTCCAGGGAAGGGCCTGGAGTGGGTCTCAGGTA<br>TTAGTTGGAATAGTGGTAGGATAGGCTATGCGGACTCTGTAAAGGGCCGA<br>TTCACCATCTCCAGAGACAACGCCAAGAACTCCCTGTTTCTGCAAATGAA<br>CAGTCTGAGAGCTGAGGACACGGCCGTGTATTACTGTGCGAGAGATCAGG<br>GGTATCATTACTATGATAGTGCCGAACATGCTTTGATATCTGGGGCCAAG<br>GGACAATGGTCACCGTCTCCTCAGGTGGAGGCGGTTCAGGCGGAGGTGGC<br>TCTGGCGGTGGCGGATCGCAGGCTGTGCTGACTCAGCCTCGCTCAGTGTC<br>CGGGTCTCCTGGACAGTCAGTCACCATCTCCTGCACTGGAATCAGCAGTG<br>GTGTTGATAGTCATAGGTATGTCTCCTGGTACCAACACCACCCAGGCAAA<br>GCCCCCAAACTCATGATTTATGATTTCAGTAAGCGGCCCTCAGGGGTCCCT<br>GATCGTTTCTCTGGCTCCAAGTCTGGCAACACGGCCTCCCTGACCATCTCT<br>GGGCTCCAGGCTGAGGATGAGGCTGATTACTATTGCTGCTCATATGCAGC<br>CATCTCCCCTAATTATGTCTTCGGAACTGGGACCAAGCTGACCGTCCTA | Clone 192 scFv (nt) |
| 87 | EVQLVESGGGLVQPGRSLRLSCAASGFTFDDYAMHWVRQAPGKGLEWVSGI<br>SWNSGRIGYADSVKGRFTISRDNAKNSLFLQMNSLRAEDTAVYYCARDQGY<br>HYYDSAEHAFDIWGQGTMVTVSSGGGGSGGGGSGGGGSQAVLTQPRSVSGS<br>PGQSVTISCTGISSGVDSHRYVSWYQHHPGKAPKLMIYDFSKRPSGVPDRF<br>SGSKSGNTASLTISGLQAEDEADYYCCSYAAISPNYVFGTGTKLTVL | Clone 192 scFv (aa) |
| 88 | GAAGTGCAGCTGGTGCAGTCTGGGGGAGGCTTGGTACAGCCTGGCAGGTC<br>CCTGAGACTCTCCTGTGCAGCCTCTGGATTCACCTTTGATGATTATGCCAT<br>GCACTGGGTCCGGCAAGCTCCAGGGAAGGGCCTGGAGTGGGTCTCAGGTA<br>TTAGTTGGAATAGTGGTAGCATAGGCTATGCGGACTCTGTGAAGGGCCGA<br>TTCACCATCTCCAGAGACAACGCCAAGAACTCCCTGTATCTGCAAATGAA<br>CAGTCTGAGAGCTGAGGACACGGCCGTGTATTACTGTGCGAGAGATCAGG<br>GGTATCATTACTATGATAGTGCCGAACATGCTTTGATATCTGGGGCCAAG<br>GGACAGTGGTCACCGTCTCCTCAGGTGGAGGCGGTTCAGGCGGAGGTGGC<br>TCTGGCGGTGGCGGATCGGCCATCCGGATGACCCAGTCTCCATCCTCCCTG<br>TCTGCATCTGTAGGAGACAGAGTCACCGTCACTTGCCAGGCGAGTCAGGA<br>CATTAGCAACTATTTAAATTGGTATCAGCAGAAACCAGGGAGAGCCCCTA<br>AGCTCCTGATCTACGATGCATCCAATGTGAAAGCAGGGGTCCCATCAAGG<br>TTCAGTGGGGGTGGATCTGGGACAGATTTCACTCTCACCATCAGCAGTCTG<br>CAACCTGAAGATTTTGCAACTTACTACTGTCAACAGAGTTACAGTACCCCT<br>CAGGCGTACACTTTTGGCCAGGGGACCAAGCTGGATATCAAA | Clone 241 scFv (nt) |
| 89 | EVQLVQSGGGLVQPGRSLRLSCAASGFTFDDYAMHWVRQAPGKGLEWVSGI<br>SWNSGSIGYADSVKGRFTISRDNAKNSLYLQMNSLRAEDTAVYYCARDQGY<br>HYYDSAEHAFDIWGQGTVVTVSSGGGGSGGGGSGGGGSAIRMTQSPSSLSA<br>SVGDRVTVTCQASQDISNYLNWYQQKPGRAPKLLIYDASNVKAGVPSRFSG<br>GGSGTDFTLTISSLQPEDFATYYCQQSYSTPQAYTFGQGTKLDIK | Clone 241 scFv (aa) |
| 90 | AIRMTQSPSSLSASVGDRVTVTCQASQDISNYLNWYQQKPGRAPKLLIYDAS<br>NVKAGVPSRFSGGGSGTDFTLTISSLQPEDFATYYCQQSYSTPQAYTFGQGT<br>KLDIK | VL Clone 241 (aa) |
| 91 | QAVLTQPRSVSGSPGQSVTISCTGISSGVDSHRYVSWYQHHPGKAPKLMIYD<br>FSKRPSGVPDRFSGSKSGNTASLTISGLQAEDEADYYCCSYAAISPNYVFGT<br>GTKLTVL | VL Clone 192 |

TABLE 9-continued

SEQUENCES

| SEQ ID NO. | Sequence | Description |
|---|---|---|
| 92 | MPPPRLLFFLLFLTPMEVRPEEPLVVKVEEGDNAVLQCLKGTSDGPTQQLTW<br>SRESPLKPFLKLSLGLPGLGIHMRPLAIWLFIFNVSQQMGGFYLCQPGPPSE<br>KAWQPGWTVNVEGSGELFRWNVSDLGGLGCGLKNRSSEGPSSPSGKLMSPKL<br>YVWAKDRPEIWEGEPPCLPPRDSLNQSLSQDLTMAPGSTWLSCGVPPDSVS<br>RGPLSWTHVHPKGPKSLLSLELKDDRPARDMWVMETGLLLPRATAQDAGKY<br>YCHRGNLTMSFHLEITARPVLWHWLLRTGGWKVSAVTLAYLIFCLCSLVGIL<br>HLQRALVLRRKRKRMTDPTRRFFKVTPPPGSGPQNQYGNVLSLPTPTSGLGR<br>AQRWAAGLGGTAPSYGNPSSDVQADGALGSRSPPGVGPEEEEGEGYEEPDSE<br>EDSEFYENDSNLGQDQLSQDGSGYENPEDEPLGPEDEDSFSNAESYENEDEEL<br>TQPVARTMDFLSPHGSAWDPSREATSLGSQSYEDMRGILYAAPQLRSIRGQP<br>GPNHEEDADSYENMDNPDGPDPAWGGGGRMGTWSTR | CD19<br>Accession No.<br>P15391<br>*Homo Sapiens* |
| 93 | DFSKRPS | CDR-L2<br>Clone 192B,<br>Clone 192 |
| 94 | DVTVRPS | CDR-L2<br>Clone 285 |
| 95 | DVTKRPS | CDR-L2<br>Clone 328 |
| 96 | DNNKRPP | CDR-L2<br>Clone 1 |
| 97 | DASNVKA | CDR-L2<br>Clone 1304<br>Clone 241 |
| 98 | DASRLAS | CDR-L2<br>Clone 1300 |
| 99 | DASNLET | CDR-L2<br>Clone 227 |
| 100 | DASNRAT | CDR-L2<br>Clone 488 |
| 101 | SSYAAISPNYV | CDR-L3<br>Clone 192B |
| 102 | CSYAAISPNYV | CDR-L3<br>Clone 192 |
| 103 | GSYTSSSTLLWV | CDR-L3<br>Clone 285 |
| 104 | TSYRPGPTFV | CDR-L3<br>Clone 328 |
| 105 | ATWDSGLSAVV | CDR-L3<br>Clone 1 |
| 106 | QQSYSTPQAYT | CDR-L3<br>Clone 1304<br>Clone 241 |
| 107 | QQSYGAPMFT | CDR-L3<br>Clone 1300 |
| 108 | QQYDNLPLT | CDR-L3<br>Clone 227 |
| 109 | QQSYSHPRMYT | CDR-L3<br>Clone 488 |
| 110 | $X_1X_2X_3X_4X_5X_6X_7X_8X_9X_{10}X_{11}X_{12}X_{13}X_{14}$<br>$X_1$ = T, Q, S, or R;<br>$X_2$ = G or A;<br>$X_3$ = I, T, D, or S;<br>$X_4$ = S, R, T, or Q;<br>$X_5$ = null or S;<br>$X_6$ = null, D, D, or G; | CDR-L1<br>consensus |

TABLE 9-continued

SEQUENCES

| SEQ ID NO. | Sequence | Description |
|---|---|---|
| | $X_7$ = null, V, or L;<br>$X_8$ = X or null;<br>$X_9$ = X or null;<br>$X_{10}$ = X;<br>$X_{11}$ = X;<br>$X_{12}$ = Y, F, D, or W;<br>$X_{13}$ = V, A, or L;<br>$X_{14}$ = S, N, or A | |
| 111 | $X_1X_2X_3X_4X_5X_6X_7X_8X_9X_{10}X_{11}X_{12}X_{13}X_{14}$<br>$X_1$ = T, Q, S, or R;<br>$X_2$ = G or A;<br>$X_3$ = I, T, D, or S;<br>$X_4$ = S, R, T, or Q;<br>$X_5$ = null or S;<br>$X_6$ = G, D, N, or null;<br>$X_7$ = null, V, or L;<br>$X_8$ = D, G, I, L, S, or null;<br>$X_9$ = S, G, A, I, R, or null;<br>$X_{10}$ = H, Y, F, S, or N;<br>$X_{11}$ = R, N, D, H, or Y;<br>$X_{12}$ = Y, F, D, or W;<br>$X_{13}$ = V, A, or L;<br>$X_{14}$ = S, N, or A | CDR-L1 consensus |
| 112 | $X_1X_2X_3X_4X_5X_6X_7$<br>$X_1$ = D or S;<br>$X_2$ = F, V, N, K, or A;<br>$X_3$ = S, T, D, or N;<br>$X_4$ = K, V, N, Q, or R;<br>$X_5$ = R, V, or L;<br>$X_6$ = P, K, A, or E;<br>$X_7$ = S, P, A, or T | CDR-L2 Consensus |
| 113 | $X_1X_2X_3X_4X_5X_6X_7X_8X_9X_{10}X_{11}$<br>$X_1$ = C, S, A, G, or N;<br>$X_2$ = S, A, or T;<br>$X_3$ = Y, W, or R;<br>$X_4$ = A or D;<br>$X_5$ = G, D, or S;<br>$X_6$ = R, S, or N;<br>$X_7$ = Y, L, or G;<br>$X_8$ = N or S;<br>$X_9$ = S, N, or null;<br>$X_{10}$ = V, A, or W;<br>$X_{11}$ = L or V | CDR-L3 |
| 114 | $X_1X_2X_3X_4X_5X_6X_7X_8X_9X_{10}X_{11}X_{12}$<br>$X_1$ = S, G, T, A, Q, C, or N;<br>$X_2$ = S, Q, A, or T;<br>$X_3$ = Y, S, W, R;<br>$X_4$ = A, D, R, T, or Y;<br>$X_5$ = A, S, P, G, N, or D;<br>$X_6$ = I, S, G, T, A, L, H, R, N;<br>$X_7$ = S, P, L, Y, G;<br>$X_8$ = P, T, S, Q, M, R, N or null;<br>$X_9$ = S, L, N, A, M or null;<br>$X_{10}$ = L or null;<br>$X_{11}$ = Y, W, F, V, A, or L;<br>$X_{12}$ = V, T, or L | CDR-L3 consensus |
| 115 | $X_1X_2X_3X_4X_5X_6X_7X_8X_9X_{10}X_{11}X_{12}$<br>$X_1$ = X;<br>$X_2$ = S, Q, A, or T;<br>$X_3$ = Y, S, W, R;<br>$X_4$ = A, D, R, T, or Y;<br>$X_5$ = X<br>$X_6$ = X<br>$X_7$ = S, P, L, Y, G;<br>$X_8$ = X or null<br>$X_9$ = X or null<br>$X_{10}$ = L or null;<br>$X_{11}$ = X<br>$X_{12}$ = V, T, or L | CDR-L3 consensus |

TABLE 9-continued

SEQUENCES

| SEQ ID NO. | Sequence | Description |
|---|---|---|
| 116 | GTWDISLRFGV | CDR-L3 Clone 79 |
| 117 | CSYEAPTHTYV | CDR-L3 Clone 835 |
| 118 | AAWDDSLNVV | CDR-L3 Clone 184 |
| 119 | CSYAGSYTFEV | CDR-L3 Clone 505 |
| 120 | CSFAGYYTYWL | CDR-L3 Clone 506 |
| 121 | SSXAGRKYV | CDR-L3 Clone 305 |
| 122 | GGGS | Linker artificial |
| 123 | GGGGS | Linker artificial |
| 124 | ESKYGPPCPPCP | spacer (IgG4hinge) (aa) *homo sapien* |
| 125 | GAATCTAAGTACGGACCGCCCTGCCCCCCTTGCCCT | spacer (IgG4hinge) (nt) *homo sapien* |
| 126 | ESKYGPPCPPCPGQPREPQVYTLPPSQEEMTKNQVSLTCLVKGFYPSDIAVEW ESNGQPENNYKTTPPVLDSDGSFFLYSRLTVDKSRWQEGNVFSCSVMHEALH NHYTQKSLSLSLGK | Hinge-CH3 spacer *Homo sapien* |
| 127 | ESKYGPPCPPCPAPEFLGGPSVFLFPPKPKDTLMISRTPEVTCVVVDVSQEDP EVQFNWYVDGVEVHNAKTKPREEQFNSTYRVVSVLTVLHQDWLNGKEYKCK VSNKGLPSSIEKTISKAKGQPREPQVYTLPPSQEEMTKNQVSLTCLVKGFYPS DIAVEWESNGQPENNYKTTPPVLDSDGSFFLYSRLTVDKSRWQEGNVFSCSV MHEALHNHYTQKSLSLSLGK | Hinge-CH2—CH3 spacer *Homo sapien* |
| 128 | RWPESPKAQASSVPTAQPQAEGSLAKATTAPATTRNTGRGGEEKKKEKEKEE QEERETKTPECPSHTQPLGVYLLTPAVQDLWLRDKATFTCFVVGSDLKDAHL TWEVAGKVPTGGVEEGLLERHSNGSQSQHSRLTLPRSL WNAGTSVTCTLNHPSLPPQRLMALREPAAQAPVKLSLNLLASSDPPEAASWL LCEVSGFSPPNILLMWLEDQREVNTSGFAPARPPPQPGSTTFWAWSVLRVPAP PSPQPATYTCVVSHEDSRTLLNASRSLEVSYVTDH | IgD-hinge-Fc *Homo sapien* |
| 129 | FWVLVVVGGVLACYSLLVTVAFIIFWV | CD28 (amino acids 153-179 of Accession No. P10747) *Homo sapien* |
| 130 | IEVMYPPPYLDNEKSNGTIIHVKGKHLCPSPLFPGPSKP FWVLVVVGGVLACYSLLVTVAFIIFWV | CD28 (amino acids 114-179 of Accession No. P10747) *Homo sapien* *Homo sapien* |
| 131 | RSKRSRLLHSDYMNMTPRRPGPTRKHYQPYAPPRDFAAYRS | CD28 (amino acids 180-220 of P10747) *Homo sapien* |
| 132 | RSKRSRGGHSDYMNMTPRRPGPTRKHYQPYAPPRDFAAYRS | CD28 (LL to GG) *Homo sapien* |

TABLE 9-continued

SEQUENCES

| SEQ ID NO. | Sequence | Description |
|---|---|---|
| 133 | KRGRKKLLYIFKQPFMRPVQTTQEEDGCSCRFPEEEEGGCEL | 4-1BB (amino acids 214-255 of Q07011.1) *Homo sapien* |
| 134 | RVKFSRSADAPAYQQGQNQLYNELNLGRREEYDVLDKRRGRDPEMGGKPR RKNPQEGLYNELQKDKMAEA YSEIGMKGER RRGKGHDGLY QGLSTATKDTYDALHMQALP PR | CD3 zeta *Homo sapien* |
| 135 | RVKFSRSAEPPAYQQGQNQLYNELNLGRREEYDVLDKRRGRDPEMGGKPRR KNPQEGLYN ELQKDKMAEA YSEIGMKGER RRGKGHDGLY QGLSTATKDTYDALHMQALP PR | CD3 zeta *Homo sapien* |
| 136 | RVKFSRSADAPAYKQGQNQLYNELNLGRREEYDVLDKRRGRDPEMGGKPR RKNPQEGLYNELQKDKMAEA YSEIGMKGER RRGKGHDGLY QGLSTATKDTYDALHMQALP PR | CD3 zeta *Homo sapien* |
| 137 | LEGGGEGRGSLLTCGDVEENPGPR | T2A artificial |
| 138 | MLLLVTSLLLCELPHPAFLLIPRKVCNGIGIGEFKDSLSINATNIKHFKNCTSISG DLHILPVAFRGDSFTHTPPLDPQELDILKTVKEITGFLLIQAWPENRTDLHAFE NLEIIRGRTKQHGQFSLAVVSLNITSLGLRSLKEISDGDVIISGNKNLCYANTIN WKKLFGTSGQKTKIISNRGENSCKATGQVCHALCSPEGCWGPEPRDCVSCRN VSRGRECVDKCNLLEGEPREFVENSECIQCHPECLPQAMNITCTGRGPDNCIQ CAHYIDGPHCVKTCPAGVMGENNTLVWKYADAGHVCHLCHPNCTYGCTGP GLEGCPTNGPKIPSIATGMVGALLLLLVVALGIGLFM | tEGFR artificial |
| 139 | MPPPCLLFFLLFLTPMEVRPQEPLVVKVEEGDNAVLQCLEGTSDGPTQQLVW CRDSPFEPFLNLSLGLPGMGIRMGPLGIWLLIFNVSNQTGGFYLCQPGLPSEKA WQPGWTVSVEGSGELFRWNVSDLGGLGCGLKNRSSEGPSSPSGKLNSSQLY VWAKDRPEMWEGEPVCGPPRDSLNQSLSQDLTMAPGSTLWLSCGVPPDSVS RGPLSWTHVRPKGPKSSLLSLELKDDRPDRDMWVVDTGLLLTRATAQDAGK YYCHRGNWTKSFYLEITARPALWHWLLRIGGWKVPAVTLTYLIFCLCSLVGI LQLQRALVLRRKRKRMTDPTRRFFKVTPPPGSGPQNQYGNVLSLPTPTSGLG RAQRWAAGLGGTAPSYGNPSSDVQVDGAVGSRSPPGAGPEEEEGEGYEEPD SEEGSEFYENDSNFGQDQLSQDGSGYENPEDEPLGPEDEDSFSNAESYENEDE ELTQPVARTMDFLSPHGSAWDPSREATSLGSQSYEDMRGLLYAAPQLRTIRG QPGPNHEEDADSYENMDNPDGPDPAWGGGRMGTWSAR | Rhesus macaque CD19 Accession No. F7F486 |
| 140 | HPKGPKSLLSLELKDDRPARDMWVMETGLLLPRATAQDAGKYYCHRGNLT MSFHLEITARPVLWHWLLRTGGWK | V1 chimeric/rhesus human corresponding to residues 218 to 291 of human CD19 |
| 141 | RPKGPKSSLLSLELKDDRPDRDMWVVDTGLLLTRATAQDAGKYYCHRGNLT MSFHLEITARPVLWHWLLRTGGWK | V2 chimeric/rhesus human corresponding to residues 218 to 291 of human CD19 |
| 142 | HPKGPKSLLSLELKDDRPARDMWVMETGLLLPRATAQDAGKYYCHRGNWT KSFYLEITARPALWHWLLRIGGWK | V3 chimeric/rhesus human corresponding to residues 218 to 291 of human CD19 |
| 143 | HPKGPKSLLSLELKDDRPARDMWVMETGLLLP | Artificial |
| 144 | RPKGPKSSLLSLELKDDRPDRDMWVVDTGLLLT | Artificial |
| 145 | DQGXHXYDSAEHAFXI | CDR-H3 clone 305 |
| 146 | QASQDISNYLN | CDR-L1 Clone 255 |

TABLE 9-continued

SEQUENCES

| SEQ ID NO. | Sequence | Description |
|---|---|---|
| 147 | TGTGRDIGAYDYVS | CDR-L1 Clone 305 |
| 148 | TETSSDLGGYNYVS | CDR-L1 Clone 327 |
| 149 | TGASTDVGGYNYVS | CDR-L1 Clone 505 |
| 150 | TGASSDVGGYDHVS | CDR-L1 Clone 506 |
| 151 | SGSSSNIGSNTVN | CDR-L1 Clone 184 |
| 152 | TGPISGVGDYTSVS | CDR-L1 Clone 835 |
| 153 | DNNKRPS | CDR-L2 Clone 272 |
| 154 | GVNKRPS | CDR-L2 Clone 305 |
| 155 | DVNKRPS | CDR-L2 Clone 505 |
| 156 | DNNKRPS | CDR-L2 Clone 79 |
| 157 | DVTQRPS | CDR-L2 Clone 835 |
| 158 | GTWDSSLNRDWV | CDR-L3 Clone 272 |
| 159 | CSYAGRYNSVP | CDR-L3 Clone 508 |
| 160 | TSGVGVG | CDR-H1 Clone 1265 |
| 161 | LIYWDDDKRYSPSLKS | CDR-H2 Clone 1265 |
| 162 | IDYGSGSYSPRTSYYYYMSV | CDR-H3 Clone 1265 |
| 163 | RASQGISSYLN | CDR-L1 Clone 1265 |
| 164 | AASNLQS | CDR-L2 Clone 1265 |
| 165 | QQGDAFPLT | CDR-L3 Clone 1265 |
| 166 | QITLKESGPTLVKPTQTLTLTCTFSGFSLSTSGVGVGWIRQPPGKALEWLALIY WDDDKRYSPSLKSRLTITKDTSKNQVVLTMTNMDPVDTATYYCAHIDYGSG SYSPRTSYYYYMSVWGKGTTVTVSS | VH Clone 1265 |
| 167 | QVQLVQSGGGVVQPGRSLRLSCAASGFTFDDYAMHWVRQAPGKGLEWVSG ISWNSGSIGYADSVKGRFTISRDNAKNSLYLQMNSLRAEDTAVYYCARDQGY HYYDSAEHAFDIWGQGTVVTVSS | VH Clone 213 |
| 168 | EVQLVQSGGGLVQPGRSLRLSCAASGFTFDDYAMHWVRQAPGKGLEWVSGI SWNSGSIGYADSVKGRFTISRDNAKNSLYLQMNSLRAEDTAVYYCARDQGY HYYDSAEHAFDIWGQGTVVTVSS | VH Clone 255 |
| 169 | EVQLVESGGGLVQPGRSLRLSCAASGFTFDDYAMHWVRQAPGKGLEWVSGI SWNSGRIGYADSVKGRFTISRDNAKNSLFLQMNSLRAEDTAVYYCARDQGY HYYDSAEHAFDIWGQGTVVTVSS | VH Clone 272 |

TABLE 9-continued

SEQUENCES

| SEQ ID NO. | Sequence | Description |
|---|---|---|
| 170 | QVQLVESGGGLVQPGRSLRLSCAASGFTFDDYAMHWVRQAPGKGLEWVSGI SWNSGRIGYADSVKGRFTISRDNAKNSLFLQMNSLRAEDTAVYYCARDQGY HYYDSAEHAFDIWGQGTVVTVSS | VH Clone 283 |
| 171 | QVQLVESGGGLVQPGRSLRLSCAASGFTFDDYAMHWVRQAPGKGLEWVSGI SWNSGRIGYADSVKGRFTISRDNAKNSLFLQMNSLRAEDTAVYYCARDQGY HYYDSAEHAFDIWGQGTVVTVSS | VH Clone 302 |
| 172 | QVQLVESGGGLVQPGRSLRLSCAASGFTFDDYAMHWVRQAPGKGLEWVSGI SWNSGRIGYADSXXGRXXISRDNAKNSLFLQMNSLRAEDTAXYYCAXDQGX HXYDSAEHAFXIWGQGTVVTVSS | VH Clone 305 |
| 173 | EVQLVESGGGLVQPGRSLRLSCAASGFTFDDYAMHWVRQAPGKGLEWVSGI SWNSGRIGYADSVKGRFTISRDNAKNSLFLQMNSLRAEDTAVYYCARDQGY HYYDSAEHAFDIWGQGTVVTVSS | VH Clone 314 |
| 174 | EVQLVESGGGLVQPGRSLRLSCAASGFTFDDYAMHWVRQAPGKGLEWVSGI SWNSGRIGYADSVKGRFTISRDNAKNSLFLQMNSLRAEDTAVYYCARDQGY HYYDSAEHAFDIWGQGTVVTVSS | VH Clone 379 |
| 175 | EVQLVESGGGLVQPGRSLRLSCAASGFTFDDYAMHWVRQAPGKGLEWVSGI SWNSGRIGYADSVKGRFTISRDNAKNSLFLQMNSLRAEDTAVYYCARDQGY HYYDSAEHAFDIWGQGTVVTVSS | VH Clone 324 |
| 176 | QVQLVESGGGLVQPGRSLRLSCAASGFTFDDYAMHWVRQAPGKGLEWVSGI SWNSGRIGYADSVKGRFTISRDNAXNSLFLQMNSLRAEDTAVYYCARDQGY HYYDSAEHAFDIWGQGTVVTVSS | VH Clone 327 |
| 177 | QVQLVESGGGLVQPGRSLRLSCAASGFTFDDYAMHWVRQAPGKGLEWVSGI SWNSGRIGYADSVKGRFTISRDNAKNSLFLQMNSLRAEDTAVYYCARDQGY HYYDSAEHAFDIWGQGTVVTVSS | VH Clone 336 |
| 178 | QVQLVESGGGLVQPGRSLRLSCAASGFTFDDYAMHWVRQAPGKGLEWVSGI SWNSGRIGYADSVKGRFTISRDNAKNSLFLQMNSLRAEDTAVYYCARDQGY HYYDSAEHAFDIWGQGTVVTVSS | VH Clone 440 |
| 179 | QVQLVESGGGLVQPGRSLRLSCAASGFTFDDYAMHWVRQAPGKGLEWVSGI SWNSGRIGYADSVKGRFTISRDNAKNSLFLQMNSLRAEDTAVYYCARDQGY HYYDSAEHAFDIWGQGTVVTVSS | VH Clone 448 |
| 180 | EVQLVESGGGLVQPGRSLRLSCAASGFTFDDYAMHWVRQAPGKGLEWVSGI SWNSGRIGYADSVKGRFTISRDNAKNSLFLQMNSLRAEDTAVYYCARDQGY HYYDSAEHAFDIWGQGTMVTVSS | VH Clone 505 |
| 181 | EVQLVESGGGLVQPGRSLRLSCAASGFTFDDYAMHWVRQAPGKGLEWVSGI SWNSGRIGYADSVKGRFTISRDNAKNSLFLQMNSLRAEDTAVYYCARDQGY HYYDSAEHAFDIWGQGTMVTVSS | VH Clone 506 |
| 182 | EVQLVESGGGLVQPGRSLRLSCAASGFTFDDYAMHWVRQAPGKGLEWVSGI SWNSGRIGYADSVKGRFTISRDNAKNSLFLQMNSLRAEDTAVYYCARDQGY HYYDSAEHAFDIWGQGTVVTVSS | VH Clone 508 |
| 183 | QVQLVESGGGLVQPGRSLRLSCAASGFTFDDYAMHWVRQAPGKGLEWVSGI SWNSGRIGYADSVKGRFTISRDNAKNSLFLQMNSLRAEDTAVYYCARDQGY HYYDSAEHAFDIWGQGTMVTVSS | VH Clone 184 |
| 184 | EVQLVESGGGLVQPGRSLRLSCAASGFTFDDYAMHWVRQAPGKGLEWVSGI SWNSGRIGYADSVKGRFTISRDNAKNSLFLQMNSLRAEDTAVYYCARDQGY HYYDSAEHAFDIWGQGTVVTVSS | VH Clone 79 |
| 185 | EVQLVESGGGLVQPGRSLRLSCAASGFTFDDYAMHWVRLAPGKGLEWVSGI SWNSGRIGYADSVKGRFTISRDNAKNSLFLQMNSLRAKDTAVYYCARDQGY HYYDSAEHAFDIWGQGTMVTVSS | VH Clone 835 |
| 186 | AIQLTQSPSFLSASVGDRVTITCRASQGISSYLNWYQQRAGKAPELLIYAA SNLQSGVPSRFSGSGSGTDFTLTITSVQPEDFATYFCQQGDAFPLTFGPGT KVTIR | VL Clone 1265 |
| 187 | EIVLTQSPATLSLSPGETATLSCRASQSINHYLAWYQQKPGQAPRLLIYDA SNRATGIPARFSGSGSGTDFTLTISSLEPEDFATYYCQQSYSHPRMYTFGQ GTKLEIK | VL Clone 213 |

TABLE 9-continued

SEQUENCES

| SEQ ID NO. | Sequence | Description |
|---|---|---|
| 188 | AIRMTQSPSSLSASVGDRVTVTCQASQDISNYLNWYQQKPGRAPKLLIYDA SNVKAGVPSRFSGGGSGTDFTLTISSLQPEDFATYYCQQSYSTPQAYTFGQ GTKLDIK | VL Clone 255 |
| 189 | QSVLTQPPSVSAAPGQKVTISCSGSSSNIGNNYVSWYQQLPGTAPKLLIYD NNKRPSGIPDRFSGSKSGTSATLGITGLQTGDEADYYCGTWDSSLNRDWVF GGGTKLTVL | VL Clone 272 |
| 190 | QSALTQPASVSGSPGQSITISCTGTSSDLGGYNYVSWYQHRPGKAPKLIIY DVTVRPSGVSDRFSGSKSGNTASLTISGLQAEDEADYYCGSYTSSSTLLWV FGGGTKLTVL | VL Clone 283 |
| 191 | QSALTQPASVSGSPGQSITISCTGTSSDLGGYNYVSWYQHRPGKAPKLIIY DVTVRPSGVSDRFSGSKSGNTASLTISGLQAEDEADYYCGSYTSSSTLLWV FGGGTKLTVL | VL Clone 302 |
| 192 | QSVLXXPXXASGSPGQSVTVSCTGTGRDIGAYDYVSWYQQHPGKAPKLLIY GVNKRPSGVPDRFSGSKSDNTASLTVSGLQVEDEADYYCSXAGRKYVFGT GXKVTVL | VL Clone 305 |
| 193 | QSALTQPASVSGSPGQSITISCTGTSSDLGGYNYVSWYQHRPGKAPKLIIY DVTVRPSGVSDRFSGSKSGNTASLTISGLQAEDEADYYCGSYTSSSTLLWV FGGGTKLTVL | VL Clone 314 |
| 194 | QSALTQPASVSGSPGQSITISCTGTSSDLGGYNYVSWYQHRPGKAPKLIIY DVTVRPSGVSDRFSGSKSGNTASLTISGLQAEDEADYYCGSYTSSSTLLWV FGGGTKLTVL | VL Clone 379 |
| 195 | QSALTQPASVSGSPGQSITISCTGTSSDLGGYNYVSWYQHRPGKAPKLIIY DVTVRPSGVSDRFSGSKSGNTASLTISGLQAEDEADYYCGSYTSSSTLLWV FGGGTKLTVL | VL Clone 324 |
| 196 | QSALTQPASVSGSPGQSITISCTETSSDLGGYNYVSWYQHRPGKAPKLIIY DVTVRPSGVXDRFSGSKSGNTASLTISGLQAEDEADYYCGSYTSSSTLLWV FGGGTKLTVL | VL Clone 327 |
| 197 | QSALTQPASVSGSPGQSITISCTGTSSDLGGYNYVSWYQHRPGKAPKLIIYD VTVRPSGVSDRFSGSKSGNTASLTISGLQAEDEADYYCGSYTSSSTLLWVFG GGTKLTVL | VL Clone 336 |
| 198 | QSALTQPASVSGSPGHSITISCTGTRSDVGGFDYVSWYQHNPGKAPKLIIYD VTKRPSGVSNRFSGAKSGITASLTISGLQAEDEADYYCTSYRPGPTFVFGTG TKLDIK | VL Clone 440 |
| 199 | QSALTQPASVSGSPGQSITISCTGTSSDLGGYNYVSWYQHRPGKAPKLIIYD VTVRPSGVSDRFSGSKSGNTASLTISGLQAEDEADYYCGSYTSSSTLLWVFG GGTKLDIK | VL Clone 448 |
| 200 | QSVLTQPRSLSGSPGQSVTIACTGASTDVGGYNYVSWYQQHPGKAPKLMIYD VNKRPSGVPDRFSGSKSGNTAFLTISGLQAEDEADYYCCSYAGSYTFEVFGG GTKLTVL | VL Clone 505 |
| 201 | QLVLTQPPSVSGSPGQSVTFSCTGASSDVGGYDHVSWYQHHPGKGPKLLIYD VSKRPSGVPDRFSGSKSGNTASLTISGLQAEDEADYYCCSFAGYYTYWLFGG GTKVTVL | VL Clone 506 |
| 202 | QSALTQPRSVSGFPGQSVTISCTGTTSDDVSWYQQHPGKAPQLMLYDVSKRP SGVPHRFSGSRSGRAASLIISGLQTEDEADYFCCSYAGRYNSVPFGGGTKLT VL | VL Clone 508 |
| 203 | SYVLTQPPSASGTPGQRVTISCSGSSSNIGSNTVNWYQQFPGTAPKLLIYSN NQRPSGVPDRFSGSKSGTSASLAISGLQSEDEAEYYCAAWDDSLNVV | VL Clone 184 |
| 204 | QSVLTQPPSVSAAPGQKVTISCSGSSSNIGNNYVSWYQQLPGTAPKLLIYDN NKRPSGIPDRFSGSKSGTSATLGITGLQTGDEGDYYCGTWDISLRFGVFGGG TKVTVL | VL Clone 79 |
| 205 | QSVLTQPRSVSGSPGQSVTISCTGPISGVGDYTSVSWYQHYPGKTPKLIIYD VTQRPSGVPNRFSGSKSGNTASLTISGLQADDEADYYCCSYEAPTHTYVFGT GTKLTVL | VL Clone 835 |

TABLE 9-continued

SEQUENCES

| SEQ ID NO. | Sequence | Description |
|---|---|---|
| 206 | QITLKESGPTLVKPTQTLTLTCTFSGFSLSTSGVGVGWIRQPPGKALEWLAL IYWDDDKRYSPSLKSRLTITKDTSKNQVVLTMTNMDPVDTATYYCAHIDYGS GSYSPRTSYYYMSVWGKGTTVTVSSGGGGSGGGGSGGGGSAIQLTQSPSFL SASVGDRVTITCRASQGISSYLNWYQQRAGKAPELLIYAASNLQSGVPSRFS GSGSGTDFTLTITSVQPEDFATYFCQQGDAFPLTFGPGTKVTIR | scFv Clone 1265 |
| 207 | QVQLVQSGGGVVQPGRSLRLSCAASGFTFDDYAMHWVRQAPGKGLEWVSGIS WNSGSIGYADSVKGRFTISRDNAKNSLYLQMNSLRAEDTAVYYCARDQGYHY YDSAEHAFDIWGQGTVVTVSSGGGGSGGGGSGGGGSEIVLTQSPATLSLSPG ETATLSCRASQSINHYLAWYQQKPGQAPRLLIYDASNRATGIPARFSGSGSG TDFTLTISSLEPEDFATYYCQQSYSHPRMYTFGQGTKLEIK | scFv Clone 213 |
| 208 | EVQLVQSGGGLVQPGRSLRLSCAASGFTFDDYAMHWVRQAPGKGLEWVSGIS WNSGSIGYADSVKGRFTISRDNAKNSLYLQMNSLRAEDTAVYYCARDQGYHY YDSAEHAFDIWGQGTVVTVSSGGGGSGGGGSGGGGSAIRMTQSPSSLSASVG DRVTVTCQASQDISNYLNWYQQKPGRAPKLLIYDASNVKAGVPSRFSGGGSG TDFTLTISSLQPEDFATYYCQQSYSTPQAYTFGQGTKLDIK | scFv Clone 255 |
| 209 | EVQLVESGGGLVQPGRSLRLSCAASGFTFDDYAMHWVRQAPGKGLEWVSGIS WNSGRIGYADSVKGRFTISRDNAKNSLFLQMNSLRAEDTAVYYCARDQGYHY YDSAEHAFDIWGQGTVVTVSSGGGGSGGGGSGGGGSQSVLTQPPSVSAAPGQ KVTISCSGSSSNIGNNYVSWYQQLPGTAPKLLIYDNNKRPSGIPDRFSGSKS GTSATLGITGLQTGDEADYYCGTWDSSLNRDWVFGGGTKLTVL | scFv Clone 272 |
| 210 | QVQLVESGGGLVQPGRSLRLSCAASGFTFDDYAMHWVRQAPGKGLEWVSGIS WNSGRIGYADSVKGRFTISRDNAKNSLFLQMNSLRAEDTAVYYCARDQGYHY YDSAEHAFDIWGQGTVVTVSSGGGGSGGGGSGGGGSQSALTQPASVSGSPGQ SITISCTGTSSDLGGYNYVSWYQHRPGKAPKLIIYDVTVRPSGVSDRFSGSK SGNTASLTISGLQAEDEADYYCGSYTSSSTLLWVFGGGTKLTVL | scFv Clone 283 |
| 211 | QVQLVESGGGLVQPGRSLRLSCAASGFTFDDYAMHWVRQAPGKGLEWVSGIS WNSGRIGYADSVKGRFTISRDNAKNSLFLQMNSLRAEDTAVYYCARDQGYHY YDSAEHAFDIWGQGTVVTVSSGGGGSGGGGSGGGGSQSALTQPASVSGSPGQ SITISCTGTSSDLGGYNYVSWYQHRPGKAPKLIIYDVTVRPSGVSDRFSGSK SGNTASLTISGLQAEDEADYYCGSYTSSSTLLWVFGGGTKLTVL | scFv Clone 302 |
| 212 | QVQLVESGGGLVQPGRSLRLSCAASGFTFDDYAMHWVRQAPGKGLEWVSGIS WNSGRIGYADSXXGRXXISRDNAKNSLFLQMNSLRAEDTAXYYCAXDQGXHX YDSAEHAFXIWGQGTVVTVSSGGGGSGGGGSGGGGSQSVLXXPXXASGSPGQ SVTVSCTGTGRDIGAYDYVSWYQQHPGKAPKLLIYGVNKRPSGVPDRFSGSK SDNTASLTVSGLQVEDEADYYCSSXAGRKYVFGTGXKVTVL | scFv Clone 305 |
| 213 | EVQLVESGGGLVQPGRSLRLSCAASGFTFDDYAMHWVRQAPGKGLEWVSGIS WNSGRIGYADSVKGRFTISRDNAKNSLFLQMNSLRAEDTAVYYCARDQGYHY YDSAEHAFDIWGQGTVVTVSSGGGGSGGGGSGGGGSQSALTQPASVSGSPGQ SITISCTGTSSDLGGYNYVSWYQHRPGKAPKLIIYDVTVRPSGVSDRFSGSK SGNTASLTISGLQAEDEADYYCGSYTSSSTLLWVFGGGTKLTVL | scFv Clone 314 |
| 214 | EVQLVESGGGLVQPGRSLRLSCAASGFTFDDYAMHWVRQAPGKGLEWVSGIS WNSGRIGYADSVKGRFTISRDNAKNSLFLQMNSLRAEDTAVYYCARDQGYHY YDSAEHAFDIWGQGTVVTVSSGGGGSGGGGSGGGGSQSALTQPASVSGSPGQ SITISCTGTSSDLGGYNYVSWYQHRPGKAPKLIIYDVTVRPSGVSDRFSGSK SGNTASLTISGLQAEDEADYYCGSYTSSSTLLWVFGGGTKLTVL | scFv Clone 379 |
| 215 | EVQLVESGGGLVQPGRSLRLSCAASGFTFDDYAMHWVRQAPGKGLEWVSGIS WNSGRIGYADSVKGRFTISRDNAKNSLFLQMNSLRAEDTAVYYCARDQGYHY YDSAEHAFDIWGQGTVVTVSSGGGGSGGGGSGGGGSQSALTQPASVSGSPGQ SITISCTGTSSDLGGYNYVSWYQHRPGKAPKLIIYDVTVRPSGVSDRFSGSK SGNTASLTISGLQAEDEADYYCGSYTSSSTLLWVFGGGTKLTVL | scFv Clone 324 |
| 216 | QVQLVESGGGLVQPGRSLRLSCAASGFTFDDYAMHWVRQAPGKGLEWVSGIS WNSGRIGYADSVKGRFTISRDNAXNSLFLQMNSLRAEDTAVYYCARDQGYHY YDSAEHAFDIWGQGTVVTVSSGGGGSGGGGSGGGGSQSALTQPASVSGSPGQ SITISCTETSSDLGGYNYVSWYQHRPGKAPKLIIYDVTVRPSGVXDRFSGSK SGNTASLTISGLQAEDEADYYCGSYTSSSTLLWVFGGGTKLTVL | scFv Clone 327 |
| 217 | QVQLVESGGGLVQPGRSLRLSCAASGFTFDDYAMHWVRQAPGKGLEWVSGIS WNSGRIGYADSVKGRFTISRDNAKNSLFLQMNSLRAEDTAVYYCARDQGYHY YDSAEHAFDIWGQGTVVTVSSGGGGSGGGGSGGGGSQSALTQPASVSGSPGQ SITISCTGTSSDLGGYNYVSWYQHRPGKAPKLIIYDVTVRPSGVSDRFSGSK SGNTASLTISGLQAEDEADYYCGSYTSSSTLLWVFGGGTKLTVL | scFv Clone 336 |

TABLE 9-continued

SEQUENCES

| SEQ ID NO. | Sequence | Description |
|---|---|---|
| 218 | QVQLVESGGGLVQPGRSLRLSCAASGFTFDDYAMHWVRQAPGKGLEWVSGIS WNSGRIGYADSVKGRFTISRDNAKNSLFLQMNSLRAEDTAVYYCARDQGYHY YDSAEHAFDIWGQGTVVTVSSGGGGSGGGGSGGGGSQSALTQPASVSGSPGH SITISCTGTRSDVGGFDYVSWYQHNPGKAPKLIIYDVTKRPSGVSNRFSGAK SGITASLTISGLQAEDEADYYCTSYRPGPTFVFGTGTKLDIK | scFv Clone 440 |
| 219 | QVQLVESGGGLVQPGRSLRLSCAASGFTFDDYAMHWVRQAPGKGLEWVSGIS WNSGRIGYADSVKGRFTISRDNAKNSLFLQMNSLRAEDTAVYYCARDQGYHY YDSAEHAFDIWGQGTVVTVSSGGGGSGGGGSGGGGSQSALTQPASVSGSPGQ SITISCTGTSSDLGGYNYVSWYQHRPGKAPKLIIYDVTVRPSGVSDRFSGSK SGNTASLTISGLQAEDEADYYCGSYTSSSTLLWVFGGGTKLDIK | scFv Clone 448 |
| 220 | EVQLVESGGGLVQPGRSLRLSCAASGFTFDDYAMHWVRQAPGKGLEWVSGIS WNSGRIGYADSVKGRFTISRDNAKNSLFLQMNSLRAEDTAVYYCARDQGYHY YDSAEHAFDIWGQGTMVTVSSQSVLTQPRSLSGSPGQSVTIACTGASTDVGG YNYVSWYQQHPGKAPKLMIYDVNKRPSGVPDRFSGSKSGNTAFLTISGLQAE DEADYYCCSYAGSYTFEVFGGGTKLTVL | scFv Clone 505 |
| 221 | EVQLVESGGGLVQPGRSLRLSCAASGFTFDDYAMHWVRQAPGKGLEWVSGIS WNSGRIGYADSVKGRFTISRDNAKNSLFLQMNSLRAEDTAVYYCARDQGYHY YDSAEHAFDIWGQGTMVTVSSGGGGSGGGGSGGGGSQLVLTQPPSVSGSPGQ SVTFSCTGASSDVGGYDHVSWYQHHPGKGPKLLIYDVSKRPSGVPDRFSGSK SGNTASLTISGLQAEDEADYYCCSFAGYYTYWLFGGGTKVTVL | scFv Clone 506 |
| 222 | EVQLVESGGGLVQPGRSLRLSCAASGFTFDDYAMHWVRQAPGKGLEWVSGIS WNSGRIGYADSVKGRFTISRDNAKNSLFLQMNSLRAEDTAVYYCARDQGYHY YDSAEHAFDIWGQGTVVTVSSGGGGSGGGGSGGGGSQSALTQPRSVSGFPGQ SVTISCTGTTSDDVSWYQHPGKAPQLMLYDVSKRPSGVPHRFSGSRSGRAA SLIISGLQTEDEADYFCCSYAGRYNSVPFGGGTKLTVL | scFv Clone 508 |
| 223 | QVQLVESGGGLVQPGRSLRLSCAASGFTFDDYAMHWVRQAPGKGLEWVSGIS WNSGRIGYADSVKGRFTISRDNAKNSLFLQMNSLRAEDTAVYYCARDQGYHY YDSAEHAFDIWGQGTMVTVSSGGGGSGGGGSGGGGSSYVLTQPPSASGTPGQ RVTISCSGSSSNIGSNTVNWYQQFPGTAPKLLIYSNNQRPSGVPDRFSGSKS GTSASLAISGLQSEDEAEYYCAAWDDSLNVV | scFv Clone 184 |
| 224 | EVQLVESGGGLVQPGRSLRLSCAASGFTFDDYAMHWVRQAPGKGLEWVSGI SWNSGRIGYADSVKGRFTISRDNAKNSLFLQMNSLRAEDTAVYYCARDQGY HYYDSAEHAFDIWGQGTVVTVSSGGGGSGGGGSGGGGSQSVLTQPPSVSAA PGQKVTISCSGSSSNIGNNYVSWYQQLPGTAPKLLIYDNNKRPSGIPDRFS GSKSGTSATLGITGLQTGDEGDYYCGTWDISLRFGVFGGGTKVTVL | scFv Clone 79 |
| 225 | EVQLVESGGGLVQPGRSLRLSCAASGFTFDDYAMHWVRLAPGKGLEWVSGI SWNSGRIGYADSVKGRFTISRDNAKNSLFLQMNSLRAKDTAVYYCARDQGY HYYDSAEHAFDIWGQGTMVTVSSGGGGSGGGGSGGGGSQSVLTQPRSVSGS PGQSVTISCTGPISGVGDYTSVSWYQHYPGKTPKLIIYDVTQRPSGVPNRF SGSKSGNTASLTISGLQADDEADYYCCSYEAPTHTYVFGTGTKLTVL | scFv Clone 835 |
| 226 | X1X2X3X4X5X6X7X8X9X10X11X12X13X14 X1 = T, Q, R, or S; X2 = G, A, or E; X3 = I, T, S, D, A, or P; X4 = S, R, Q, G, or I ; X5 = null, S, R, or T; X6 = G, D, N, or null; X7 = V, L, null, or I; X8 = D, G, S, I, L, or null; X9 = S, G, A, I, null, or D; X10 = H, Y, F, S, or N; X11 = R, N, D, H, Y, or T; X12 = Y, F, W, D, H, T, or S; X13 = V, A, or L; X14 = S, N, or A | CDR-L1 consensus |
| 227 | X1X2X3X4X5X6X7 X1 = D, S, or G; X2 = F, V, N, K, or A; X3 = S, T, N, or D; X4 = K, V, N, R, or Q; X5 = R, V, or L; X6 = P, K, A, or E; X7 = S, P, A, or T | CDR-L2 consensus |

TABLE 9-continued

SEQUENCES

| SEQ ID NO. | Sequence | Description |
|---|---|---|
| 228 | X1X2X3X4X5X6X7X8X9X10X11X12<br>X1 = S, G, T, A, Q, C, or N;<br>X2 = S, Q, A, or T;<br>X3 = Y, S, W, or R;<br>X4 = A, D, R, T, or Y;<br>X5 = A, S, P, G, N, or D;<br>X6 = I, S, G, T, A, L, H, R, or N;<br>X7 = S, P, L, Y, or G;<br>X8 = P, T, S, Q, M, R, or N;<br>X9 = S, L, N, A, M, null, or R;<br>X10 = L, null, or D;<br>X11 = Y, W, F, V, A, or L;<br>X12 = V, T, L, or P | CDR-L3 consensus |

The invention claimed is:

1. An anti-CD19 antibody or antigen-binding fragment thereof, comprising a heavy chain variable (VH) region and a light chain variable (VL) region, wherein:
the VH region comprises a heavy chain complementarity determining region 1 (CDR-H1), a CDR-H2, and a CDR-H3 comprising the amino acid sequence set forth in SEQ ID NOs: 18, 19, and 20, respectively, and
the VL region comprises a light chain complementarity determining region 1 (CDR-L1), a CDR-L2, and a CDR-L3 comprising the amino acid sequence set forth in SEQ ID NOs: 21, 22, and 23, respectively; SEQ ID NOs: 21, 22, and 24, respectively; SEQ ID NOs: 25, 26, and 27, respectively; SEQ ID NOs: 28, 29, and 30, respectively; SEQ ID NOs: 31, 32, and 33, respectively; SEQ ID NOs: 74, 94, and 103, respectively; SEQ ID NOs: 73, 93, and 101, respectively; SEQ ID NOs: 75, 95, and 104, respectively; SEQ ID NOs: 76, 96, and 105, respectively; or SEQ ID NOs: 73, 93, and 102, respectively.

2. An anti-CD19 antibody or antigen-binding fragment thereof, comprising a heavy chain variable (VH) region and a light chain variable (VL) region, wherein:
(a) the VH region comprises a heavy chain complementarity determining region 1 (CDR-H1) 1, a CDR-H2, and a CDR-H3, respectively, comprising the amino acid sequences of CDR-H1, CDR-H2, and CDR-H3 sequences contained within the VH region amino acid sequence set forth in SEQ ID NO: 11; and
the VL region comprises a light chain complementarity determining region 1 (CDR-L1), a CDR-L2, and a CDR-L3, respectively, comprising the amino acid sequences of CDR-L1, CDR-L2, and CDR-L3 sequences contained within the light chain variable (VL) region amino acid sequence set forth in any one of SEQ ID NOs: 13, 14, 16, and 65; or
(b) the VH region comprises a heavy chain complementarity determining region 1 (CDR-H1) 1, a CDR-H2, and a CDR-H3, respectively, comprising the amino acid sequences of CDR-H1, CDR-H2, and CDR-H3 sequences contained within the VH region amino acid sequence set forth in SEQ ID NO: 12; and
the VL region comprises a light chain complementarity determining region 1 (CDR-L1), a CDR-L2, and a CDR-L3, respectively, comprising the amino acid sequences of CDR-L1, CDR-L2, and CDR-L3 sequences contained within the light chain variable (VL) region amino acid sequence set forth in any one of SEQ ID NOs: 15, 17, 67, and 91; or
(c) the VH region comprises a heavy chain complementarity determining region 1 (CDR-H1) 1, a CDR-H2, and a CDR-H3, respectively, comprising the amino acid sequences of CDR-H1, CDR-H2, and CDR-H3 sequences contained within the VH region amino acid sequence set forth in SEQ ID NO: 60; and the VL region comprises a light chain complementarity determining region 1 (CDR-L1), a CDR-L2, and a CDR-L3, respectively, comprising the amino acid sequences of CDR-L1, CDR-L2, and CDR-L3 sequences contained within the light chain variable (VL) region amino acid sequence set forth in SEQ ID NO: 64; or (d) the VH region comprises a heavy chain complementarity determining region 1 (CDR-H1) 1, a CDR-H2, and a CDR-H3, respectively, comprising the amino acid sequences of CDR-H1, CDR-H2, and CDR-H3 sequences contained within the VH region amino acid sequence set forth in SEQ ID NO: 61; and the VL region comprises a light chain complementarity determining region 1 (CDR-L1), a CDR-L2, and a CDR-L3, respectively, comprising the amino acid sequences of CDR-L1, CDR-L2, and CDR-L3 sequences contained within the light chain variable (VL) region amino acid sequence set forth in SEQ ID NO: 66.

3. An anti-CD19 antibody or antigen-binding fragment thereof, comprising a heavy chain variable (VH) region and a light chain variable (VL) region, wherein:

the VH region comprises a heavy chain complementarity determining region 1 (CDR-H1), a CDR-H2, and a CDR-H3 comprising the amino acid sequence set forth in SEQ ID NOs: 18, 72, and 20, respectively, and the VL region comprises a CDR-L1, a CDR-L2, and a CDR-L3 comprising the amino acid sequence set forth in SEQ ID NOs: 80, 100, and 109, respectively; SEQ ID NOs: 77, 97, and 106, respectively; SEQ ID NOs: 79, 99, and 108, respectively; or SEQ ID NOs: 78, 98, and 107, respectively.

4. The anti-CD19 antibody or antigen-binding fragment thereof of claim 1, wherein:

the VH and VL regions of the antibody or fragment comprise amino acid sequences that have at least 90% identity to the sequences set forth in SEQ ID NOs: 12 and 17, respectively;

the VH and VL regions of the antibody or fragment comprise amino acid sequences that have at least 90% identity to the sequences set forth in SEQ ID NOs: 12 and 15, respectively;

the VH and VL regions of the antibody or fragment comprise amino acid sequences that have at least 90% identity to the sequences set forth in SEQ ID NOs: 11 and 13, respectively;

the VH and VL regions of the antibody or fragment comprise amino acid sequences that have at least 90% identity to the sequences set forth in SEQ ID NOs: 11 and 14, respectively;

the VH and VL regions of the antibody or fragment comprise amino acid sequences that have at least 90% identity to the sequences set forth in SEQ ID NOs: 11 and 16, respectively;

the VH and VL regions of the antibody or fragment comprise amino acid sequences that have at least 90% identity to the sequences set forth in SEQ ID NOs: 11 and 65, respectively;

the VH and VL regions of the antibody or fragment comprise amino acid sequences that have at least 90% identity to the sequences set forth in SEQ ID NOs: 60 and 64, respectively;

the VH and VL regions of the antibody or fragment comprise amino acid sequences that have at least 90% identity to the sequences set forth in SEQ ID NOs: 61 and 66, respectively;

the VH and VL regions of the antibody or fragment comprise amino acid sequences that have at least 90% identity to the sequences set forth in SEQ ID NOs: 12 and 67, respectively;

the VH and VL regions of the antibody or fragment comprise amino acid sequences that have at least 90% identity to the sequences set forth in SEQ ID NOs: 12 and 91, respectively;

the VH and VL regions of the antibody or fragment comprise amino acid sequences that have at least 90% identity to the sequences set forth in SEQ ID NOs: 170 and 190, respectively;

the VH and VL regions of the antibody or fragment comprise amino acid sequences that have at least 90% identity to the sequences set forth in SEQ ID NOs: 171 and 191, respectively;

the VH and VL regions of the antibody or fragment comprise amino acid sequences that have at least 90% identity to the sequences set forth in SEQ ID NOs: 173 and 193, respectively;

the VH and VL regions of the antibody or fragment comprise amino acid sequences that have at least 90% identity to the sequences set forth in SEQ ID NOs: 174 and 194, respectively;

the VH and VL regions of the antibody or fragment comprise amino acid sequences that have at least 90% identity to the sequences set forth in SEQ ID NOs: 175 and 195, respectively;

the VH and VL regions of the antibody or fragment comprise amino acid sequences that have at least 90% identity to the sequences set forth in SEQ ID NOs: 177 and 197, respectively; or the VH and VL regions of the antibody or fragment comprise amino acid sequences that have at least 90% identity to the sequences set forth in SEQ ID NOs: 179 and 199, respectively.

5. The anti-CD19 antibody or antigen-binding fragment thereof of claim 3, wherein:

the VH and VL regions of the antibody or fragment comprise amino acid sequences that have at least 90% identity to the sequences set forth in SEQ ID NOs: 63 and 71, respectively;

the VH and VL regions of the antibody or fragment comprise amino acid sequences that have at least 90% identity to the sequences set forth in SEQ ID NOs: 62 and 68, respectively;

the VH and VL regions of the antibody or fragment comprise amino acid sequences that have at least 90% identity to the sequences set forth in SEQ ID NOs: 63 and 70, respectively;

the VH and VL regions of the antibody or fragment comprise amino acid sequences that have at least 90% identity to the sequences set forth in SEQ ID NOs: 62 and 69, respectively; or the VH and VL regions of the antibody or fragment comprise amino acid sequences that have at least 90% identity to the sequences set forth in SEQ ID NOs: 63 and 90, respectively.

6. The anti-CD19 antibody or antigen-binding fragment thereof of claim 1, wherein:

the VH and VL regions of the antibody or fragment comprise the amino acid sequences of SEQ ID NOs: 12 and 17, respectively;

the VH and VL regions of the antibody or fragment comprise the amino acid sequences of SEQ ID NOs: 12 and 15, respectively;
the VH and VL regions of the antibody or fragment comprise the amino acid sequences of SEQ ID NOs: 11 and 13, respectively;
the VH and VL regions of the antibody or fragment comprise the amino acid sequences of SEQ ID NOs: 11 and 14, respectively;
the VH and VL regions of the antibody or fragment comprise the amino acid sequences of SEQ ID NOs: 11 and 16, respectively;
the VH and VL regions of the antibody or fragment comprise the amino acid sequences of SEQ ID NOs: 11 and 65, respectively;
the VH and VL regions of the antibody or fragment comprise the amino acid sequences of SEQ ID NOs: 60 and 64, respectively;
the VH and VL regions of the antibody or fragment comprise the amino acid sequences of SEQ ID NOs: 61 and 66, respectively;
the VH and VL regions of the antibody or fragment comprise the amino acid sequences of SEQ ID NOs: 12 and 67, respectively;
the VH and VL regions of the antibody or fragment comprise the amino acid sequences of SEQ ID NOs: 12 and 91, respectively;
the VH and VL regions of the antibody or fragment comprise the amino acid sequences of SEQ ID NOs: 170 and 190, respectively;
the VH and VL regions of the antibody or fragment comprise the amino acid sequences of SEQ ID NOs: 171 and 191, respectively;
the VH and VL regions of the antibody or fragment comprise the amino acid sequences of SEQ ID NOs: 173 and 193, respectively;
the VH and VL regions of the antibody or fragment comprise the amino acid sequences of SEQ ID NOs: 174 and 194, respectively;
the VH and VL regions of the antibody or fragment comprise the amino acid sequences of SEQ ID NOs: 175 and 195, respectively;
the VH and VL regions of the antibody or fragment comprise the amino acid sequences of SEQ ID NOs: 177 and 197, respectively; or
the VH and VL regions of the antibody or fragment comprise the amino acid sequences of SEQ ID NOs: 179 and 199, respectively.

7. The anti-CD19 antibody or antigen-binding fragment thereof of claim 3, wherein:
the VH and VL regions of the antibody or fragment comprise the amino acid sequences of SEQ ID NOs: 63 and 71, respectively;
the VH and VL regions of the antibody or fragment comprise the amino acid sequences of SEQ ID NOs: 62 and 68, respectively;
the VH and VL regions of the antibody or fragment comprise the amino acid sequences of SEQ ID NOs: 63 and 70, respectively;
the VH and VL regions of the antibody or fragment comprise the amino acid sequences of SEQ ID NOs: 62 and 69, respectively; or
the VH and VL regions of the antibody or fragment comprise the amino acid sequences of SEQ ID NOs: 63 and 90, respectively.

8. The anti-CD19 antibody or antigen-binding fragment thereof of claim 1, wherein the antibody specifically binds to human CD19.

9. The anti-CD19 antibody or antigen-binding fragment thereof of claim 3, wherein the antibody specifically binds to human CD19.

10. The anti-CD19 antibody or antigen-binding fragment thereof of claim 1, wherein the antibody or fragment is monoclonal and/or recombinant.

11. The anti-CD19 antibody or antigen-binding fragment thereof of claim 1, wherein the antibody or fragment is human.

12. The anti-CD19 antibody or antigen-binding fragment thereof of claim 1, which is a single chain molecule.

13. The anti-CD19 antibody or antigen-binding fragment thereof of claim 3, which is a single chain molecule.

14. The anti-CD19 antibody or antigen-binding fragment thereof of claim 12, wherein the single chain molecule comprises an scFv.

15. The anti-CD19 antibody or antigen-binding fragment thereof of claim 13, wherein the single chain molecule comprises an scFv.

16. The anti-CD19 antibody or antigen-binding fragment thereof of claim 14, wherein the scFv comprises a sequence that exhibits at least 95% sequence identity to the amino acid sequence set forth in any one of SEQ ID NOS: 2, 4, 6, 8, 10, 49, 51, 53, 59, 87, 210, 211, 213-215, 217, and 219.

17. The anti-CD19 antibody or antigen-binding fragment thereof of claim 14, wherein the scFv comprises the amino acid sequence set forth in any one of SEQ ID NOS: 2, 4, 6, 8, 10, 49, 51, 53, 59, 87, 210, 211, 213-215, 217, and 219.

18. The anti-CD19 antibody or antigen-binding fragment thereof of claim 1, which further comprises at least a portion of an immunoglobulin constant region.

19. The anti-CD19 antibody or antigen-binding fragment thereof of claim 18, wherein the at least a portion comprises a hinge region and/or an Fc region.

20. The anti-CD19 antibody or antigen-binding fragment thereof of claim 15, wherein the scFv comprises a sequence that exhibits at least 95% sequence identity to the amino acid sequence set forth in any one of SEQ ID NOs: 45, 47, 55, 57, and 89.

21. The anti-CD19 antibody or antigen-binding fragment thereof of claim 15, wherein the scFv comprises the amino acid sequence set forth in any one of SEQ ID NOs: 45, 47, 55, 57, and 89.

22. A composition, comprising the anti-CD19 antibody or antigen-binding fragment thereof of claim 1 and a pharmaceutically acceptable excipient.

23. A composition, comprising the anti-CD19 antibody or antigen-binding fragment thereof of claim 2 and a pharmaceutically acceptable excipient.

24. A composition, comprising the anti-CD19 antibody or antigen-binding fragment thereof of claim 3 and a pharmaceutically acceptable excipient.

25. The anti-CD19 antibody or antigen-binding fragment thereof of claim 1, wherein:
the VH and VL regions of the antibody or fragment comprise the amino acid sequences of SEQ ID NOs: 12 and 17, respectively;
the VH and VL regions of the antibody or fragment comprise the amino acid sequences of SEQ ID NOs: 12 and 15, respectively;
the VH and VL regions of the antibody or fragment comprise the amino acid sequences of SEQ ID NOs: 11 and 13, respectively;

the VH and VL regions of the antibody or fragment comprise the amino acid sequences of SEQ ID NOs: 11 and 14, respectively; or the VH and VL regions of the antibody or fragment comprise the amino acid sequences of SEQ ID NOs: 11 and 16, respectively.

26. The anti-CD19 antibody or antigen-binding fragment thereof of claim 14, wherein the scFv comprises the amino acid sequence set forth in any one of SEQ ID NOS: 2, 4, 6, 8, or 10.

27. The anti-CD19 antibody or antigen-binding fragment thereof of claim 14, wherein the scFv comprises a sequence that exhibits at least 95% sequence identity to the amino acid sequence set forth in any one of SEQ ID NOS: 2, 4, 6, 8, or 10.

28. The anti-CD19 antibody or antigen-binding fragment thereof of claim 3, wherein the antibody or fragment is monoclonal and/or recombinant.

29. The anti-CD19 antibody or antigen-binding fragment thereof of claim 3, wherein the antibody or fragment is human.

30. The anti-CD19 antibody or antigen-binding fragment thereof of claim 2, wherein:
   (a) the VH region comprises a CDR-H1, a CDR-H2, and a CDR-H3, respectively, comprising the amino acid sequences of CDR-H1, CDR-H2, and CDR-H3 sequences contained within the VH region amino acid sequence set forth in SEQ ID NO: 11; and
   the VL region comprises a CDR-L1, a CDR-L2, and a CDR-L3, respectively, comprising the amino acid sequences of CDR-L1, CDR-L2, and CDR-L3 sequences contained within the VL region amino acid sequence set forth in any one of SEQ ID NOs: 13, 14, and 16; or
   (b) the VH region comprises a CDR-H1, a CDR-H2, and a CDR-H3, respectively, comprising the amino acid sequences of CDR-H1, CDR-H2, and CDR-H3 sequences contained within the VH region amino acid sequence set forth in SEQ ID NO: 12; and
   the VL region comprises a CDR-L1, a CDR-L2, and a CDR-L3, respectively, comprising the amino acid sequences of CDR-L1, CDR-L2, and CDR-L3 sequences contained within the VL region amino acid sequence set forth in SEQ ID NO: 15 or 17.

31. The anti-CD19 antibody or antigen-binding fragment thereof of claim 1, wherein the VH region comprises a CDR-H1, a CDR-H2, and a CDR-H3 comprising the amino acid sequence set forth in SEQ ID NOs: 18, 19, and 20, respectively; and the VL region comprises a CDR-L1, a CDR-L2, and a CDR-L3 comprising the amino acid sequence set forth in SEQ ID NOs: 21, 22, and 23, respectively; SEQ ID NOs: 21, 22, and 24, respectively; SEQ ID NOs: 25, 26, and 27, respectively; SEQ ID NOs: 28, 29, and 30, respectively; or SEQ ID NOs: 31, 32, and 33, respectively.

* * * * *